(12) United States Patent
Zhou et al.

(10) Patent No.: US 12,115,226 B2
(45) Date of Patent: Oct. 15, 2024

(54) LINKER CONTAINING ARYLNITRO, ANTIBODY-DRUG CONJUGATE CONTAINING LINKER AND USE OF LINKER

(71) Applicant: Academy of Military Medical Sciences, Beijing (CN)

(72) Inventors: Xinbo Zhou, Beijing (CN); Yanming Wang, Beijing (CN); Song Li, Beijing (CN); Wu Zhong, Beijing (CN); Shiyong Fan, Beijing (CN); Dian Xiao, Beijing (CN); Junhai Xiao, Beijing (CN); Zhibing Zheng, Beijing (CN); Xingzhou Li, Beijing (CN); Yunde Xie, Beijing (CN); Ruiyuan Cao, Beijing (CN); Xiaokui Wang, Beijing (CN)

(73) Assignee: Academy of Military Medical Sciences, Beijing (CN)

( * ) Notice: Subject to any disclaimer, the term of this patent is extended or adjusted under 35 U.S.C. 154(b) by 899 days.

(21) Appl. No.: 17/271,882

(22) PCT Filed: Aug. 28, 2019

(86) PCT No.: PCT/CN2019/103053
§ 371 (c)(1),
(2) Date: Feb. 26, 2021

(87) PCT Pub. No.: WO2020/043129
PCT Pub. Date: Mar. 5, 2020

(65) Prior Publication Data
US 2021/0205464 A1 Jul. 8, 2021

(30) Foreign Application Priority Data

Aug. 30, 2018 (CN) .......................... 201811002559.2

(51) Int. Cl.
| | | |
|---|---|---|
| A61K 47/68 | (2017.01) |
| A61K 31/337 | (2006.01) |
| A61K 31/4745 | (2006.01) |
| A61K 31/537 | (2006.01) |
| A61K 31/5517 | (2006.01) |
| A61K 31/704 | (2006.01) |
| A61K 38/07 | (2006.01) |
| A61K 47/54 | (2017.01) |
| A61P 35/00 | (2006.01) |
| C07C 237/04 | (2006.01) |
| C07D 207/452 | (2006.01) |
| C07D 233/94 | (2006.01) |
| C07D 307/71 | (2006.01) |
| C07D 333/44 | (2006.01) |
| C07D 403/04 | (2006.01) |
| C07D 405/12 | (2006.01) |
| C07D 409/12 | (2006.01) |

(52) U.S. Cl.
CPC ........ *A61K 47/6811* (2017.08); *A61K 31/337* (2013.01); *A61K 31/4745* (2013.01); *A61K 31/537* (2013.01); *A61K 31/5517* (2013.01); *A61K 31/704* (2013.01); *A61K 38/07* (2013.01); *A61K 47/545* (2017.08); *A61K 47/6803* (2017.08); *A61K 47/6809* (2017.08); *A61P 35/00* (2018.01); *C07C 237/04* (2013.01); *C07D 207/452* (2013.01); *C07D 233/94* (2013.01); *C07D 307/71* (2013.01); *C07D 333/44* (2013.01); *C07D 403/04* (2013.01); *C07D 405/12* (2013.01); *C07D 409/12* (2013.01)

(58) Field of Classification Search
None
See application file for complete search history.

(56) References Cited

FOREIGN PATENT DOCUMENTS

| CN | 106661123 A | 5/2017 |
|---|---|---|
| CN | 107789630 A | 3/2018 |
| EP | 3524273 A1 | 8/2019 |
| WO | 2009151687 A2 | 12/2009 |
| WO | 2015196089 A1 | 12/2015 |
| WO | 2016094505 A1 | 6/2016 |
| WO | 2017214301 A1 | 12/2017 |

OTHER PUBLICATIONS

International Search Report, Application No. PCT/CN2019/103053, mailed Nov. 27, 2019. ISA/China National Intellectual Property Administration.

*Primary Examiner* — Zinna Northington Davis
(74) *Attorney, Agent, or Firm* — Honigman LLP

(57) ABSTRACT

The present application relates to a linker containing arylnitro, an antibody-drug conjugate the linker and use of the linker, as well as a pharmaceutical composition comprising the antibody-drug conjugate and use of the antibody-drug conjugate for treatment and/or prevention of a disease

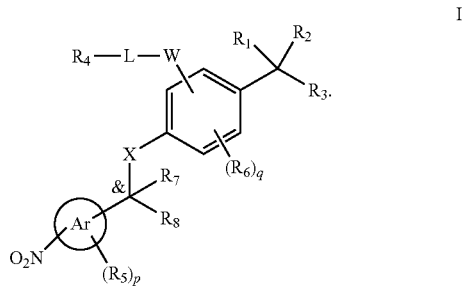

18 Claims, 7 Drawing Sheets

LINKER CONTAINING ARYLNITRO, ANTIBODY-DRUG CONJUGATE CONTAINING LINKER AND USE OF LINKER

CROSS-REFERENCE TO RELATED APPLICATIONS

This application is a National Stage Application and claims priority under 35 U.S.C. § 371 to Patent Cooperation Treaty application PCT/CN2019/103053, filed Aug. 28, 2019, which claims the benefit of Chinese Patent Application No. 201811002559.2, filed Aug. 30, 2018. Priority is claimed to these applications and the disclosures of these prior applications are considered part of the disclosure of this application and to the extent allowed the entire contents of the aforementioned applications are incorporated herein.

TECHNICAL FIELD

The present application belongs to the field of medicinal chemistry, specifically relates to a linker containing arylnitro, an antibody-drug conjugate containing the linker and use of the linker, as well as a pharmaceutical composition comprising the antibody-drug conjugate and use of the antibody-drug conjugate for treatment and/or prevention of a disease.

BACKGROUND ART

An antibody-drug conjugate (ADC) organically combines a monoclonal antibody with a cytotoxin, thereby combines the advantages of both antibody and cytotoxic drug and has characteristics such as strong targeting, high cytotoxicity, low toxic and side effect, long degradation half-life. ADC structurally comprises three components: an antibody, a small molecule cytotoxin and a linker, in which the role of antibody is to achieve targeting, the role of cytotoxin is to kill target cells, and the role of linker is to realize the organic combination of antibody and cytotoxin in structure so as to form an organic entirety. The design of linker is of great significance to ADC drugs. As a junction and bridge connecting the monoclonal antibody and the small molecule cytotoxin, the linker has a nature that directly affects the efficacy and safety of ADC. As the linker of ADC, it must make the drug stable in the blood circulation system and release the active toxin quickly and effectively after reaching the target tissue. The construction of linkers has become a core element and a major challenge restricting the development of ADCs.

Regarding the development of ADC linkers, there are many important considerations, including the coupling site of antibody, the average number of cytotoxins linked to each antibody molecule (drug to antibody ratio, DAR), the cleavability of linker, the hydrophilicity of linker, etc. The linker should have a long-term stability in the circulatory system, and can release cytotoxin quickly and effectively after reaching the target cells, so as to exert the two advantages of antibody targeting and high toxin efficiency. At the present stage, the design idea of linker is mainly to utilize the difference between tumor cells and blood circulation system environment to achieve selective release of toxin in tumor tissues.

According to the different cleavage modes to release toxins, the linkers can be divided into two categories: cleavable linkers and non-cleavable linkers. Regarding the ADCs containing cleavable linkers, after being degraded in target cells, they can release the free parent toxin itself to exert its effectiveness, while regarding the ADCs containing non-cleavable linkers, after they are degraded in target cells, the active substance exerting effectiveness is often not the cytotoxin itself, but a complex formed by the toxin and the amino acid residue at the linker-antibody coupling site.

According to the different cleavage mechanisms, the cleavable linkers are classified into chemically cleavable linkers and enzymatically cleavable linkers. The enzymatically cleavable linkers have significant advantages over the chemically cleavable linkers in terms of stability and drug release selectivity. At the present stage, the enzymatically cleavable linkers have become the mainstream choice for ADCs. The relatively mature enzymatically cleavable linkers studied are dipeptide linkers whose cleavage depends on cathepsin B.

The existing ADC drug-releasing enzymes such as cathepsin B or β-glucuronidase are non-tumor specific enzymes, which are widely present in the lysosomes of most cells of mammal. For those unavoidable off-target ADCs, they can be degraded by the drug-releasing enzymes in the lysosomes of normal tissues and release highly lethal cytotoxin drugs such as MMAE, which are toxic to normal tissues, and the non-ionic free cytotoxins can further penetrate the normal cell membrane usually via the bystander effect to cause systemic toxicity to surrounding tissues.

For the current mainstream enzymatically cleavable ADCs, the lack of tumor specificity and the off-target toxicity caused by non-specific enzymolysis are common problems during drug release process.

Contents of the Disclosure

The present application relates to a compound represented by Formula I or a salt thereof,

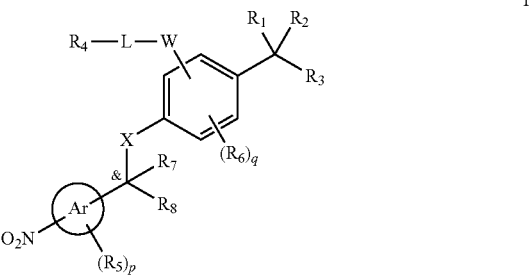

wherein:

$R_1$ is hydrogen, methyl, ethyl, n-propyl or isopropyl;

$R_2$ is hydrogen, methyl, ethyl, n-propyl or isopropyl;

$R_3$ is fluorine, chlorine, bromine, iodine or

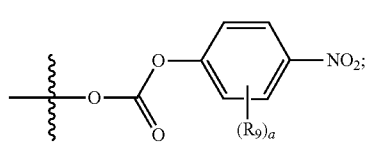

R$_4$ is and in the two carbonyl groups are located on the same side of the C=C double bond, which is a cis structure, R$_{11}$ is a C$_{1-6}$ linear or branched alkyl, and R$_{11}$ is optionally mono- or multi-substituted by one or more substituents selected from the group consisting of: halogen and C$_{1-4}$ alkoxy;

X is oxygen atom (O), nitrogen atom (N) or sulfur atom (S);

Ar is aryl, heteroaryl, aryl-fused-heterocyclyl or heteroaryl-fused-heterocyclyl, preferably 5- or 6-membered aryl, or 5- or 6-membered heteroaryl; preferably, the nitro on Ar and the C atom at & site are located at the conjugation positions of the aromatic system, and more preferably, Ar is 6-membered aryl or 6-membered heteroaryl, and the nitro on Ar and the C atom at & site are at para- or ortho-positions;

R$_5$ is hydrogen, methyl, ethyl, n-propyl, isopropyl, fluorine, chlorine, bromine, iodine, hydroxyl or cyano;

R$_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;

R$_7$ is hydrogen, methyl, ethyl, n-propyl or isopropyl;

R$_8$ is hydrogen, methyl, ethyl, n-propyl or isopropyl;

R$_9$ is hydrogen, methyl, ethyl, n-propyl, isopropyl, fluorine, chlorine, bromine, iodine, hydroxyl or cyano;

q is 0, 1, 2 or 3;

p is 0, 1, 2 or 3;

a is 0, 1, 2, 3 or 4;

L is —(CH$_2$)$_i$O(CH$_2$)$_j$—, —(CH$_2$)$_i$O(CH$_2$)$_j$—C(O)—, —(CH$_2$)$_i$—C(O)NH—(CH$_2$)$_j$—, —(CH$_2$CH$_2$O)$_i$—(CH$_2$)$_j$—C(O)—, —(CH$_2$)$_i$—(CH$_2$CH$_2$O)$_j$—C(O)—, —(OCH$_2$CH$_2$)$_i$—, —(CH$_2$)$_m$—, —(CH$_2$)$_r$C(O)—, —(CH$_2$)$_k$—C(O)NH—(CH$_2$CH$_2$O)—(CH$_2$)$_h$—C(O)—, —(CH$_2$)$_b$—C(O)NH—CH[(CH$_2$)$_a$—NHC(O)—(CH$_2$CH$_2$O)$_e$—(CH$_2$)$_f$CH$_3$]—,

W represents a linking group, preferably is —NH—CH$_2$—C(O)—NH—, —NH—CH$_2$—CH$_2$—C(O)—NH—, —C(O)—NH—, —NH—C(O)—, —O—, —S—, —NH—, —N(CH$_3$)—, —C(O)— or —NH—CH(R$_{10}$)—C(O)—NH—, more preferably —NH—CH$_2$—C(O)—NH—, —C(O)—NH—, —NH—C(O)— or —O—;

R$_{10}$ is —H, —CH$_3$, —C$_3$H$_6$, —CH—(CH$_3$)$_2$, —CH$_2$—CH(CH$_3$)$_2$, —CH(CH$_3$)—CH$_2$—CH$_3$, —CH$_2$—C$_6$H$_5$, —C$_8$NH$_6$, —CH$_2$—C$_6$H$_4$—OH, —CH$_2$—COOH, —CH$_2$—CONH$_2$, —(CH$_2$)$_2$—COOH, —(CH$_2$)$_4$—NH$_2$, —(CH$_2$)$_2$—CONH$_2$, —(CH$_2$)—S—CH$_3$, —CH$_2$—OH, —CH(CH$_3$)—OH or —CH$_2$—SH, preferably —H or —CH$_3$;

m is 1, 2, 3, 4, 5, 6, 7, 8 or 9;

each i is independently 1, 2, 3, 4, 5, 6, 7, 8 or 9;

each j is independently 1, 2, 3, 4, 5, 6, 7, 8 or 9;

r is 1, 2, 3, 4, 5, 6, 7, 8 or 9;

k is 1, 2, 3, 4, 5 or 6;

g is 1, 2, 3, 4, 5, 6, 7, 8, 9, 10, 11 or 12;

h is 1, 2, 3, 4, 5 or 6;

b is 1, 2, 3, 4, 5 or 6;

d is 1, 2, 3, 4, 5 or 6;

e is 1, 2, 3, 4, 5, 6, 7, 8, 9, 10, 11 or 12;

f is 1, 2, 3, 4, 5 or 6.

In some embodiments, in the compound represented by Formula I, W is —NH—CH$_2$—C(O)—NH—.

In some embodiments, in the compound represented by Formula I, W is —NH—CH(R$_{10}$)—C(O)—NH—, wherein R$_{10}$ is defined as described in the present application.

In some embodiments, in the compound represented by Formula I, R$_{10}$ is —H.

In some embodiments, in the compound represented by Formula I, R$_{10}$ is —CH$_3$.

In some embodiments, in the compound represented by Formula I, R$_{10}$ is —C$_3$H$_6$, —CH—(CH$_3$)$_2$, —CH$_2$—CH(CH$_3$)$_2$, —CH(CH$_3$)—CH$_2$—CH$_3$ or —CH$_2$—C$_6$H$_5$.

In some embodiments, in the compound represented by Formula I, R$_{10}$ is —C$_8$NH$_6$, —CH$_2$—C$_6$H$_4$—OH, —CH$_2$—COOH, —CH$_2$—CONH$_2$ or —(CH$_2$)$_2$—COOH.

In some embodiments, in the compound represented by Formula I, R$_{10}$ is —(CH$_2$)$_4$—NH$_2$, —(CH$_2$)$_2$—CONH$_2$, —(CH$_2$)—S—CH$_3$, —CH$_2$—OH, —CH(CH$_3$)—OH or —CH$_2$—SH.

In some embodiments, the compound represented by Formula I or a salt thereof has a structure represented by Formula Ia,

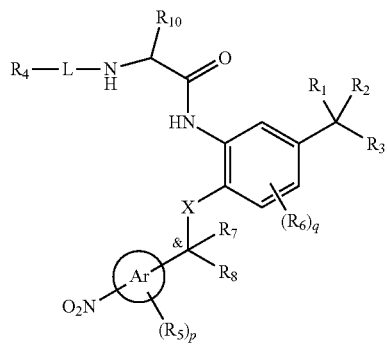

Ia wherein:
R₁ is hydrogen, methyl, ethyl, n-propyl or isopropyl;
R₂ is hydrogen, methyl, ethyl, n-propyl or isopropyl;
R₃ is fluorine, chlorine, bromine, iodine or

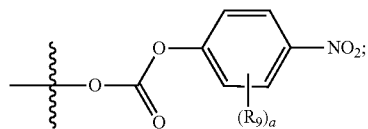

R₄ is

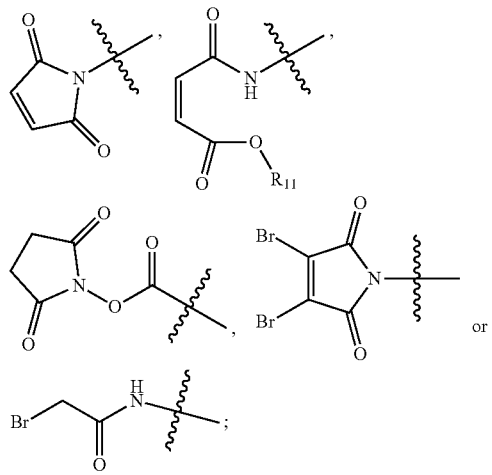

and in

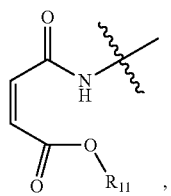

the two carbonyl groups are located on the same side of the C=C double bond, which is a cis structure, R₁₁ is a C₁₋₆ linear or branched alkyl, and R₁₁ is optionally mono- or multi-substituted by one or more substituents selected from the group consisting of: halogen and C₁₋₄ alkoxy;

X is oxygen atom (O), nitrogen atom (N) or sulfur atom (S);

Ar is aryl, heteroaryl, aryl-fused-heterocyclyl or heteroaryl-fused-heterocyclyl, preferably a 5- or 6-membered aryl, or 5- or 6-membered heteroaryl;

preferably, the nitro on Ar and the C atome at & site are at the conjugation positions of the aromatic system, and more preferably, Ar is 6-membered aryl or 6-membered heteroaryl, and the nitro on Ar and the C atom at & site are at para- or ortho-positions;

R₅ is hydrogen, methyl, ethyl, n-propyl, isopropyl, fluorine, chlorine, bromine, iodine, hydroxyl or cyano;

R₆ is hydrogen, methyl, ethyl, n-propyl, isopropyl, n-butyl, isobutyl, sec-butyl, tert-butyl, fluorine, chlorine, bromine, iodine, hydroxyl, nitro or cyano;

R₇ is hydrogen, methyl, ethyl, n-propyl or isopropyl;
R₈ is hydrogen, methyl, ethyl, n-propyl or isopropyl;
R₉ is hydrogen, methyl, ethyl, n-propyl, isopropyl, fluorine, chlorine, bromine, iodine, hydroxyl or cyano;
R₁₀ is —H, —CH₃, —C₃H₆, —CH—(CH₃)₂, —CH₂—CH(CH₃)₂, —CH(CH₃)—CH₂—CH₃, —CH₂—C₆H₅, —C₈NH₆, —CH₂—C₆H₄—OH, —CH₂—COOH, —CH₂—CONH₂, —(CH₂)₂—COOH, —(CH₂)₄—NH₂, —(CH₂)₂—CONH₂, —(CH₂)—S—CH₃, —CH₂—OH, —CH(CH₃)—OH or —CH₂—SH, preferably —H or —CH₃;

q is 0, 1, 2 or 3;
p is 0, 1, 2 or 3;
a is 0, 1, 2, 3 or 4;
L is —(CH₂)ᵢO(CH₂)ⱼ—, —(CH₂)ᵢO(CH₂)ⱼ—C(O)—, —(CH₂)ᵢ—C(O)NH—(CH₂)ⱼ—, —(CH₂CH₂O)ᵢ—(CH₂)ⱼ—C(O)—, —(CH₂)ᵢ—(CH₂CH₂O)ⱼ—C(O)—, —(OCH₂CH₂)ᵢ—, —(CH₂)ₘ—, —(CH₂)ᵣ—C(O)—, —(CH₂)ₖ—C(O)NH—(CH₂CH₂O)ᵍ—(CH₂)ₕ—C(O)—, —(CH₂)ᵦ—C(O)NH—CH[(CH₂)ₐ—NHC(O)—(CH₂CH₂O)ₑ—(CH₂)ᵣCH₃]—,

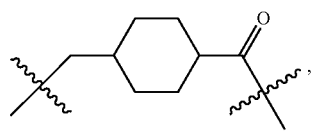

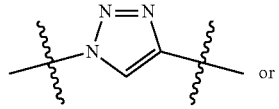

m is 1, 2, 3, 4, 5, 6, 7, 8 or 9;
i is 1, 2, 3, 4, 5, 6, 7, 8 or 9;
j is 1, 2, 3, 4, 5, 6, 7, 8 or 9;
r is 1, 2, 3, 4, 5, 6, 7, 8 or 9;
k is 1, 2, 3, 4, 5 or 6;

g is 1, 2, 3, 4, 5, 6, 7, 8, 9, 10, 11 or 12;
h is 1, 2, 3, 4, 5 or 6;
b is 1, 2, 3, 4, 5 or 6;
d is 1, 2, 3, 4, 5 or 6;
e is 1, 2, 3, 4, 5, 6, 7, 8, 9, 10, 11 or 12;
f is 1, 2, 3, 4, 5 or 6.

In some embodiments, in the compound represented by Formula I or Formula Ia or a salt thereof, $R_1$ is hydrogen or methyl.

In some embodiments, in the compound represented by Formula I or Formula Ia or a salt thereof, $R_1$ is hydrogen.

In some embodiments, in the compound represented by Formula I or Formula Ia or a salt thereof, $R_1$ is methyl.

In some embodiments, in the compound represented by Formula I or Formula Ia or a salt thereof, $R_1$ is ethyl.

In some embodiments, in the compound represented by Formula I or Formula Ia or a salt thereof, $R_1$ is n-propyl.

In some embodiments, in the compound represented by Formula I or Formula Ia or a salt thereof, $R_1$ is isopropyl.

In some embodiments, in the compound represented by Formula I or Formula Ia or a salt thereof, $R_2$ is hydrogen.

In some embodiments, in the compound represented by Formula I or Formula Ia or a salt thereof, $R_2$ is methyl.

In some embodiments, in the compound represented by Formula I or Formula Ia or a salt thereof, $R_2$ is ethyl.

In some embodiments, in the compound represented by Formula I or Formula Ia or a salt thereof, $R_2$ is n-propyl.

In some embodiments, in the compound represented by Formula I or Formula Ia or a salt thereof, $R_2$ is isopropyl.

In some embodiments, in the compound represented by Formula I or Formula Ia or a salt thereof, $R_2$ is hydrogen or methyl.

In some embodiments, in the compound represented by Formula I or Formula Ia or a salt thereof, $R_3$ is

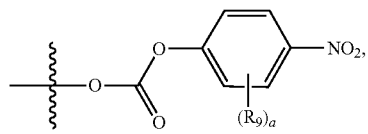

wherein $R_9$ is hydrogen, methyl, ethyl, n-propyl, isopropyl, fluorine, chlorine, bromine, iodine, hydroxyl or cyano; a is 0, 1, 2, 3 or 4; preferably, $R_9$ is hydrogen, methyl, ethyl, fluorine, chlorine or bromine; preferably, a is 0 or 1.

In some embodiments, in the compound represented by Formula I or Formula Ia or a salt thereof, $R_9$ is hydrogen.

In some embodiments, in the compound represented by Formula I or Formula Ia or a salt thereof, $R_9$ is methyl or ethyl.

In some embodiments, in the compound represented by Formula I or Formula Ia or a salt thereof, $R_9$ is n-propyl or isopropyl.

In some embodiments, in the compound represented by Formula I or Formula Ia or a salt thereof, $R_9$ is fluorine, chlorine, bromine or iodine.

In some embodiments, in the compound represented by Formula I or Formula Ia or a salt thereof, $R_9$ is hydroxy or cyano.

In some embodiments, in the compound represented by Formula I or Formula Ia or a salt thereof, a is 0.

In some embodiments, in the compound represented by Formula I or Formula Ia or a salt thereof, a is 1.

In some embodiments, in the compound represented by Formula I or Formula Ia or a salt thereof, a is 2.

In some embodiments, in the compound represented by Formula I or Formula Ia or a salt thereof, a is 3 or 4.

In some embodiments, in the compound represented by Formula I or Formula Ia or a salt thereof, $R_9$ is hydrogen, methyl or ethyl.

In some embodiments, in the compound represented by Formula I or Formula Ia or a salt thereof, $R_9$ is fluorine, chlorine or bromine.

In some embodiments, in the compound represented by Formula I or Formula Ia or a salt thereof, $R_4$ is

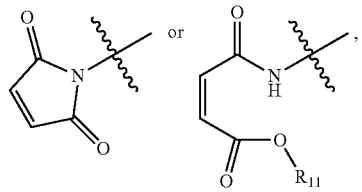

$R_{11}$ is preferably methyl, ethyl, n-propyl or isopropyl, more preferably methyl.

In some embodiments, in the compound represented by Formula I or Formula Ia or a salt thereof, $R_4$ is

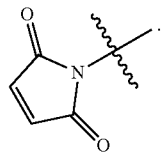 [SMILES: *N1C(=O)C=CC1=O ; "."]

In some embodiments, in the compound represented by Formula I or Formula Ia or a salt thereof, $R_4$ is

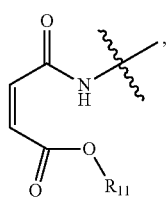

wherein $R_{11}$ is defined as in the present application.

In some embodiments, in the compound represented by Formula II or Formula IIa or a salt thereof, $R_{11}$ is methyl.

In some embodiments, in the compound represented by Formula I or Formula Ia or a salt thereof, $R_{11}$ is ethyl.

In some embodiments, in the compound represented by Formula I or Formula Ia or a salt thereof, $R_{11}$ is n-propyl.

In some embodiments, in the compound represented by Formula I or Formula Ia or a salt thereof, $R_{11}$ is isopropyl.

In some embodiments, in the compound represented by Formula I or Formula Ia or a salt thereof, X is oxygen atom (O) or nitrogen atom (N), preferably oxygen atom (O).

In some embodiments, in the compound represented by Formula I or Formula Ia or a salt thereof, Ar is benzene ring, furan ring, imidazole ring or thiophene ring.

In some embodiments, in the compound represented by Formula I or Formula Ia or a salt thereof, Ar is benzene ring.

In some embodiments, in the compound represented by Formula I or Formula Ia or a salt thereof, Ar is furan ring.

In some embodiments, in the compound represented by Formula I or Formula Ia or a salt thereof, Ar is imidazole ring.

In some embodiments, in the compound represented by Formula I or Formula Ia or a salt thereof, Ar is thiophene ring.

In some embodiments, in the compound represented by Formula I or Formula Ia or a salt thereof, $R_5$ is hydrogen, methyl, fluorine, chlorine or bromine; more preferably, $R_5$ is hydrogen or methyl.

In some embodiments, in the compound represented by Formula I or Formula Ia or a salt thereof, $R_5$ is hydrogen.

In some embodiments, in the compound represented by Formula I or Formula Ia or a salt thereof, $R_5$ is methyl.

In some embodiments, in the compound represented by Formula I or Formula Ia or a salt thereof, $R_5$ is ethyl.

In some embodiments, in the compound represented by Formula I or Formula Ia or a salt thereof, $R_5$ is fluorine.

In some embodiments, in the compound represented by Formula I or Formula Ia or a salt thereof, $R_5$ is chlorine.

In some embodiments, in the compound represented by Formula I or Formula Ia or a salt thereof, $R_5$ is bromine.

In some embodiments, in the compound represented by Formula I or Formula Ia or a salt thereof, $R_6$ is hydrogen, methyl, ethyl, fluorine, chlorine or bromine.

In some embodiments, in the compound represented by Formula I or Formula Ia or a salt thereof, $R_6$ is hydrogen.

In some embodiments, in the compound represented by Formula I or Formula Ia or a salt thereof, $R_6$ is methyl.

In some embodiments, in the compound represented by Formula I or Formula Ia or a salt thereof, $R_6$ is ethyl.

In some embodiments, in the compound represented by Formula I or Formula Ia or a salt thereof, $R_6$ is fluorine.

In some embodiments, in the compound represented by Formula I or Formula Ia or a salt thereof, $R_6$ is chlorine.

In some embodiments, in the compound represented by Formula I or Formula Ia or a salt thereof, $R_6$ is bromine.

In some embodiments, in the compound represented by Formula I or Formula Ia or a salt thereof, $R_7$ is hydrogen or methyl.

In some embodiments, in the compound represented by Formula I or Formula Ia or a salt thereof, $R_7$ is hydrogen.

In some embodiments, in the compound represented by Formula I or Formula Ia or a salt thereof, $R_7$ is methyl.

In some embodiments, in the compound represented by Formula I or Formula Ia or a salt thereof, $R_7$ is ethyl.

In some embodiments, in the compound represented by Formula I or Formula Ia or a salt thereof, $R_7$ is n-propyl.

In some embodiments, in the compound represented by Formula I or Formula Ia or a salt thereof, $R_7$ is isopropyl.

In some embodiments, in the compound represented by Formula I or Formula Ia or a salt thereof, $R_8$ is hydrogen or methyl.

In some embodiments, in the compound represented by Formula I or Formula Ia or a salt thereof, $R_8$ is hydrogen.

In some embodiments, in the compound represented by Formula I or Formula Ia or a salt thereof, $R_8$ is methyl.

In some embodiments, in the compound represented by Formula I or Formula Ia or a salt thereof, $R_8$ is ethyl.

In some embodiments, in the compound represented by Formula I or Formula Ia or a salt thereof, $R_8$ is n-propyl.

In some embodiments, in the compound represented by Formula I or Formula Ia or a salt thereof, $R_8$ is isopropyl.

In some embodiments, in the compound represented by Formula I or Formula Ia or a salt thereof, $R_{10}$ is hydrogen or methyl.

In some embodiments, in the compound represented by Formula I or Formula Ia or a salt thereof, $R_{10}$ is methyl.

In some embodiments, in the compound represented by Formula I or Formula Ia or a salt thereof, $R_{10}$ is hydrogen.

In some embodiments, in the compound represented by Formula I or Formula Ia or a salt thereof, q is 0 or 1.

In some embodiments, in the compound represented by Formula I or Formula Ia or a salt thereof, q is 0.

In some embodiments, in the compound represented by Formula I or Formula Ia or a salt thereof, p is 0 or 1.

In some embodiments, in the compound represented by Formula I or Formula Ia or a salt thereof, p is 1.

In some embodiments, in the compound represented by Formula I or Formula Ia or a salt thereof, L is —$(CH_2)_iO(CH_2)_j$—, —$(CH_2)_iO(CH_2)_j$—C(O)—, —$(CH_2)_i$—C(O)NH—$(CH_2)_j$—, —$(CH_2CH_2O)_i$—$(CH_2)_j$—C(O)—, —$(CH_2)_i$—$(CH_2CH_2O)_j$—C(O)—, —$(OCH_2CH_2)_i$—, —$(CH_2)_m$—, —$(CH_2)_r$—C(O)—,

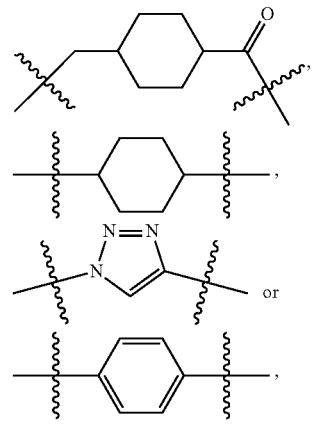

wherein i, j, m, k, g, h and r are defined as in the present application.

In some embodiments, in the compound represented by Formula I or Formula Ia or a salt thereof, L is —$(CH_2)_iO(CH_2)_j$—C(O)—, —$(CH_2CH_2O)_i$—$(CH_2)_j$—C(O)—, —$(CH_2)_i$—$(CH_2CH_2O)_j$—C(O)—, —$(CH_2)_m$—, —$(CH_2)_r$—C(O)—,

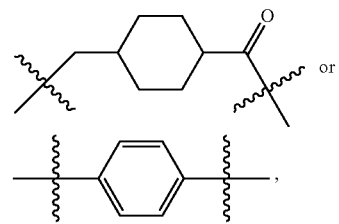

wherein m is 1, 2, 3, 4, 5, 6, 7, 8 or 9, preferably 4, 5, 6 or 7; i is 1, 2, 3, 4, 5, 6, 7, 8 or 9, preferably 4, 5, 6 or 7; j is 1, 2, 3, 4, 5, 6, 7, 8 or 9, preferably 4, 5, 6 or 7; r is 1, 2, 3, 4, 5, 6, 7, 8 or 9, preferably 4, 5 or 6.

In some embodiments, in the compound represented by Formula I or Formula Ia or a salt thereof, L is —$(CH_2)_m$—, —$(CH_2)_r$—C(O)—,

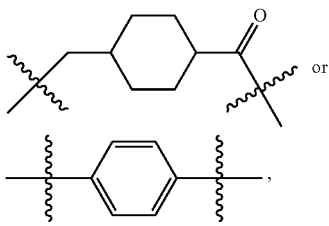

wherein m is 1, 2, 3, 4, 5, 6, 7, 8 or 9, preferably 4, 5, 6 or 7; i is 1, 2, 3, 4, 5, 6, 7, 8 or 9, preferably 4, 5, 6 or 7; j is 1, 2, 3, 4, 5, 6, 7, 8 or 9, preferably 4, 5, 6 or 7; r is 1, 2, 3, 4, 5, 6, 7, 8 or 9, preferably 4, 5 or 6.

In some embodiments, in the compound represented by Formula I or Formula Ia or a salt thereof, L is —$(CH_2)_m$—, wherein m is defined as in the present application.

In some embodiments, in the compound represented by Formula I or Formula Ia or a salt thereof, m is 1 or 2.

In some embodiments, in the compound represented by Formula I or Formula Ia or a salt thereof, m is 3 or 4.

In some embodiments, in the compound represented by Formula I or Formula Ia or a salt thereof, m is 5.

In some embodiments, in the compound represented by Formula I or Formula Ia or a salt thereof, m is 6.

In some embodiments, in the compound represented by Formula I or Formula Ia or a salt thereof, m is 7.

In some embodiments, in the compound represented by Formula I or Formula Ia or a salt thereof, m is 8 or 9.

In some embodiments, in the compound represented by Formula I or Formula Ia or a salt thereof, L is —$(CH_2)_r$—C(O)—, wherein r is defined as in the present application.

In some embodiments, in the compound represented by Formula I or Formula Ia or a salt thereof, r is 1 or 2.

In some embodiments, in the compound represented by Formula I or Formula Ia or a salt thereof, r is 3.

In some embodiments, in the compound represented by Formula I or Formula Ia or a salt thereof, r is 4.

In some embodiments, in the compound represented by Formula I or Formula Ia or a salt thereof, r is 5.

In some embodiments, in the compound represented by Formula I or Formula Ia or a salt thereof, r is 6.

In some embodiments, in the compound represented by Formula I or Formula Ia or a salt thereof, r is 7.

In some embodiments, in the compound represented by Formula I or Formula Ia or a salt thereof, r is 8 or 9.

In some embodiments, in the compound represented by Formula I or Formula Ia or a salt thereof, L is

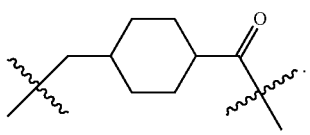

In some embodiments, in the compound represented by Formula I or Formula Ia or a salt thereof, L is

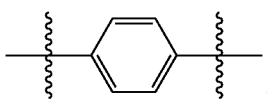

In some embodiments, in the compound represented by Formula I or Formula Ia or a salt thereof, L is —$(CH_2)_k$—C(O)NH—$(CH_2CH_2O)_g$—$(CH_2)_h$—C(O)—, wherein k, g and h are defined as in the present application.

In some embodiments, in the compound represented by Formula I or Formula Ia or a salt thereof, k is 1 or 2.

In some embodiments, in the compound represented by Formula I or Formula Ia or a salt thereof, k is 3 or 4.

In some embodiments, in the compound represented by Formula I or Formula Ia or a salt thereof, k is 5 or 6.

In some embodiments, in the compound represented by Formula I or Formula Ia or a salt thereof, g is 1, 2, 3 or 4.

In some embodiments, in the compound represented by Formula I or Formula Ia or a salt thereof, g is 5, 6, 7 or 8.

In some embodiments, in the compound represented by Formula I or Formula Ia or a salt thereof, g is 9, 10, 11 or 12.

In some embodiments, in the compound represented by Formula I or Formula Ia or a salt thereof, h is 1 or 2.

In some embodiments, in the compound represented by Formula I or Formula Ia or a salt thereof, h is 3 or 4.

In some embodiments, in the compound represented by Formula I or Formula Ia or a salt thereof, h is 5 or 6.

In some embodiments, in the compound represented by Formula I or Formula Ia or a salt thereof, L is —$(CH_2)_2$—C(O)NH—$(CH_2CH_2O)_g$—$(CH_2)_2$—C(O)—, wherein g is defined as in the present application.

In some embodiments, in the compound represented by Formula I or Formula Ia or a salt thereof, L is —$(CH_2)_2$—C(O)NH—$(CH_2CH_2O)_2$—$(CH_2)_2$—C(O)—, —$(CH_2)_2$—C(O)NH—$(CH_2CH_2O)_4$—$(CH_2)_2$—C(O)—, —$(CH_2)_2$—C(O)NH—$(CH_2CH_2O)_6$—$(CH_2)_2$—C(O)—, or —$(CH_2)_2$—C(O)NH—$(CH_2CH_2O)_5$—$(CH_2)_2$—C(O)—.

In some embodiments, in the compound represented by Formula I or Formula Ia or a salt thereof, L is —$(CH_2)_2$—C(O)NH—$(CH_2CH_2O)_3$—$(CH_2)_2$—C(O)—.

In some embodiments, in the compound represented by Formula I or Formula Ia or a salt thereof, L is —$(CH_2)_2$—C(O)NH—$(CH_2CH_2O)_5$—$(CH_2)_2$—C(O)—.

In some embodiments, in the compound represented by Formula I or Formula Ia or a salt thereof, L is —$(CH_2)_2$—C(O)NH—$(CH_2CH_2O)_7$—$(CH_2)_2$—C(O)—.

In some embodiments, in the compound represented by Formula I or Formula Ia or a salt thereof, L is —$(CH_2)_2$—C(O)NH—$(CH_2CH_2O)_9$—$(CH_2)_2$—C(O)—.

In some embodiments, in the compound represented by Formula I or Formula Ia, L is —$(CH_2)_b$—C(O)NH—CH[$(CH_2)_a$—NHC(O)—$(CH_2CH_2O)_e$—$(CH_2)_f$—$CH_3$]—, wherein b, d, e and f are defined as in the present application.

In some embodiments, in the compound represented by Formula I or Formula Ia or a salt thereof, b is 1.

In some embodiments, in the compound represented by Formula I or Formula Ia or a salt thereof, b is 2.

In some embodiments, in the compound represented by Formula I or Formula Ia or a salt thereof, b is 3.

In some embodiments, in the compound represented by Formula I or Formula Ia or a salt thereof, b is 4.

In some embodiments, in the compound represented by Formula I or Formula Ia or a salt thereof, b is 5.

In some embodiments, in the compound represented by Formula I or Formula Ia or a salt thereof, b is 6.

In some embodiments, in the compound represented by Formula I or Formula Ia or a salt thereof, d is 1.

In some embodiments, in the compound represented by Formula I or Formula Ia or a salt thereof, d is 2.

In some embodiments, in the compound represented by Formula I or Formula Ia or a salt thereof, d is 3.

In some embodiments, in the compound represented by Formula I or Formula Ia or a salt thereof, d is 4.

In some embodiments, in the compound represented by Formula I or Formula Ia or a salt thereof, d is 5.

In some embodiments, in the compound represented by Formula I or Formula Ia or a salt thereof, d is 6.

In some embodiments, in the compound represented by Formula I or Formula Ia or a salt thereof, e is 1 or 2.

In some embodiments, in the compound represented by Formula I or Formula Ia or a salt thereof, e is 3 or 4.

In some embodiments, in the compound represented by Formula I or Formula Ia or a salt thereof, e is 5 or 6.

In some embodiments, in the compound represented by Formula I or Formula Ia or a salt thereof, e is 7 or 8.

In some embodiments, in the compound represented by Formula I or Formula Ia or a salt thereof, e is 9 or 10.

In some embodiments, in the compound represented by Formula I or Formula Ia or a salt thereof, e is 11 or 12.

In some embodiments, in the compound represented by Formula I or Formula Ia or a salt thereof, f is 1.

In some embodiments, in the compound represented by Formula I or Formula Ia or a salt thereof, f is 2.

In some embodiments, in the compound represented by Formula I or Formula Ia or a salt thereof, f is 3.

In some embodiments, in the compound represented by Formula I or Formula Ia or a salt thereof, f is 4.

In some embodiments, in the compound represented by Formula I or Formula Ia or a salt thereof, f is 5.

In some embodiments, in the compound represented by Formula I or Formula Ia or a salt thereof, f is 6.

In some embodiments, in the compound represented by Formula I or Formula Ia or a salt thereof,

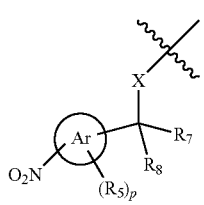

is selected from the group consisting of:

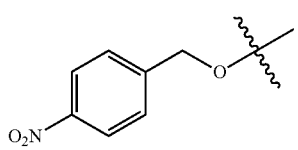

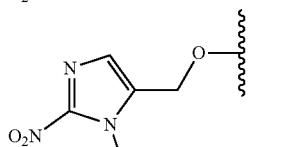

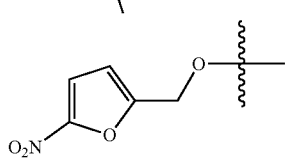

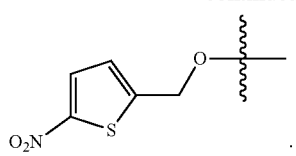

In some embodiments, in the compound represented by Formula I or Formula Ia or a salt thereof,

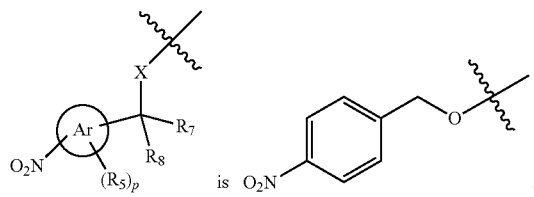

In some embodiments, in the compound represented by Formula I or Formula Ia or a salt thereof,

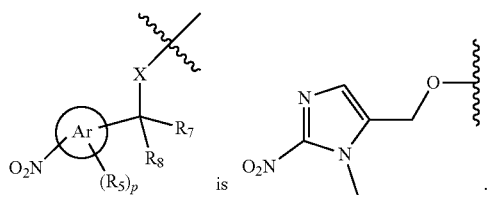

In some embodiments, in the compound represented by Formula I or Formula Ia or a salt thereof,

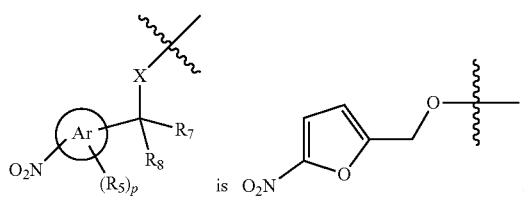

In some embodiments, in the compound represented by Formula I or Formula Ia or a salt thereof,

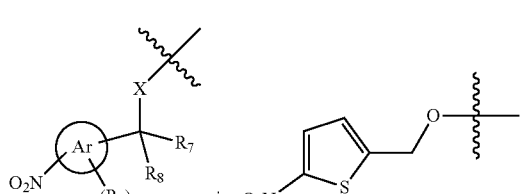

In some embodiments, the compound represented by Formula I or Formula Ia has a structure represented by Formula I-1, Formula I-2, Formula I-3 or Formula I-4,

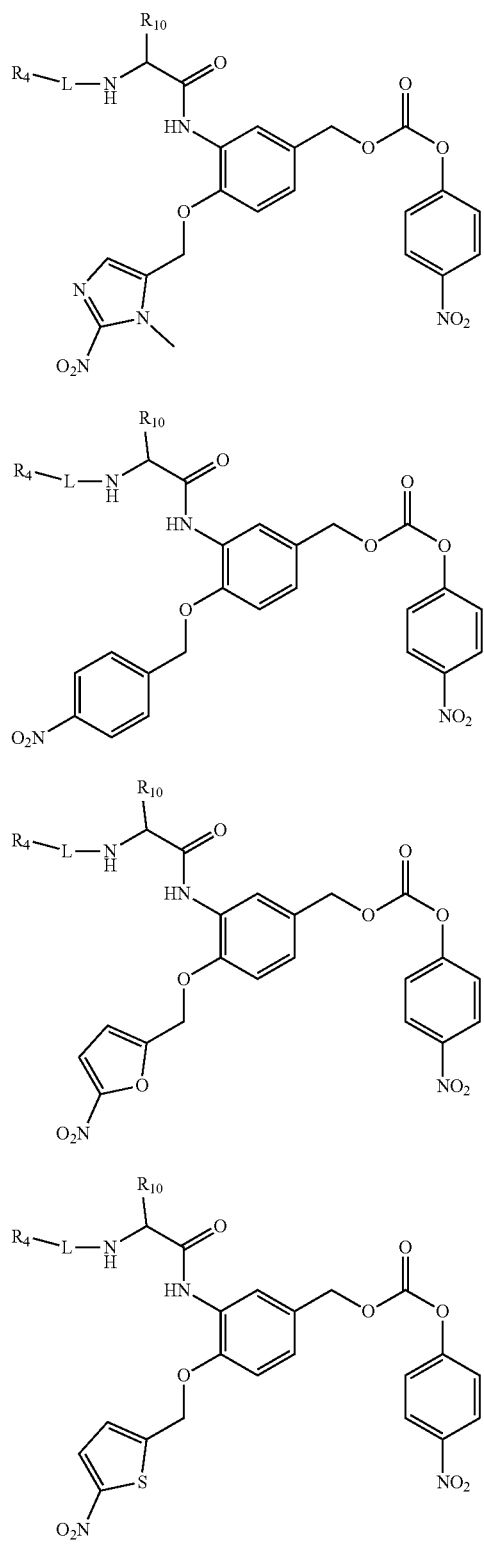
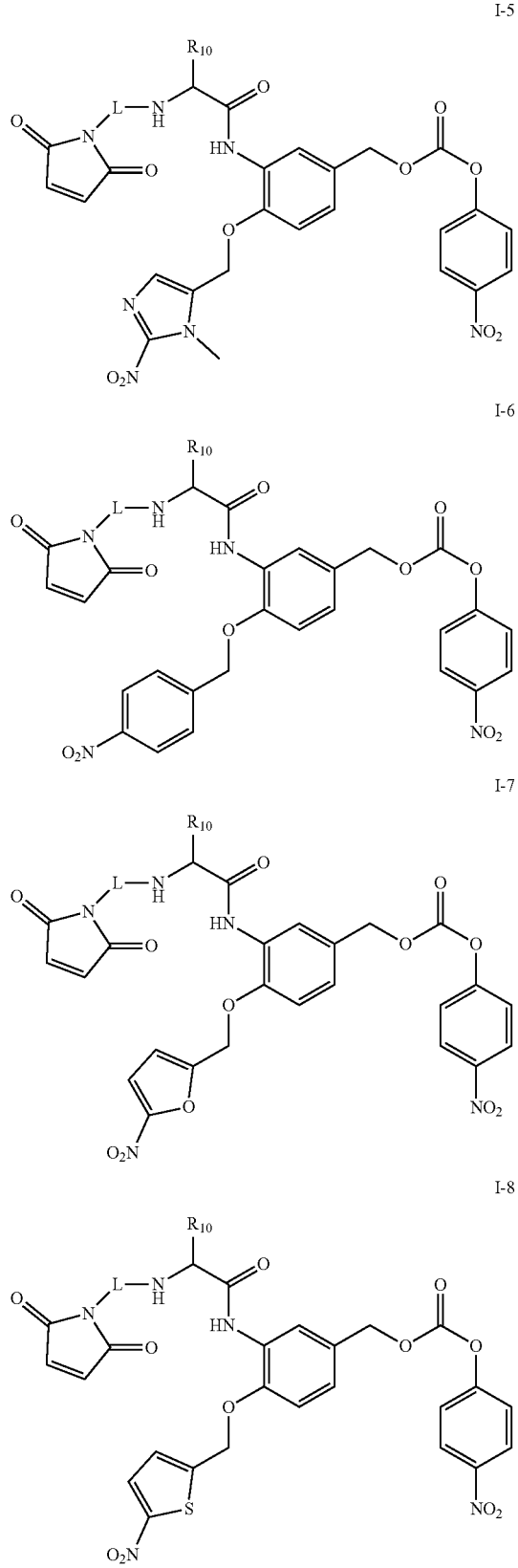
wherein, $R_4$, $R_{10}$ and L are defined as in the present application.
In some embodiments, the compound represented by Formula I or Formula Ia has a structure represented by Formula I-5, Formula I-6, Formula I-7 or Formula I-8,
wherein, $R_{10}$ and L are defined as in the present application.

In some embodiments, the compound represented by Formula I or Formula Ia has a structure represented by Formula I-9, Formula I-10, Formula I-11 or Formula I-12,
I-9
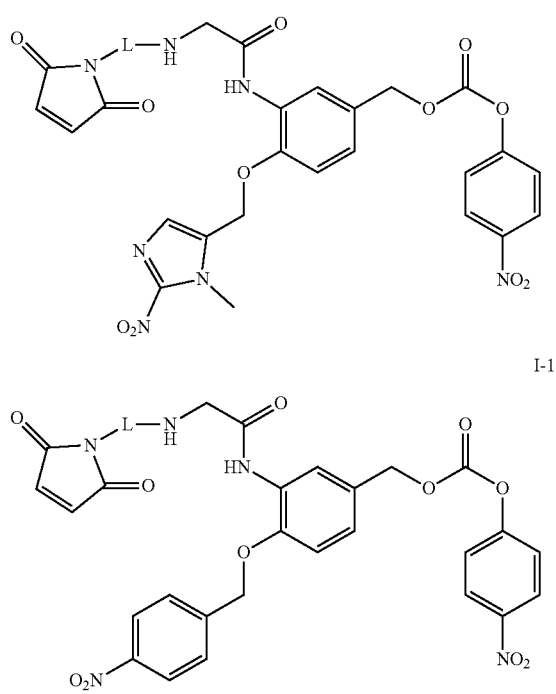
I-10
I-11
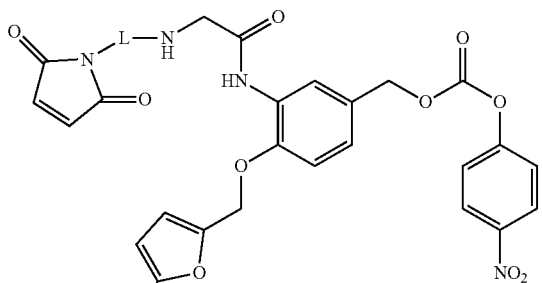
I-12
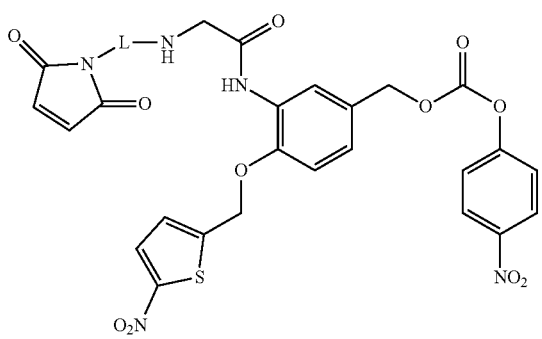
wherein, L is defined as in the present application.
In some embodiments, the compound represented by Formula I or Formula Ia is selected from the group consisting of:
L01
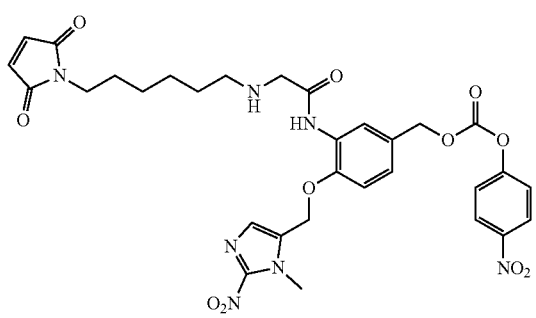
L02
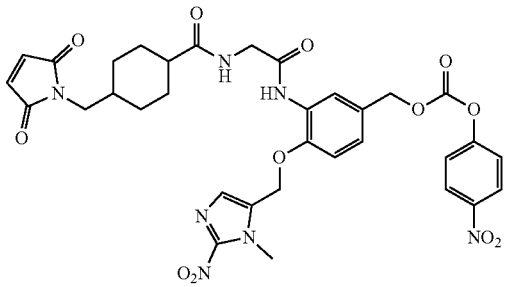
L03
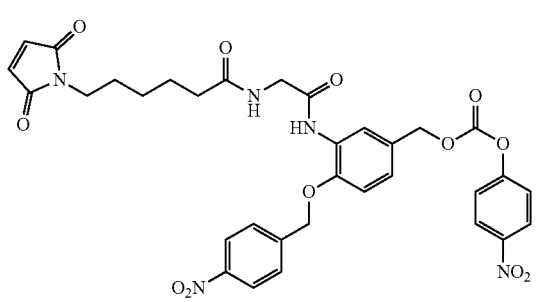
L04
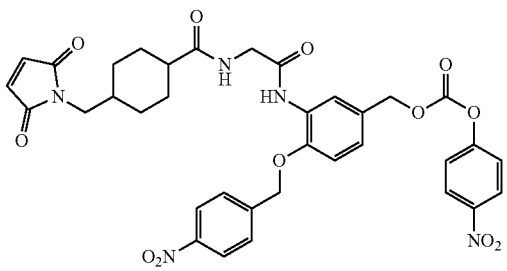

-continued
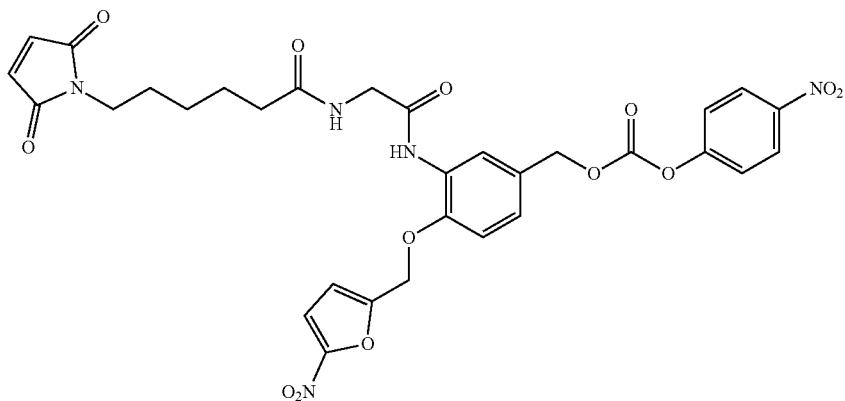
L05
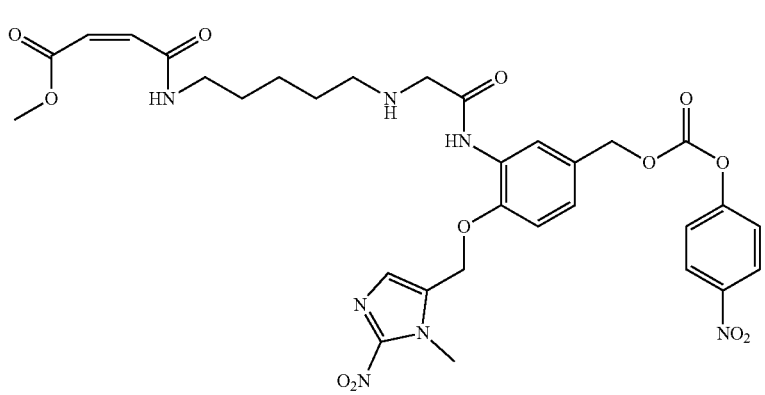
L06
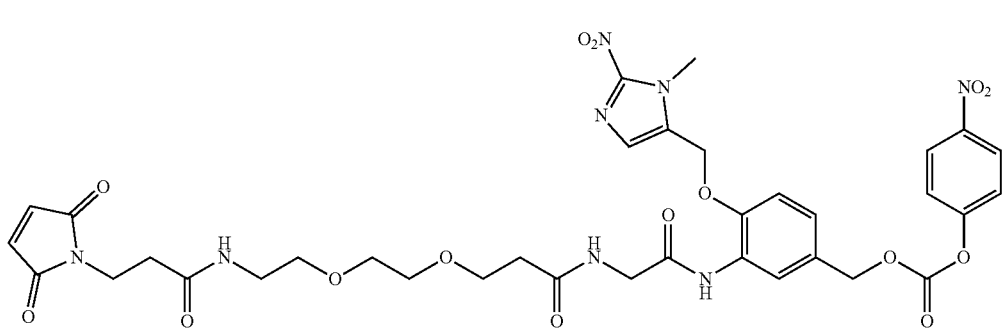
L07
1p;2p
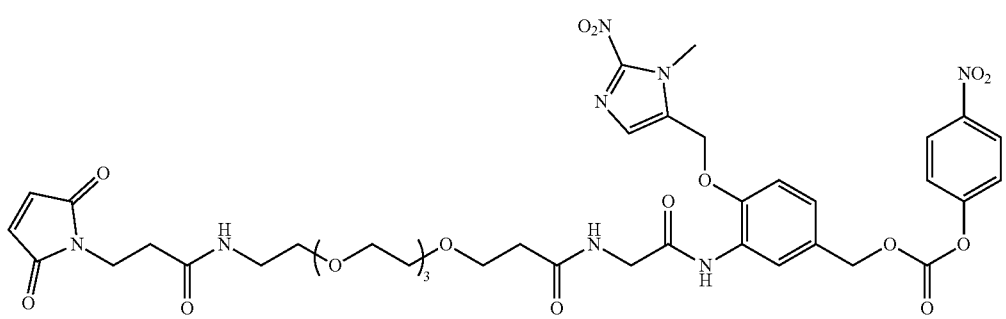
L08

-continued

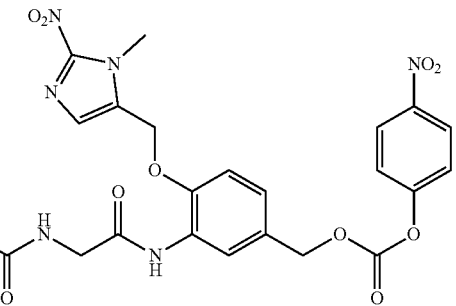
L09

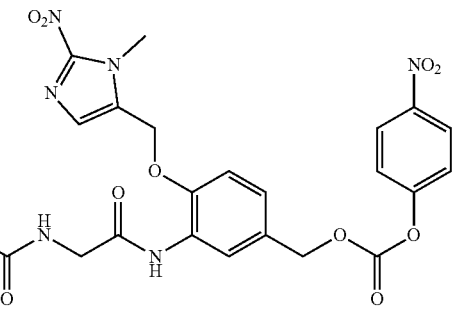
L10

The present application also relates to use of the compound represented by Formula I or Formula Ia or a salt thereof in preparation of an antibody-drug conjugate.

The present application also relates to a compound represented by Formula II or a salt thereof,

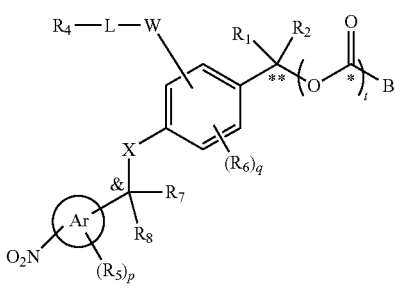
II wherein:

$R_1$ is hydrogen, methyl, ethyl, n-propyl or isopropyl;
$R_2$ is hydrogen, methyl, ethyl, n-propyl or isopropyl;
$R_4$ is

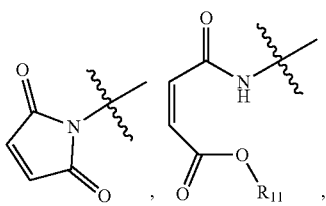

-continued

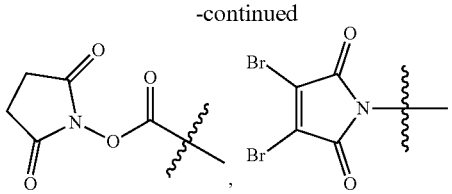

and in

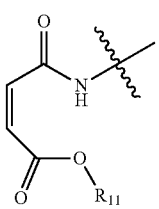

the two carbonyl groups are located on the same side of the C=C double bond, which is a cis structure, $R_{11}$ is a $C_{1-6}$ linear or branched alkyl, and $R_{11}$ is optionally mono- or multi-substituted by one or more substituents selected from the group consisting of: halogen and $C_{1-4}$ alkoxy;

X is oxygen atom (O), nitrogen atom (N) or sulfur atom (S);

Ar is aryl, heteroaryl, aryl-fused-heterocyclyl or heteroaryl-fused-heterocyclyl, preferably a 5- or 6-membered aryl, or 5- or 6-membered heteroaryl; preferably, the nitro on Ar and the C atom at & site are located at the conjugation positions of the aromatic system, and more preferably, Ar is 6-membered aryl or 6-membered heteroaryl, and the nitro on Ar and the C atom at & site are at para- or ortho-positions;

$R_5$ is hydrogen, methyl, ethyl, n-propyl, isopropyl, fluorine, chlorine, bromine, iodine, hydroxyl or cyano;

$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;

$R_7$ is hydrogen, methyl, ethyl, n-propyl or isopropyl;

$R_8$ is hydrogen, methyl, ethyl, n-propyl or isopropyl;

q is 0, 1, 2 or 3;

p is 0, 1, 2 or 3;

L is —$(CH_2)_iO(CH_2)_j$—, —$(CH_2)_iO(CH_2)_j$—C(O)—, —$(CH_2)_i$—C(O)NH—$(CH_2)_j$—, —$(CH_2CH_2O)_i$—$(CH_2)_j$—C(O)—, —$(CH_2)_i$—$(CH_2CH_2O)_j$—C(O)—, —$(OCH_2CH_2)_i$—, —$(CH_2)_m$—, —$(CH_2)_r$—C(O)—, —$(CH_2)_k$—C(O)NH—$(CH_2CH_2O)_g$—$(CH_2)_h$—C(O)—, —$(CH_2)_b$—C(O)NH—CH[$(CH_2)_a$—NHC(O)—$(CH_2CH_2O)_e$—$(CH_2)_r$—$CH_3$]—,

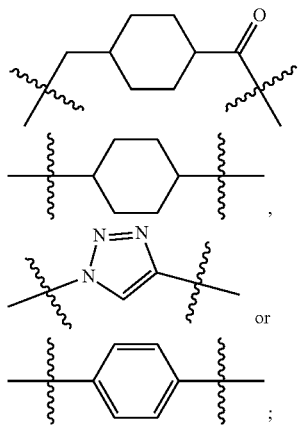

W represents a linking group, preferably is —NH—$CH_2$—C(O)—NH—, —NH—$CH_2$—$CH_2$—C(O)—NH—, —C(O)—NH—, —NH—C(O)—, —O—, —S—, —NH—, —N($CH_3$)— or —C(O)—, further preferably —NH—$CH_2$—C(O)—NH—, —C(O)—NH—, —NH—C(O)—, —O— or —NH—CH($R_{10}$)—C(O)—NH—;

$R_{10}$ is —H, —$CH_3$, —$C_3H_6$, —CH—$(CH_3)_2$, —$CH_2$—CH($CH_3)_2$, —CH($CH_3$)—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH($CH_3$)—OH or —$CH_2$—SH; further preferably —H or —$CH_3$;

m is 1, 2, 3, 4, 5, 6, 7, 8 or 9;

each i is independently 1, 2, 3, 4, 5, 6, 7, 8 or 9;

each j is independently 1, 2, 3, 4, 5, 6, 7, 8 or 9;

r is 1, 2, 3, 4, 5, 6, 7, 8 or 9;

k is 1, 2, 3, 4, 5 or 6;

g is 1, 2, 3, 4, 5, 6, 7, 8, 9, 10, 11 or 12;

h is 1, 2, 3, 4, 5 or 6;

b is 1, 2, 3, 4, 5 or 6;

d is 1, 2, 3, 4, 5 or 6;

e is 1, 2, 3, 4, 5, 6, 7, 8, 9, 10, 11 or 12;

f is 1, 2, 3, 4, 5 or 6;

B is an active compound, selected from the group consisting of drug, cytotoxin, detection reagent, diagnostic reagent and targeting carrier; preferably, B is a cytotoxin, an antitumor drug, an antiviral drug, an anti-infective drug or an immunomodulator drug; further preferably, B is a cytotoxin, such as a tubulin inhibitor, a DNA alkylating agent, a DNA intercalator, an enzyme inhibitor, an antimetabolite, a peptide or a nucleotide; preferably, B is coupled to the site* or site** through a N atom or O atom in the active compound molecule;

t is 0 or 1.

In some embodiments, in the compound represented by Formula II, W is —NH—$CH_2$—C(O)—NH—.

In some embodiments, in the compound represented by Formula II, W is —NH—CH($R_{10}$)—C(O)—NH—, wherein $R_{10}$ is defined as described in the present application.

In some embodiments, in the compound represented by Formula II, $R_{10}$ is —H.

In some embodiments, in the compound represented by Formula II, $R_{10}$ is —$CH_3$.

In some embodiments, in the compound represented by Formula II, $R_{10}$ is —$C_3H_6$, —CH—$(CH_3)_2$, —$CH_2$—CH$(CH_3)_2$, —CH($CH_3$)—$CH_2$—$CH_3$ or —$CH_2$—$C_6H_5$.

In some embodiments, in the compound represented by Formula II, $R_{10}$ is —$C_8NH_6$, —$CH_2$—$C_6H_4$—OH, —$CH_2$—COOH, —$CH_2$—$CONH_2$ or —$(CH_2)_2$—COOH.

In some embodiments, in the compound represented by Formula II, $R_{10}$ is —$(CH_2)_4$—$NH_2$, —$(CH_2)_2$—$CONH_2$, —$(CH_2)$—S—$CH_3$, —$CH_2$—OH, —CH($CH_3$)—OH or —$CH_2$—SH.

In some embodiments, the compound represented by Formula II or a salt thereof has a structure represented by Formula IIa,

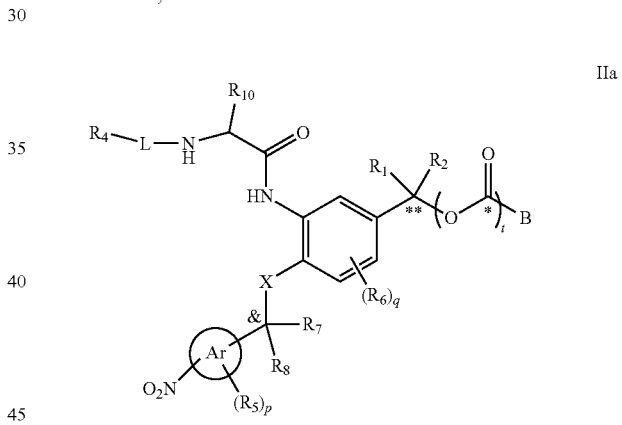

IIa wherein:

$R_1$ is hydrogen, methyl, ethyl, n-propyl or isopropyl;

$R_2$ is hydrogen, methyl, ethyl, n-propyl or isopropyl;

$R_4$ is

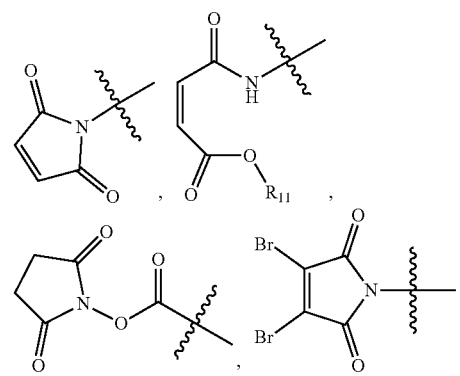

or

-continued

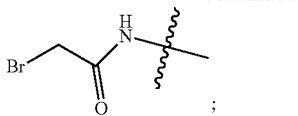

and in

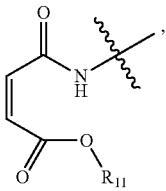

the two carbonyl groups are located on the same side of the C=C double bond, which is a cis structure, $R_{11}$ is a $C_{1-6}$ linear or branched alkyl, and $R_{11}$ is optionally mono- or multi-substituted by one or more substituents selected from the group consisting of: halogen and $C_{1-4}$ alkoxy;

X is oxygen atom (O), nitrogen atom (N) or sulfur atom (S);

Ar is aryl, heteroaryl, aryl-fused-heterocyclyl or heteroaryl-fused-heterocyclyl, preferably a 5- or 6-membered aryl, or 5- or 6-membered heteroaryl; preferably, the nitro on Ar and the C atom at & site are located at the conjugation positions of the aromatic system, and more preferably, Ar is 6-membered aryl or 6-membered heteroaryl, the nitro group on Ar and the C atom at & site are at para- or ortho-positions;

$R_5$ is hydrogen, methyl, ethyl, n-propyl, isopropyl, fluorine, chlorine, bromine, iodine, hydroxyl or cyano;

$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;

$R_7$ is hydrogen, methyl, ethyl, n-propyl or isopropyl;

$R_8$ is hydrogen, methyl, ethyl, n-propyl or isopropyl;

$R_{10}$ is —H, —CH₃, —C₃H₆, —CH—(CH₃)₂, —CH₂—CH(CH₃)₂, —CH(CH₃)—CH₂—CH₃, —CH₂—C₆H₅, —C₈NH₆, —CH₂—C₆H₄—OH, —CH₂—COOH, —CH₂—CONH₂, —(CH₂)₂—COOH, —(CH₂)₄—NH₂, —(CH₂)₂—CONH₂, —(CH₂)—S—CH₃, —CH₂—OH, —CH(CH₃)—OH or —CH₂—SH, preferably —H or —CH₃; q is 0, 1, 2 or 3;

p is 0, 1, 2 or 3;

L is —(CH₂)ᵢO(CH₂)ⱼ—, —(CH₂)ᵢO(CH₂)ⱼ—C(O)—, —(CH₂)ᵢ—C(O)NH—(CH₂)ⱼ—, —(CH₂CH₂O)ᵢ—(CH₂)ⱼ—C(O)—, —(CH₂)ᵢ—(CH₂CH₂O)ⱼ—C(O)—, —(OCH₂CH₂)ᵢ—, —(CH₂)ₘ—, —(CH₂)ᵣ—C(O)—, —(CH₂)ₖ—C(O)NH—(CH₂CH₂O)g—(CH₂)ₕ—C(O)—, —(CH₂)ᵦ—C(O)NH—CH[(CH₂)ₐ—NHC(O)—(CH₂CH₂O)ₑ—(CH₂)ᵣCH₃]—,

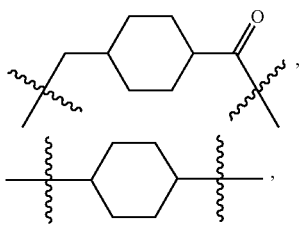

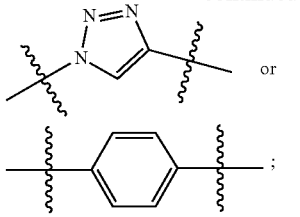

or m is 1, 2, 3, 4, 5, 6, 7, 8 or 9;
each i is independently 1, 2, 3, 4, 5, 6, 7, 8 or 9;
each j is independently 1, 2, 3, 4, 5, 6, 7, 8 or 9;
r is 1, 2, 3, 4, 5, 6, 7, 8 or 9;
k is 1, 2, 3, 4, 5 or 6;
g is 1, 2, 3, 4, 5, 6, 7, 8, 9, 10, 11 or 12;
h is 1, 2, 3, 4, 5 or 6;
b is 1, 2, 3, 4, 5 or 6;
d is 1, 2, 3, 4, 5 or 6;
e is 1, 2, 3, 4, 5, 6, 7, 8, 9, 10, 11 or 12;
f is 1, 2, 3, 4, 5 or 6;

B is an active compound, selected from the group consisting of drug, cytotoxin, detection reagent, diagnostic reagent and targeting carrier; preferably, B is a cytotoxin, an antitumor drug, an antiviral drug, an anti-infective drug or an immunomodulator drug; further preferably, B is a cytotoxin, such as a tubulin inhibitor, a DNA alkylating agent, a DNA intercalator, an enzyme inhibitor, an antimetabolite, a peptide or a nucleotide; preferably, B is coupled to the site* or site** through a N atom or O atom in the active compound molecule;

t is 0 or 1.

In some embodiments, in the compound represented by Formula II or Formula IIa or a salt thereof, $R_1$ is hydrogen or methyl.

In some embodiments, in the compound represented by Formula II or Formula IIa or a salt thereof, $R_2$ is hydrogen or methyl.

In some embodiments, in the compound represented by Formula II or Formula IIa or a salt thereof, $R_1$ is hydrogen.

In some embodiments, in the compound represented by Formula II or Formula IIa or a salt thereof, $R_1$ is methyl.

In some embodiments, in the compound represented by Formula II or Formula IIa or a salt thereof, $R_1$ is ethyl.

In some embodiments, in the compound represented by Formula II or Formula IIa or a salt thereof, $R_1$ is n-propyl.

In some embodiments, in the compound represented by Formula II or Formula IIa or a salt thereof, $R_1$ is isopropyl.

In some embodiments, in the compound represented by Formula II or Formula IIa or a salt thereof, $R_2$ is hydrogen.

In some embodiments, in the compound represented by Formula II or Formula IIa or a salt thereof, $R_2$ is methyl.

In some embodiments, in the compound represented by Formula II or Formula IIa or a salt thereof, $R_2$ is ethyl.

In some embodiments, in the compound represented by Formula II or Formula IIa or a salt thereof, $R_2$ is n-propyl.

In some embodiments, in the compound represented by Formula II or Formula IIa or a salt thereof, $R_2$ is isopropyl.

In some embodiments, in the compound represented by Formula II or Formula IIa or a salt thereof, $R_4$ is

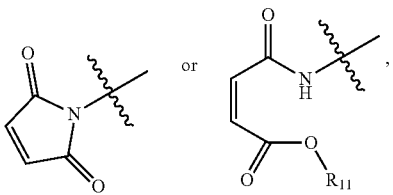

$R_{11}$ is preferably methyl, ethyl, n-propyl or isopropyl, more preferably methyl.

In some embodiments, in the compound represented by Formula II or Formula IIa or a salt thereof, $R_4$

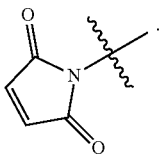 [SMILES: *N1C(=O)C=CC1=O]

In some embodiments, in the compound represented by Formula II or Formula IIa or a salt thereof, $R_4$ is

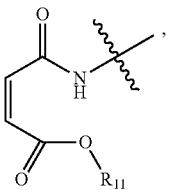

wherein $R_{11}$ is defined as in the present application.

In some embodiments, in the compound represented by Formula II or Formula IIa or a salt thereof, $R_{11}$ is methyl.

In some embodiments, in the compound represented by Formula II or Formula IIa or a salt thereof, $R_{11}$ is ethyl.

In some embodiments, in the compound represented by Formula II or Formula IIa or a salt thereof, $R_{11}$ is n-propyl.

In some embodiments, in the compound represented by Formula II or Formula IIa or a salt thereof, $R_{11}$ is isopropyl.

In some embodiments, in the compound represented by Formula II or Formula IIa or a salt thereof, X is oxygen atom (O) or nitrogen atom (N), preferably oxygen atom (O).

In some embodiments, in the compound represented by Formula II or Formula IIa or a salt thereof, Ar is benzene ring, furan ring, imidazole ring or thiophene ring.

In some embodiments, in the compound represented by Formula II or Formula IIa or a salt thereof, Ar is benzene ring.

In some embodiments, in the compound represented by Formula II or Formula IIa or a salt thereof, Ar is furan ring.

In some embodiments, in the compound represented by Formula II or Formula IIa or a salt thereof, Ar is imidazole ring.

In some embodiments, in the compound represented by Formula II or Formula IIa or a salt thereof, Ar is thiophene ring.

In some embodiments, in the compound represented by Formula II or Formula IIa or a salt thereof, $R_5$ is hydrogen, methyl, fluorine, chlorine or bromine; more preferably, $R_5$ is hydrogen or methyl.

In some embodiments, in the compound represented by Formula II or Formula IIa or a salt thereof, $R_5$ is hydrogen.

In some embodiments, in the compound represented by Formula II or Formula IIa or a salt thereof, $R_5$ is methyl.

In some embodiments, in the compound represented by Formula II or Formula IIa or a salt thereof, $R_5$ is ethyl.

In some embodiments, in the compound represented by Formula II or Formula IIa or a salt thereof, $R_5$ is fluorine.

In some embodiments, in the compound represented by Formula II or Formula IIa or a salt thereof, $R_5$ is chlorine.

In some embodiments, in the compound represented by Formula II or Formula IIa or a salt thereof, $R_5$ is bromine.

In some embodiments, in the compound represented by Formula II or Formula IIa or a salt thereof, $R_6$ is hydrogen, methyl, ethyl, fluorine, chlorine or bromine.

In some embodiments, in the compound represented by Formula II or Formula IIa or a salt thereof, $R_6$ is hydrogen.

In some embodiments, in the compound represented by Formula II or Formula IIa or a salt thereof, $R_6$ is methyl.

In some embodiments, in the compound represented by Formula II or Formula IIa or a salt thereof, $R_6$ is ethyl.

In some embodiments, in the compound represented by Formula II or Formula IIa or a salt thereof, $R_6$ is fluorine.

In some embodiments, in the compound represented by Formula II or Formula IIa or a salt thereof, $R_6$ is chlorine.

In some embodiments, in the compound represented by Formula II or Formula IIa or a salt thereof, $R_6$ is bromine.

In some embodiments, in the compound represented by Formula II or Formula IIa or a salt thereof, $R_7$ is hydrogen or methyl.

In some embodiments, in the compound represented by Formula II or Formula IIa or a salt thereof, $R_7$ is hydrogen.

In some embodiments, in the compound represented by Formula II or Formula IIa or a salt thereof, $R_7$ is methyl.

In some embodiments, in the compound represented by Formula II or Formula IIa or a salt thereof, $R_7$ is ethyl.

In some embodiments, in the compound represented by Formula II or Formula IIa or a salt thereof, $R_7$ is n-propyl.

In some embodiments, in the compound represented by Formula II or Formula IIa or a salt thereof, $R_7$ is isopropyl.

In some embodiments, in the compound represented by Formula II or Formula IIa or a salt thereof, $R_8$ is hydrogen or methyl.

In some embodiments, in the compound represented by Formula II or Formula IIa or a salt thereof, $R_8$ is hydrogen.

In some embodiments, in the compound represented by Formula II or Formula IIa or a salt thereof, $R_8$ is methyl.

In some embodiments, in the compound represented by Formula II or Formula IIa or a salt thereof, $R_8$ is ethyl.

In some embodiments, in the compound represented by Formula II or Formula IIa or a salt thereof, $R_8$ is n-propyl.

In some embodiments, in the compound represented by Formula II or Formula IIa or a salt thereof, $R_8$ is isopropyl.

In some embodiments, in the compound represented by Formula II or Formula IIa or a salt thereof, $R_{10}$ is hydrogen or methyl.

In some embodiments, in the compound represented by Formula II or Formula IIa or a salt thereof, $R_{10}$ is methyl.

In some embodiments, in the compound represented by Formula II or Formula IIa or a salt thereof, $R_{10}$ is hydrogen.

In some embodiments, in the compound represented by Formula II or Formula IIa or a salt thereof, $R_{11}$ is methyl, ethyl, n-propyl or isopropyl, preferably methyl.

In some embodiments, in the compound represented by Formula II or Formula IIa or a salt thereof, q is 0 or 1.

In some embodiments, in the compound represented by Formula II or Formula IIa or a salt thereof, q is 0.

In some embodiments, in the compound represented by Formula II or Formula IIa or a salt thereof, p is 0 or 1.

In some embodiments, in the compound represented by Formula II or Formula IIa or a salt thereof, p is 1.

In some embodiments, in the compound represented by Formula II or Formula IIa or a salt thereof, L is —(CH$_2$)$_i$O(CH$_2$)$_j$—, —(CH$_2$)$_i$O(CH$_2$)$_j$—C(O)—, —(CH$_2$)$_i$—C(O)NH—(CH$_2$)$_j$—, —(CH$_2$CH$_2$O)$_i$—(CH$_2$)$_j$—C(O)—, —(CH$_2$)$_i$—(CH$_2$CH$_2$O)$_j$—C(O)—, —(OCH$_2$CH$_2$)$_i$—, —(CH$_2$)$_m$—, —(CH$_2$)$_r$—C(O)—,

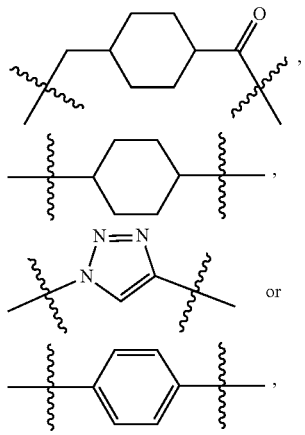

wherein i, j, m, k, g, h and r are defined as in the present application.

In some embodiments, in the compound represented by Formula II or Formula IIa or a salt thereof, L is —(CH$_2$)$_i$O(CH$_2$)$_j$—C(O)—, —(CH$_2$CH$_2$O)$_i$—(CH$_2$)$_j$—C(O)—, —(CH$_2$)$_i$—(CH$_2$CH$_2$O)$_j$—C(O)—, —(CH$_2$)$_m$—, —(CH$_2$)$_r$—C(O)—,

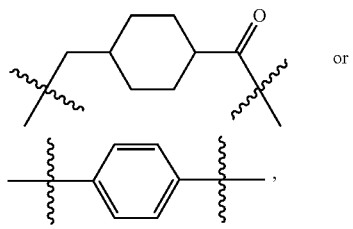

wherein m is 1, 2, 3, 4, 5, 6, 7, 8 or 9, preferably 4, 5, 6 or 7; i is 1, 2, 3, 4, 5, 6, 7, 8 or 9, preferably 4, 5, 6 or 7; j is 1, 2, 3, 4, 5, 6, 7, 8 or 9, preferably 4, 5, 6 or 7; r is 1, 2, 3, 4, 5, 6, 7, 8 or 9, preferably 4, 5 or 6.

In some embodiments, in the compound represented by Formula II or Formula IIa or a salt thereof, L is —(CH$_2$)$_m$—, wherein m is defined as in the present application.

In some embodiments, in the compound represented by Formula II or Formula IIa or a salt thereof, m is 1 or 2.

In some embodiments, in the compound represented by Formula II or Formula IIa or a salt thereof, m is 3 or 4.

In some embodiments, in the compound represented by Formula II or Formula IIa or a salt thereof, m is 5.

In some embodiments, in the compound represented by Formula II or Formula IIa or a salt thereof, m is 6.

In some embodiments, in the compound represented by Formula II or Formula IIa or a salt thereof, m is 7.

In some embodiments, in the compound represented by Formula II or Formula IIa or a salt thereof, m is 8 or 9.

In some embodiments, in the compound represented by Formula II or Formula IIa or a salt thereof, L is —(CH$_2$)$_r$—C(O)—, wherein r is defined as in the present application.

In some embodiments, in the compound represented by Formula II or Formula IIa or a salt thereof, r is 1 or 2.

In some embodiments, in the compound represented by Formula II or Formula IIa or a salt thereof, r is 3.

In some embodiments, in the compound represented by Formula II or Formula IIa or a salt thereof, r is 4.

In some embodiments, in the compound represented by Formula II or Formula IIa or a salt thereof, r is 5.

In some embodiments, in the compound represented by Formula II or Formula IIa or a salt thereof, r is 6.

In some embodiments, in the compound represented by Formula II or Formula IIa or a salt thereof, r is 7.

In some embodiments, in the compound represented by Formula II or Formula IIa or a salt thereof, r is 8 or 9.

In some embodiments, in the compound represented by Formula II or Formula IIa or a salt thereof, L is

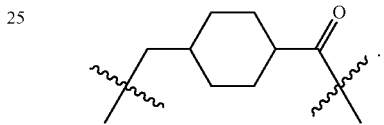

In some embodiments, in the compound represented by Formula II or Formula IIa or a salt thereof, L is

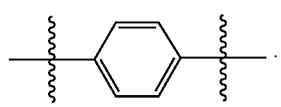

In some embodiments, in the compound represented by Formula II or Formula IIa or a salt thereof, L is —(CH$_2$)$_k$—C(O)NH—(CH$_2$CH$_2$O)$_g$—(CH$_2$)$_h$—C(O)—, wherein k, g and h are defined as in the present application.

In some embodiments, in the compound represented by Formula II or Formula IIa or a salt thereof, k is 1 or 2.

In some embodiments, in the compound represented by Formula II or Formula IIa or a salt thereof, k is 3 or 4.

In some embodiments, in the compound represented by Formula II or Formula IIa or a salt thereof, k is 5 or 6.

In some embodiments, in the compound represented by Formula II or Formula IIa or a salt thereof, g is 1, 2, 3 or 4.

In some embodiments, in the compound represented by Formula II or Formula IIa or a salt thereof, g is 5, 6, 7 or 8.

In some embodiments, in the compound represented by Formula II or Formula IIa or a salt thereof, g is 9, 10, 11 or 12.

In some embodiments, in the compound represented by Formula II or Formula IIa or a salt thereof, h is 1 or 2.

In some embodiments, in the compound represented by Formula II or Formula IIa or a salt thereof, h is 3 or 4.

In some embodiments, in the compound represented by Formula II or Formula IIa or a salt thereof, h is 5 or 6.

In some embodiments, in the compound represented by Formula II or Formula IIa or a salt thereof, L is —(CH$_2$)$_2$—C(O)NH—(CH$_2$CH$_2$O)$_g$—(CH$_2$)$_2$—C(O)—, wherein g is defined as in the present application.

In some embodiments, in the compound represented by Formula II or Formula IIa or a salt thereof, L is —(CH$_2$)$_2$—C(O)NH—(CH$_2$CH$_2$O)$_2$—(CH$_2$)$_2$—C(O)—, —(CH$_2$)$_2$—C(O)NH—(CH$_2$CH$_2$O)$_4$—(CH$_2$)$_2$—C(O)—, —(CH$_2$)$_2$—C(O)NH—(CH$_2$CH$_2$O)$_6$—(CH$_2$)$_2$—C(O)—, or —(CH$_2$)$_2$—C(O)NH—(CH$_2$CH$_2$O)$_5$—(CH$_2$)$_2$—C(O)—.

In some embodiments, in the compound represented by Formula II or Formula IIa or a salt thereof, L is —(CH$_2$)$_2$—C(O)NH—(CH$_2$CH$_2$O)$_3$—(CH$_2$)$_2$—C(O)—.

In some embodiments, in the compound represented by Formula II or Formula IIa or a salt thereof, L is —(CH$_2$)$_2$—C(O)NH—(CH$_2$CH$_2$O)$_5$—(CH$_2$)$_2$—C(O)—.

In some embodiments, in the compound represented by Formula II or Formula IIa or a salt thereof, L is —(CH$_2$)$_2$—C(O)NH—(CH$_2$CH$_2$O)$_7$—(CH$_2$)$_2$—C(O)—.

In some embodiments, in the compound represented by Formula II or Formula IIa or a salt thereof, L is —(CH$_2$)$_2$—C(O)NH—(CH$_2$CH$_2$O)$_9$—(CH$_2$)$_2$—C(O)—.

In some embodiments, in the compound represented by Formula II or Formula IIa, L is —(CH$_2$)$_b$—C(O)NH—CH[(CH$_2$)$_a$—NHC(O)—(CH$_2$CH$_2$O)$_e$—(CH$_2$)$_f$—CH$_3$]—, wherein b, d, e and f are defined as in the present application.

In some embodiments, in the compound represented by Formula II or Formula IIa or a salt thereof, b is 1.

In some embodiments, in the compound represented by Formula II or Formula IIa or a salt thereof, b is 3.

In some embodiments, in the compound represented by Formula II or Formula IIa or a salt thereof, b is 5.

In some embodiments, in the compound represented by Formula II or Formula IIa or a salt thereof, b is 6.

In some embodiments, in the compound represented by Formula II or Formula IIa or a salt thereof, d is 1.

In some embodiments, in the compound represented by Formula II or Formula IIa or a salt thereof, d is 2.

In some embodiments, in the compound represented by Formula II or Formula IIa or a salt thereof, d is 3.

In some embodiments, in the compound represented by Formula II or Formula IIa or a salt thereof, d is 4.

In some embodiments, in the compound represented by Formula II or Formula IIa or a salt thereof, d is 5.

In some embodiments, in the compound represented by Formula II or Formula IIa or a salt thereof, d is 6.

In some embodiments, in the compound represented by Formula II or Formula IIa or a salt thereof, e is 1 or 2.

In some embodiments, in the compound represented by Formula II or Formula IIa or a salt thereof, e is 3 or 4.

In some embodiments, in the compound represented by Formula II or Formula IIa or a salt thereof, e is 5 or 6.

In some embodiments, in the compound represented by Formula I or Formula Ia or a salt thereof, e is 7 or 8.

In some embodiments, in the compound represented by Formula II or Formula IIa or a salt thereof, e is 9 or 10.

In some embodiments, in the compound represented by Formula II or Formula IIa or a salt thereof, e is 11 or 12.

In some embodiments, in the compound represented by Formula II or Formula IIa or a salt thereof, f is 1.

In some embodiments, in the compound represented by Formula II or Formula IIa or a salt thereof, f is 2.

In some embodiments, in the compound represented by Formula II or Formula IIa or a salt thereof, f is 3.

In some embodiments, in the compound represented by Formula II or Formula IIa or a salt thereof, f is 4.

In some embodiments, in the compound represented by Formula II or Formula IIa or a salt thereof, f is 5.

In some embodiments, in the compound represented by Formula II or Formula IIa or a salt thereof, f is 6.

In some embodiments, in the compound represented by Formula II or Formula IIa or a salt thereof, L is —(CH$_2$)$_m$—, —(CH$_2$)$_r$C(O)—,

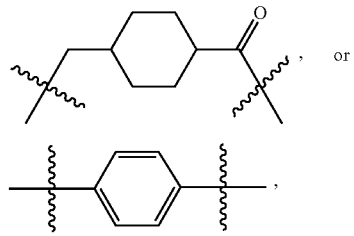

wherein m is 1, 2, 3, 4, 5, 6, 7, 8 or 9, preferably 4, 5, 6 or 7; i is 1, 2, 3, 4, 5, 6, 7, 8 or 9, preferably 4, 5, 6 or 7; j is 1, 2, 3, 4, 5, 6, 7, 8 or 9, preferably 4, 5, 6 or 7; r is 1, 2, 3, 4, 5, 6, 7, 8 or 9, preferably 4, 5 or 6.

In some embodiments, in the compound represented by Formula II or a salt thereof, t is 1.

In some embodiments, in the compound represented by Formula II or Formula IIa or a salt thereof, B is selected from the group consisting of: auristatin, monomethyl-auristatin E (MMAE), maytansine or its derivatives (such as maytansinoids, DM1, DM3, DM4), paclitaxel, calicheamicin, duocarmycin, doxorubicin, camptothecin, PBD (pyrrolobenzodiazepines) cytotoxin and its derivatives; preferably, B is monomethyl-auristatin E (MMAE).

In some embodiments, in the compound represented by Formula II or Formula IIa or a salt thereof,

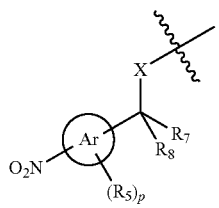

is selected from the group consisting of:

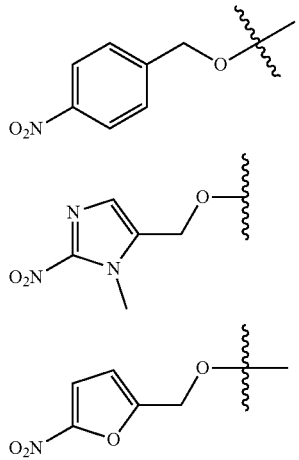

-continued

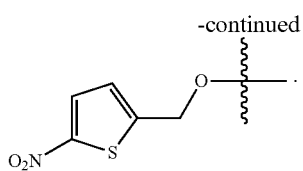

In some embodiments, in the compound represented by Formula II or Formula IIa or a salt thereof,

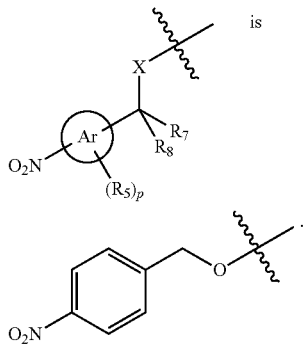

is

In some embodiments, in the compound represented by Formula II or Formula IIa or a salt thereof,

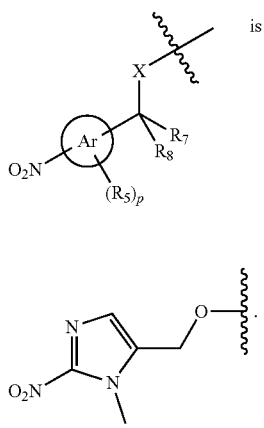

is

In some embodiments, in the compound represented by Formula II or Formula IIa or a salt thereof,

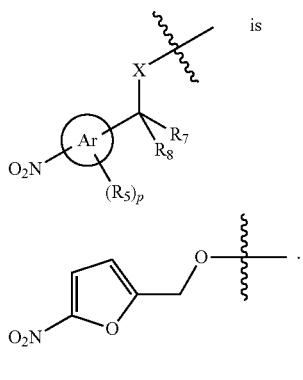

is

In some embodiments, in the compound represented by Formula II or Formula IIa or a salt thereof,

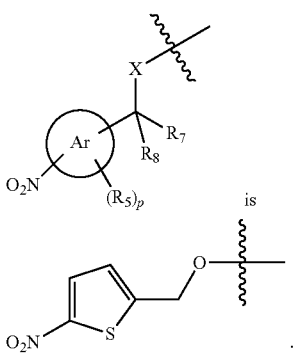

is

In some embodiments, the compound represented by Formula II or Formula IIa has a structure represented by Formula II-1, Formula II-2, Formula II-3 or Formula II-4,

II-1

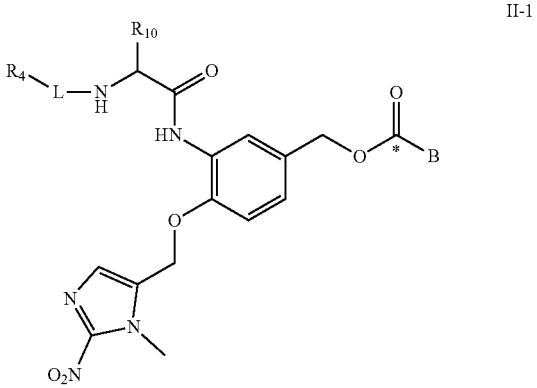

II-2

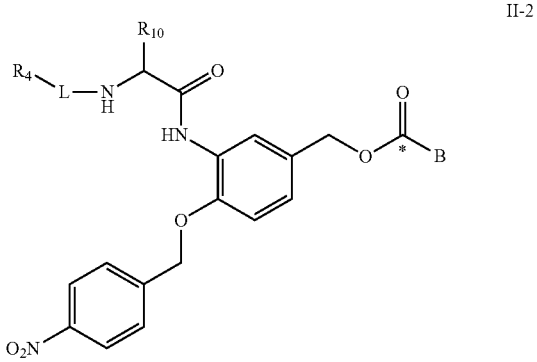

II-3

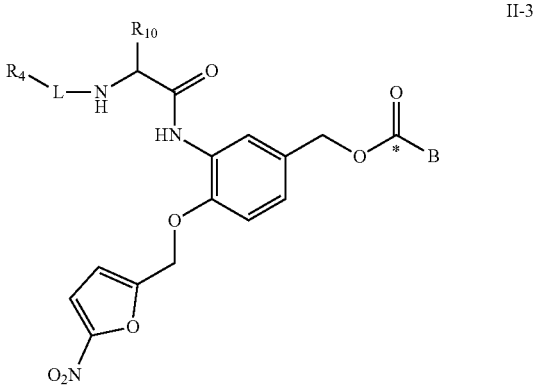

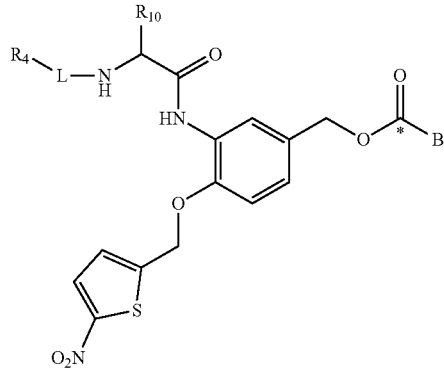

II-4

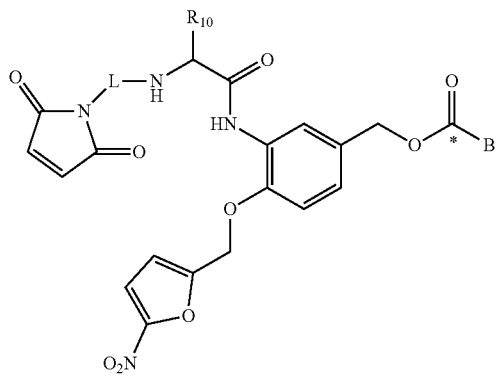

II-7 wherein, $R_4$, $R_{10}$, L and B are defined as in the present application.

In some embodiments, the compound represented by Formula II or Formula IIa has a structure represented by Formula II-5, Formula II-6, Formula II-7 or Formula II-8,

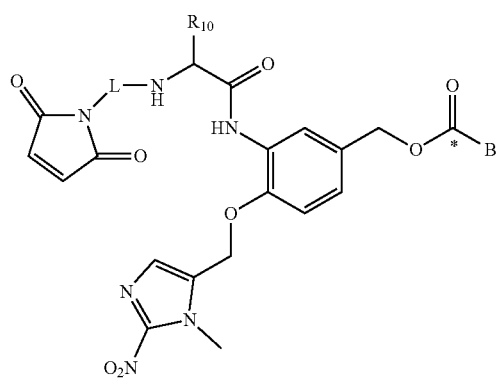

II-5

II-8

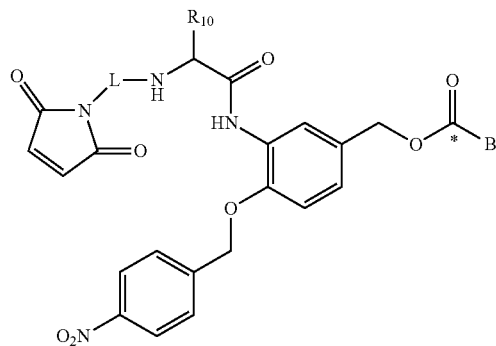

II-6 wherein, $R_{10}$, L and B are defined as in the present application.

In some embodiments, the compound represented by Formula II or Formula IIa has a structure represented by Formula II-9, Formula II-10, Formula II-11, Formula II-12 or Formula II-13,

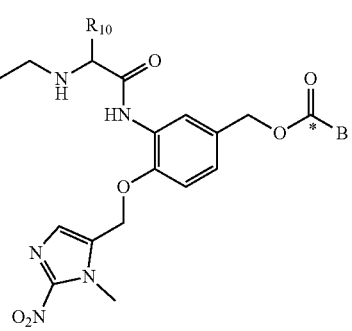

II-9

II-10
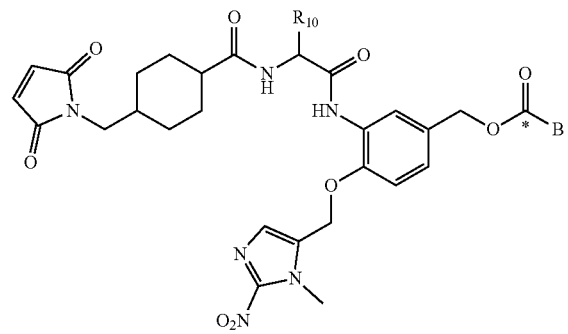
II-14
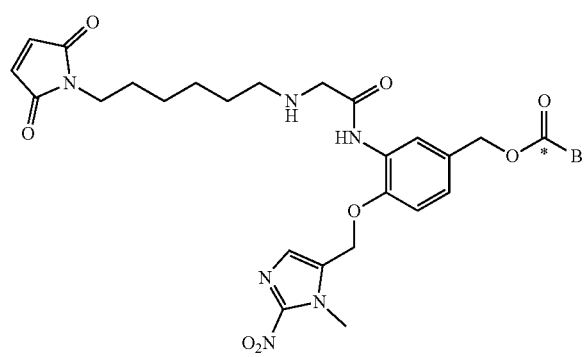
II-11
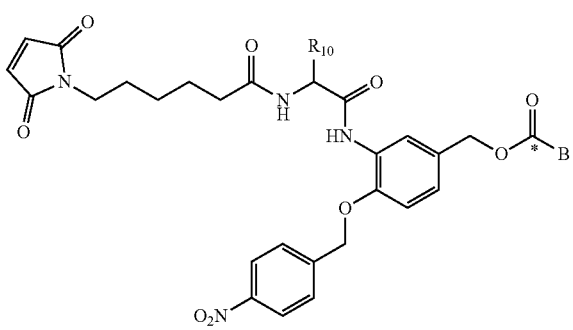
II-15
II-12
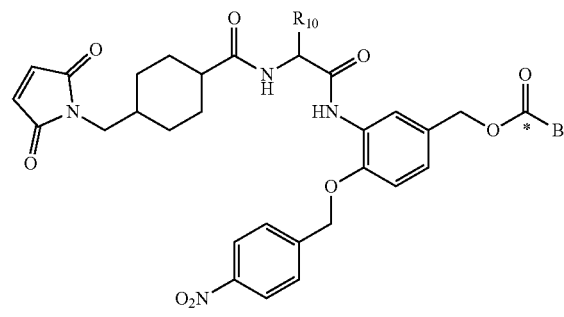
II-13
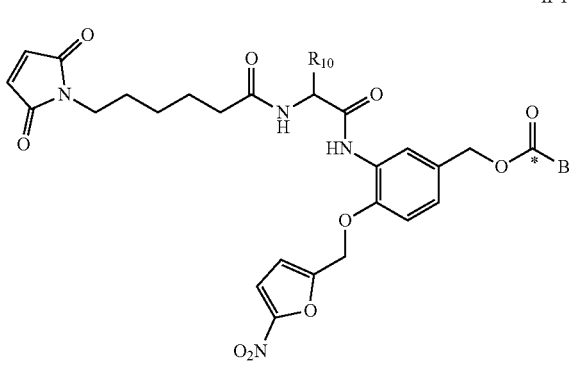
II-16
II-17
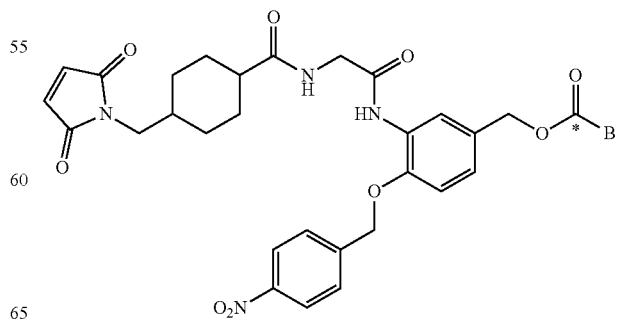
wherein, $R_{10}$ and B are defined as in the present application.
In some embodiments, the compound represented by Formula II or Formula IIa has a structure represented by Formula II-14, Formula II-15, Formula II-16, Formula II-17 or Formula II-18, II-18
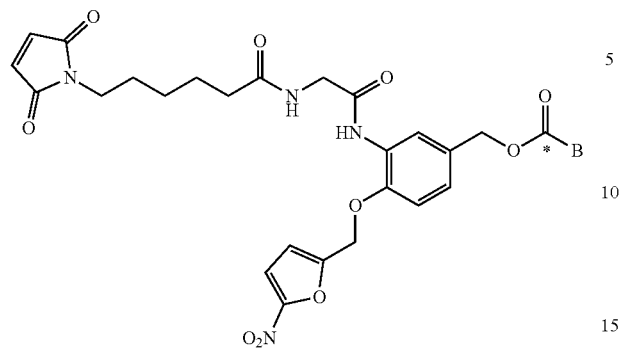
wherein, B is defined as in the present application.
In some embodiments, the compound represented by Formula II or Formula IIa is selected from the group consisting of:
L01-MMAE
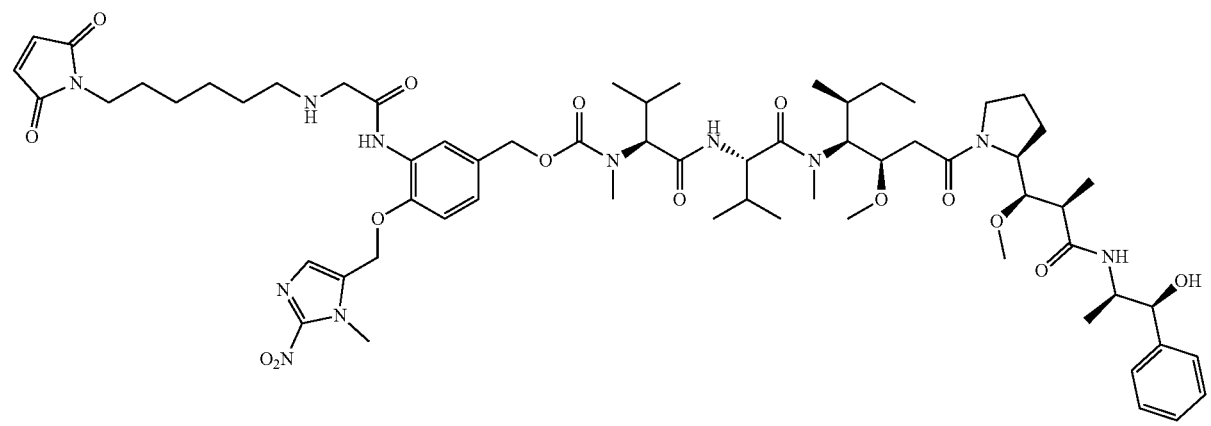
L02-MMAE
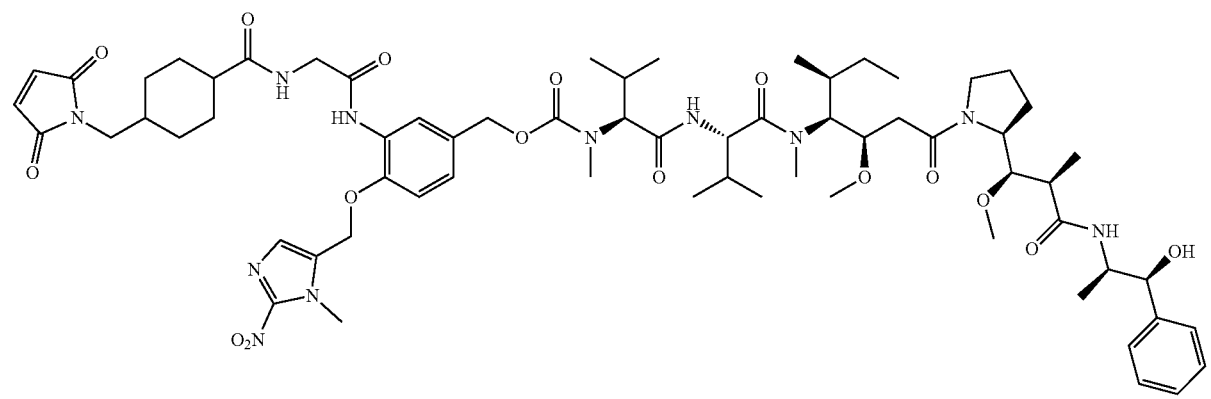

L03-MMEA
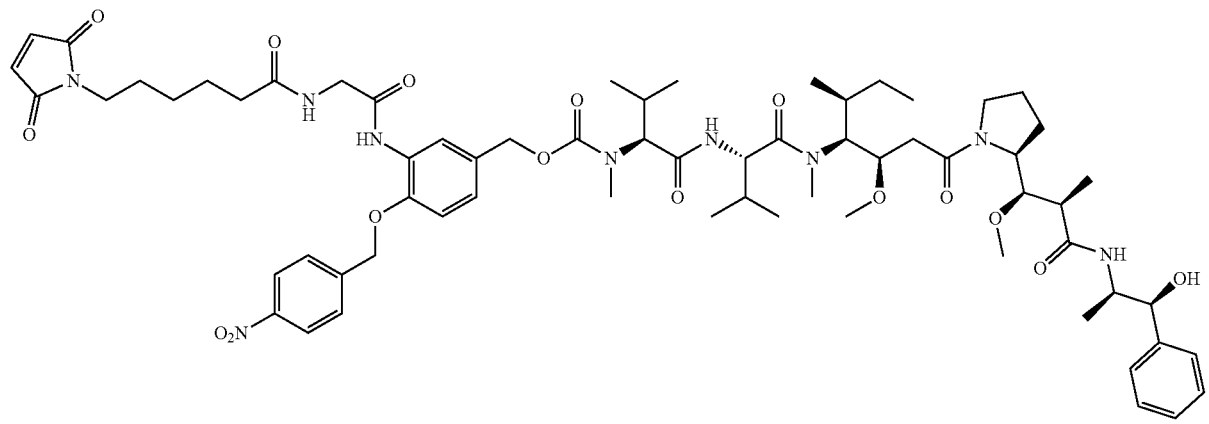
L04-MMAE
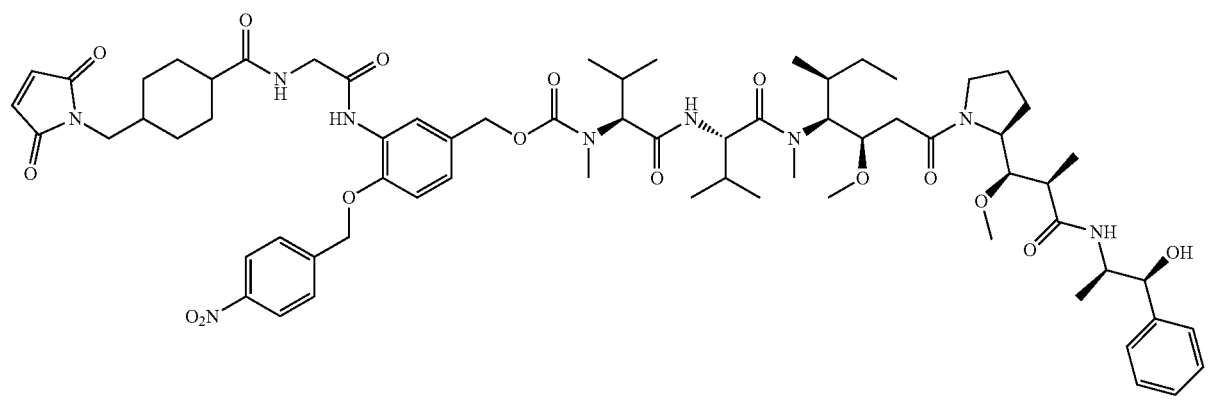
L05-MMAE
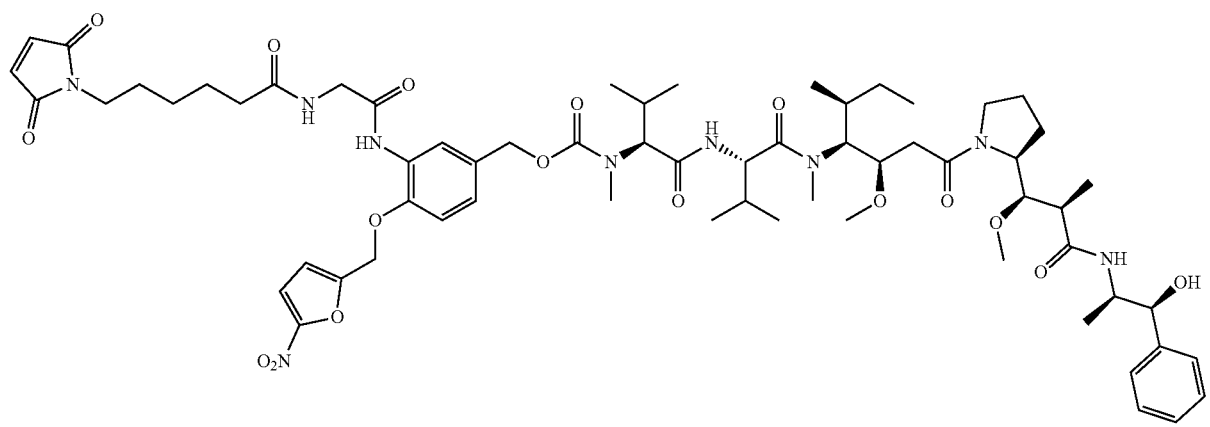

-continued
L6-MMAE
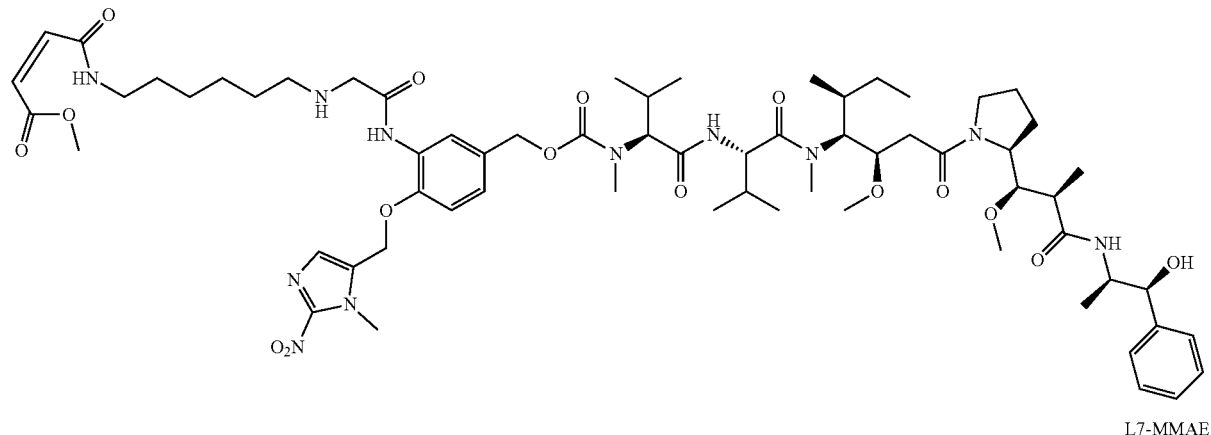
L7-MMAE
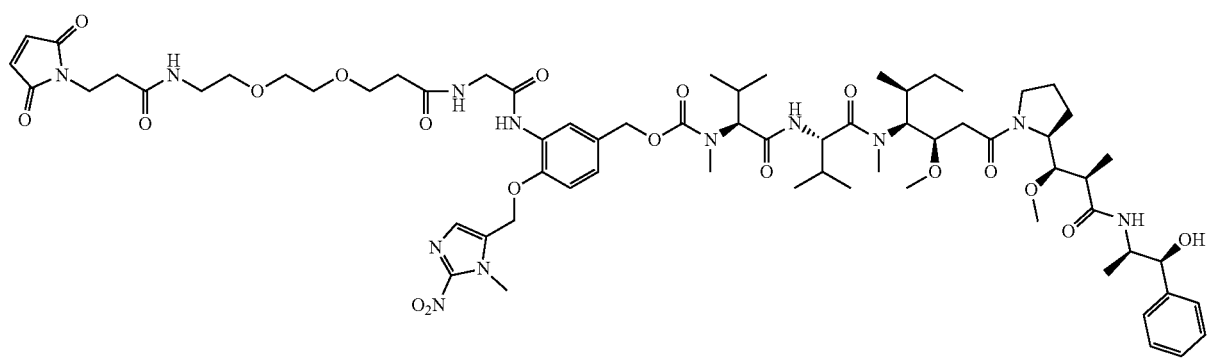
L8-MMAE
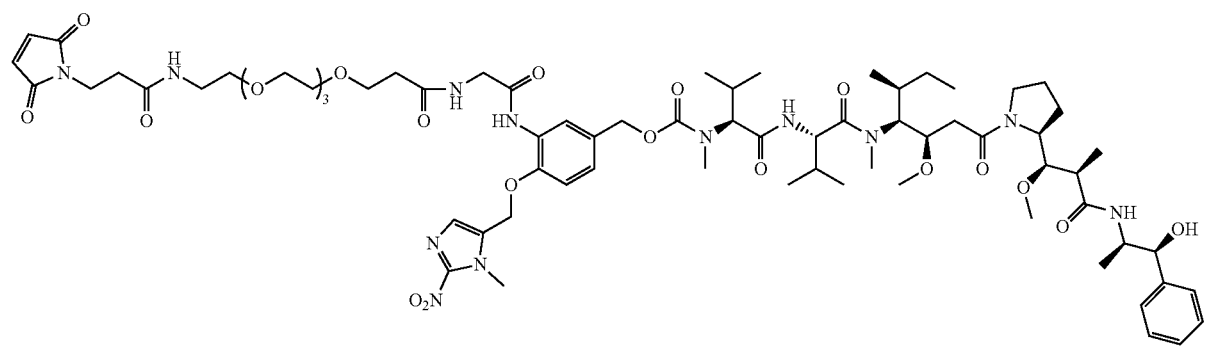
L9-MMAE
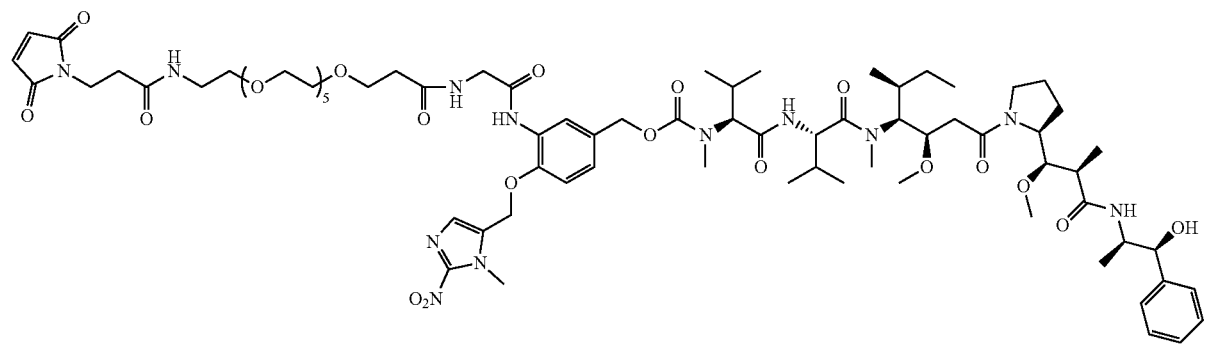

L10-MMAE

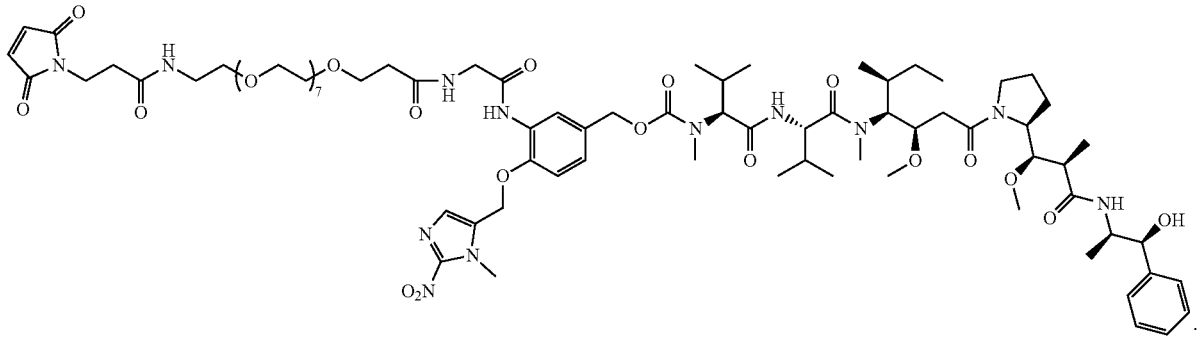

The present application also relates to use of the compound represented by Formula II or Formula IIa or a salt thereof in preparation of an antibody-drug conjugate.

The present application also relates to a compound represented by Formula III or Formula III' or a salt thereof,

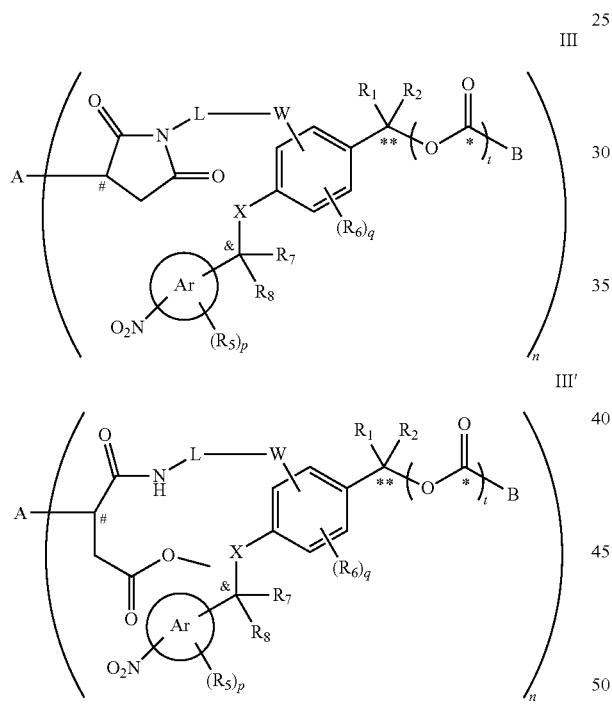

wherein:
$R_1$ is hydrogen, methyl, ethyl, n-propyl or isopropyl;
$R_2$ is hydrogen, methyl, ethyl, n-propyl or isopropyl;
X is oxygen atom (O), nitrogen atom (N) or sulfur atom (S);
Ar is aryl, heteroaryl, aryl-fused-heterocyclyl or heteroaryl-fused-heterocyclyl, preferably a 5- or 6-membered aryl, or 5- or 6-membered heteroaryl; preferably, the nitro on Ar and the C atom at & site are located at the conjugation positions of the aromatic system, and more preferably, Ar is 6-membered aryl or 6-membered heteroaryl, and the nitro on Ar and the C atom at & site are at para- or ortho-positions;
$R_5$ is hydrogen, methyl, ethyl, n-propyl, isopropyl, fluorine, chlorine, bromine, iodine, hydroxyl or cyano;
$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;
$R_7$ is hydrogen, methyl, ethyl, n-propyl or isopropyl;
$R_8$ is hydrogen, methyl, ethyl, n-propyl or isopropyl;
q is 0, 1, 2 or 3;
p is 0, 1, 2 or 3;
L is —$(CH_2)_iO(CH_2)_j$—, —$(CH_2)_iO(CH_2)_j$—C(O)—, —$(CH_2)_i$—C(O)NH—$(CH_2)_j$—, —$(CH_2CH_2O)_i$—$(CH_2)_j$—C(O)—, —$(CH_2)_i$—$(CH_2CH_2O)_j$—C(O)—, —$(OCH_2CH_2)_i$—, —$(CH_2)_m$—, —$(CH_2)_r$—C(O)—, —$(CH_2)_k$—C(O)NH—$(CH_2CH_2O)_g$—$(CH_2)_h$—C(O)—, —$(CH_2)_b$—C(O)NH—CH[$(CH_2)_a$—NHC(O)—$(CH_2CH_2O)_e$—$(CH_2)_r$—CH_3]—,

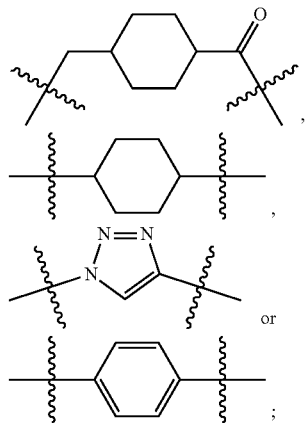

W represents a linking group, preferably is —NH—$CH_2$—C(O)—NH—, —NH—$CH_2$—$CH_2$—C(O)—NH—, —C(O)—NH—, —NH—C(O)—, —O—, —S—, —NH—, —N($CH_3$)— or —C(O)—, further preferably —NH—$CH_2$—C(O)—NH, —C(O)—NH—, —NH—C(O)—, —O— or —NH—CH($R_{10}$)—C(O)—NH—;
$R_{10}$ is —H, —$CH_3$, —$C_3H_6$, —CH—$(CH_3)_2$, —$CH_2$—CH$(CH_3)_2$, —CH$(CH_3)$—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH($CH_3$)—OH or —$CH_2$—SH, preferably —H or —$CH_3$;
m is 1, 2, 3, 4, 5, 6, 7, 8 or 9;
each i is independently 1, 2, 3, 4, 5, 6, 7, 8 or 9;

each j is independently 1, 2, 3, 4, 5, 6, 7, 8 or 9;

r is 1, 2, 3, 4, 5, 6, 7, 8 or 9;

k is 1, 2, 3, 4, 5 or 6;

g is 1, 2, 3, 4, 5, 6, 7, 8, 9, 10, 11 or 12;

h is 1, 2, 3, 4, 5 or 6;

b is 1, 2, 3, 4, 5 or 6;

d is 1, 2, 3, 4, 5 or 6;

e is 1, 2, 3, 4, 5, 6, 7, 8, 9, 10, 11 or 12;

f is 1, 2, 3, 4, 5 or 6;

B is an active compound, selected from the group consisting of drug, cytotoxin, detection reagent, diagnostic reagent and targeting carrier; preferably, B is a cytotoxin, an antitumor drug, an antiviral drug, an antiinfective drug or an immunomodulator drug; further preferably, B is a cytotoxin, such as a tubulin inhibitor, a DNA alkylating agent, a DNA intercalator, an enzyme inhibitor, an antimetabolite, a peptide or a nucleotide; preferably, B is coupled to the site* or site** through a N atom or O atom in the active compound molecule;

t is 0 or 1;

A is a targeting compound, selected from the group consisting of: protein, antibody, polypeptide, enzyme and small molecule; preferably, A is coupled to the site # through a S atom in the targeting compound molecule;

n is a number between 0.5 and 8.5, such as a number between 0.8 and 5, a number between 1 and 4, a number between 2 and 6, a number between 3 and 7, a number between 4 and 8, a number between 3.5 and 8.5, a number between 3.5 and 4.5, or a number between 6.5 and 8.5, preferably n is about 4, 5, 6, 7 or 8;

In some embodiments, in the compound represented by Formula III or Formula III', W is —NH—CH$_2$—C(O)—NH—.

In some embodiments, in the compound represented by Formula III or Formula III', W is —NH—CH(R$_{10}$)—C(O)—NH—, wherein R$_{10}$ is defined as described in the present application.

In some embodiments, in the compound represented by Formula III or Formula III', R$_{10}$ is —H.

In some embodiments, in the compound represented by Formula III or Formula III', R$_{10}$ is —CH$_3$.

In some embodiments, in the compound represented by Formula III or Formula III', R$_{10}$ is —C$_3$H$_6$, —CH—(CH$_3$)$_2$, —CH$_2$—CH(CH$_3$)$_2$, —CH(CH$_3$)—CH$_2$—CH$_3$ or —CH$_2$—C$_6$H$_5$.

In some embodiments, in the compound represented by Formula III or Formula III', R$_{10}$ is —C$_8$NH$_6$, —CH$_2$—C$_6$H$_4$—OH, —CH$_2$—COOH, —CH$_2$—CONH$_2$ or —(CH$_2$)$_2$—COOH.

In some embodiments, in the compound represented by Formula III or Formula III', R$_{10}$ is —(CH$_2$)$_4$—NH$_2$, —(CH$_2$)$_2$—CONH$_2$, —(CH$_2$)—S—CH$_3$, —CH$_2$—OH, —CH(CH$_3$)—OH or —CH$_2$—SH.

In some embodiments, the compound represented by Formula III or a salt thereof has a structure represented by Formula IIIa,

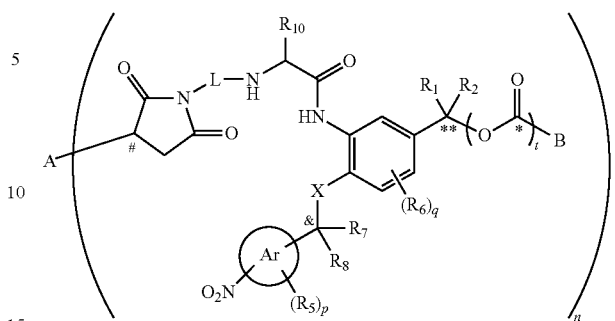

IIIa wherein:

R$_1$ is hydrogen, methyl, ethyl, n-propyl or isopropyl;

R$_2$ is hydrogen, methyl, ethyl, n-propyl or isopropyl;

X is oxygen atom (O), nitrogen atom (N) or sulfur atom (S);

Ar is aryl, heteroaryl, aryl-fused-heterocyclyl or heteroaryl-fused-heterocyclyl, preferably a 5- or 6-membered aryl, or 5- or 6-membered heteroaryl; preferably, the nitro on Ar and the C atom at & site are located at the conjugation positions of the aromatic system, and more preferably, Ar is 6-membered aryl or 6-membered heteroaryl, and the nitro on Ar and the C atom at & site are at para- or ortho-positions;

R$_5$ is hydrogen, methyl, ethyl, n-propyl, isopropyl, fluorine, chlorine, bromine, iodine, hydroxyl or cyano;

R$_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;

R$_7$ is hydrogen, methyl, ethyl, n-propyl or isopropyl;

R$_8$ is hydrogen, methyl, ethyl, n-propyl or isopropyl;

R$_{10}$ is —H, —CH$_3$, —C$_3$H$_6$, —CH—(CH$_3$)$_2$, —CH$_2$—CH(CH$_3$)$_2$, —CH(CH$_3$)—CH$_2$—CH$_3$, —CH$_2$—C$_6$H$_5$, —C$_8$NH$_6$, —CH$_2$—C$_6$H$_4$—OH, —CH$_2$—COOH, —CH$_2$—CONH$_2$, —(CH$_2$)$_2$—COOH, —(CH$_2$)$_4$—NH$_2$, —(CH$_2$)$_2$—CONH$_2$, —(CH$_2$)—S—CH$_3$, —CH$_2$—OH, —CH(CH$_3$)—OH or —CH$_2$—SH, preferably —H or —CH$_3$;

q is 0, 1, 2 or 3;

p is 0, 1, 2 or 3;

L is —(CH$_2$)$_i$O(CH$_2$)$_j$—, —(CH$_2$)$_i$O(CH$_2$)$_j$—C(O)—, —(CH$_2$)$_i$—C(O)NH—(CH$_2$)$_j$—, —(CH$_2$CH$_2$O)$_i$—(CH$_2$)$_j$—C(O)—, —(CH$_2$)$_i$—(CH$_2$CH$_2$O)$_j$—C(O)—, —(OCH$_2$CH$_2$)$_i$—, —(CH$_2$)$_m$—, —(CH$_2$)$_r$—C(O)—, —(CH$_2$)$_k$—C(O)NH—(CH$_2$CH$_2$O)$_g$—(CH$_2$)$_h$—C(O)—, —(CH$_2$)$_b$—C(O)NH—CH[(CH$_2$)$_a$—NHC(O)—(CH$_2$CH$_2$O)$_e$—(CH$_2$)$_r$CH$_3$]—,

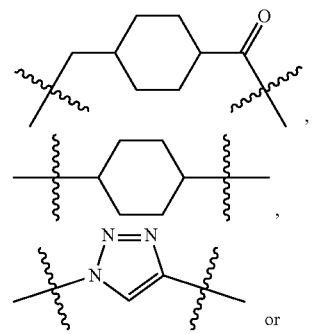

or

-continued

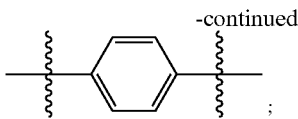

m is 1, 2, 3, 4, 5, 6, 7, 8 or 9;
each i is independently 1, 2, 3, 4, 5, 6, 7, 8 or 9;
each j is independently 1, 2, 3, 4, 5, 6, 7, 8 or 9;
r is 1, 2, 3, 4, 5, 6, 7, 8 or 9;
k is 1, 2, 3, 4, 5 or 6;
g is 1, 2, 3, 4, 5, 6, 7, 8, 9, 10, 11 or 12;
h is 1, 2, 3, 4, 5 or 6;
b is 1, 2, 3, 4, 5 or 6;
d is 1, 2, 3, 4, 5 or 6;
e is 1, 2, 3, 4, 5, 6, 7, 8, 9, 10, 11 or 12;
f is 1, 2, 3, 4, 5 or 6;
B is an active compound, selected from the group consisting of drug, cytotoxin, detection reagent, diagnostic reagent and targeting carrier; preferably, B is a cytotoxin, an antitumor drug, an antiviral drug, an anti-infective drug or an immunomodulator drug; further preferably, B is a cytotoxin, such as a tubulin inhibitor, a DNA alkylating agent, a DNA intercalator, an enzyme inhibitor, an antimetabolite, a peptide or a nucleotide; preferably, B is coupled to the site* or site** through a N atom or O atom in the active compound molecule;
t is 0 or 1;
A is a targeting compound, selected from the group consisting of: protein, antibody, polypeptide, enzyme and small molecule; preferably, A is coupled to the site # through a S atom in the targeting compound molecule;
n is a number between 0.5 and 8.5, such as a number between 0.8 and 5, a number between 1 and 4, a number between 2 and 6, a number between 3 and 7, a number between 4 and 8, a number between 3.5 and 8.5, a number between 3.5 and 4.5, or a number between 6.5 and 8.5, preferably n is about 4, 5, 6, 7 or 8.

In some embodiments, in the compound represented by Formula III, Formula III' or Formula IIIa, or a salt thereof, $R_1$ is hydrogen or methyl.

In some embodiments, in the compound represented by Formula III, Formula III' or Formula IIIa, or a salt thereof, $R_1$ is hydrogen.

In some embodiments, in the compound represented by Formula III, Formula III' or Formula IIIa, or a salt thereof, $R_1$ is methyl.

In some embodiments, in the compound represented by Formula III, Formula III' or Formula IIIa, or a salt thereof, $R_1$ is ethyl.

In some embodiments, in the compound represented by Formula III, Formula III' or Formula IIIa, or a salt thereof, $R_1$ is n-propyl.

In some embodiments, in the compound represented by Formula III, Formula III' or Formula IIIa, or a salt thereof, $R_1$ is isopropyl.

In some embodiments, in the compound represented by Formula III, Formula III' or Formula IIIa, or a salt thereof, $R_2$ is hydrogen or methyl.

In some embodiments, in the compound represented by Formula III, Formula III' or Formula IIIa, or a salt thereof, $R_2$ is hydrogen.

In some embodiments, in the compound represented by Formula III, Formula III' or Formula IIIa, or a salt thereof, $R_2$ is methyl.

In some embodiments, in the compound represented by Formula III, Formula III' or Formula IIIa, or a salt thereof, $R_2$ is ethyl.

In some embodiments, in the compound represented by Formula III, Formula III' or Formula IIIa, or a salt thereof, $R_2$ is n-propyl.

In some embodiments, in the compound represented by Formula III, Formula III' or Formula IIIa, or a salt thereof, $R_2$ is isopropyl.

In some embodiments, in the compound represented by Formula III, Formula III' or Formula IIIa, or a salt thereof, X is oxygen atom (O) or nitrogen atom (N), preferably oxygen atom (O).

In some embodiments, in the compound represented by Formula III, Formula III' or Formula IIIa, or a salt thereof, Ar is benzene ring, furan ring, imidazole ring or thiophene ring.

In some embodiments, in the compound represented by Formula III, Formula III' or Formula IIIa, or a salt thereof, Ar is benzene ring.

In some embodiments, in the compound represented by Formula III, Formula III' or Formula IIIa, or a salt thereof, Ar is furan ring.

In some embodiments, in the compound represented by Formula III, Formula III' or Formula IIIa, or a salt thereof, Ar is imidazole ring.

In some embodiments, in the compound represented by Formula III, Formula III' or Formula IIIa, or a salt thereof, Ar is thiophene ring.

In some embodiments, in the compound represented by Formula III, Formula III' or Formula IIIa, or a salt thereof, $R_5$ is hydrogen, methyl, fluorine, chlorine or bromine; more preferably, $R_5$ is hydrogen or methyl.

In some embodiments, in the compound represented by Formula III, Formula III' or Formula IIIa, or a salt thereof, $R_5$ is hydrogen.

In some embodiments, in the compound represented by Formula III, Formula III' or Formula IIIa, or a salt thereof, $R_5$ is methyl.

In some embodiments, in the compound represented by Formula III, Formula III' or Formula IIIa, or a salt thereof, $R_5$ is ethyl.

In some embodiments, in the compound represented by Formula III, Formula III' or Formula IIIa, or a salt thereof, $R_5$ is fluorine.

In some embodiments, in the compound represented by Formula III, Formula III' or Formula IIIa, or a salt thereof, $R_5$ is chlorine.

In some embodiments, in the compound represented by Formula III, Formula III' or Formula IIIa, or a salt thereof, $R_5$ is bromine.

In some embodiments, in the compound represented by Formula III, Formula III' or Formula IIIa, or a salt thereof, $R_6$ is hydrogen, methyl, ethyl, fluorine, chlorine or bromine.

In some embodiments, in the compound represented by Formula III, Formula III' or Formula IIIa, or a salt thereof, $R_6$ is hydrogen.

In some embodiments, in the compound represented by Formula III, Formula III' or Formula IIIa, or a salt thereof, $R_6$ is methyl.

In some embodiments, in the compound represented by Formula III, Formula III' or Formula IIIa, or a salt thereof, $R_6$ is ethyl.

In some embodiments, in the compound represented by Formula III, Formula III' or Formula IIIa, or a salt thereof, $R_6$ is fluorine.

In some embodiments, in the compound represented by Formula III, Formula III' or Formula IIIa, or a salt thereof, $R_6$ is chlorine.

In some embodiments, in the compound represented by Formula III, Formula III' or Formula IIIa, or a salt thereof, $R_6$ is bromine.

In some embodiments, in the compound represented by Formula III, Formula III' or Formula IIIa, or a salt thereof, $R_7$ is hydrogen or methyl.

In some embodiments, in the compound represented by Formula III, Formula III' or Formula IIIa, or a salt thereof, $R_7$ is hydrogen.

In some embodiments, in the compound represented by Formula III, Formula III' or Formula IIIa, or a salt thereof, $R_7$ is methyl.

In some embodiments, in the compound represented by Formula III, Formula III' or Formula IIIa, or a salt thereof, $R_7$ is ethyl.

In some embodiments, in the compound represented by Formula III, Formula III' or Formula IIIa, or a salt thereof, $R_7$ is n-propyl.

In some embodiments, in the compound represented by Formula III, Formula III' or Formula IIIa, or a salt thereof, $R_7$ is isopropyl.

In some embodiments, in the compound represented by Formula III, Formula III' or Formula IIIa, or a salt thereof, $R_8$ is hydrogen or methyl.

In some embodiments, in the compound represented by Formula III, Formula III' or Formula IIIa, or a salt thereof, $R_8$ is hydrogen.

In some embodiments, in the compound represented by Formula III, Formula III' or Formula IIIa, or a salt thereof, $R_8$ is methyl.

In some embodiments, in the compound represented by Formula III, Formula III' or Formula IIIa, or a salt thereof, $R_8$ is ethyl.

In some embodiments, in the compound represented by Formula III, Formula III' or Formula IIIa, or a salt thereof, $R_8$ is n-propyl.

In some embodiments, in the compound represented by Formula III, Formula III' or Formula IIIa, or a salt thereof, $R_8$ is isopropyl.

In some embodiments, in the compound represented by Formula III, Formula III' or Formula IIIa, or a salt thereof, $R_{10}$ is hydrogen or methyl.

In some embodiments, in the compound represented by Formula III, Formula III' or Formula IIIa, or a salt thereof, $R_{10}$ is methyl.

In some embodiments, in the compound represented by Formula III, Formula III' or Formula IIIa, or a salt thereof, $R_{10}$ is hydrogen.

In some embodiments, in the compound represented by Formula III, Formula III' or Formula IIIa, or a salt thereof, q is 0 or 1.

In some embodiments, in the compound represented by Formula III, Formula III' or Formula IIIa, or a salt thereof, q is 0.

In some embodiments, in the compound represented by Formula III, Formula III' or Formula IIIa, or a salt thereof, p is 0 or 1.

In some embodiments, in the compound represented by Formula III, Formula III' or Formula IIIa, or a salt thereof, p is 1.

In some embodiments, in the compound represented by Formula III, Formula III' or Formula IIIa, or a salt thereof, L is —(CH$_2$)$_i$O(CH$_2$)$_j$—, —(CH$_2$)$_i$O(CH$_2$)$_j$—C(O)—, —(CH$_2$)$_i$—C(O)NH—(CH$_2$)$_j$—, —(CH$_2$CH$_2$O)$_i$—(CH$_2$)$_j$—C(O)—, —(CH$_2$)$_i$—(CH$_2$CH$_2$O)$_j$—C(O)—, —(OCH$_2$CH$_2$)$_i$—, —(CH$_2$)$_m$—, —(CH$_2$)$_r$—C(O)—,

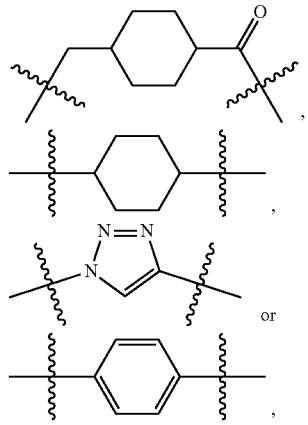

wherein i, j, m, k, g, h and r are defined as in the present application.

In some embodiments, in the compound represented by Formula III, Formula III' or Formula IIIa, or a salt thereof, L is —(CH$_2$)$_i$O(CH$_2$)$_j$—C(O)—, —(CH$_2$CH$_2$O)$_i$—(CH$_2$)$_j$—C(O)—, —(CH$_2$)$_i$—(CH$_2$CH$_2$O)$_j$—C(O)—, —(CH$_2$)$_m$—, —(CH$_2$)$_r$—C(O)—,

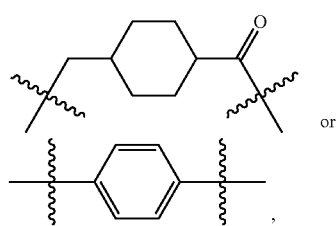

wherein m is 1, 2, 3, 4, 5, 6, 7, 8 or 9, preferably 4, 5, 6 or 7; i is 1, 2, 3, 4, 5, 6, 7, 8 or 9, preferably 4, 5, 6 or 7; j is 1, 2, 3, 4, 5, 6, 7, 8 or 9, preferably 4, 5, 6 or 7; r is 1, 2, 3, 4, 5, 6, 7, 8 or 9, preferably 4, 5 or 6.

In some embodiments, in the compound represented by Formula III, Formula III' or Formula IIIa, or a salt thereof, L is —(CH$_2$)$_m$—, —(CH$_2$)$_r$—C(O)—,

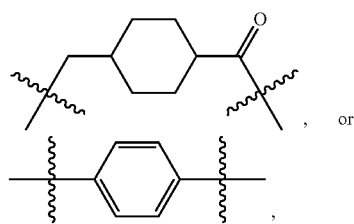

wherein m is 1, 2, 3, 4, 5, 6, 7, 8 or 9, preferably 4, 5, 6 or 7; i is 1, 2, 3, 4, 5, 6, 7, 8 or 9, preferably 4, 5, 6 or 7; j is 1, 2, 3, 4, 5, 6, 7, 8 or 9, preferably 4, 5, 6 or 7; r is 1, 2, 3, 4, 5, 6, 7, 8 or 9, preferably 4, 5 or 6.

In some embodiments, in the compound represented by Formula III, Formula III' or Formula IIIa, or a salt thereof, L is —(CH$_2$)$_m$—, wherein m is defined as in the present application.

In some embodiments, in the compound represented by Formula III, Formula III' or Formula IIIa, or a salt thereof, m is 1 or 2.

In some embodiments, in the compound represented by Formula III, Formula III' or Formula IIIa, or a salt thereof, m is 3 or 4.

In some embodiments, in the compound represented by Formula III, Formula III' or Formula IIIa, or a salt thereof, m is 5.

In some embodiments, in the compound represented by Formula III, Formula III' or Formula IIIa, or a salt thereof, m is 6.

In some embodiments, in the compound represented by Formula III, Formula III' or Formula IIIa, or a salt thereof, m is 7.

In some embodiments, in the compound represented by Formula III, Formula III' or Formula IIIa, or a salt thereof, m is 8 or 9.

In some embodiments, in the compound represented by Formula III, Formula III' or Formula IIIa, or a salt thereof, L is —$(CH_2)_r$—C(O)—, wherein r is defined as in the present application.

In some embodiments, in the compound represented by Formula III, Formula III' or Formula IIIa, or a salt thereof, r is 1 or 2.

In some embodiments, in the compound represented by Formula III, Formula III' or Formula IIIa, or a salt thereof, r is 3.

In some embodiments, in the compound represented by Formula III, Formula III' or Formula IIIa, or a salt thereof, r is 4.

In some embodiments, in the compound represented by Formula III, Formula III' or Formula IIIa, or a salt thereof, r is 5.

In some embodiments, in the compound represented by Formula III, Formula III' or Formula IIIa, or a salt thereof, r is 6.

In some embodiments, in the compound represented by Formula III, Formula III' or Formula IIIa, or a salt thereof, r is 7.

In some embodiments, in the compound represented by Formula III, Formula III' or Formula IIIa, or a salt thereof, r is 8 or 9.

In some embodiments, in the compound represented by Formula III, Formula III' or Formula IIIa, or a salt thereof, L is In some embodiments, in the compound represented by Formula III, Formula III' or Formula IIIa, or a salt thereof, L is In some embodiments, in the compound represented by Formula III, Formula III' or Formula IIIa, or a salt thereof, L is —$(CH_2)_k$—C(O)NH—$(CH_2CH_2O)_g$—$(CH_2)_h$—C(O)—, wherein k, g and h are defined as in the present application.

In some embodiments, in the compound represented by Formula III, Formula III' or Formula IIIa, or a salt thereof, k is 1 or 2.

In some embodiments, in the compound represented by Formula III, Formula III' or Formula IIIa, or a salt thereof, k is 3 or 4.

In some embodiments, in the compound represented by Formula III, Formula III' or Formula IIIa, or a salt thereof, k is 5 or 6.

In some embodiments, in the compound represented by Formula III, Formula III' or Formula IIIa, or a salt thereof, g is 1, 2, 3 or 4.

In some embodiments, in the compound represented by Formula III, Formula III' or Formula IIIa, or a salt thereof, g is 5, 6, 7 or 8.

In some embodiments, in the compound represented by Formula III, Formula III' or Formula IIIa, or a salt thereof, g is 9, 10, 11 or 12.

In some embodiments, in the compound represented by Formula III, Formula III' or Formula IIIa, or a salt thereof, h is 1 or 2.

In some embodiments, in the compound represented by Formula III, Formula III' or Formula IIIa, or a salt thereof, h is 3 or 4.

In some embodiments, in the compound represented by Formula III, Formula III' or Formula IIIa, or a salt thereof, h is 5 or 6.

In some embodiments, in the compound represented by Formula III, Formula III' or Formula IIIa, or a salt thereof, L is —$(CH_2)_2$—C(O)NH—$(CH_2CH_2O)_g$—$(CH_2)_2$—C(O)—, wherein g is defined as in the present application.

In some embodiments, in the compound represented by Formula III, Formula III' or Formula IIIa, or a salt thereof, L is

—$(CH_2)_2$—C(O)NH—$(CH_2CH_2O)_2$—$(CH_2)_2$—C(O)—,

—$(CH_2)_2$—C(O)NH—$(CH_2CH_2O)_4$—$(CH_2)_2$—C(O)—,

—$(CH_2)_2$—C(O)NH—$(CH_2CH_2O)_6$—$(CH_2)_2$—C(O)—, or

—$(CH_2)_2$—C(O)NH—$(CH_2CH_2O)_5$—$(CH_2)_2$—C(O)—.

In some embodiments, in the compound represented by Formula III, Formula III' or Formula IIIa, or a salt thereof, L is —$(CH_2)_2$—C(O)NH—$(CH_2CH_2O)_3$—$(CH_2)_2$—C(O)—.

In some embodiments, in the compound represented by Formula III, Formula III' or Formula IIIa, or a salt thereof, L is —$(CH_2)_2$—C(O)NH—$(CH_2CH_2O)_5$—$(CH_2)_2$—C(O)—.

In some embodiments, in the compound represented by Formula III, Formula III' or Formula IIIa, or a salt thereof, L is —$(CH_2)_2$—C(O)NH—$(CH_2CH_2O)_7$—$(CH_2)_2$—C(O)—.

In some embodiments, in the compound represented by Formula III, Formula III' or Formula IIIa, or a salt thereof, L is —$(CH_2)_2$—C(O)NH—$(CH_2CH_2O)_9$—$(CH_2)_2$—C(O)—.

In some embodiments, in the compound represented by Formula III, Formula III' or Formula IIIa, L is —$(CH_2)_b$—

C(O)NH—CH[(CH$_2$)$_d$—NHC(O)—(CH$_2$CH$_2$O)$_e$—(CH$_2$)$_f$—CH$_3$]—, wherein b, d, e and f are defined as in the present application.

In some embodiments, in the compound represented by Formula III, Formula III' or Formula IIIa, or a salt thereof, b is 1.

In some embodiments, in the compound represented by Formula III, Formula III' or Formula IIIa, or a salt thereof, b is 3.

In some embodiments, in the compound represented by Formula III, Formula III' or Formula IIIa, or a salt thereof, b is 5.

In some embodiments, in the compound represented by Formula III, Formula III' or Formula IIIa, or a salt thereof, b is 6.

In some embodiments, in the compound represented by Formula III, Formula III' or Formula IIIa, or a salt thereof, d is 1.

In some embodiments, in the compound represented by Formula III, Formula III' or Formula IIIa, or a salt thereof, d is 2.

In some embodiments, in the compound represented by Formula III, Formula III' or Formula IIIa, or a salt thereof, d is 3.

In some embodiments, in the compound represented by Formula III, Formula III' or Formula IIIa, or a salt thereof, d is 4.

In some embodiments, in the compound represented by Formula III, Formula III' or Formula IIIa, or a salt thereof, d is 5.

In some embodiments, in the compound represented by Formula III, Formula III' or Formula IIIa, or a salt thereof, d is 6.

In some embodiments, in the compound represented by Formula III, Formula III' or Formula IIIa, or a salt thereof, e is 1 or 2.

In some embodiments, in the compound represented by Formula III, Formula III' or Formula IIIa, or a salt thereof, e is 3 or 4.

In some embodiments, in the compound represented by Formula III, Formula III' or Formula IIIa, or a salt thereof, e is 5 or 6.

In some embodiments, in the compound represented by Formula III, Formula III' or Formula IIIa, or a salt thereof, e is 7 or 8.

In some embodiments, in the compound represented by Formula III, Formula III' or Formula IIIa, or a salt thereof, e is 9 or 10.

In some embodiments, in the compound represented by Formula III, Formula III' or Formula IIIa, or a salt thereof, e is 11 or 12.

In some embodiments, in the compound represented by Formula III, Formula III' or Formula IIIa, or a salt thereof, f is 1.

In some embodiments, in the compound represented by Formula III, Formula III' or Formula IIIa, or a salt thereof, f is 2.

In some embodiments, in the compound represented by Formula III, Formula III' or Formula IIIa, or a salt thereof, f is 3.

In some embodiments, in the compound represented by Formula III, Formula III' or Formula IIIa, or a salt thereof, f is 4.

In some embodiments, in the compound represented by Formula III, Formula III' or Formula IIIa, or a salt thereof, f is 5.

In some embodiments, in the compound represented by Formula III, Formula III' or Formula IIIa, or a salt thereof, f is 6.

In some embodiments, in the compound represented by Formula III, Formula III' or Formula IIIa, or a salt thereof, t is 1.

In some embodiments, in the compound represented by Formula III, Formula III' or Formula IIIa, or a salt thereof, B is selected from the group consisting of: auristatin, monomethyl-auristatin E (MMAE), maytansine or its derivatives (such as maytansinoids, DM1, DM3, DM4), paclitaxel, calicheamicin, duocarmycin, doxorubicin, camptothecin, PBD (pyrrolobenzodiazepines) cytotoxin and its derivatives; more preferably, B is monomethyl-auristatin E (MMAE).

In some embodiments, in the compound represented by Formula III, Formula III' or Formula IIIa, or a salt thereof, A is a monoclonal antibody with sulfhydryl as the coupling site, or a monoclonal antibody with site-directed mutation or modification and with sulfhydryl as the coupling site, preferably, A is selected from the group consisting of: anti-HER2 humanized monoclonal antibody mil40, trastuzumab (HERCEPTIN), pertuzumab (PERJETA), cetuximab (ERBITUX), panitumumab (VECTIBIX), rituximab (RITUXAN), alemtuzumab (CAMPATH), ibritumomab (ZEVALIN), tositumomab (BEXXAR), ofatumumab (ARZERRA), bevacizumab (AVASTIN), ipilimumab (YERVOY), denosumab (XGEVA), pembrolizumab (KEYTRUDA), nivolumab (Opdivo), Avelumab (Bavencio), Atezolizumab (Tecentriq), durvalumab (Imfinzi), sacituzumab, rovalpituzumab, and biological analogues thereof more preferably, A is anti-HER2 humanized monoclonal antibody mil40.

In some embodiments, in the compound represented by Formula III, Formula III' or Formula IIIa, or a salt thereof, n is a number between 2 and 7, or n is a number between 3 and 6, or between 4 and 5, preferably, n is about 4, 5, 6, 7 or 8.

In some embodiments, in the compound represented by Formula III, Formula III' or Formula IIIa, or a salt thereof,

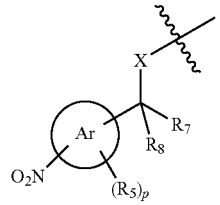

is selected from the group consisting of:

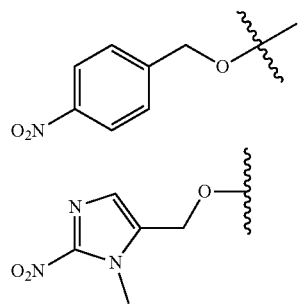

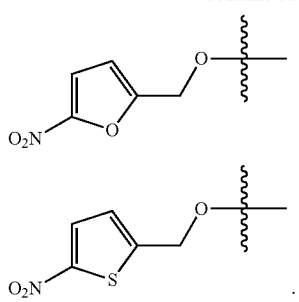

In some embodiments, in the compound represented by Formula III, Formula III' or Formula IIIa, or a salt thereof,

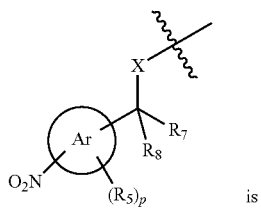 is

In some embodiments, in the compound represented by Formula III, Formula III' or Formula IIIa, or a salt thereof,

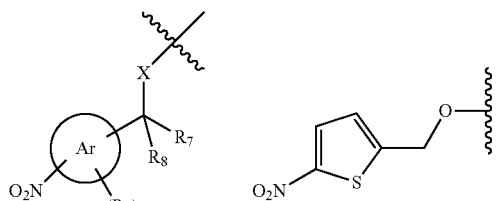 is

In some embodiments, in the compound represented by Formula III, Formula III' or Formula IIIa, or a salt thereof,

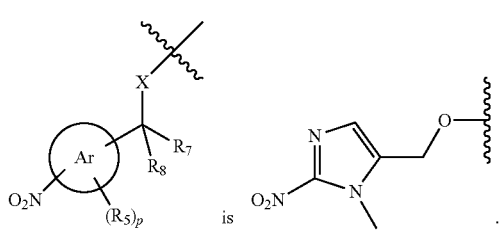 is

In some embodiments, in the compound represented by Formula III, Formula III' or Formula IIIa, or a salt thereof, n is about 4.

In some embodiments, in the compound represented by Formula III, Formula III' or Formula IIIa, or a salt thereof, n is about 5.

In some embodiments, in the compound represented by Formula III, Formula III' or Formula IIIa, or a salt thereof, n is about 6.

In some embodiments, in the compound represented by Formula III, Formula III' or Formula IIIa, or a salt thereof, n is about 7.

In some embodiments, in the compound represented by Formula III, Formula III' or Formula IIIa, or a salt thereof, n is about 8.

In some embodiments, the compound represented by Formula III or Formula IIIa has a structure represented by Formula III-1, Formula III-2, Formula III-3 or Formula III-4,

III-1

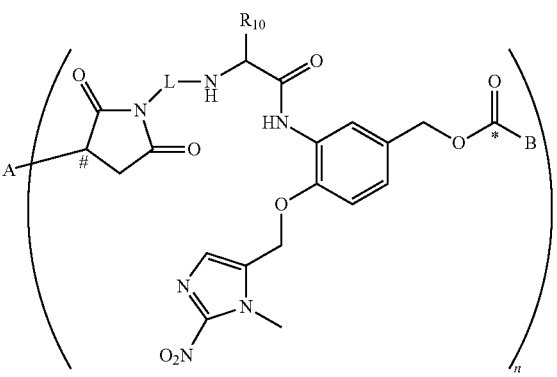

III-2

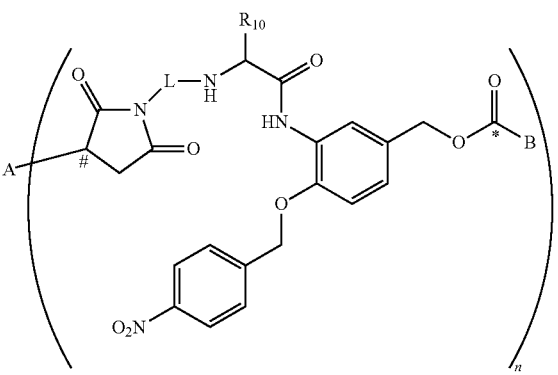

III-3

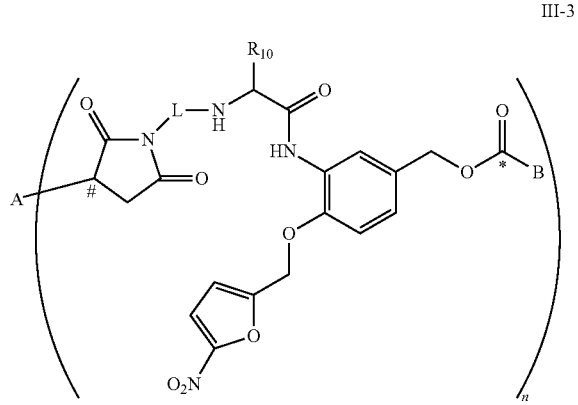

III-4

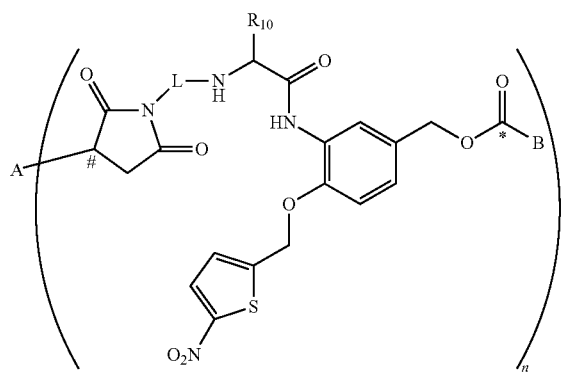

wherein, A, $R_{10}$, L, B, n is defined as in the present application.

In some embodiments, the compound represented by Formula III or Formula IIIa has a structure represented by Formula III-5, Formula III-6, Formula III-7, Formula III-8 or Formula III-9,

III-5

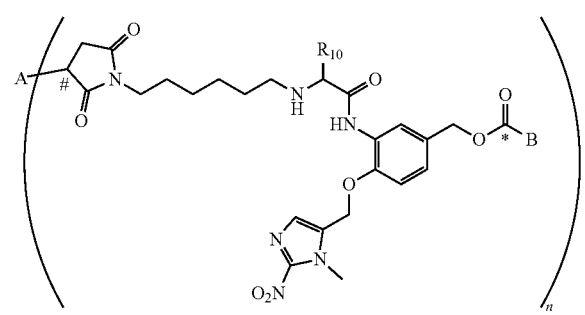

III-6

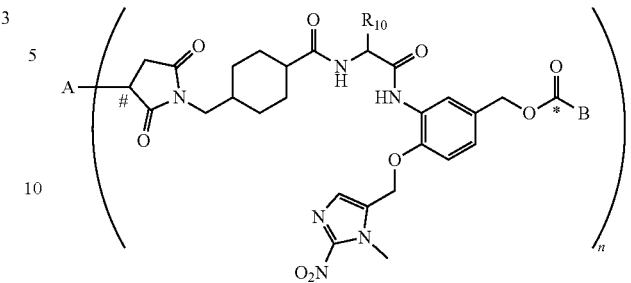

III-7

III-8

III-9

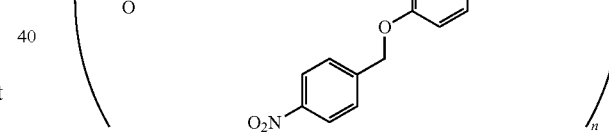

wherein, A, B, $R_{10}$ and n are defined as in the present application.

In some embodiments, the compound represented by Formula III or Formula IIIa has a structure represented by Formula III-10, Formula III-11, Formula III-12, Formula III-13 or Formula III-14,

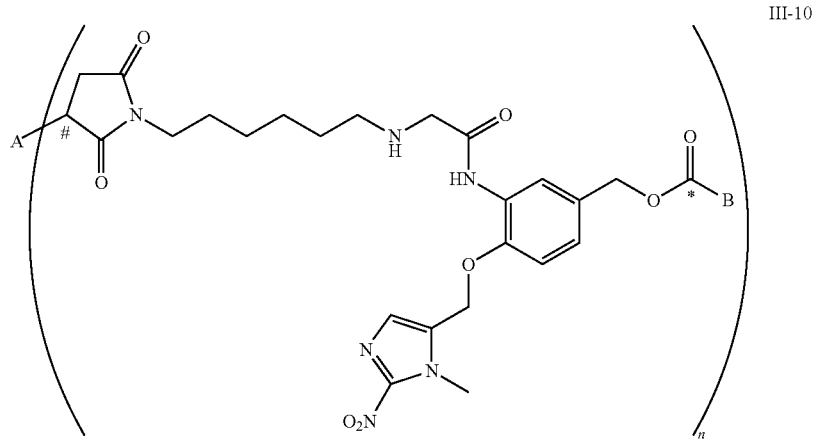
III-10
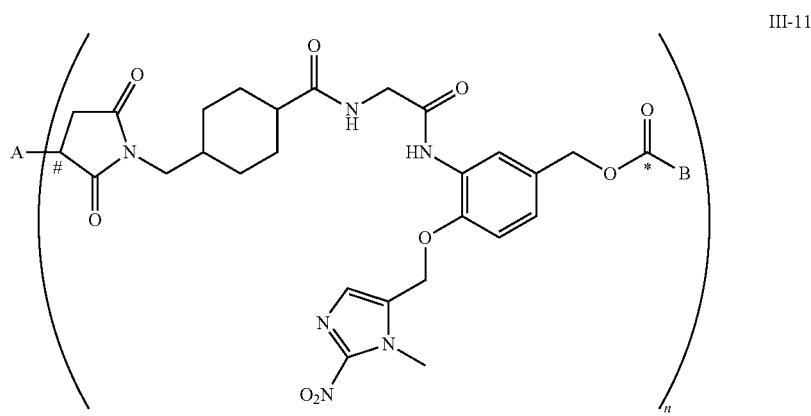
III-11
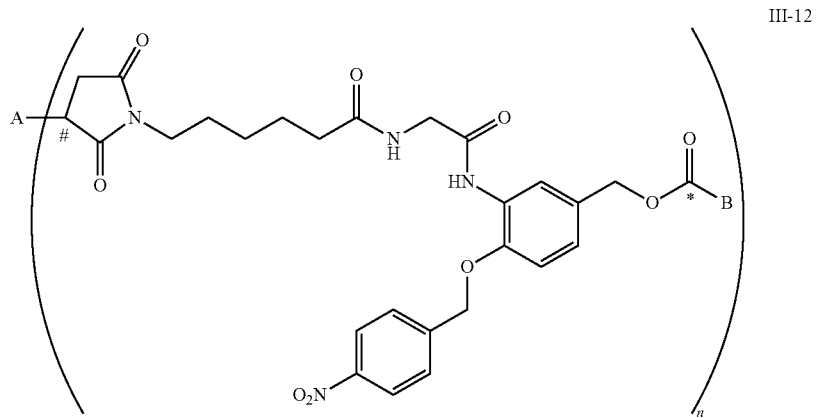
III-12
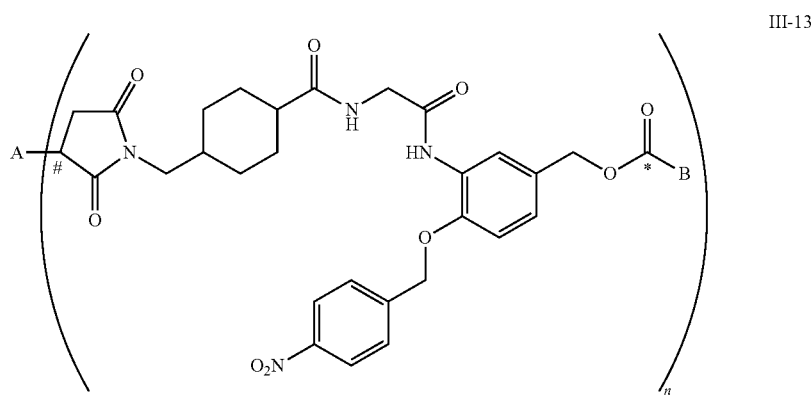
III-13

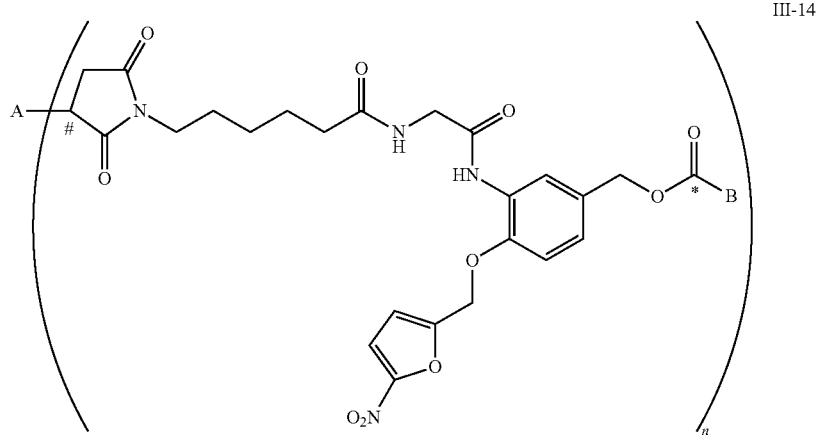
III-14
wherein, A, B and n are defined as in the present application.
In some embodiments, the compound of Formula III is selected from the group consisting of:
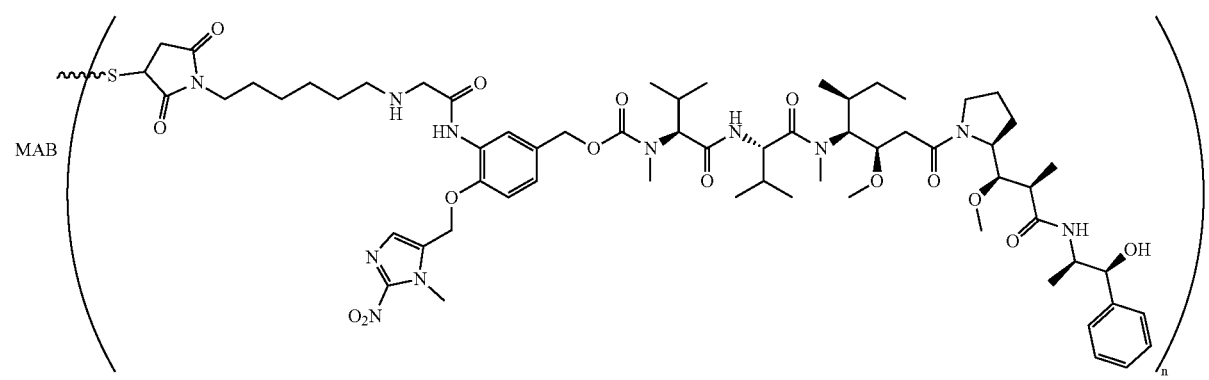
ADC-1
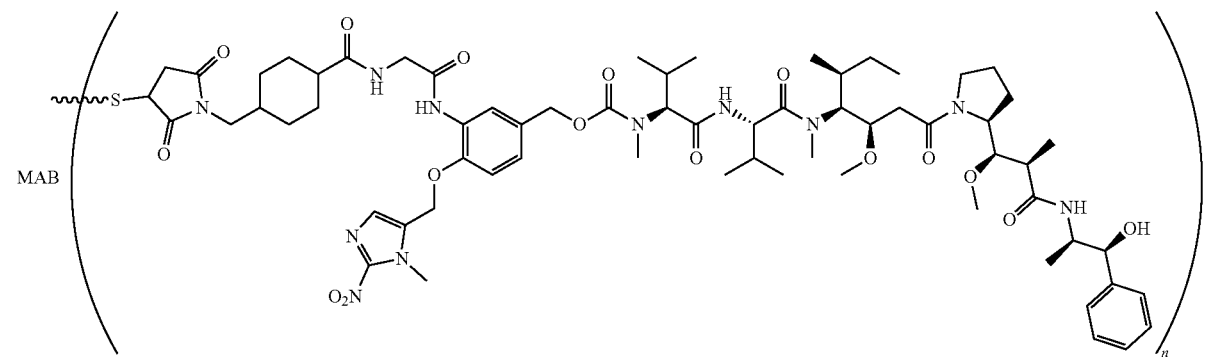
ADC-2

ADC-3
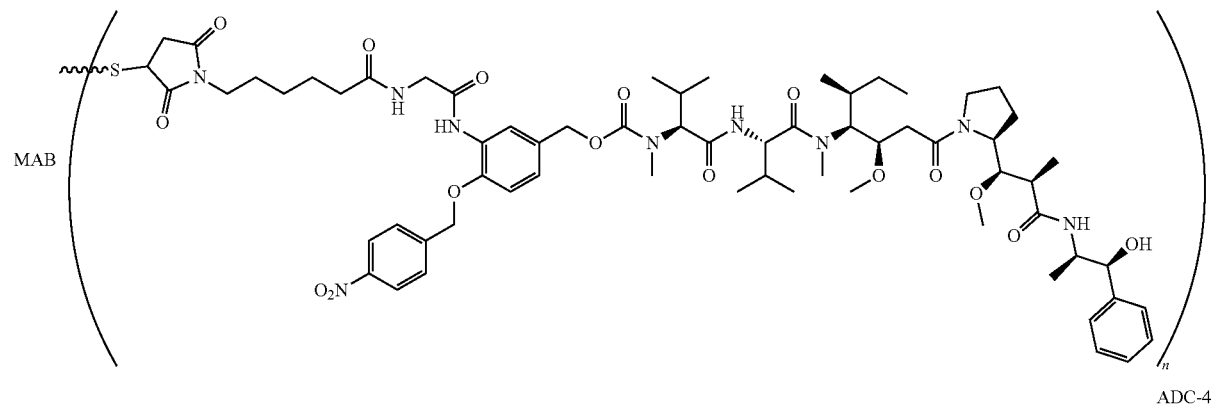
ADC-4
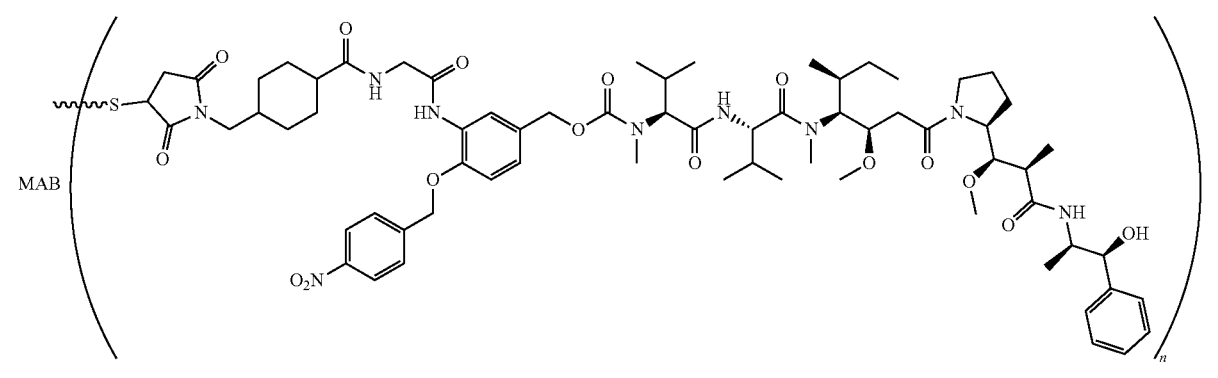
ADC-5
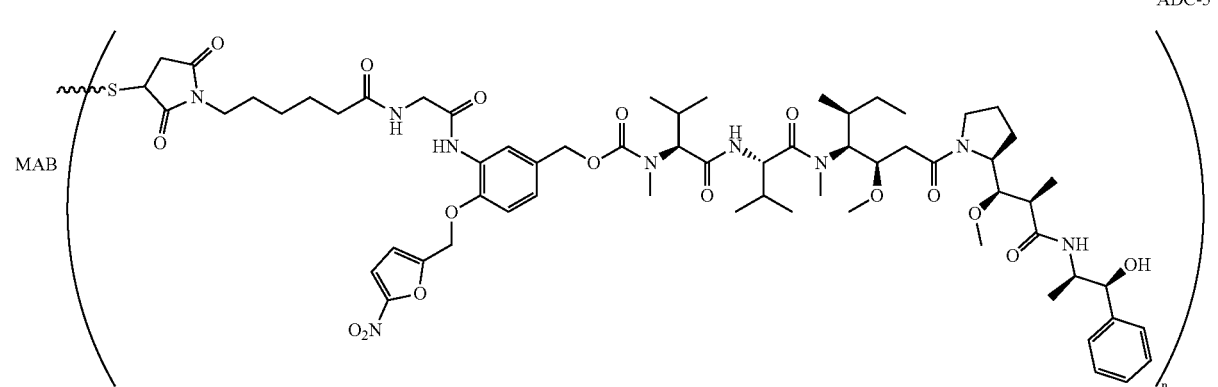
ADC-6
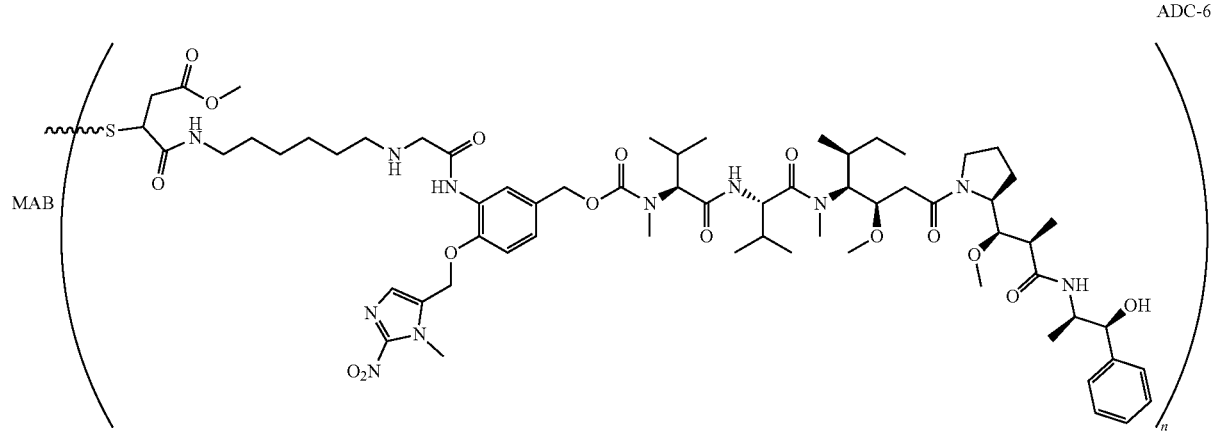

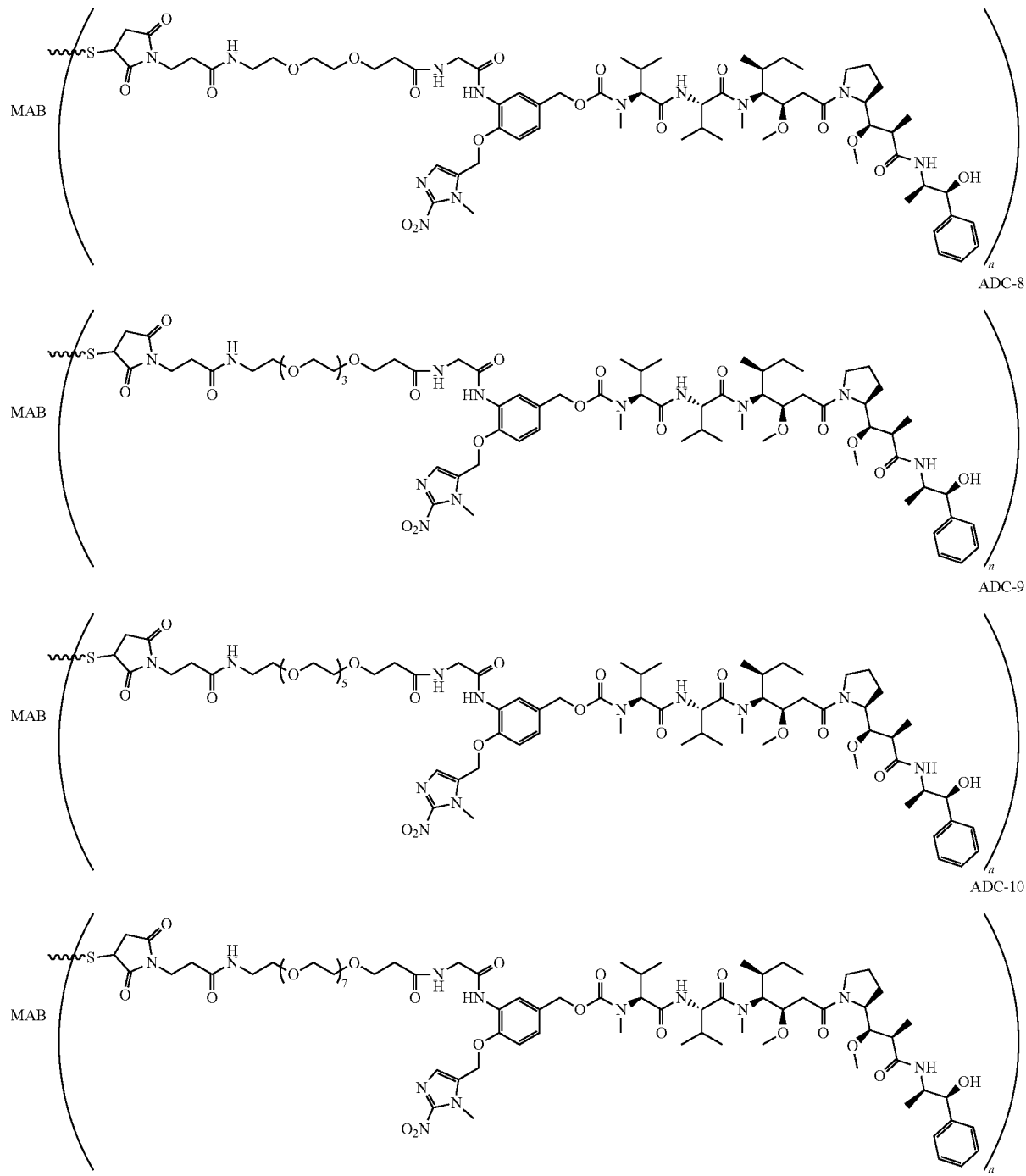

wherein, MAB is a monoclonal antibody, preferably an anti-HER2 humanized monoclonal antibody mil40, and n is defined as described in this application.

The present application also relates to a pharmaceutical composition, which comprises at least one compound represented by Formula III, Formula III' or Formula IIIa, or a salt thereof, and one or more pharmaceutically acceptable carriers or excipients.

The present application also relates to use of the compound represented by Formula III, Formula III' or Formula IIIa, or a salt thereof in manufacture of a medicament for diagnosing, preventing or treating a disease or condition or alleviating a severity of the disease or condition.

The present application also relates to a method for diagnosis, prevention or treatment of a disease or condition or alleviation of a severity of the disease or condition, the method comprising administering to a patient in need of such treatment a therapeutically effective amount of the compound represented by Formula III, Formula III' or Formula IIIa, or a salt thereof.

The present application also relates to the compound represented by Formula III, Formula III' or Formula IIIa, or a salt thereof, for use in the diagnosis, prevention or treatment of a disease or condition or the alleviation of a severity of the disease or condition.

This application also relates to a method for diagnosis, prevention or treatment of a disease or condition, comprising administering a therapeutically effective amount of the compound represented by Formula III, Formula III' or Formula IIIa or a salt thereof to a patient in need of such treatment.

In some embodiments, the disease or condition is selected from the group consisting of tumor, infectious disease, hematological disease, metabolic disease and an inflammation.

In some embodiments, the tumor is selected from the group consisting of cancer, lymphoma, lymphoid tumor, blastoma, sarcoma and leukemia.

In some embodiments, the cancer is selected from the group consisting of: breast cancer (for example, HER2-positive breast cancer); squamous cell carcinoma (for example, epithelial squamous cell carcinoma); lung cancer, including small cell lung cancer, non-small cell lung cancer, adenocarcinoma of lung and squamous cell carcinoma of lung; peritoneal cancer; liver cancer; gastric cancer; gastrointestinal cancer; pancreatic cancer; glioblastoma; cervical cancer; ovarian cancer; liver cancer; bladder cancer; urethral cancer; hepatocellular tumor; breast cancer; intestinal cancer; colon cancer; rectal cancer; colorectal cancer; endometrial cancer; uterine cancer; salivary gland cancer; kidney cancer; prostate cancer; vulvar cancer; thyroid cancer; liver cancer; anal cancer; penile cancer; melanoma; multiple myeloma and B-cell lymphoma; brain cancer; gallbladder cancer; esophageal cancer; cholangiocarcinoma; head and neck cancer and related metastatic tumor.

Definitions

As used herein, the term "antibody" is a common immunoglobulin, and a Y-shaped protein used by the immune system to recognize and neutralize a foreign object (e.g., bacteria and viruses). Antibody can specifically recognize the unique part of foreign target (called antigen), because each tip of the Y-shaped protein antibody contains a site that can specifically recognize the antigen. After the antibody binds to the specific antigen, it can mediate multiple related biological effects. Antibody is composed of two identical heavy chains and two identical light chains, and the chains are connected by disulfide bonds formed by sulfhydryl groups in cysteine residues. "Monoclonal antibody" is a single specific antibody in which all antibody molecules are composed of the same immune cells that are clones of the only parent cell, so all antibody molecules are the same.

As used herein, the term "cytotoxin" refers to a molecule that can be toxic to a cancer cell after being released in the cell. The toxins of particular concern in the present application include methyl-auristatin E (MMAE), auristatin, maytansine or its derivatives (e.g., maytansinoids, DM1, DM3, DM4), calicheamicin, duocarmycin, doxorubicin, camptothecin or PBD type cytotoxins.

As used herein, the term "linker" is a molecule with two reactive ends, one end of which can be coupled to an antibody and the other end is used to couple to an active compound, such as a cytotoxin. The antibody coupling end of the linker is usually a site that can be coupled through a sulfhydryl of cysteine or an amino of lysine in the antibody, and the toxin coupling end of the linker is usually a site that can be coupled through an active site such as sulfhydryl, amino, carboxyl or hydroxyl in the toxin molecule. When the term "linker" is used to describe a linker in the coupling form, since the linker has reacted with one or two of the antibody and cytotoxin to form covalent bond, it can no longer comprise one or two reactive sites at reactive ends (e.g., a leaving group for sulfhydryl reactive group, a leaving group for amino reactive group).

As used herein, the term "antibody-drug conjugate" or "ADC" is a product formed by an antibody molecule to which multiple molecules (usually 1 to 8) of cytotoxin are each coupled via linker, i.e., an antibody conjugated to one or more cytotoxins. The antibody is usually a monoclonal antibody showing a selectivity to a cancer-specific antigen.

As used herein, the term "about" can be understood as a value which is within +/−20%, +/−18%, +/−15%, +/−12%, +/−10%, +/−9%, +/−8%, +/−7%, +/−6%, +/−5%, +/−4%, +/−3%, +/−2%, +/−1%, +/−0.5%, +/−0.4%, +/−0.3%, +/−0.2%, +/−0.1% of the mentioned value. Unless obvious from the context, all numerical values provided herein are modified by the term "about".

The types of tumor diseases that the antibody-drug conjugates described herein focus on include, but are not limited to cancer, breast cancer, lymphoma, lymphoid tumor, blastoma, sarcoma, and leukemia. More specific examples of such cancer include squamous cell carcinoma (for example, epithelial squamous cell carcinoma); lung cancer, including small cell lung cancer, non-small cell lung cancer, adenocarcinoma of lung and squamous cell carcinoma of lung; peritoneal cancer; liver cancer; gastric cancer, including gastrointestinal cancer; pancreatic cancer; glioblastoma; cervical cancer; ovarian cancer; liver cancer; bladder cancer; urethral cancer; hepatocellular tumor; breast cancer, including, for example, HER2-positive breast cancer; colon cancer; rectal cancer; colorectal cancer; endometrial or uterine cancer; salivary gland cancer; kidney cancer; prostate cancer; vulvar cancer; thyroid cancer; liver cancer; anal cancer; penile cancer; melanoma; myeloma and B-cell lymphoma; brain cancer; head and neck cancer and related metastatic tumor.

As used herein, the term "salt" refers to a salt that retains the biological effectiveness and properties of a compound, and regarding use in medicine, it is not biologically or otherwise undesirable. In many cases, the compound disclosed herein is capable of forming an acid and/or base salt through the presence of amino and/or carboxyl or a similar group. The pharmaceutically acceptable acid addition salt can be formed with an inorganic acid or organic acid. The inorganic acid that can be derivatized to form a salt includes, for example, hydrochloric acid, hydrobromic acid, sulfuric acid, nitric acid, phosphoric acid, etc. The organic acid that can be derivatized to form a salt includes, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, etc. The pharmaceutically acceptable base addition salt can be formed with an inorganic base or organic base. The inorganic base that can be derivatized to form a salt includes, for example, sodium, potassium, lithium, ammonium, calcium, magnesium, iron, zinc, copper, manganese, aluminum, etc.; particularly preferred is a salt of ammonium, potassium, sodium, calcium and magnesium. The organic base that can be derivatized to form a salt includes, for example, primary, secondary and tertiary amines, substituted amines, including naturally-occurring substituted amines, cyclic amines, basic ion exchange resins, etc., specifically including, for example, isopropylamine, trimethylamine, diethylamine, triethylamine, tripropylamine and ethanolamine. Many such salts are known in the art, as described in WO87/05297, Johnston et al., published on Sep. 11, 1987 (which is incorporated herein by reference in its entirety).

As used herein, the term "aryl" refers to an unsaturated aromatic carbocyclic ring group having 5 to 14 carbon atoms and one monocyclic ring or two or more fused rings with a conjugated 7-electron system. The "aryl" preferably has 5 to 10, 5 to 8, or 5 to 6 carbon atoms. Typical examples of "aryl" include, but are not limited to, phenyl, naphthyl, anthryl and the like.

As used herein, the term "heteroaryl" refers to an aryl as defined herein in which at least one ring member is a heteroatom selected from the group consisting of nitrogen, oxygen and sulfur. The "heteroaryl" preferably has 5 to 10, 5 to 8 or 5 to 6 ring members. Typical examples of "heteroaryl" include, but are not limited to, furyl, imidazolyl, thienyl, triazolyl, indolyl, tetrazolyl, pyridyl, pteridyl, pyrimidyl, triazolyl, quinolyl, isoquinolyl, quinazolinyl, quinoxalinyl and the like.

As used herein, the term "aryl-fused-heterocyclyl" refers to a cyclic group having two or more fused rings, in which two or more carbon atoms are shared by two adjacent rings, and at least one ring is aryl as defined herein, and at least one ring is heterocyclyl.

As used herein, the term "heteroaryl-fused-heterocyclyl" refers to a cyclic group having two or more fused rings, in which two or more carbon atoms are shared by two adjacent rings, and at least one ring is heteroaryl as defined herein, and at least one ring is heterocyclyl.

As used herein, the term "heterocyclyl" refers to a saturated or partially unsaturated cyclic hydrocarbyl having 3 to 12 ring members and monocyclic or bicyclic or multiple condensed (including condensed, bridged and spiro) rings, in which at least one ring member is a heteroatom selected from the group consisting of nitrogen, oxygen and sulfur. The "heterocyclyl" preferably has 3 to 10, 3 to 8, 5 to 8, 3 to 6 or 5 to 6 ring members. Typical examples of "heterocyclyl" include, but are not limited to, tetrahydrofuryl, tetrahydrothienyl, pyrrolidinyl, piperazinyl, thiazinyl, piperidinyl, morpholinyl and the like.

Acronyms/Abbreviations
  ADC: antibody-drug conjugate;
  DAR (Drug to antibody ratio): molar ratio of antibody to drug;
  DCM: dichloromethane;
  DIPEA (N,N-Diisopropylethylamine): diisopropylethylamine;
  NHS/SuOH: N-hydroxysuccinimide;
  MMAE: monomethyl auristatin E;
  TFA: trifluoroacetic acid;
  THF: tetrahydrofuran;
  DMF: N,N-dimethylformamide;
  DMSO: dimethyl sulphoxide;
  HER2: human epidermal growth factor receptor 2;
  MAB: monoclonal antibody
  MMAE: monomethyl auristatin E;
  NAC: N-acetyl-L-cysteine;
  TFAA: trifluoroacetic anhydride;
  EA: ethyl acetate;
  EDCI: 1-(3-dimethylaminopropyl)-3-ethylcarbodiimide hydrochloride;
  HOBt: 1-hydroxybenzotriazole;
  DCC: dicyclohexylcarbodiimide;
  EDCI: 1-(3-dimethylaminopropyl)-3-ethylcarbodiimide hydrochloride;

When the names of the compounds used herein are inconsistent with the chemical structural formula, the chemical structural formula shall prevail.

The pharmaceutical composition as described herein comprises the compound represented by Formula III, Formula III' or Formula IIIa of the present application, or a salt or solvate thereof, and a conventional pharmaceutical carrier or excipient. The pharmaceutical composition can be administered orally or parenterally, such as intravenous injection, intraperitoneal injection, intramuscular injection, subcutaneous injection, and the like.

As used herein, the term "effective amount" refers to an amount sufficient to achieve a desired therapeutic effect, for example, an amount that achieves alleviation of symptoms associated with the disease to be treated.

In addition, it should be pointed out that the dosage and method of using the compound of the present application depend on many factors, including age, weight, gender, natural health status and nutritional status of patient, active strength of compound, time of administration, metabolic rate, severity of disease, and subjective judgment of physician in diagnosis and treatment. The preferred dosage is between 0.01 to 100 mg/kg body weight/day.

The linker provided in the present application contains an arylnitro segment, which has good enzymatic cleavage performance. The antibody-drug conjugate (ADC) containing the linker provided in the present application has good structural stability, ideal enzymatic drug-release performance, hypoxic dependence, and relatively ideal in vivo and in vitro drug efficacy and safety.

In some specific embodiments, the synthetic route of the ADC described in the present application is as follows:

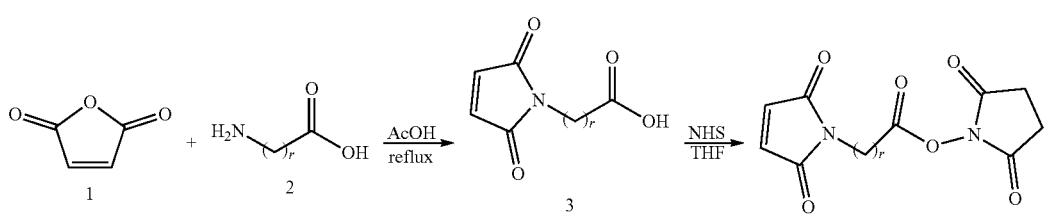

-continued
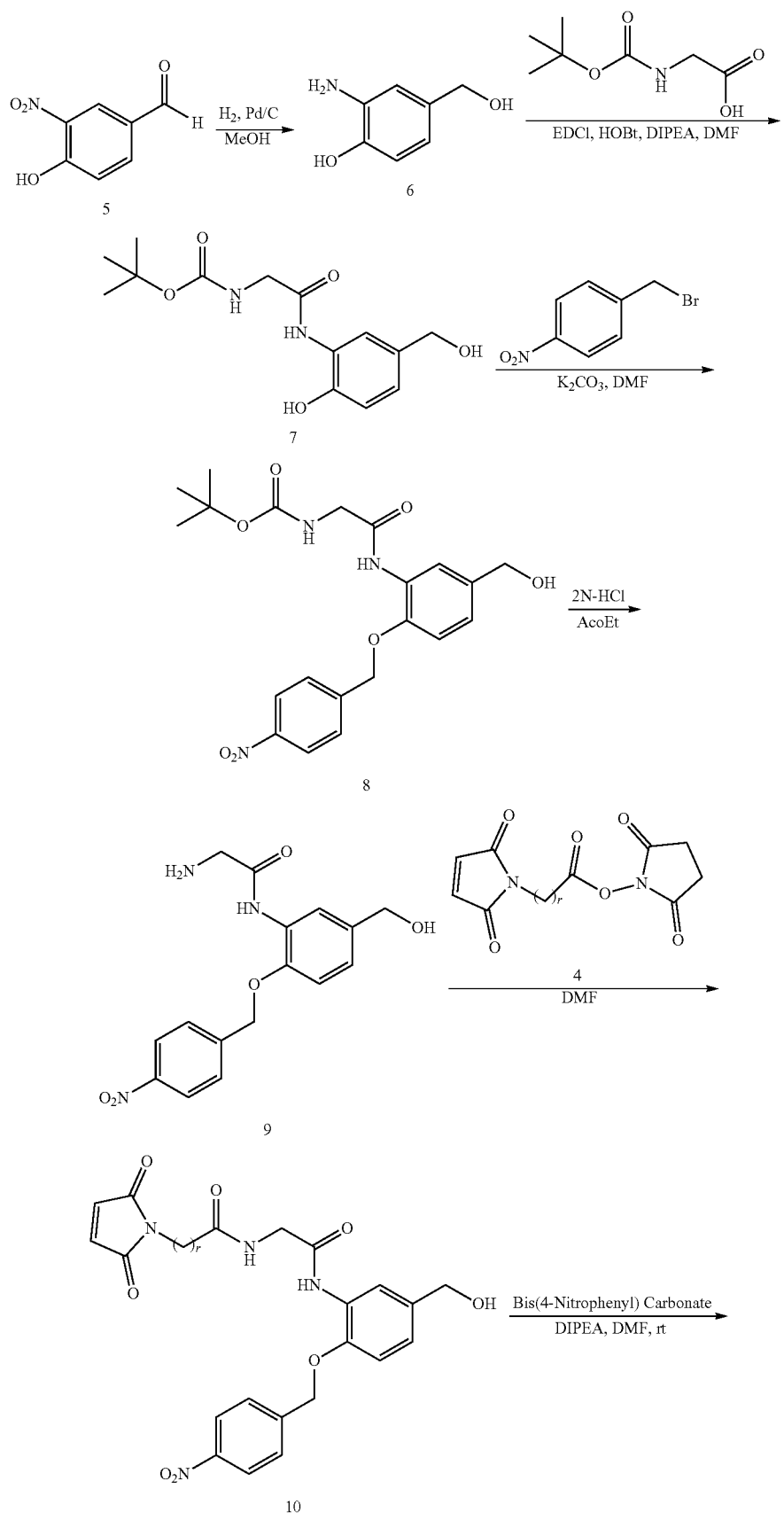

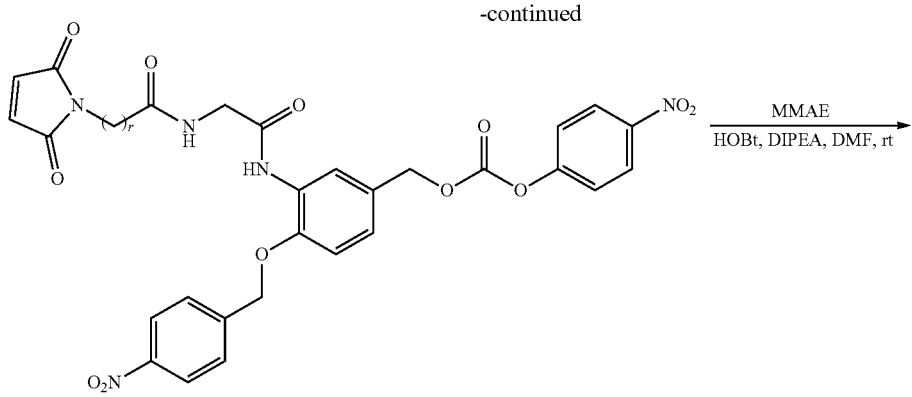

11

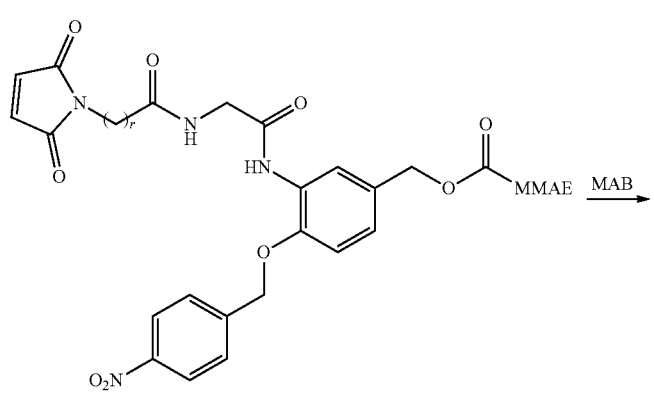

12

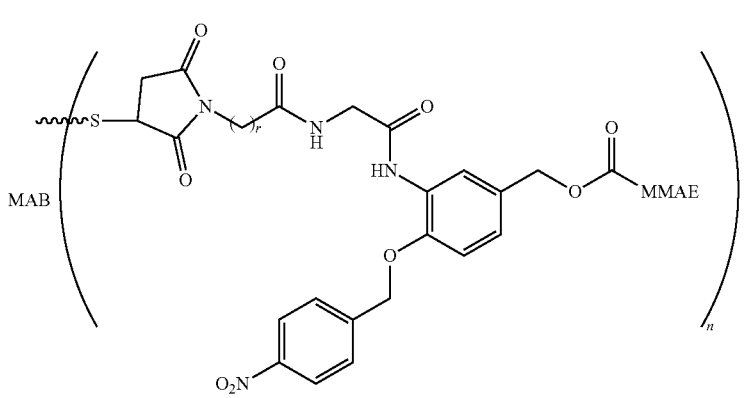

13 wherein: r and n are defined as described in the present application, by using maleic anhydride (1) and a corresponding amino acid (2) as starting materials, a compound (3) is prepared by acylation and dehydration under heating condition, and further condensed with N-hydroxysuccinimide (NHS) under the action of trifluoroacetic anhydride to prepare a maleic amide-type linker compound (4); 4-hydroxy-3-nitrobenzaldehyde (5) is used as starting material, and subjected to reduction reaction to obtain a compound (6), the compound (6) is acylated with Boc-glycine to obtain a compound (7), the compound (7) reacts with p-nitrobenzyl bromide to form an ether under alkaline condition to obtain a compound (8), the compound (8) is subjected to the removal of Boc protecting group under acidic condition to obtain a compound (9), the compound (9) reacts with a linker (4) to obtain a compound (10), and the compound (10) reacts with bis(p-nitrophenyl) carbonate to obtain a linker (11); the linker (11) is connected with MMAE to obtain a corresponding ADC load (12), which is further coupled to an antibody to obtain a final ADC product (13).

In some specific embodiments, another synthetic route of the ADC described in the present application is as follows:

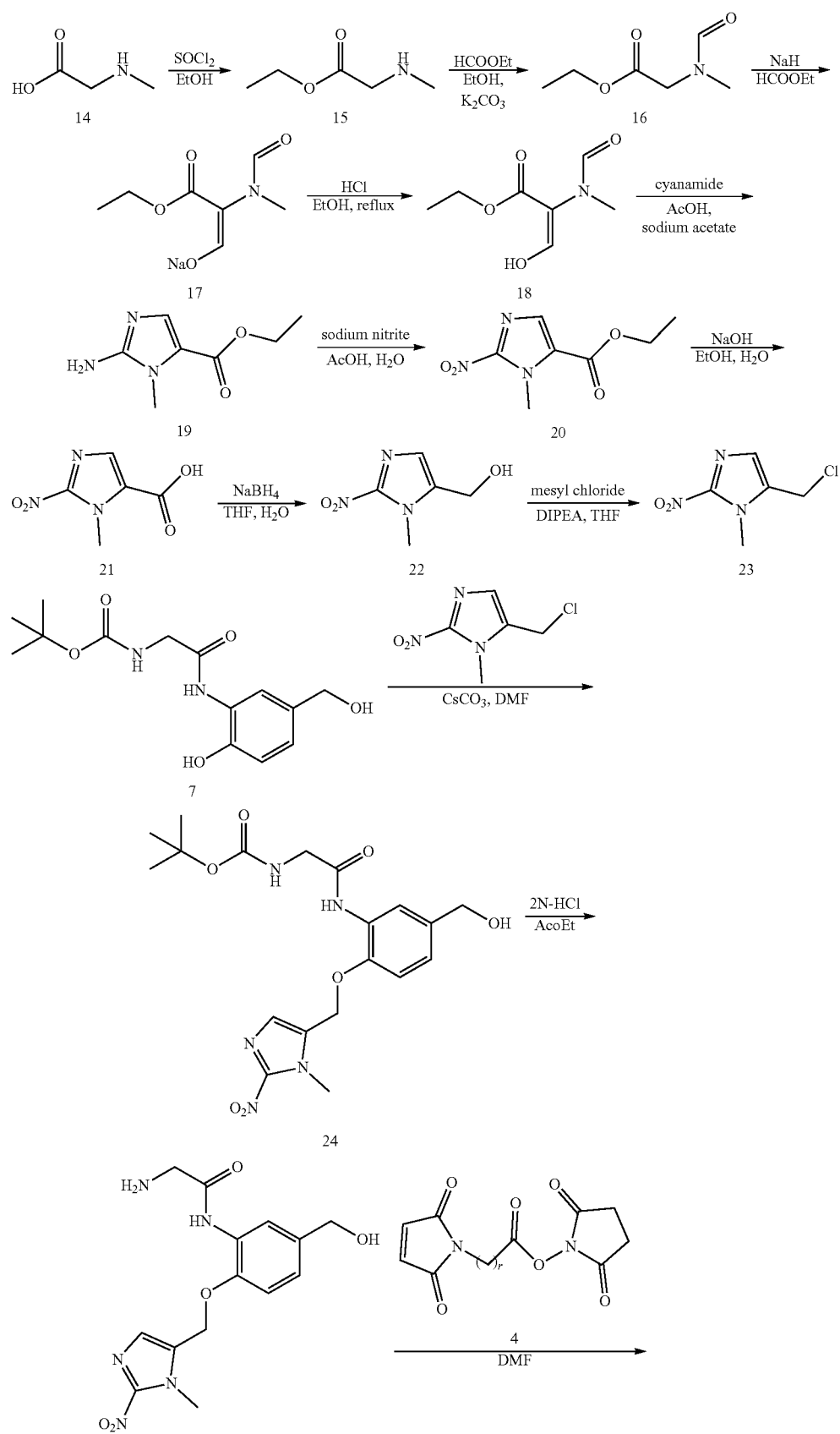

-continued
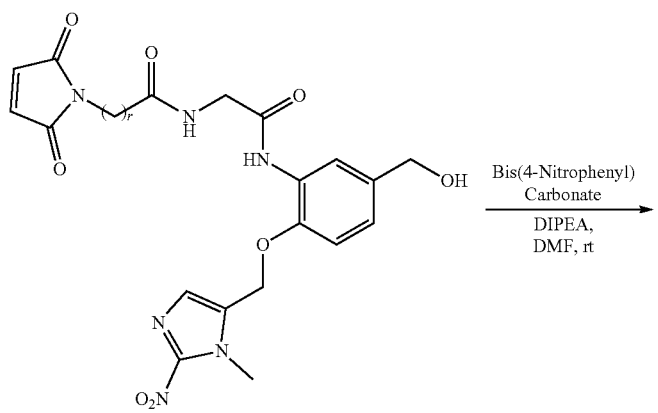
26
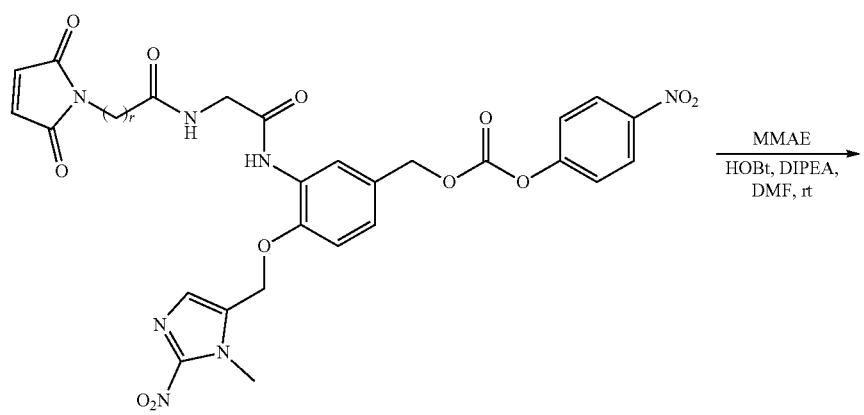
27
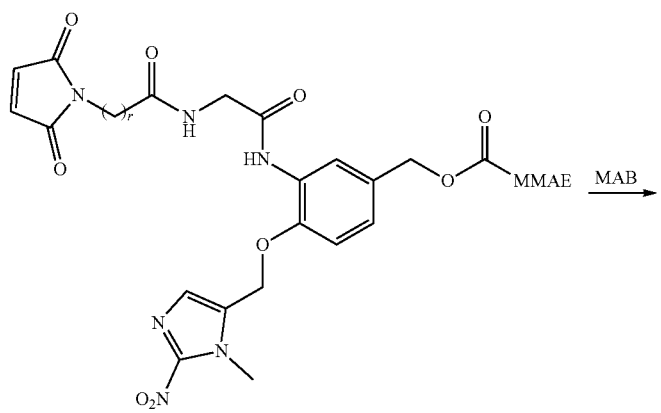
28

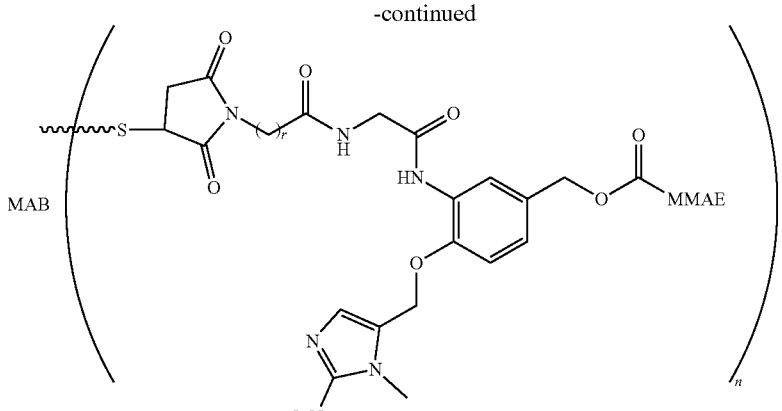

29 wherein: r and n are defined as described in the present application, by using sarcosine (14) as starting material, a compound (15) is prepared by esterification reaction under heating condition, and then compound (15) reacts with ethyl formate to obtain an acylated compound (16), the compound (16) further reacts with ethyl formate under the action of sodium hydride to produce a compound (17), the compound (17) reacts with HCl under heating condition to obtain an intermediate compound (18), the compound (18) reacts with cyanamide to obtain a cyclization product (19), the product (19) reacts with NaNO₂ under acidic condition to obtain a nitration product (20), the product (20) is subjected to hydrolysis reaction to obtain a compound (21), the compound (21) is subjected to a reduction reaction to obtain an intermediate compound (22), and the compound (22) reacts with mesyl chloride to obtain a chlorination product (23). The intermediate compound (7) reacts with the chlorination product (23) to form an ether under alkaline condition to obtain an intermediate (24), the intermediate (24) is subjected to the removal of Boc protecting group under acidic condition to obtain an intermediate (25), the intermediate (25) reacts with a linker (4) to obtain an intermediate compound (26), the compound (26) reacts with bis(p-nitrophenyl) carbonate to obtain a linker (27); the linker (27) is connected with MMAE to obtain a corresponding ADC load (28), which is further coupled to an antibody to obtain a final ADC product (29).

In some specific embodiments, another synthetic route of the ADC described in the present application is as follows:

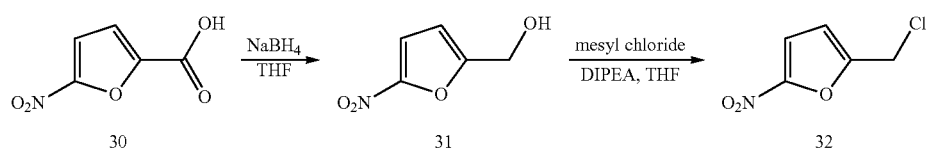

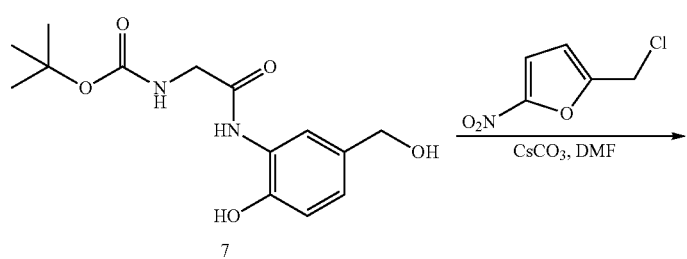

-continued
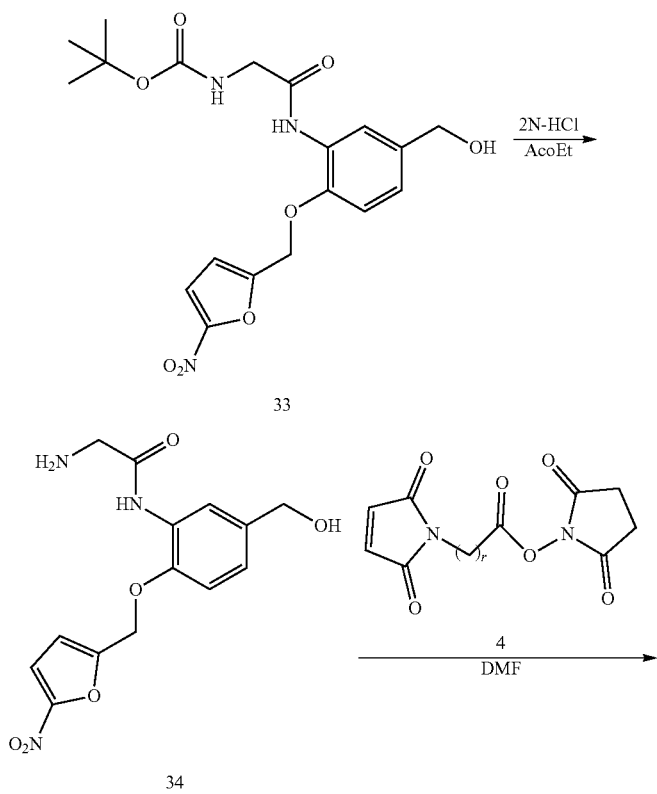
33
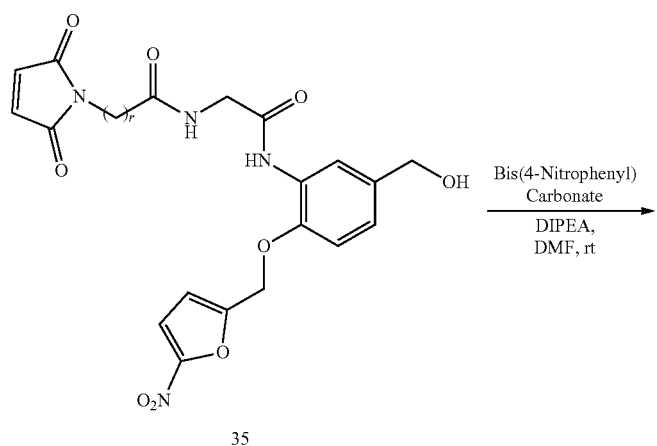
34
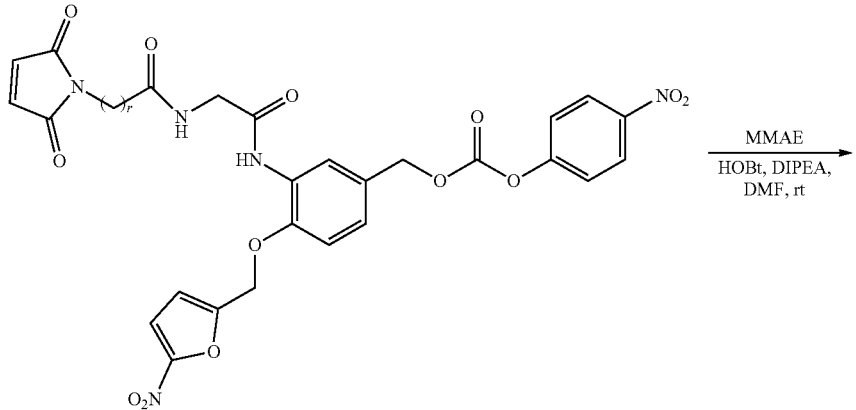
35
36

-continued

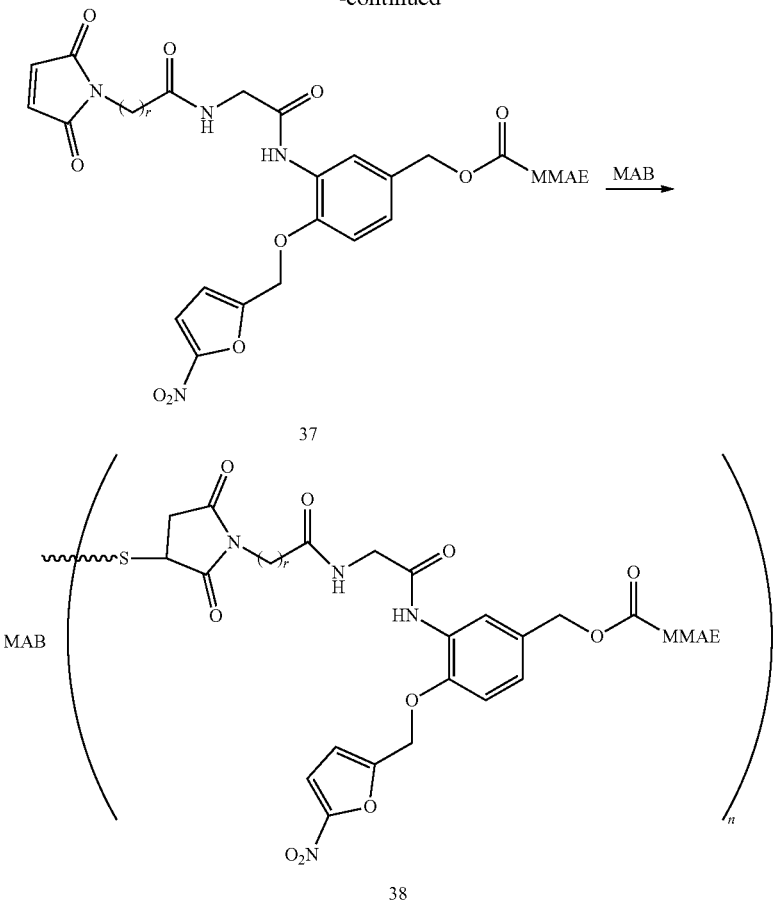

wherein: r and n are defined as described in the present application, the reaction process is similar to the synthetic route 3: 4-nitro-1-furancarboxylic acid (30) is reduced by sodium borohydride to obtain a reduction product 4-nitro-1-furanmethanol (31), is the 4-nitro-1-furanmethanol (31) reacts with mesyl chloride to obtain a chlorination product (32). The intermediate compound (7) reacts with the chlorination product (32) to form an ether under alkaline condition to obtain an intermediate (33), the intermediate (33) is subjected to the removal of Boc protecting group under acidic condition to obtain an intermediate (34), the intermediate (34) reacts with a linker (4) to obtain an intermediate compound (35), and the compound (35) is reacted with bis(p-nitrophenyl) carbonate to obtain a linker (36); the linker (36) is connected with MMAE to obtain a corresponding ADC load (37), which is further coupled to an antibody to obtain a final ADC product (38).

SPECIFIC MODELS FOR CARRYING OUT THE DISCLOSURE

Figure 1:
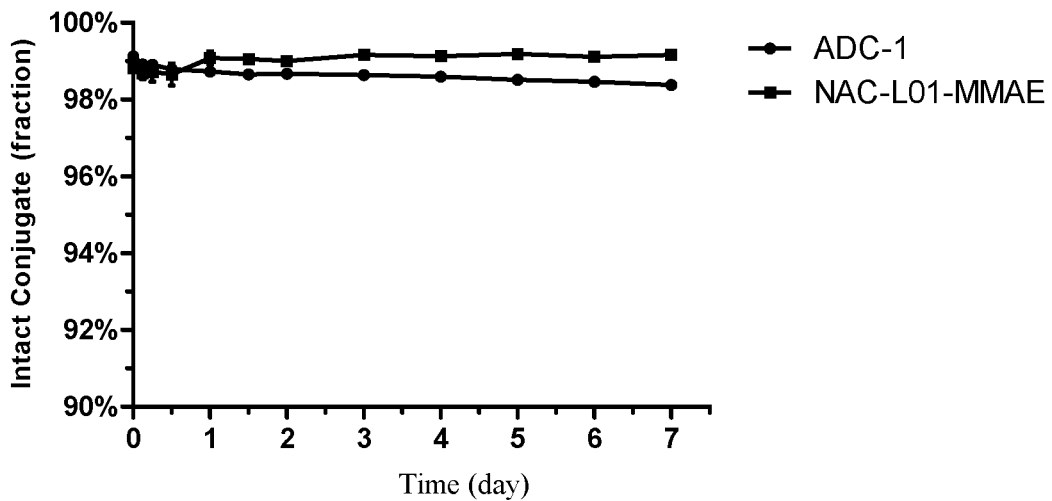
FIG. 1 shows the stability evaluation results of ADC-1 and NAC-L01-MMEA in plasma.

The embodiments of the present application will be described in detail below in combination with examples, but those skilled in the art will understand that the following examples are only used to illustrate the present application and should not be regarded as limiting the scope of the present application. If specific conditions are not indicated in the examples, they shall be carried out in accordance with conventional conditions or conditions recommended by the manufacturers. The reagents or instruments used without giving manufacturers are all conventional products that were commercially available.

Example 1: Preparation of ADC-1

1) Preparation of 6-(2,5-dioxo-2,5-dihydro-1H-pyrrol-1-yl)hexanoic acid (MCOH)

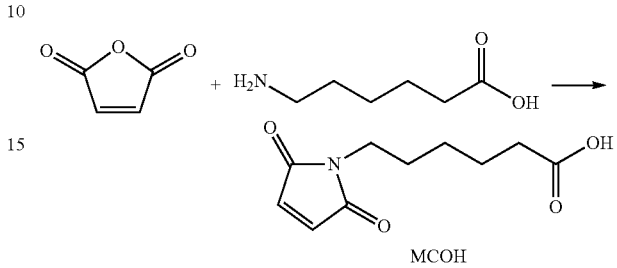

Maleic anhydride (4.86 g, 49.55 mmol) was added into a 500 mL three-necked flask, dissolved with acetic acid (150 mL), after the dissolution was completed, 6-aminohexanoic acid (5.0 g, 38.11 mmol) was added, the resulting reaction solution was heated to 120° C. and refluxed for 6 hours. After the reaction was completed, the reaction solution was cooled to room temperature, poured into distilled water, and extracted with an appropriate amount of ethyl acetate for several times. The organic phases were combined, washed with saturated NaCl solution, dried over anhydrous $Na_2SO_4$ overnight, concentrated, and purified by chromatography to obtain a white powdery solid (5.92 g, 74% yield). $^1$H-NMR (400 MHz, DMSO-d6) δ 11.98 (br, 1H), 7.01 (s, 2H), 3.39 (t, J=7.3 Hz, 2H), 2.17 (t, J=7.3 Hz, 2H), 1.51-1.44 (m, 2H), 1.24-1.17 (m, 2H). MS (ESI) m/z: 210.0 [M−H]$^-$.

2) Preparation of (2,5-dioxo-2,5-dihydro-1H-pyrrol-1-yl)hexanoic acid 2,5-dioxopyrrolidin-1-yl ester (MCOSu)

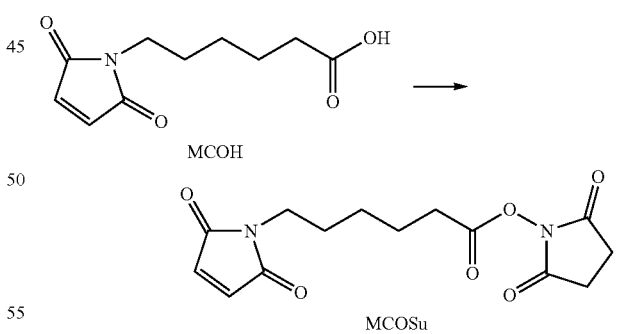

MCOH (4.66 g, 22 mmol) was added into a 250 mL three-necked flask, dissolved with THF (100 mL), after the dissolution was completed, NHS (5.08 g, 44 mmol) and 2,4,6-trimethylpyridine (10.65 g, 88 mmol) were added in sequence. After the addition was completed, the three-necked flask was transferred to a low temperature reaction tank at −5° C. and the resulting mixture was cooled down at stirring; trifluoroacetic anhydride (TFAA, 9.24 g, 44 mmol) was slowly added dropwise. After the addition was completed, the three-necked flask was transferred to room temperature and the reaction was continued for 1 hour. The solvent was removed by evaporation under reduced pressure, and the residue obtained was re-dissolved with EA (200 mL), and washed with 1N hydrochloric acid, saturated NaHCO$_3$ and saturated NaCl for 3 times. The concentrated crude product was further purified by column chromatography to obtain a viscous oil, which was placed at a low temperature and became a white lumpy solid (5.03 g, 69% yield). $^1$H-NMR (400 MHz, DMSO-d6) δ 6.69 (s, 2H), 3.53 (t, J=7.3 Hz, 2H), 2.84 (s, J=3.6 Hz, 2H), 2.61 (t, J=7.3 Hz, 2H), 1.78 (m, 2H), 1.63 (m, 2H), 1.45-1.37 (m, 2H). MS (ESI) m/z: 309.4 [M+H]$^+$; 331.2 [M+Na]$^+$.

3) Preparation of ethyl methylaminoacetate hydrochloride

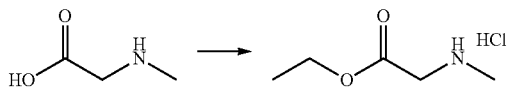

SOCl$_2$ (107 mL, 1.48 mol) was slowly added dropwise to a 500 mL eggplant-shaped flask containing 0° C. ethanol solution, sarcosine (120 g, 1.35 mol) was added in batches under stirring, continuously stirred for 30 minutes, then slowly heated to reflux, and the reaction was continued for 2 hours. The reaction solution was cooled to room temperature, then the solvent was removed by evaporation under reduced pressure to obtain a white crystalline solid, which showed basically no raw material remained in TLC detection (close to a quantitative reaction) and was directed used in the next step without further purification (Procedure of Methyl sarcosine hydrochloride; Meng F, ect. Mol Cancer Ther, 2012, 11(3): 740-751).

4) Preparation of ethyl (formyl-methyl-amino)acetate

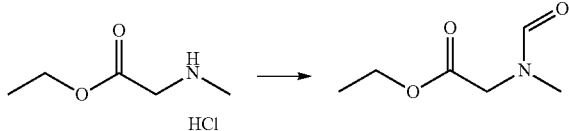

Ethyl methylaminoacetate hydrochloride (188 g, 1.35 mol) was added into a 1000 mL three-necked flask, and dissolved by adding ethanol (250 mL), and then anhydrous K$_2$CO$_3$ (186 g, 1.35 mol) and ethyl formate (163 mL, 2.0 mol) were respectively added to the reaction solution. The resulting reaction solution was heated and refluxed for 3 hours, then filtered to remove insoluble salts, the filtrate was concentrated to obtain a crude target product as a pale yellow oil, which was not further purified and directly used in the next reaction (Procedure of Methyl 2-(N-methylformamido)acetate; Meng F, ect. Mol Cancer Ther, 2012, 11(3): 740-751).

5) Preparation of (E)-2-carbethoxy-2-(formyl-methyl-amino)vinyl alcohol sodium salt

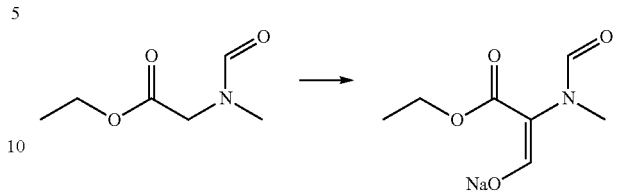

Ethyl (formyl-methyl-amino)acetate (31.4 g, 0.24 mol) was added to a 500 mL three-necked flask, and dissolved with ethyl formate (100 mL), the three-necked flask was placed in a low temperature reaction tank to be cooled to 0° C., then NaH (11.5 g, 0.36 mol) was added in batches. The reaction was carried out for 1 hour, then the reaction solution was slowly heated to room temperature, and then the reaction was continued under stirring overnight. The reaction solution was concentrated, a yellow sticky substance like chewing gum was obtained, which was not further purified and directly used in the next step of reaction (Procedure of Sodium 3-methoxy-2-(N-methylformamido)-3-oxoprop-1-en-1-olate; Meng F, ect. Mol Cancer Ther, 2012, 11 (3): 740-751).

6) Preparation of ethyl (E)-2-(formyl-methyl-amino)-3-hydroxyacrylate

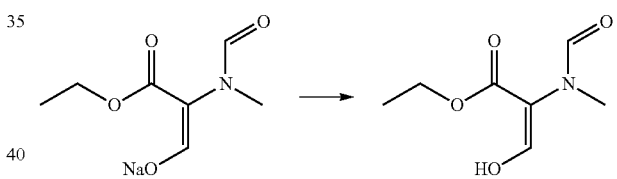

(E)-2-carbethoxy-2-(formyl-methyl-amino)vinyl alcohol sodium salt (43.3 g, 0.24 mol) was added into a 500 mL three-necked flask and dissolved with ethanol (150 mL), concentrated hydrochloric acid (66 mL) was added, and the resulting reaction solution was heated and refluxed for 2 hours. The reaction solution was filtered to remove insoluble substance, and the filtrate was concentrated to obtain about 40 g of a crude product as a black oil, which was not further purified and directly used in the next reaction (Procedure of Ethyl 3-hydroxy-2-(methylamino)acrylate; Meng F, ect. Mol Cancer Ther, 2012, 11(3): 740-751).

7) Preparation of ethyl 2-amino-3-methyl-3H-imidazole-4-carboxylate

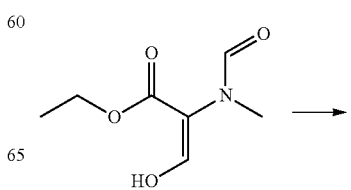

-continued

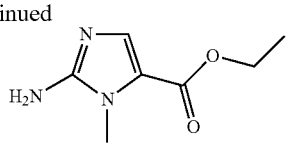

Ethyl (E)-2-(formyl-methyl-amino)-3-hydroxyacrylate (65.3 g, 0.45 mol) was added to a 500 mL three-necked flask and dissolved with 10% acetic acid (250 mL), and sodium acetate (111 g, 1.35 mol) and cyanamide (37.8 g, 0.9 mol) were added. The resulting reaction solution was heated and refluxed for 2 hours. The reaction solution was concentrated under reduced pressure to remove acetic acid, and NaHCO$_3$ solid was added to the resulting filtrate to adjust the pH to about 8. The aqueous phase was extracted with EA for several times, the organic phases were combined and washed with saturated NaCl for 3 times, dried over Na$_2$SO$_4$. The solvent was removed by evaporation under reduced pressure, and the obtained crude product was purified by column chromatography to obtain an orange solid powder (15 g, the total yield of the above reactions was 19%). $^1$H-NMR (400 MHz, DMSO-d6) δ 7.28 (s, 1H), 6.20 (s, 1H), 4.15 (q, J=7.0 Hz, 2H), 3.52 (s, 3H), 1.23 (t, J=7.0 Hz, 3H). MS (EI) m/z: 170.3 [M+H]$^+$; 192.1 [M+Na]$^+$.

8) Preparation of ethyl 3-methyl-2-nitro-3H-imidazole-4-carboxylate

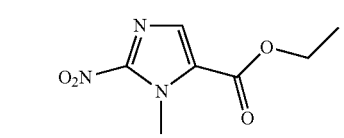

Sodium nitrite (42 g, 0.6 mol) was added to a 1000 mL three-necked flask, dissolved with distilled water (250 mL) and cooled to −5° C., then ethyl 2-amino-3-methyl-3H-imidazole-4-carboxylate (8.5 g, 50 mol) in acetic acid solution (70 mL) was added dropwise, after the addition was completed, the resulting reaction solution was slowly heated to room temperature and the reaction was continued for 16 hours. The reaction solution was extracted with DCM for several times, then the organic phases were combined, washed with saturated NaCl for 3 times, and dried over Na$_2$SO$_4$. The solvent was removed by evaporation under reduced pressure, and the obtained crude product was purified by column chromatography to obtain a pale yellow solid powder (6.25 g, 63% yield). $^1$H-NMR (400 MHz, CDCl$_3$) δ 7.75 (s, 1H), 4.40 (q, J=7.0 Hz, 2H), 4.30 (s, 3H), 1.41 (t, J=7.0 Hz, 3H). MS (ESI) m/z: 200.2 [M+H]$^+$; 222.1 [M+Na]$^+$.

9) Preparation of 3-methyl-2-nitro-3H-imidazole-4-carboxylic acid

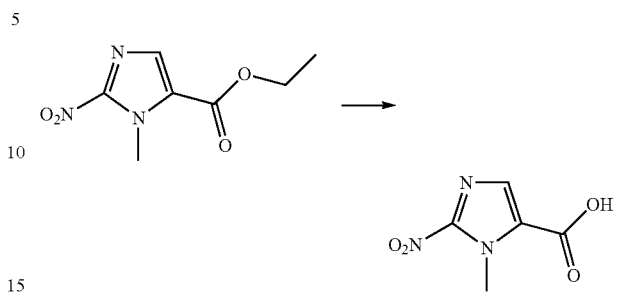

Ethyl 3-methyl-2-nitro-3H-imidazole-4-carboxylate (6.6 g, 33 mol) was added into a 250 mL three-necked flask, dissolved with an aqueous ethanol solution (120 mL), and NaOH (4 g, 100 mmol) was added. The reaction was carried out under stirring at room temperature for 16 hours, then concentrated HCl was added to adjust the pH to about 1. The reaction solution was extracted with EA for several times, the organic phases were combined, washed with saturated NaCl for 3 times, and dried over Na$_2$SO$_4$. The solvent was removed by evaporation under reduced pressure to obtain a pale yellow solid powder (5.56 g, 97% yield). $^1$H-NMR (400 MHz, DMSO-d6) δ 13.83 (br, 1H), 7.74 (s, 1H), 4.18 (s, 1H). MS (ESI) m/z: 172.2 [M+H]$^+$; 169.9 [M−H]$^−$.

10) Preparation of (3-methyl-2-nitro-3H-imidazol-4-yl)methanol

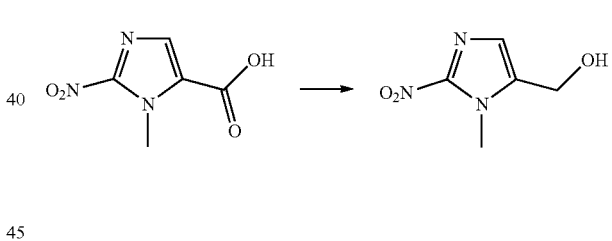

3-Methyl-2-nitro-3H-imidazole-4-carboxylic acid (1.0 g, 5.8 mol) was added into a 250 mL three-necked flask, and dissolved with anhydrous THF (100 mL), then triethylamine (1.3 mL, 9.3 mmol) was added, and then the three-necked flask was placed in a low temperature reaction tank to be cooled to −40° C., isobutyl chloroformate (1.2 mL, 9.3 mmol) was slowly added dropwise, after the addition was completed, the reaction solution was warmed to room temperature, and the reaction was continued under stirring for 1 hour. NaBH$_4$ (4 eq) and THF-H$_2$O (3:1, 5 mL) were added to the reaction solution. After the reaction was completed, the reaction solution was filtered and concentrated, extracted with DCM for several times, the organic phases were combined, washed with saturated NaCl for 3 times, and dried over Na$_2$SO$_4$. The solvent was removed by evaporation under reduced pressure, and the obtained crude product was purified by column chromatography to obtain a pale yellow solid powder (0.76 g, 69% yield). $^1$H-NMR (400 MHz, DMSO-d6) δ 7.12 (s, 1H), 5.51 (t, J=5.4 Hz, 1H), 4.54 (d, J=5.4 Hz, 2H), 3.92 (s, 3H). MS (ESI) m/z: 158.4 [M+H]$^+$.

11) Preparation of 5-(chloromethyl)-1-methyl-2-nitro-1H-imidazole

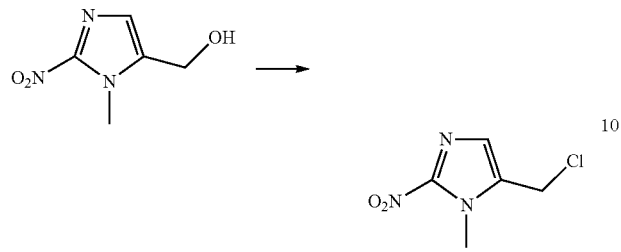

(3-Methyl-2-nitro-3H-imidazol-4-yl)methanol (0.5 g, 3.2 mol) was added into a 50 mL eggplant-shaped flask, and dissolved with anhydrous THF (10 mL), then DIPEA (0.67 mL, 3.8 mmol) and mesyl chloride (0.30 mL, 3.8 mmol) were added. The reaction was carried out at room temperature for 1 hour. After the reaction was completed, the reaction solution was diluted with EA and washed twice with 1 mol/L hydrochloric acid. The organic phase was dried with anhydrous $Na_2SO_4$. The solvent was removed by evaporation under reduced pressure to obtain a yellow solid powder (0.45 g, 81% yield). $^1$H-NMR (400 MHz, DMSO-d6) δ 7.30 (s, 1H), 5.03 (s, 2H), 3.94 (s, 3H). MS (ESI) m/z: 176.2 $[M+H]^+$.

12) Preparation of 2-amino-4-(hydroxymethyl)phenol

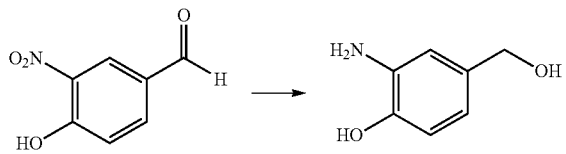 [SMILES: O=Cc1ccc(O)c([N+](=O)[O-])c1 ; Nc1cc(CO)ccc1O]

4-Hydroxy-3-nitrobenzaldehyde (0.55 g, 3.3 mmol) was added into a 100 mL three-necked flask, and dissolved with methanol (10 mL), then a catalytic amount of Pd/C was added; the air in the reaction solution was replaced with hydrogen gas, the reaction was carried out under stirring at room temperature for 4 hours in hydrogen environment. After the reaction was completed, the insoluble substance was removed by filtration, and the obtained filtrate was concentrated and purified by column chromatography to obtain a brown solid powder (0.38 g, 84% yield). $^1$H-NMR (400 MHz, DMSO-d6) δ 8.83 (s, 1H), 6.56-6.65 (m, 2H), 6.32 (dd, 1H), 4.82 (t, J=5.7 Hz, 1H), 4.47 (br, 2H), 4.25 (d, J=5.7 Hz, 2H). MS (ESI) m/z: 140.2 $[M+H]^+$; 138.0 $[M-H]^-$.

13) Preparation of tert-butyl [(2-hydroxy-5-hydroxymethyl-phenylcarbamoyl)-methyl]-carbamate

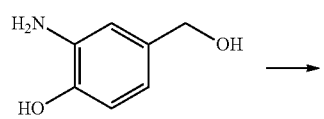

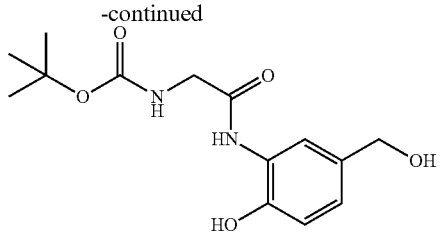

N-Boc-glycine (0.40 g, 2.28 mmol) was added into a 50 mL eggplant-shaped flask, and dissolved with DMF (15 mL), EDCI (0.53 g, 2.74 mmol), HOBt (0.37 g, 2.74 mmol) and DIPEA (0.44 g, 3.42 mmol) were added in sequence. The reaction was carried out under stirring at room temperature for 90 minutes, then 2-amino-4-(hydroxymethyl)phenol (0.32 g, 2.28 mmol) was added, and then the reaction was carried out under stirring overnight at room temperature. After the reaction was completed, the reaction solution was poured into 10 times the volume of water, and extracted with EA for several times, the organic phases were combined and washed with saturated NaCl for 3 times, and dried over $Na_2SO_4$. The solvent was removed by evaporation under reduced pressure, and the obtained crude product was purified by column chromatography to obtain an orange solid powder (0.57 g, 84% yield). $^1$H-NMR (400 MHz, DMSO-d6) δ 9.81 (s, 1H), 8.98 (s, 1H), 7.92 (s, 1H), 7.32 (s, 1H), 6.85 (d, J=8.2 Hz, 1H), 6.79 (d, J=8.2 Hz, 1H), 5.00 (br, 1H), 4.35 (s, 2H), 3.72 (s, 2H), 1.40 (s, 9H). MS (ESI) m/z: 297.2 $[M+H]^+$; 319.1 $[M+Na]+$.

14) Preparation of tert-butyl {[5-hydroxymethyl-2-(3-methyl-2-nitro-3H-imidazol-4-yl-methoxy)-phenylcarbamoyl]methyl}-carbamate

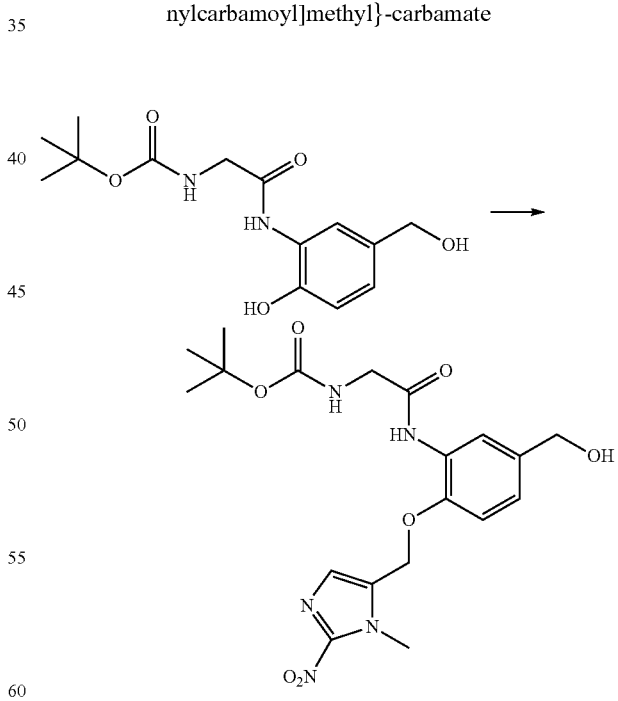

Tert-butyl [(2-Hydroxy-5-hydroxymethyl-phenylcarbamoyl)-methyl]-carbamate (0.10 g, 0.34 mmol) was added to a 50 mL eggplant-shaped flask, and dissolved with anhydrous DMF (5 mL), then 5-(chloromethyl)-1-methyl-2-nitro-1H-imidazole (70 mg, 0.39 mmol) and $CsCO_3$ (165 mg, 0.51 mmol) were added in sequence. The reaction was carried out under stirring at room temperature for 4 hours, then the reaction solution was poured into distilled water (40 mL), and extracted with EA for several times, the organic phases were combined and washed for 3 times with saturated NaCl and dried over Na$_2$SO$_4$. The solvent was removed by evaporation under reduced pressure, and the obtained crude product was purified by column chromatography to obtain a yellow solid powder (0.12 g, 81% yield). $^1$H-NMR (400 MHz, DMSO-d6) δ 8.92 (s, 1H), 8.01 (s, 1H), 7.37 (s, 1H), 7.32 (br, 1H), 7.22 (d, J=8.4 Hz, 1H), 7.03 (d, J=8.4 Hz, 1H), 5.30 (s, 2H), 5.15 (t, 1H), 4.41 (d, J=5.6 Hz, 2H), 4.00 (s, 3H), 3.71 (d, J=5.9 Hz, 2H), 1.34 (s, 9H). MS (ESI) m/z: 436.4 [M+H]$^+$; 458.4 [M+Na]$^+$.

15) Preparation of 2-amino-N-[5-hydroxymethyl-2-(3-methyl-2-nitro-3H-imidazol-4-yl-methoxy)-phenyl]-acetamide 16) Preparation of 2-[6-(2,5-dioxo-2,5-dihydro-pyrrol-1-yl)-hexylamino]-N-[5-hydroxymethyl-2-(3-methyl-2-nitro-3H-imidazol-4-yl-methoxy)-phenyl]-acetamide

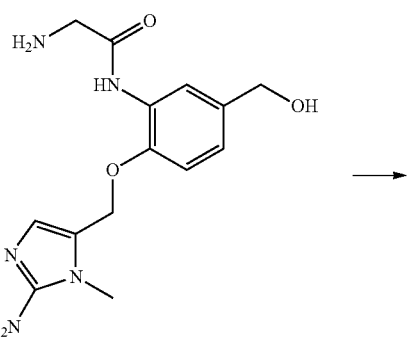

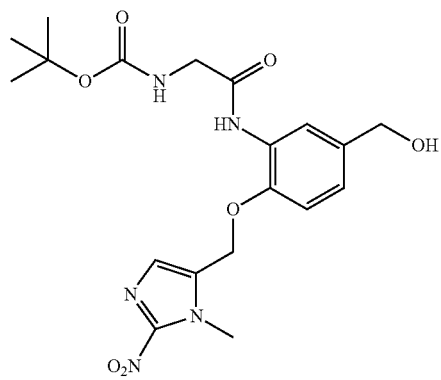

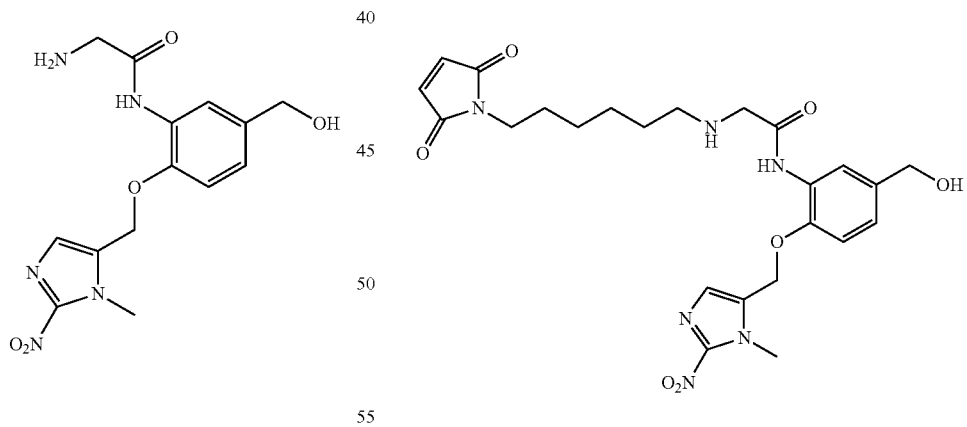

Tert-butyl{[5-hydroxymethyl-2-(3-methyl-2-nitro-3H-imidazol-4-yl-methoxy)-phenylcarbamoyl]methyl}-carbamate (1.44 g, 3.3 mmol) was added to a 50 mL eggplant-shaped flask, and dissolved with DCM (10 mL), then TFA (3.3 mL) was added. The reaction was carried out under stirring at room temperature for 2 hours, then the solvent was removed by evaporation under reduced pressure to obtain a crude target product (1.13 g, 99% yield), which was directly used in the next reaction without further purification. MS (ESI) m/z: 336.2 [M+H]$^+$.

2-Amino-N-[5-hydroxymethyl-2-(3-methyl-2-nitro-3H-imidazol-4-yl-methoxy)-phenyl]-acetamide (1.0 g, 2.2 mmol, crude product) was added to a 50 mL eggplant-shaped flask, and dissolved with DMF (15 mL), then an excess of DIPEA (1.0 g, 8.0 mmol) was added, and stirred at room temperature for 10 minutes, and then the intermediate MCOSu (0.68 g, 2.2 mmol) was added, the reaction was carried out under stirring overnight at room temperature. After the reaction was completed, the reaction solution was concentrated and purified by column chromatography to obtain a pale yellow solid (0.85 g, 73% yield). $^1$H-NMR (400 MHz, DMSO-d6) δ 8.95 (s, 1H), 8.33 (t, J=5.9 Hz, 1H), 7.97 (s, 1H), 7.38 (s, 1H), 7.20 (d, J=8.4 Hz, 1H), 7.03 (d, J=8.4 Hz, 1H), 6.99 (s, 2H), 5.27 (s, 2H), 5.15 (t, J=5.8 Hz, 1H), 4.39 (d, J=5.6 Hz, 2H), 3.83 (d, J=5.6 Hz, 2H). 1.99 (t, J=12.0 Hz, 2H), 1.43 (m, 4H), 1.14 (m, 2H). MS (ESI) m/z: 529.3 [M+H]$^+$; 551.3 [M+Na]$^+$; 527.5 [M−H]$^−$.

17) Preparation of carbonic acid 3-{2-[6-(2,5-dioxo-2,5-dihydro-pyrrol-1-yl)-hexylamino]-acetylamino}-4-(3-methyl-2-nitro-3H-imidazol-4-yl-methoxy)-benzyl ester 4-nitrophenyl ester (L01)

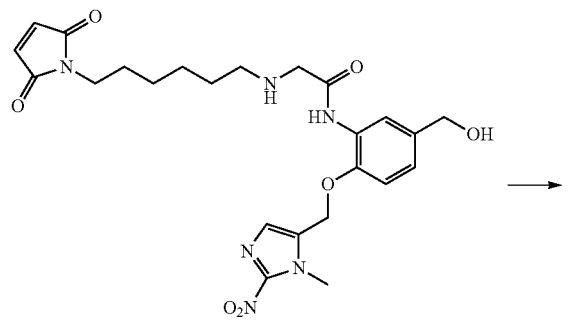

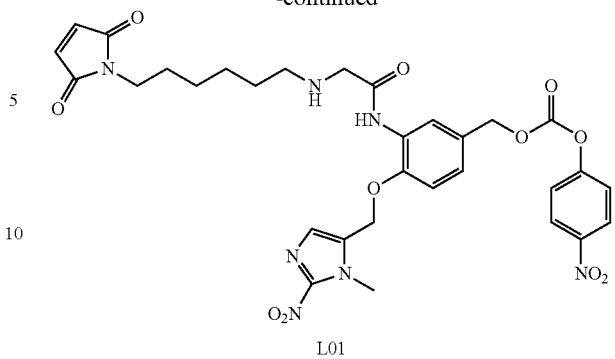

The intermediate 2-[6-(2,5-dioxo-2,5-dihydro-pyrrol-1-yl)-hexylamino]-N-[5-hydroxymethyl-2-(3-methyl-2-nitro-3H-imidazol-4-yl-methoxy)-phenyl]-acetamide (200 mg, 1 eq) was used as raw material, and dissolved with anhydrous DMF (20 mL), then bis(p-nitrophenyl) carbonate (2 eq and DIPEA (2 eq were added in sequence, and then the reaction was carried out under stirring at room temperature for 12 hours. After the reaction was completed, the solvent was removed by concentration under reduced pressure, and the residue was dispersed and slurried in diethyl ether to obtain a crude product, which was further purified by column chromatography to obtain a target product as a white solid powder (91% yield). $^1$H-NMR (400 MHz, DMSO-d6) δ 9.06 (s, 1H), 8.33 (m, 1H), 8.31 (dt, J=9.0 Hz, 2H), 8.16 (s, 1H), 7.57 (dt, J=9.0 Hz, 2H), 7.41 (s, 1H), 7.30 (d, J=8.7 Hz, 1H), 7.22 (dd, J=8.4 Hz, 1H), 6.99 (s, 2H), 5.33 (s, 2H), 5.24 (s, 2H), 3.99 (s, 3H), 3.86 (d, J=5.6 Hz, 2H), 3.32 (m, 2H), 2.00 (t, J=7.4 Hz, 1H), 1.43 (m, 4H), 1.14 (m, 2H). MS (ESI) m/z: 694.2 [M+H]+; 716.3 [M+Na]+; 692.0 [M−H]$^−$.

18) Preparation of L01-MMAE Conjugate

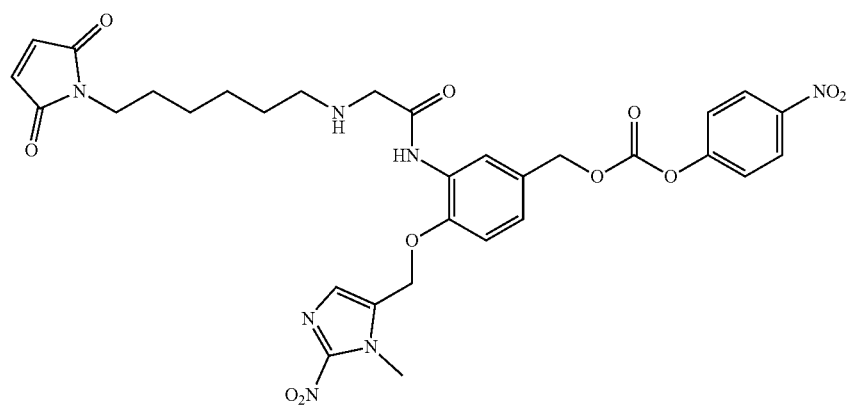

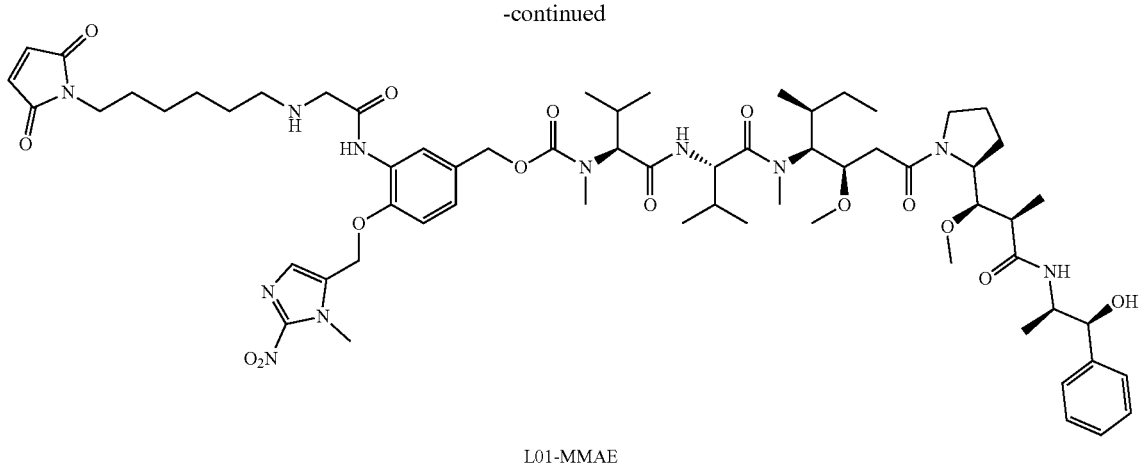

L01-MMAE

The linker L01 (53 mg, 0.06 mmol) was added to a 10 mL eggplant-shaped flask, and dissolved in anhydrous DMF (3 mL), then HOBt (9.4 mg, 0.06 mmol), MMAE (50 mg, 0.07 mmol, purchased from Concortis Biosystems) and DIPEA (18.2 μL) were added in sequence, and the reaction was carried out under stirring at room temperature for 18 hours. After the reaction was completed, the solvent was removed by concentration under reduced pressure, and the residue was further purified by column chromatography to obtain a target product as a white solid powder (75% yield). HRMS (ESI) m/z: 1272.6876 [M+H]$^+$; 1294.6697 [M+Na]$^+$; 636.8487 [M+2H]$^{2+}$.

19) Preparation of ADC-1

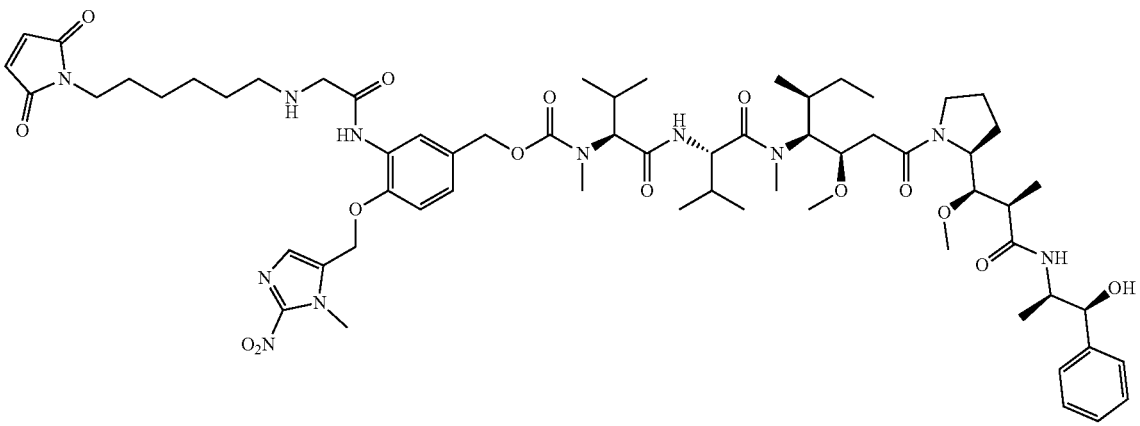

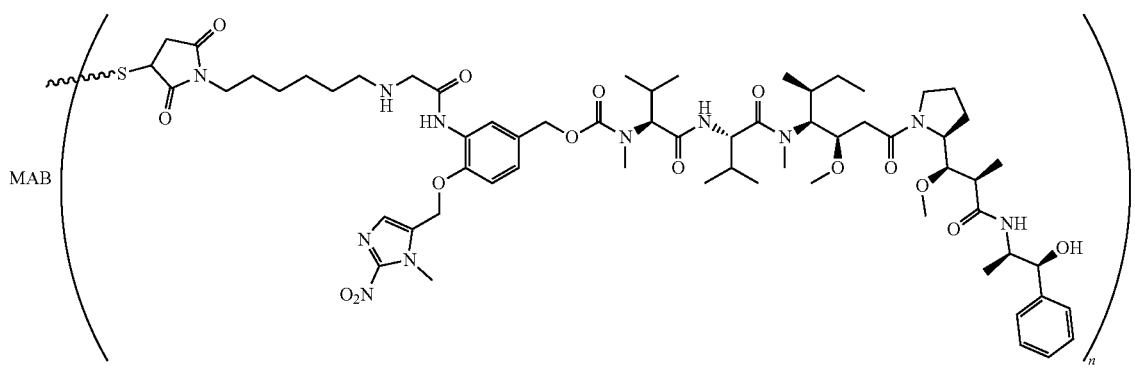

ADC-1

By using the method described in the literature (*Int J Mol Sci.* 2017, 18(9): e1860), the L01-MMAE conjugate was coupled to anti-HER2 humanized monoclonal antibody mil40 (purchased from Zhejiang Hisun Pharmaceutical Co., Ltd. Co., Ltd., a biosimilar of Herceptin) to obtain a target antibody-drug conjugate ADC-1, in which MAB represented monoclonal antibody, and the drug to antibody ratio (DAR) n was about 4.

Example 2: Preparation of ADC-2

1) Preparation of 4-[(2,5-dioxo-2,5-dihydro-pyrrol-1-yl)-methyl]-cyclohexanecarboxylic acid

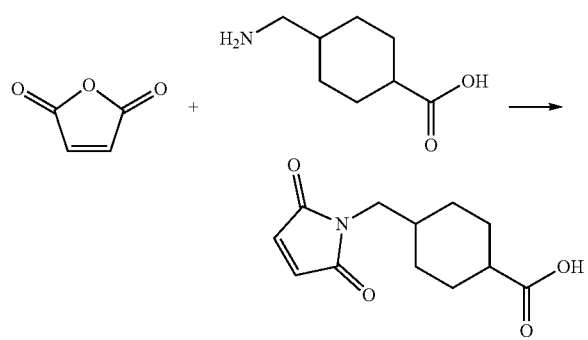

By using a method similar to that for the synthesis of MCOH, trans-4-(aminomethyl)cyclohexanecarboxylic acid (7.86 g, 50.0 mmol) and maleic anhydride (4.90 g, 50.0 mmol) were added to a 500 mL three-necked flask, dissolved with DMF (250 mL), then heated to 120° C. and refluxed for 6 hours. After the reaction was completed, the reaction solution was cooled to room temperature, poured into distilled water, and extracted with an appropriate amount of ethyl acetate for several times. The organic phases were combined, washed with saturated NaCl solution, and dried over anhydrous Na$_2$SO$_4$ overnight. The solvent was removed by concentration to obtain a white solid powder (9.96 g, 84% yield), which was used directly in the next reaction.

2) Preparation of 2,5-dioxo-pyrrolidin-1-yl 4-(2,5-dioxo-2,5-dihydro-pyrrol-1-yl-methyl)-cyclohexane carboxylate (SMCC)

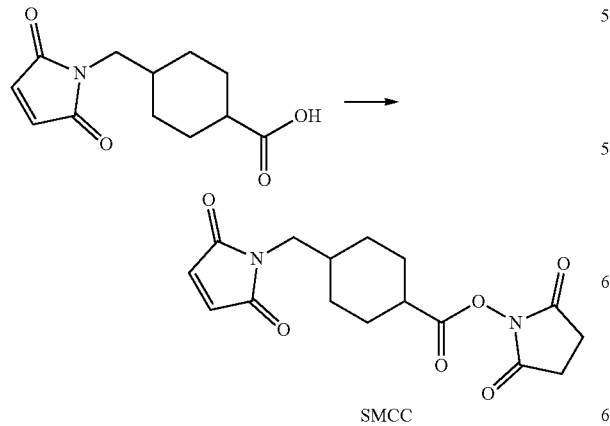

SMCC

N-hydroxysuccinimide (23.0 g, 200 mmol) was added into a 1000 mL three-necked flask, dissolved in DMF (250 mL), then stirred at 0° C. for 30 minutes, and trifluoroacetic anhydride (27.8 mL, 200 mmol) was added dropwise. The reaction mixture was stirred for 10 minutes, trimethylpyridine (26.4 mL, 200 mmol) was added dropwise, and stirred for 10 min, then 4-[(2,5-dioxo-2,5-dihydro-pyrrol-1-yl)-methyl]-cyclohexanecarboxylic acid (13.1 g, 55 mmol) was added, continuously reacted at 0° C. for 2 hours, then slowly warmed to room temperature and continuously reacted for 18 hours. After the reaction was completed, chloroform (300 mL) and hydrochloric acid solution (1 mol/L, 250 mL) were added to the reaction solution, and then the resulting mixture was extracted with DCM. The organic layer obtained by the extraction was washed twice with hydrochloric acid solution (1 mol/L) (2×250 mL), dried over anhydrous sodium sulfate and concentrated under vacuum to obtain a crude yellow solid, which was slurried in diethyl ether (3×200 mL) to obtain a white powdery solid (15 g, 90% yield). $^1$H-NMR (400 MHz, DMSO-d6) δ 6.71 (s, 1H), 3.39 (d, J=7.0 Hz, 2H), 2.82 (d, J=7.3 Hz, 4H), 2.58 (m, 1H), 2.15 (m, 2H), 1.80 (m, 2H), 1.56 (m, 1H), 1.54 (m, 2H), 1.06 (m, 2H). MS (ESI) m/z: 352.6 [M+NH$_4$]$^+$; 357.4 [M+Na]$^+$.

3) Preparation of 4-(2,5-dioxo-2,5-dihydro-pyrrol-1-yl-methyl)]-cyclohexanecarboxylic acid {[5-hydroxymethyl-2-(3-methyl-2-nitro-3H-imidazol-4-yl-methoxy)-phenylcarbamoyl]-methyl}amide

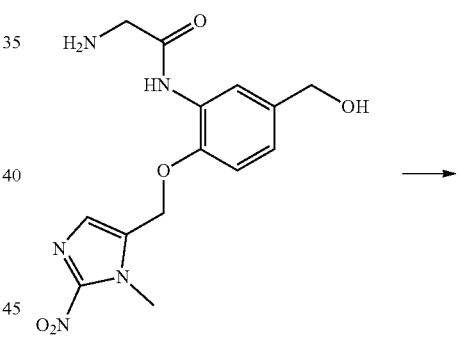

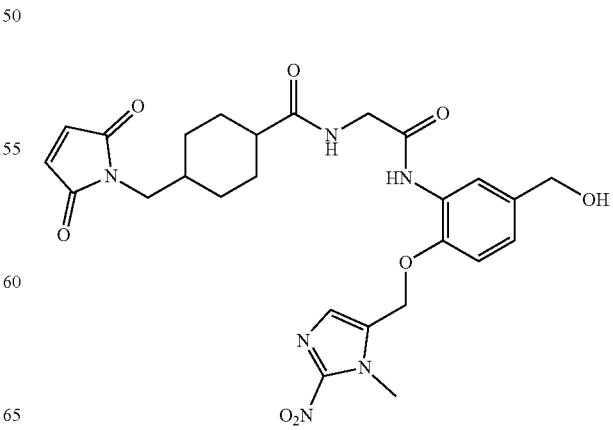

By referring to the method for preparation of 2-[6-(2,5-dioxo-2,5-dihydro-pyrrol-1-yl)-hexylamino]-N-[5-hydroxylmethyl-2-(3-methyl-2-nitro-3H-imidazol-4-yl-methoxy)-phenyl]-acetamide as described in step 16) of Example 1, a pale yellow solid powder (61% yield) was obtained. $^1$H-NMR (400 MHz, DMSO-d6) δ 9.06 (s, 1H), 8.34 (br, 1H), 8.31 (dt, J=9.0 Hz, 2H), 8.16 (s, 1H), 7.57 (dt, J=9.0 Hz, 2H), 7.40 (s, 1H), 7.30 (d, J=8.7 Hz, 1H), 7.22 (dd, J=8.4 Hz, 1H), 6.99 (s, 2H), 5.33 (s, 2H), 5.24 (s, 2H), 3.99 (s, 1H), 3.86 (d, J=5.6 Hz, 2H), 3.32 (m, 2H), 2.00 (t, J=7.4 Hz, 2H), 1.43 (m, 4H), 1.15 (m, 2H). MS (ESI) m/z: 694.2 [M+H]+; 716.3 [M+Na]+; 692.0 [M–H]−.

4) Preparation of carbonic acid 3-(2-{[4-[(2,5-dioxo-2,5-dihydro-pyrrol-1-yl-methyl) cyclohexanecarbonyl]-amino}-acetylamino)-4-(3-methyl-2-nitro-3H-imidazol-4-yl-methoxy) benzyl ester 4-nitro-phenyl ester (L02)

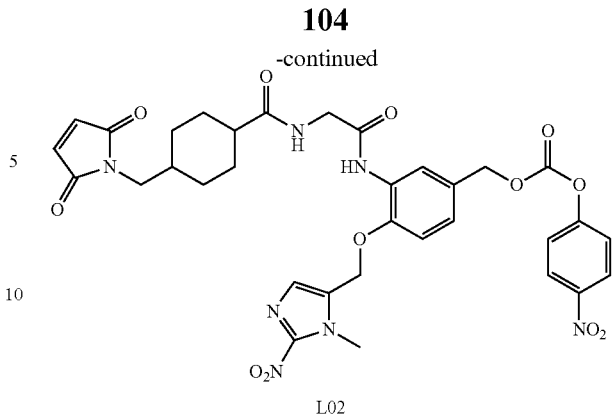

L02

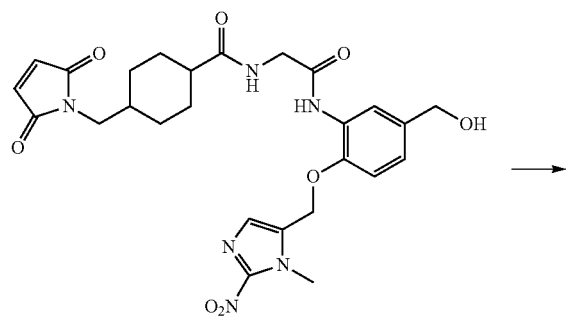

→

The intermediate 4-(2,5-dioxo-2,5-dihydro-pyrrol-1-yl-methyl)]-cyclohexanecarboxylic acid {[5-hydroxymethyl-2-(3-methyl-2-nitro-3H-imidazol-4-yl-methoxy)-phenylcarbamoyl]-methyl}amide was used as raw material, and a preparation method similar to that of L01 was used for synthesis of the target product. A pale yellow solid powder (90% yield) was obtained. $^1$H-NMR (400 MHz, DMSO-d6) δ 9.01 (s, 1H), 8.31 (dt, J=9.3 Hz, 2H), 8.22 (t, J=5.7 Hz, 1H), 8.17 (s, 1H), 7.56 (dt, J=9.3 Hz, 2H), 7.39 (s, 1H), 7.30 (d, J=8.7 Hz, 2H), 7.21 (dd, J=6.6 Hz, 1H), 7.01 (s, 2H), 5.32 (s, 2H), 5.24 (s, 2H), 3.99 (s, 3H), 3.84 (d, J=5.6 Hz, 2H), 3.23 (d, J=7.0 Hz, 2H), 2.04 (tt, J=11.8 Hz, 1H), 1.63 (m, 2H), 1.48 (m, 1H), 1.18 (m, 2H), 0.86 (qd, 2H). MS (ESI) m/z: 720.3 [M+H]+; 737.6 [M+NH4]+; 742.8 [M+Na]+.

5) Preparation of L02-MMAE Conjugate

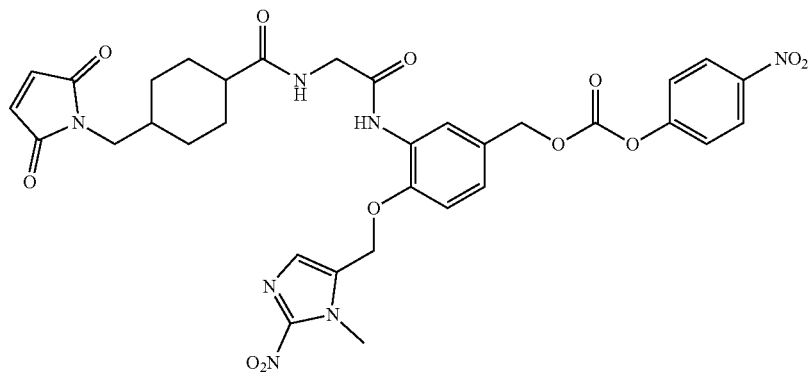

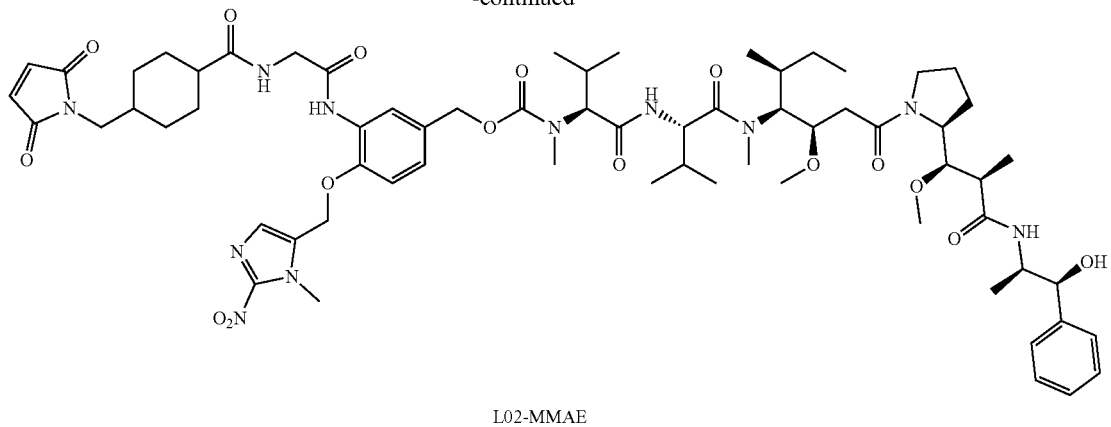

L02-MMAE

Carbonic acid 3-(2-{[4-[(2,5-dioxo-2,5-dihydro-pyrrol-1-yl-methyl)cyclohexanecarbonyl]-amino}-acetylamino)-4-(3-methyl-2-nitro-3H-imidazol-4-yl-methoxy)benzyl ester 4-nitro-phenyl ester (L02) was used as raw material, and a preparation method similar to that of L01-MMAE conjugate was used for synthesis of the target product. The target product was a white solid powder (72% yield). HRMS (ESI) m/z: 1298.7041 [M+H]$^+$; 1320.6851 [M+Na]$^+$.

6) Preparation of ADC-2

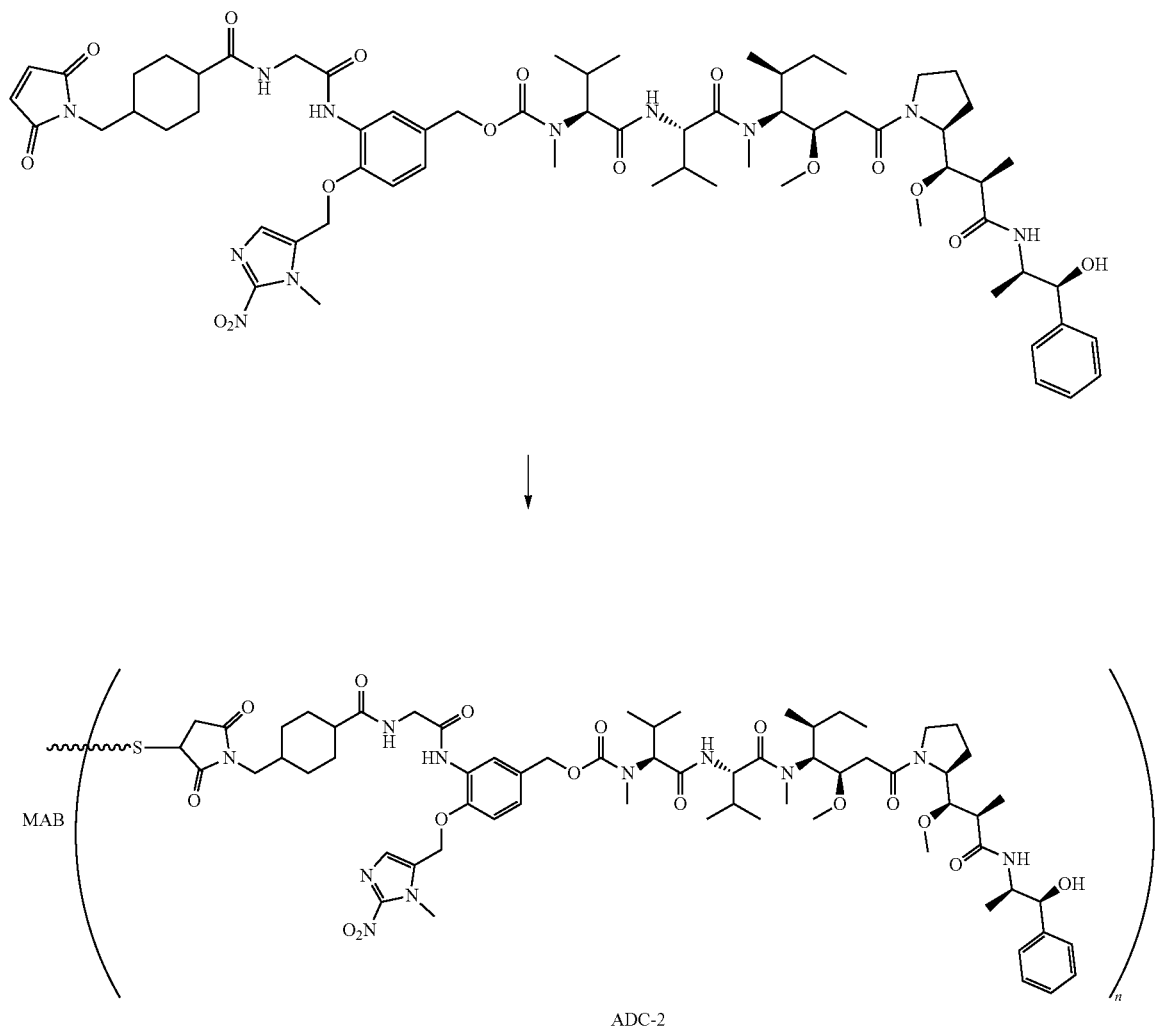

ADC-2

By using the method described in the literature (*Int J Mol Sci.* 2017, 18(9): e1860), the L02-MMAE conjugate was coupled to anti-HER2 humanized monoclonal antibody mil40 to obtain a target antibody-drug conjugate ADC-2, in which MAB represented monoclonal antibody, and the drug to antibody ratio (DAR) n was about 4.

Example 3: Preparation of ADC-3

1) Preparation of tert-butyl {[5-hydroxymethyl-2-(4-nitro-benzyloxy)phenylcarbamoyl]methyl}carbamate

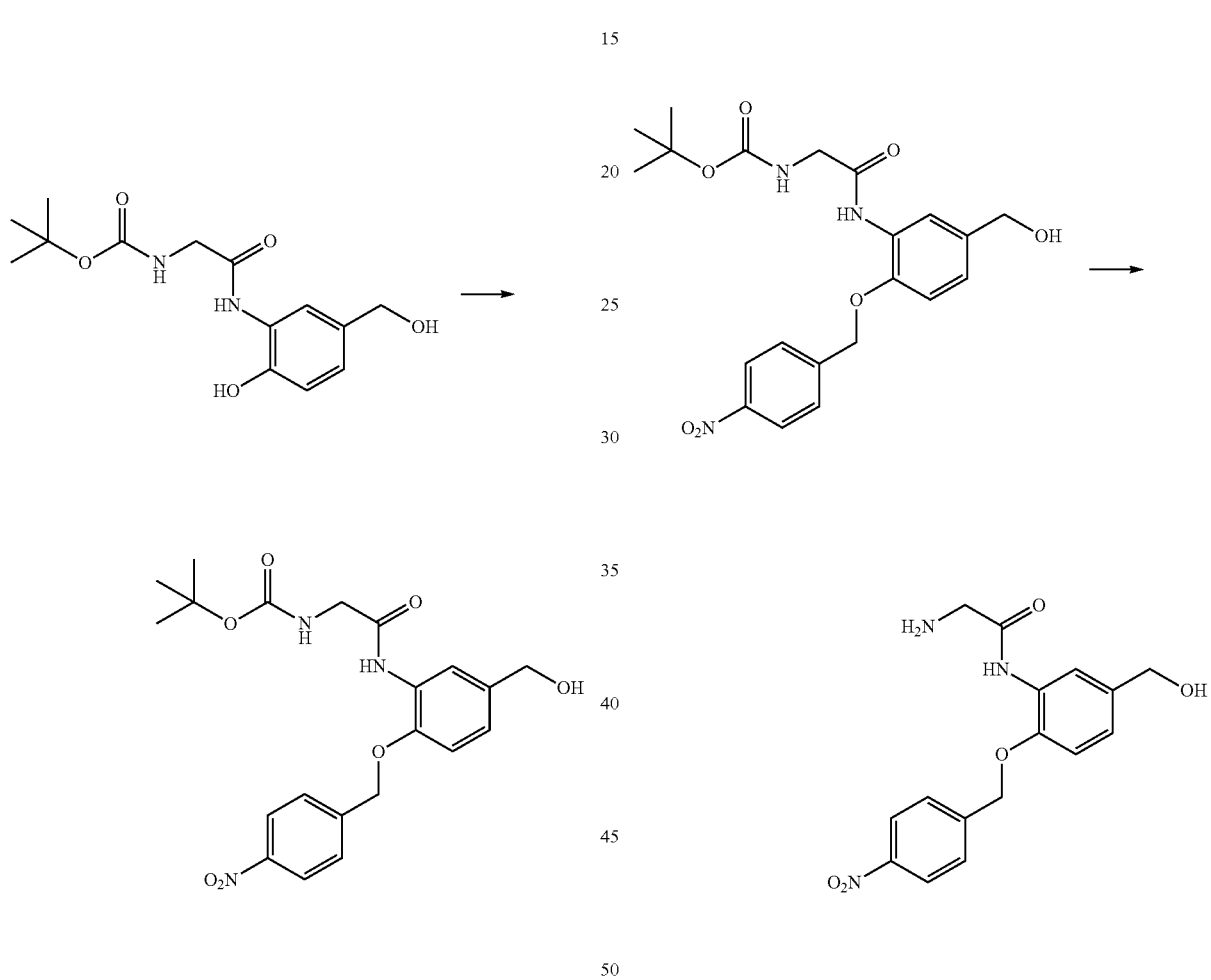

2) Preparation of 2-amino-N-[5-hydroxymethyl-2-(4-nitro-benzyloxy)-phenyl]-acetamide Tert-butyl [(2-Hydroxy-5-hydroxymethyl-phenylcarbamoyl)-methyl]-carbamate (0.15 g, 0.50 mmol) was added to a 50 mL eggplant-shaped flask and dissolved in anhydrous DMF (5 mL), then p-nitrobenzyl bromide (0.13 mg, 0.60 mmol) and $CsCO_3$ (0.26 mg, 0.8 mmol) were added in sequence. The reaction was carried out under stirring at room temperature for 5 hours, then the reaction solution was poured into distilled water (40 mL) to precipitate solid insoluble substances. The resulting mixture containing the solid insoluble substances was extracted with EA for several times, the organic phases were combined and washed for 3 times with saturated NaCl and dried over $Na_2SO_4$. The solvent was removed by evaporation under reduced pressure to obtain a pale yellow solid powder (0.12 g, 95% yield).

$^1$H-NMR (400 MHz, DMSO-d6) δ 9.11 (s, 1H), 8.27 (d, J=8.7 Hz, 2H), 8.02 (s, 1H), 7.77 (d, J=8.7 Hz, 2H), 7.38 (s, 1H), 7.04 (d, J=8.4 Hz, 1H), 6.98 (dd, J=8.4 Hz, 1H), 5.36 (s, 2H), 4.39 (s, 2H), 3.76 (d, J=5.9 Hz, 2H), 1.32 (s, 9H). MS (ESI) m/z: 432.2 [M+H]$^+$; 454.4 [M+Na]$^+$.

Tert-butyl {[5-hydroxymethyl-2-(4-nitro-benzyloxy)phenylcarbamoyl]methyl}carbamate (0.15 g, crude product) was added into a 10 mL eggplant-shaped flask, and dissolved in EA (1 mL), then 2 mol/L HCl in ethyl acetate solution (0.3 mL) was added. The reaction was carried out under stirring at room temperature for 2 hours, then the reaction solution was directly filtered with suction to obtain a crude product as a pale pink powdery solid, which was further slurried in EA to be purified to obtain the target product (0.1 g, 95% yield). $^1$H-NMR (400 MHz, DMSO-d6) δ 9.87 (s, 1H), 8.25 (t, J=4.4 Hz, 2H), 7.79 (t, J=8.6 Hz, 2H), 7.03 (m, 2H), 5.38 (s, 1H), 4.40 (s, 2H), 3.81 (m, 4H). MS (ESI) m/z: 332.12 [M+H]$^+$.

3) Preparation of 6-(2,5-dioxo-2,5-dihydro-pyrrol-1-yl)-hexanoic acid {[5-hydroxymethyl-2-(4-nitro-benzyloxy)-phenylcarbamoyl]-methyl}amide 4) Preparation of carbonic acid 3-{2-[6-(2,5-dioxo-2,5-dihydro-pyrrol-1-yl)-hexanoyl-amino]-acetylamino}-4-(4-nitro-benzyloxy)benzyl ester 4-nitrophenyl ester (L03)

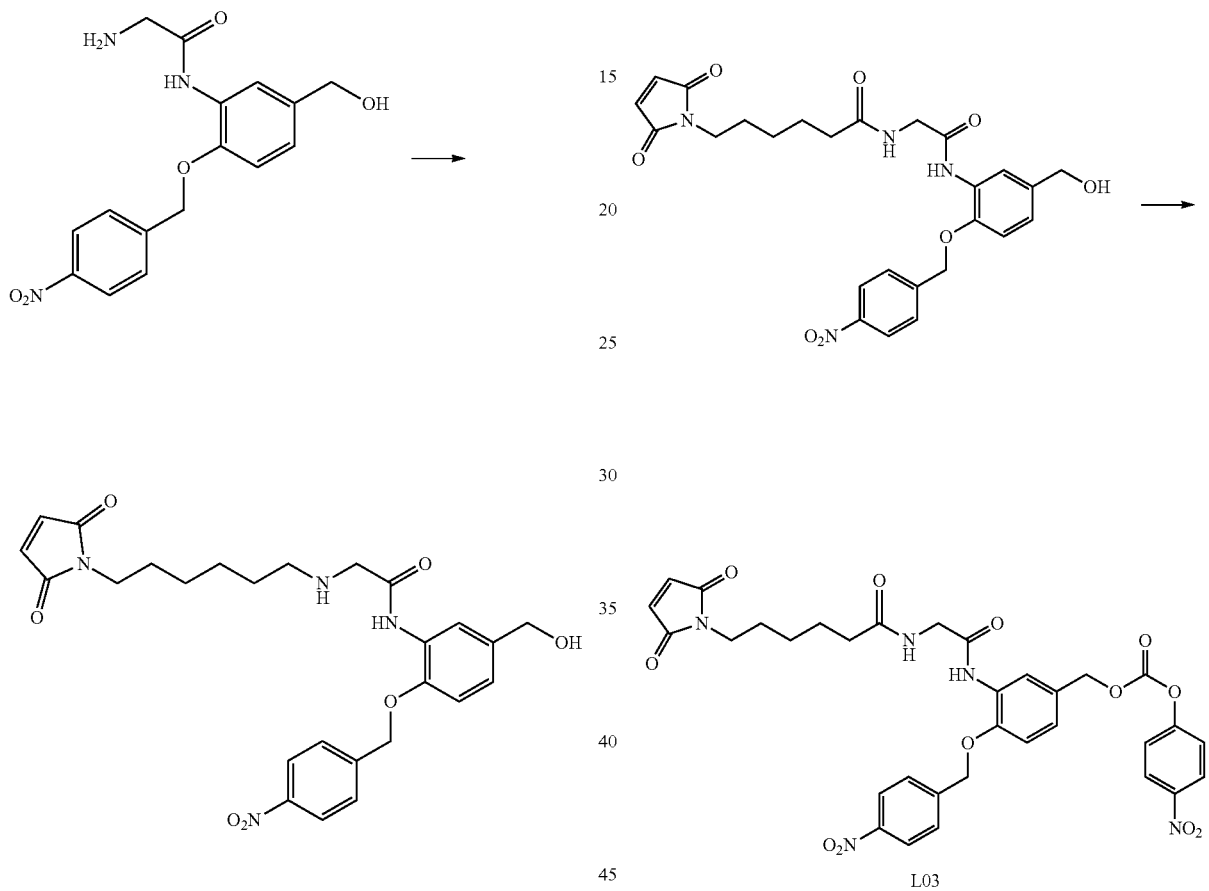

2-Amino-N-[5-hydroxymethyl-2-(4-nitro-benzyloxy)-phenyl]-acetamide (0.5 g, 1.36 mmol) was added into a 50 mL eggplant-shaped flask and dissolved in DMF (15 mL), then an excess of DIPEA (0.88 g, 6.8 mmol) was added and stirred at room temperature for 10 minutes, and then the intermediate MCOSu (0.46 g, 1.5 mmol) was added, the reaction was carried out under stirring overnight at room temperature. After the reaction was completed, the reaction solution was concentrated and purified by column chromatography to obtain a reddish brown solid (0.23 g, 43% yield). $^1$H-NMR (400 MHz, DMSO-d6) δ 9.9 (s, 1H), 8.36 (t, 1H), 8.25 (d, J=4.4 Hz, 2H), 7.98 (s, 1H), 7.78 (d, J=8.7 Hz, 2H), 7.04 (d, J=8.4 Hz, 1H), 7.01 (s, 2H), 6.98 (d, 2H), 5.34 (s, 2H), 5.12 (t, J=5.8 Hz, 1H), 4.39 (d, J=5.9 Hz, 2H), 3.89 (d, J=5.6 Hz, 2H). 3.33 (t, J=8.4 Hz, 2H), 2.06 (t, J=7.6 Hz, 2H), 1.43 (m, 4H), 1.13 (m, 2H). MS (ESI) m/z: 525.5 [M+H]$^+$; 547.5 [M+Na]$^+$.

6-(2,5-Dioxo-2,5-dihydro-pyrrol-1-yl)-hexanoic acid {[5-hydroxymethyl-2-(4-nitro-benzyloxy)-phenylcarbamoyl]-methyl}amide was used as raw material, and a preparation method similar to that of L01 was used for synthesis of the target product. A pale yellow solid powder was obtained (63% yield). $^1$H-NMR (400 MHz, DMSO-d6) δ 9.21 (s, 1H), 8.37 (t, J=5.5 Hz, 1H), 8.31 (dt, J=9.2 Hz, 2H), 8.27 (dt, J=9.0 Hz, 2H), 8.15 (s, 1H), 7.79 (d, J=8.7 Hz, 2H), 7.57 (dt, J=9.2 Hz, 2H), 7.18 (dd, J=8.4 Hz, 1H), 7.13 (d, J=8.4 Hz, 1H), 6.98 (s, 2H), 5.40 (s, 2H), 5.22 (s, 2H), 3.91 (d, J=5.6 Hz, 2H), 3.31 (m, 2H), 2.07 (t, J=7.4 Hz, 2H), 1.43 (m, 4H), 1.14 (m, 2H). MS (ESI) m/z: 690.4 [M+H]$^+$; 712.5 [M+Na]$^+$.

5) Preparation of L03-MMAE Conjugate

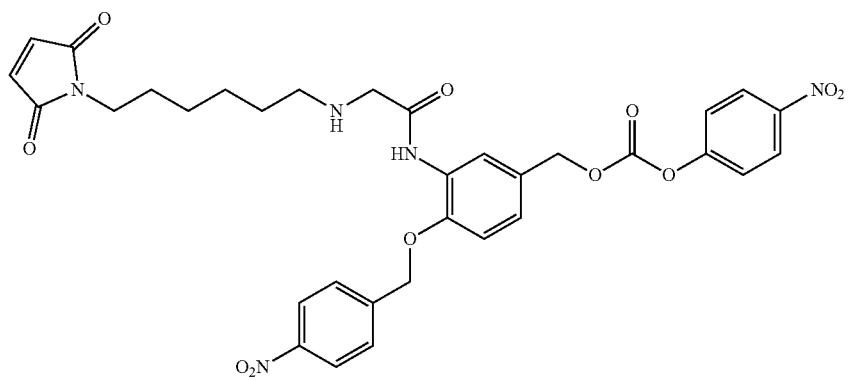

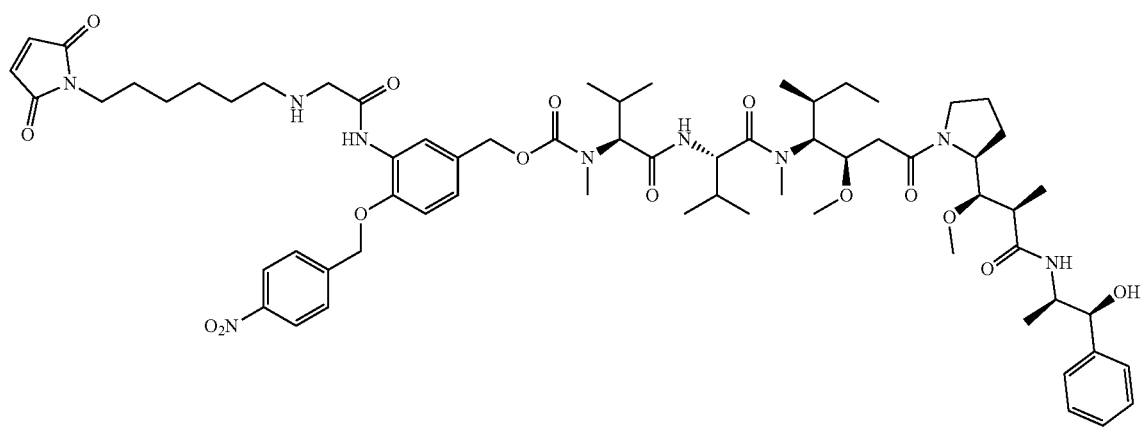

L03-MMAE

Carbonic acid 3-{2-[6-(2,5-dioxo-2,5-dihydro-pyrrol-1-yl)-hexanoylamino]-acetylamino}-4-(4-nitro-benzyloxy) benzyl ester 4-nitro-phenyl ester was used as raw material, and a preparation method similar to that of the L01-MMAE conjugate was used for synthesis of the target product. The target product was a white solid powder (72% yield). HRMS (ESI) m/z: 1268.6921 [M+H]$^+$; 1290.6636 [M+Na]$^+$.

6) Preparation of ADC-3

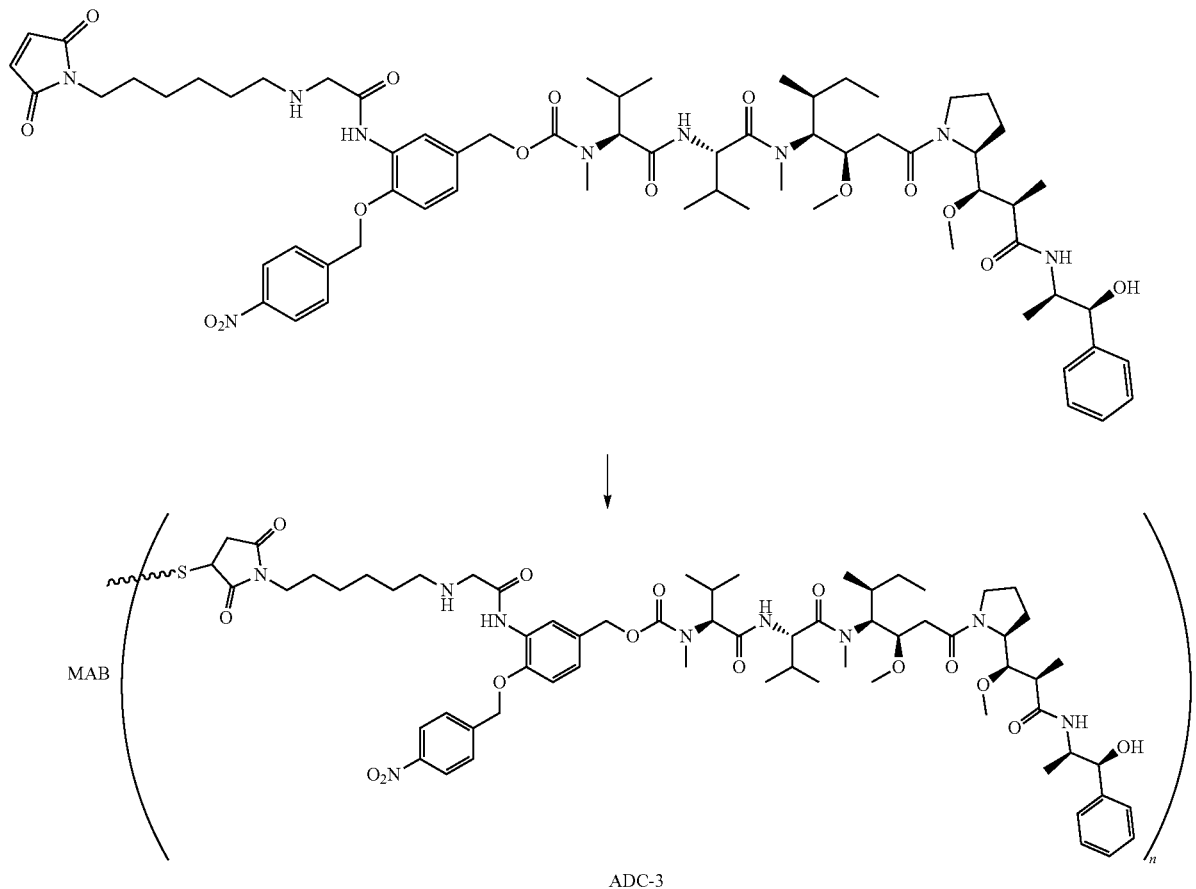

ADC-3

By using the method described in the literature (Int J Mol Sci. 2017, 18(9): e1860), the L03-MMAE conjugate was coupled to anti-HER2 humanized monoclonal antibody mil40 to obtain the target antibody-drug conjugate ADC-3, in which MAB represented monoclonal antibody, and the drug to antibody ratio (DAR) n was about 4.

Example 4: Preparation of ADC-4

1) Preparation of 4-(2,5-dioxo-2,5-dihydro-pyrrol-1-yl-methyl)-cyclohexanecarboxylic acid {[5-hydroxymethyl-2-(4-nitro-benzyloxy)-phenylcarbamoyl]-methyl}-amide

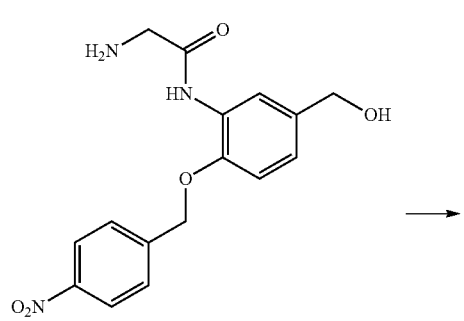

→

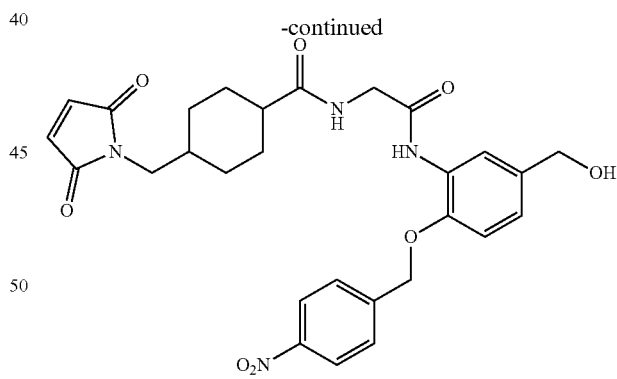

2-Amino-N-[5-hydroxymethyl-2-(4-nitro-benzyloxy)-phenyl]-acetamide was used as raw material, the intermediate MCOSu was replaced with SMCC, and the method for preparation of 6-(2,5-dioxo-2,5-dihydro-pyrrol-1-yl)-hexanoic acid {[5-hydroxymethyl-2-(4-nitro-benzyloxy)-phenylcarbamoyl]-methyl}amide as described in the step 3) of Example 3 was used for synthesis of the target product.

The target product was a pale yellow solid powder (61% yield). ¹H-NMR (400 MHz, DMSO-d6) δ 9.02 (s, 1H), 8.33 (t, J=5.6 Hz, 1H), 8.25 (d, J=8.7 Hz, 2H), 8.02 (s, 1H), 7.76 (d, J=8.7 Hz, 2H), 7.03 (d, J=8.4 Hz, 1H), 7.00 (s, 2H), 6.97 (dd, J=8.1 Hz, 1H), 5.34 (s, 2H), 5.11 (t, J=5.8 Hz, 1H), 4.38 (d, J=5.6 Hz, 2H), 3.87 (d, J=5.6 Hz, 2H), 3.19 (d, J=7.0 Hz, 2H), 2.08 (tt, J=12.1 Hz, 1H), 1.68 (d, J=12.32 Hz, 2H), 1.55 (d, J=12.9 Hz, 2H), 1.45 (m, 1H), 1.22 (qd, 2H), 0.78 (qd, 2H). MS (ESI) m/z: 551.5 [M+H]⁺; 573.5 [M+Na]⁺.

2) Preparation of carbonic acid 3-(2-{[4-(2,5-dioxo-2,5-dihydro-pyrrol-1-yl-methyl)-cyclohexanecarbonyl]-amino}-acetylamino)-4-(4-nitrobenzyloxy)benzyl ester 4-nitro-phenyl ester (L04)

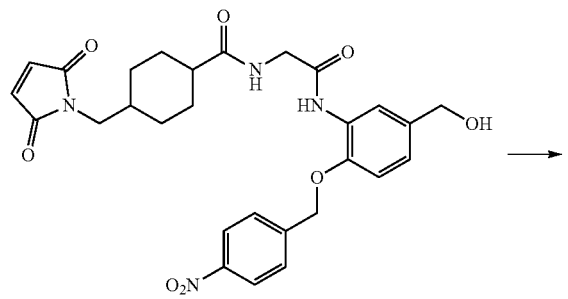

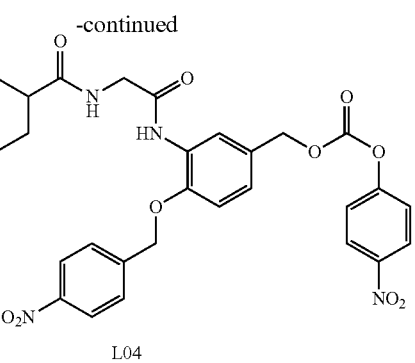

L04

The intermediate 4-(2,5-dioxo-2,5-dihydro-pyrrol-1-yl-methyl)-cyclohexanecarboxylic acid {[5-hydroxymethyl-2-(4-nitro-benzyloxy)-phenylcarbamoyl]-methyl}-amide was used as raw material, and a preparation method similar to that of L01 was used for synthesis of the target product. The target product was a pale yellow solid powder (76% yield). ¹H-NMR (400 MHz, DMSO-d6) δ 9.14 (s, 1H), 8.31 (dt, 2H), 8.27 (dt, 2H), 8.19 (s, 1H), 7.78 (d, J=8.7 Hz, 2H), 7.56 (dt, J=9.2 Hz, 2H), 7.16 (m, 2H), 7.00 (s, 2H), 5.40 (s, 2H), 5.22 (s, 2H), 3.90 (d, J=5.6 Hz, 2H), 3.19 (d, J=7.0 Hz, 2H), 2.08 (tt, J=12.0 Hz, 1H), 1.68 (d, J=13.2 Hz, 2H), 1.53 (d, J=12.9 Hz, 2H), 1.44 (m, 1H), 1.23 (m, 1H), 0.80 (qd, 2H). MS (ESI) m/z: 716.4 [M+H]⁺; 738.4 [M+Na]⁺.

3) Preparation of L04-MMAE Conjugate

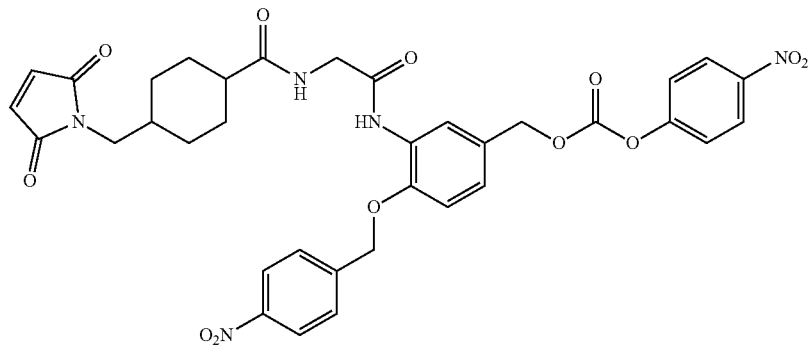

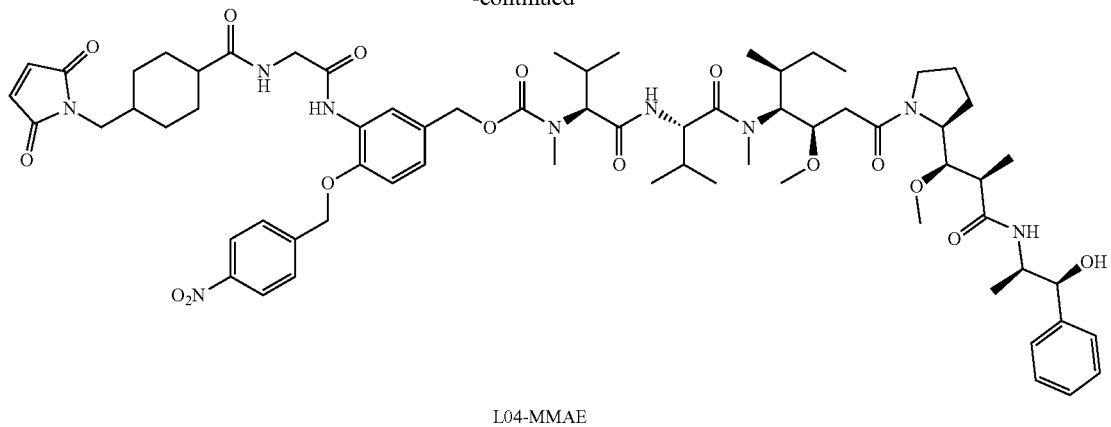

L04-MMAE

Carbonic acid 3-(2-{[4-(2,5-dioxo-2,5-dihydro-pyrrol-1-yl-methyl)-cyclohexanecarbonyl]-amino}-acetylamino)-4-(4-nitrobenzyloxy)benzyl ester 4-nitro-phenyl ester was used as raw material, and a preparation method similar to that of L01-MMAE was used for synthesis of the target product. The target product was a pale yellow solid powder (72% yield). HRMS (ESI) m/z: 1294.6976 [M+H]$^+$; 1316.6980 [M+Na]$^+$.

4) Synthesis of ADC-4

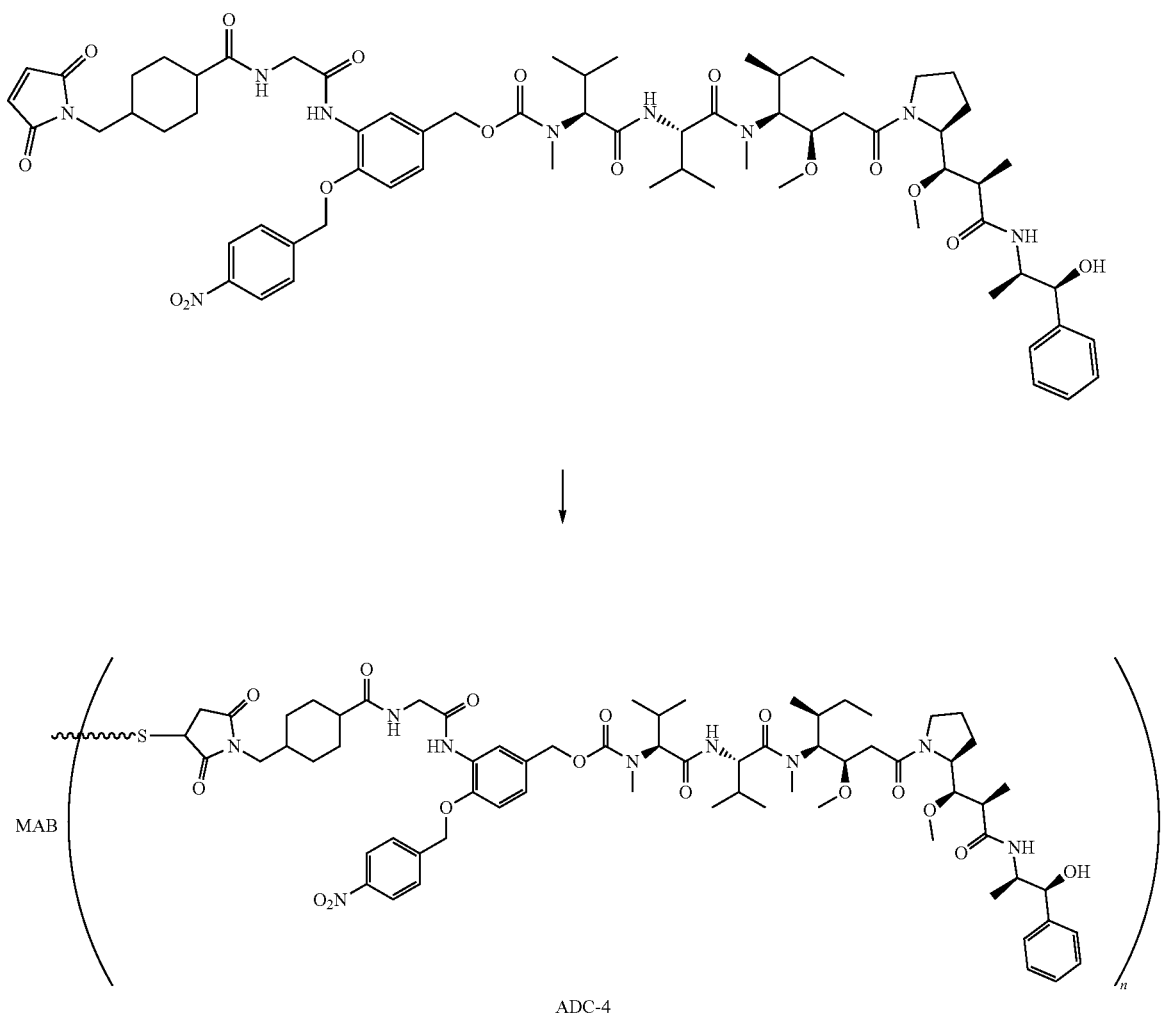

ADC-4

By using the method described in the literature (Int J Mol Sci. 2017, 18(9): e1860), the L04-MMAE conjugate was coupled to anti-HER2 humanized monoclonal antibody mil40 to obtain the target antibody-drug conjugate ADC-4, in which MAB represented monoclonal antibody, and the drug to antibody ratio (DAR) n was about 4.

Example 5: Preparation of ADC-5

1) Preparation of (5-nitrofuran-2-yl)methanol 2) 2-Chloromethyl-5-nitro-furan

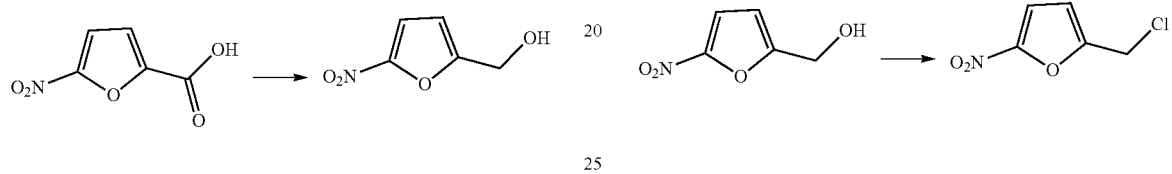

5-Nitro-furan-2-carboxylic acid (0.91 g, 5.8 mmol) was dissolved in anhydrous THF (20 mL), and placed in a low temperature reaction tank at −40° C. and cooled down after the dissolution was completed. Triethylamine (1.3 mL) and isobutyl chloroformate (1.2 mL) were slowly added dropwise, respectively, after the addition was completed, the reaction was continued for 30 minutes, the reaction solution was warmed slowly to −10° C., and the reaction was continued for 1 hour. NaBH$_4$ (1.1 g) was added in batches, and then a small amount of THF-H$_2$O (3:1, 1.2 mL) mixed solvent was added dropwise. After the reaction was completed, an appropriate amount of THF was added to the reaction solution, then THF was removed by suction filtration, the aqueous phase was extracted with EA for several times, the organic phases were combined, washed with saturated NaCl for 3 times, dried over anhydrous Na$_2$SO$_4$, and concentrated under reduced pressure to obtain a crude product, which was further purified by column chromatography to obtain a white solid powder (0.42 g, 51% yield). $^1$H-NMR (400 MHz, CDCl$_3$) δ 7.30 (d, 1H), 6.56 (d, 1H), 4.73 (s, 2H), 2.28 (m, 1H). MS (ESI) m/z: 161.0 [M+NH$_4$]f; 142.9[M−H]$^−$.

The reactant (5-nitrofuran-2-yl)methanol (0.35 g, 2.44 mmol) was dissolved in anhydrous THF (10 mL). After the dissolution was completed, DIPEA (0.51 mL, 2.93 mmol) and mesyl chloride (0.34 g, 2.93 mmol) were slowly added dropwise, respectively. After the dropwise addition was completed, the reaction was continued for 30 minutes. The reaction solution was concentrated under reduced pressure, a crude product was obtained as a yellow oil, which was further purified by column chromatography to obtain a yellow oil product (0.32 g, 81% yield). $^1$H-NMR (400 MHz, CDCl$_3$) δ 7.28 (d, 1H), 6.62 (d, 1H), 4.60 (s, 2H). MS (ESI) m/z: 324.4 [2M+H]$^+$.

3) Preparation of carbonic acid 3-{2-[6-(2,5-dioxo-2,5-dihydro-pyrrol-1-yl)-hexanoylamino]-acetylamino}-4-(5-nitro-furan-2-yl-methoxy)-benzyl ester 4-nitro-phenyl ester (L05)

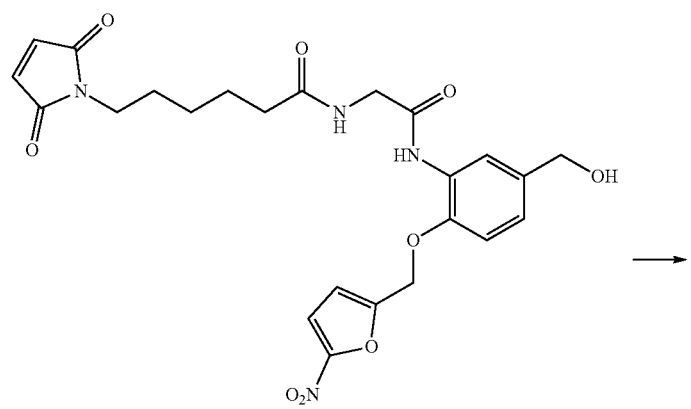

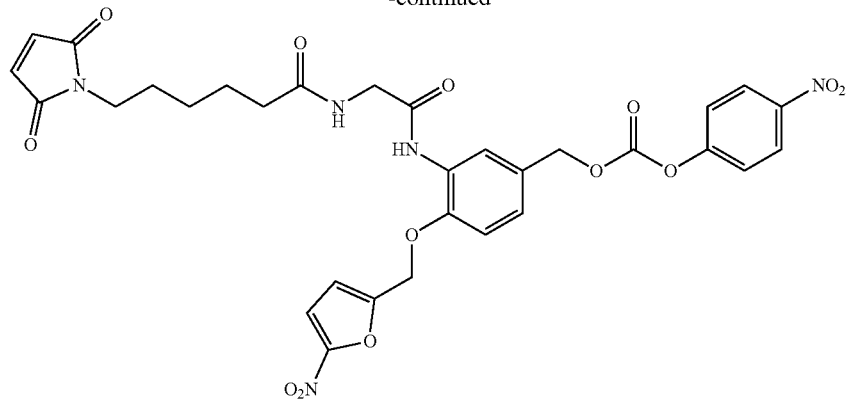

L05

By referring to the method for preparation of 2-[6-(2,5-dioxo-2,5-dihydro-pyrrol-1-yl)-hexylamino]-N-[5-hydroxymethyl-2-(3-methyl-2-nitro-3H-imidazol-4-yl-methoxy)-phenyl]-acetamide as described in the step 16) of Example 1, the raw material 6-(2,5-dioxo-2,5-dihydro-pyrrol-1-yl)-hexanoic acid {5-hydroxymethyl-2-(5-nitro-furan-2-yl-methoxy)-phenylcarbamoyl]-methyl}-amide was prepared. Then, 6-(2,5-dioxo-2,5-dihydro-pyrrol-1-yl)-hexanoic acid {5-hydroxymethyl-2-(5-nitro-furan-2-yl-methoxy)-phenylcarbamoyl]-methyl}-amide was used as raw material, and a preparation method similar to that of L01 was used to obtain the target linker product (L05) as a white solid powder (73% yield). $^1$H-NMR (400 MHz, DMSO-d6) δ 9.06 (s, 1H), 8.33 (m, 1H), 8.31 (dt, J=9.0 Hz, 2H), 8.16 (s, 1H), 7.57 (dt, J=9.0 Hz, 2H), 7.30 (d, J=8.7 Hz, 1H), 7.30 (d, 1H), 7.22 (dd, J=8.4 Hz, 1H), 6.99 (s, 2H), 6.68 (d, 1H), 5.33 (s, 2H), 5.24 (s, 2H), 3.86 (d, J=5.6 Hz, 2H), 3.32 (m, 2H), 2.00 (t, J=7.4 Hz, 1H), 1.43 (m, 4H), 1.14 (m, 2H). MS (ESI) m/z: 680.2 [M+H]$^+$; 702.1 [M+Na]$^+$.

4) Preparation of L05-MMAE Conjugate

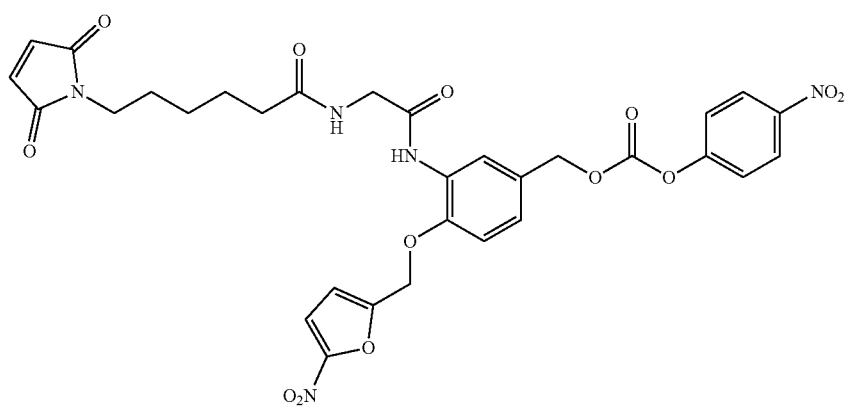

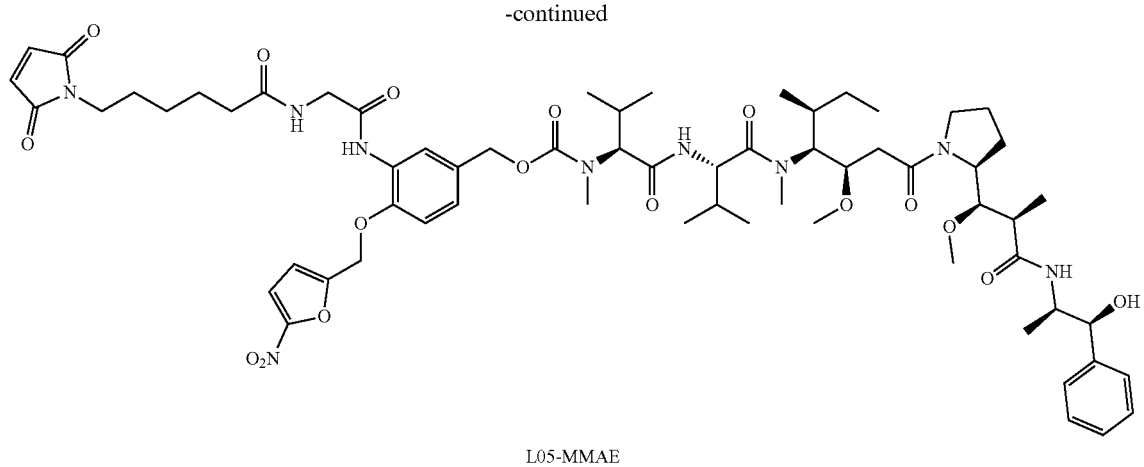
L05-MMAE
Carbonic acid 3-{2-[6-(2,5-dioxo-2,5-dihydro-pyrrol-1-yl)-hexanoylamino]-acetylamino}-4-(5-nitro-furan-2-yl-methoxy)-benzyl ester 4-nitro-phenyl ester was used as raw material, and a preparation method similar to that of L01-MMAE was used for synthesis of the target product. The target product was a white solid powder (69% yield). HRMS (ESI) m/z: 1258.6811 [M+H]$^+$; 1280.6422 [M+Na]$^+$.
5) Preparation of ADC-5
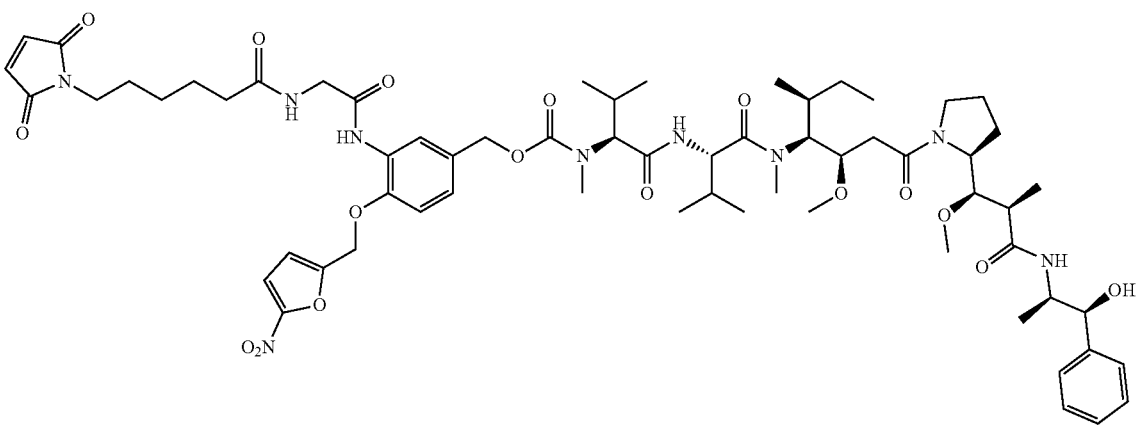
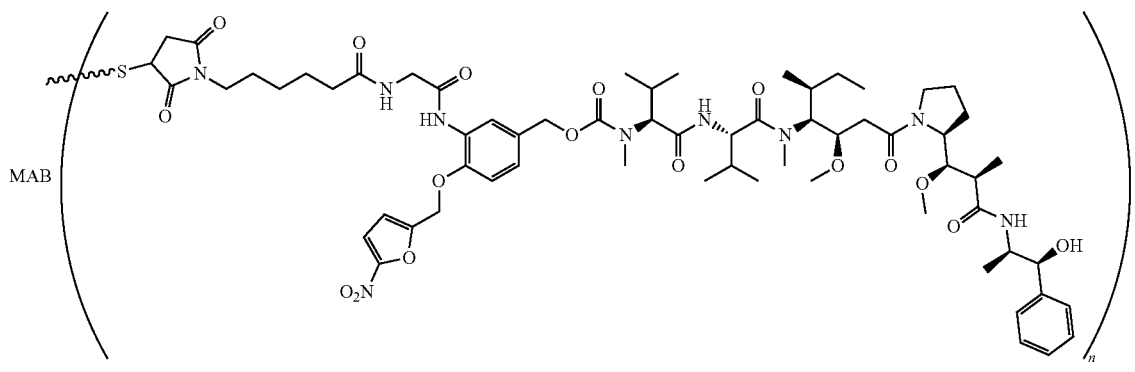
ADC-5

By using the method described in the literature (Int J Mol Sci. 2017, 18(9): e1860), the L05-MMAE conjugate was coupled to anti-HER2 humanized monoclonal antibody mil40 to obtain the target antibody-drug conjugate ADC-5, in which MAB represented monoclonal antibody, and the drug to antibody ratio (DAR) n was about 4.

Example 6: Preparation of ADC-6

1) Preparation of (Z)-6-(3-carboxyacrylamido)hexanoic acid

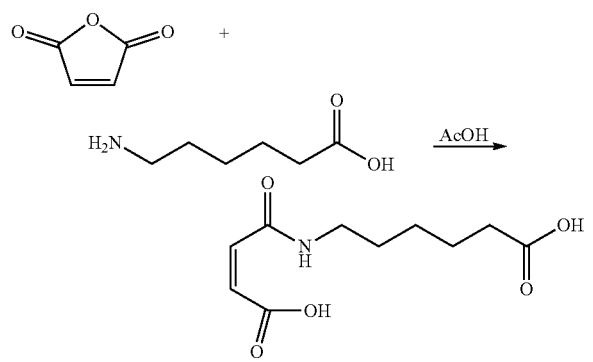

6-Aminohexanoic acid (3.94 g, 30 mM) was dissolved in acetic acid (100 mL) under stirring, maleic anhydride (2.94 g, 30 mM) was added and stirred at room temperature, the reaction solution became clear and transparent; the reaction was continued under stirring at room temperature for one hour, a white insoluble substance was precipitated out, then the reaction was continued for 10 hours, the reaction solution was filtered and the filter cake was washed with acetonitrile to obtain a white powdery solid, the white powdery solid was weighed as 5.7 g and had a yield of 82%. $^1$H-NMR (400M, DMSO-d6) δ 15.08 (br, 1H), 11.92 (br, 1H), 9.12 (t, 1H), 6.40 (d, J=12.6 Hz, 1H), 6.25 (d, J=12.6 Hz, 1H), 3.16 (t, 2H), 2.20 (t, 2H), 1.54-1.43 (m, 4H), 1.29 (m, 2H). MS m/z 228.2 ([M−H]$^-$).

2) Preparation of (Z)-4-({6-[(2,5-dioxopyrrolidin-1-yl)oxy]-6-oxohexyl}amino)-4-oxo-but-2-enoic acid

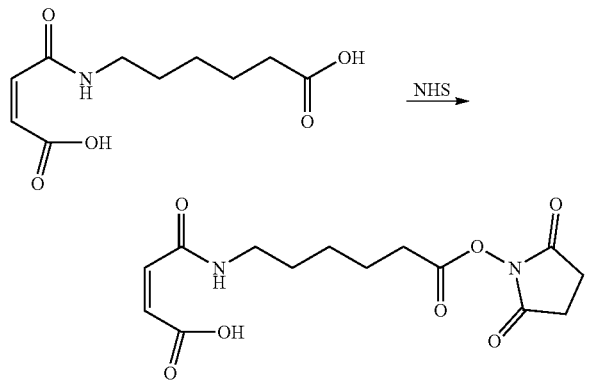

(Z)-6-(3-carboxyacrylamido)hexanoic acid (4.00 g, 17.45 mM, 1 eq) was dissolved in DMF (70 mL) under stirring, then N-hydroxysuccinimide (NHS; 8.03 g, 69.80 mM, 4 eq) was added and stirred at room temperature, and then placed in a −5° C. cold trap to be cooled for 20 minutes, then 2,4,6-trimethylpyridine (9.31 mL, 69.80 mM, 4 eq) was added and continuously stirred for 20 minutes at −5° C., trifluoroacetic anhydride (9.80 mL, 4 eq) was slowly added dropwise within half an hour. After the addition was completed, the reaction solution was dropped into 1 mol/L HCl and extracted with chloroform for 3 to 4 times. The organic phases were combined, washed with water for 3 times, washed with 1 mol/L HCl for 2 times, washed with saturated brine for 3 times, dried over anhydrous magnesium sulfate; and then the organic phase was concentrated to obtain the target product as a white solid, the white solid was dried, and weighed as 5.11 g, which had a yield of 89.74%. $^1$H-NMR (400M, DMSO-d6) δ 15.13 (1H), 9.11 (t, 1H), 6.40 (d, J=12.6 Hz, 1H), 6.25 (d, J=12.6 Hz, 1H), 3.17 (q, 2H), 2.81 (s, 4H), 2.76 (t, 2H), 1.639 (m, 2H), 1.50 (m, 2H), 1.38 (m, 2H). MS m/z 325.4 ([M−H]$^-$); 327.5 ([M+H]$^+$).

3) Preparation of 2,5-dioxopyrrolidin-1-yl (Z)-6-(4-methoxy-4-oxo-but-2-enamido)hexanoate

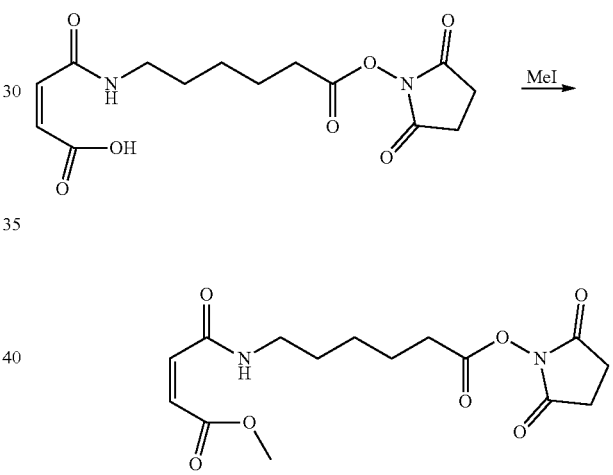

(Z)-4-({6-[(2,5-dioxopyrrolidin-1-yl)oxy]-6-oxohexyl}amino)-4-oxo-but-2-enoic acid (1.50 g, 4.6 mM, 1 eq) was dissolved in DMF (25 mL) under stirring, anhydrous potassium carbonate (1.27 g, 9.2 mM, 2 eq) was added, then iodomethane (1.3 g, 9.2 mM, 2 eq) was added dropwise, and the reaction was carried out at room temperature for 2 hours. After the reaction was completed, the insoluble substance was removed by filtration, the solvent was removed by concentration under reduced pressure, the residue was dissolved in the added ethyl acetate, the resulting mixture was filtered, the filtrate was washed with saturated brine for 3 times, dried over anhydrous magnesium sulfate, concentrated under reduced pressure, and re-dissolved in ethyl acetate, then the resulting solution was mixed with silica gel and purified by column chromatography to obtain the target product as a white solid, the white solid was dried, and weighed as 1.1 g, which had a yield of 66%. $^1$H-NMR (400M, CDCl$_3$) δ 8.21 (br, 1H), 6.35 (d, J=12.6 Hz, 1H), 6.13 (d, J=12.6 Hz, 1H), 3.80 (s, 3H), 3.35 (q, 2H), 2.84 (s, 4H), 2.63 (t, 2H), 1.80 (m, 2H), 1.63 (m, 2H), 1.49 (m, 2H). MS m/z 341.2 ([M+H]$^+$); 363.2 ([M+Na]$^+$).

4) Preparation of methyl (S)-4-[(6-{[2-({5-(hydroxymethyl)-2-[(1-methyl-2-nitro-1H-imidazol-5-yl)methoxy]phenyl}amino)-(methyl)-2-oxoethyl]amino}hexyl)amino]-4-oxo-but-2-enate

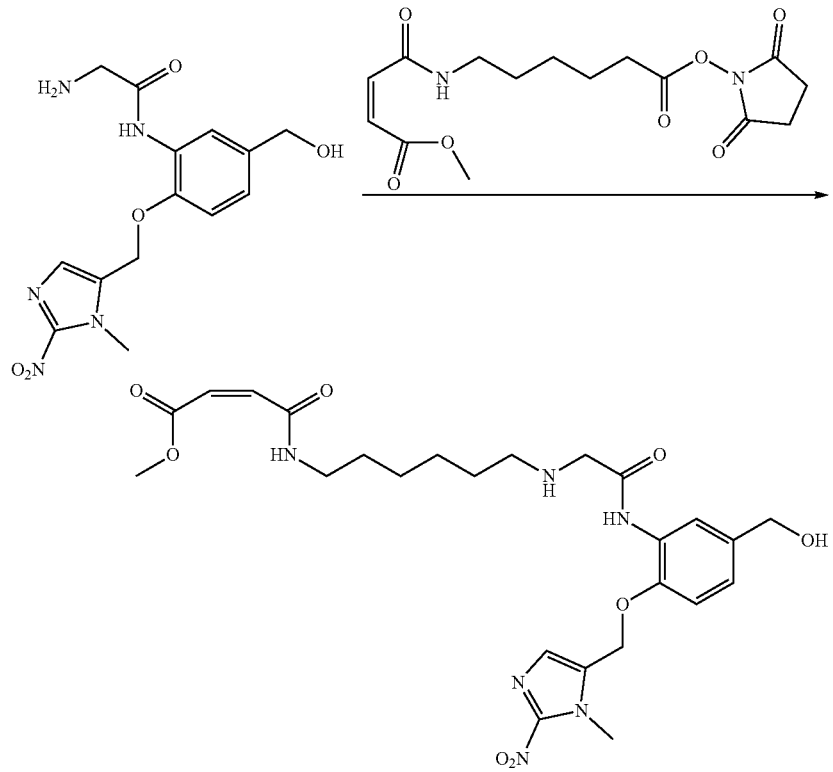

2-Amino-N-[5-hydroxymethyl-2-(3-methyl-2-nitro-3H-imidazol-4-yl-methoxy)-phenyl]-acetamide (crude product, 134 mg, 0.4 mM, 1 eq) was added to a 50 mL eggplant-shaped flask, dissolved in DMF (10 mL), then an excess of DIPEA (103 mg, 0.8 mM, 2 eq) was added and stirred at room temperature for 10 minutes, 2,5-dioxopyrrolidin-1-yl (Z)-6-(4-methoxy-4-oxo-but-2-enamido)hexanoate (136 mg, 0.4 mM, 1 eq) was added, and the reaction was carried out under stirring at room temperature overnight. After the reaction was completed, the reaction solution was concentrated and purified by column chromatography to obtain an orange-yellow viscous oil (crude product, 300 mg, >100% yield). The resulting oil was used directly in the next reaction. MS m/z 561.22 ([M+H]⁺); 583.20 ([M+Na]⁺).

5) Preparation of methyl ((S)-4-{(2-{[2-({2-[(1-methyl-2-nitro-1H-imidazol-5-yl)methoxy]-5-{[(4-nitrophenoxy)carbonyl]oxymethyl}phenyl}amino)-2-oxoethylamino]hexyl}amino)-4-oxo-but-2-enate (L06)

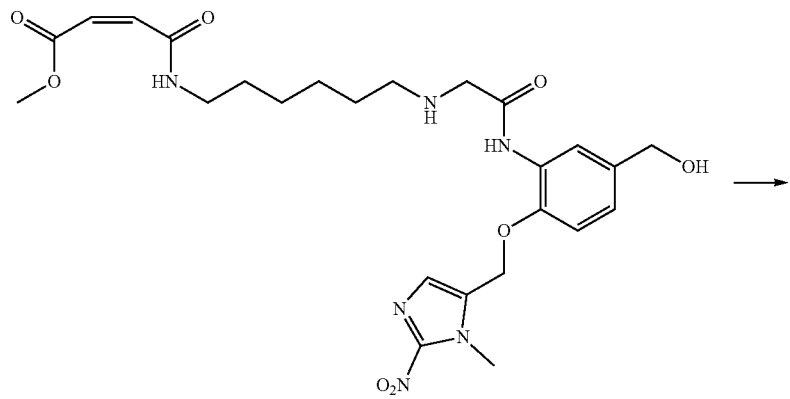

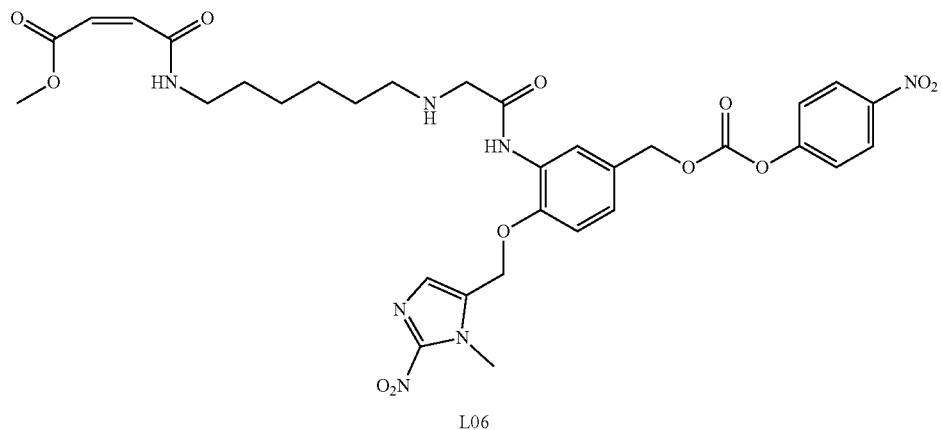

L06

According to the method described in step 17) of Example 1, methyl (S)-4-[(6-{[2-({5-(hydroxymethyl)-2-[(1-methyl-2-nitro-1H-imidazol-5-yl)methoxy]phenyl}amino)-(methyl)-2-oxoethyl]amino}hexyl)amino]-4-oxo-but-2-enate (crude product, 300 mg, 0.535 mM, 1 eq) was dissolved in DMF (10 mL), bis(p-nitrophenyl) carbonate (2 eq) and DIPEA (2 eq) were added in sequence, and the reaction was carried out under stirring for 12 hours at room temperature. After the reaction was completed, the solvent was removed by concentration under reduced pressure. The resulting residue was purified by column chromatography to obtain the target product as a white solid powder (275 mg, 71% yield). $^1$H-NMR (400M, 400M, DMSO-d6) δ 9.06 (s, 1H), 8.36-8.30 (m, 3H), 8.20-8.16 (m, 2H), 7.57 (dt, 2H), 7.41 (s, 1H), 7.30 (m, 1H), 7.22 (dd, 1H), 6.27 (d, J=12.6 Hz, 1H), 6.21 (d, J=12.6 Hz, 1H), 5.33 (s, 2H), 5.24 (s, 2H), 3.99 (s, 3H), 3.87 (d, 2H), 3.62 (s, 3H), 3.04 (m, 2H), 2.01 (m, 2H), 1.41 (m, 4H), 1.23 (m, 2H). MS m/z 726.23 ([M+H]$^+$); 748.22 ([M+Na]$^+$).

6) Preparation of L06-MMAE

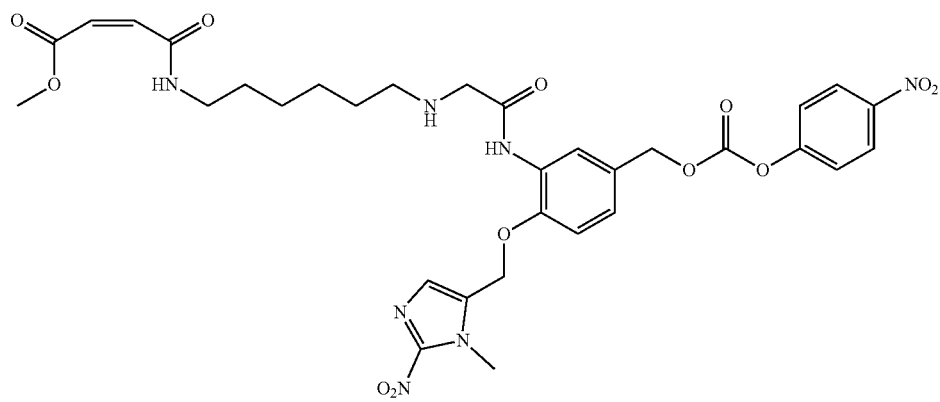

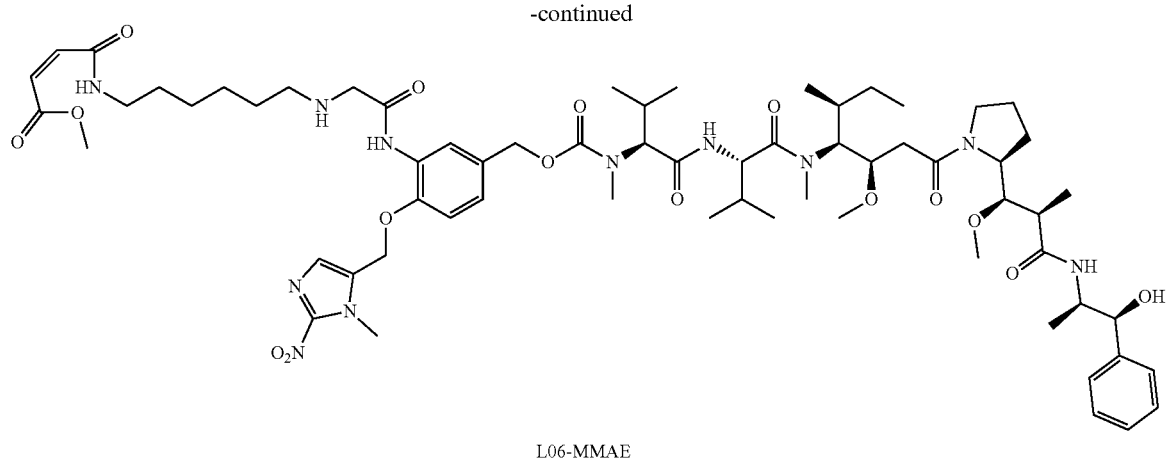

L06-MMAE

According to the method described in step 18) of Example 1, L06 (60.6 mg, 0.084 mmol) was added to a 10 mL eggplant-shaped flask, dissolved in anhydrous DMF (3 mL), and HOBt (9.46 mg, 0.07 mmol), MMAE (50 mg, 0.07 mmol, purchased from Concortis Biosystems) and DIPEA (18.1 mg) were added in sequence, and the reaction was carried out under stirring at room temperature for 18 hours. After the reaction was completed, the solvent was removed by concentration under reduced pressure, and the residue was further purified by column chromatography to obtain the target product as a white solid powder (87 mg; 95% yield). HRMS (ESI) m/z: 1304.7137 [M+H]$^+$; 1326.6957 [M+Na]$^+$.

7) Preparation of ADC-6

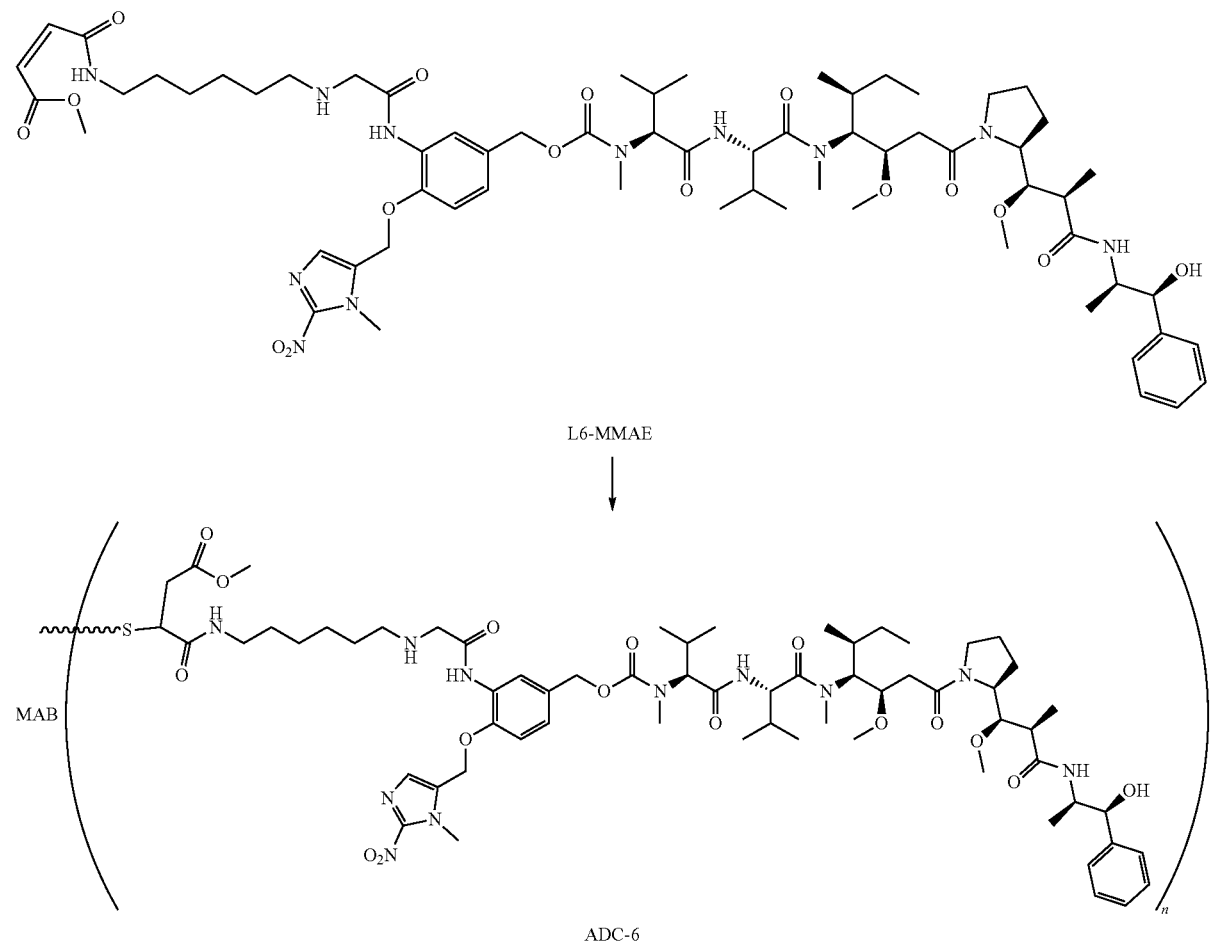

L6-MMAE

↓

ADC-6

According to the method described in step 19) of Example 1, the L06-MMAE conjugate was coupled to anti-HER2 humanized monoclonal antibody mil40 (purchased from Zhejiang Hisun Pharmaceutical Co., Ltd., a biosimilar of Herceptin) to obtain the target antibody-drug conjugate ADC-6, in which MAB represented monoclonal antibody, and the drug to antibody ratio (DAR) n was about 4.

Example 7: Preparation of ADC-7

1) Preparation of 3-(2,5-dioxo-2,5-dihydro-1H-pyrrol-1-yl)-N-{2-[2-(3-{[2-({5-(hydroxylmethyl)-2-[(1-methyl-2-nitro-1H-imidazol-5-yl)methoxy]phenyl}amino)-2-oxoethyl]amino}-3-oxo-propoxy)ethoxy]ethyl}propionamide

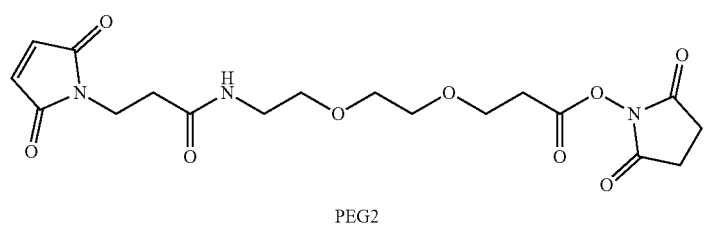
PEG2

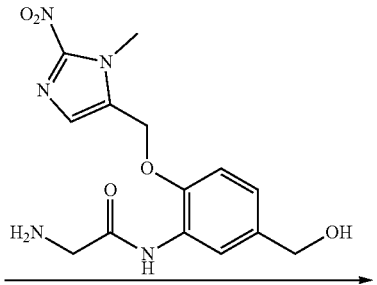

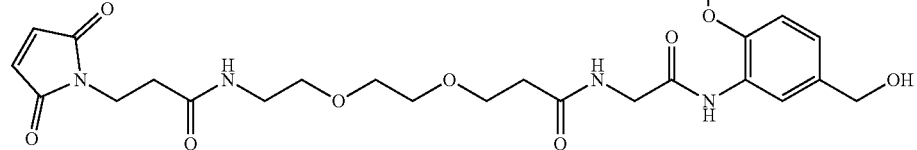

2-Amino-N-[5-hydroxymethyl-2-(3-methyl-2-nitro-3H-imidazol-4-yl-methoxy)-phenyl]-acetamide (200 mg, 0.596 mmol) was added to a 25 mL eggplant-shaped flask, dissolved in DMF (5 mL), then an excess of DIPEA (154 mg, 1.193 mmol) was added, and stirred at room temperature for 10 minutes, then intermediate PEG2 (0.68 g, 2.2 mmol) was added, and the reaction was carried out under stirring overnight at room temperature. After the reaction was completed, the reaction solution was concentrated and purified by column chromatography to obtain a pale yellow viscous oil (crude product, 380 mg, >100% yield). The resulting oil was used directly in the next reaction. MS m/z 646.24 ([M+H]$^+$); 668.22 ([M+Na]$^+$).

2) Preparation of carbonic acid 3-[16-(2,5-dioxo-2, 5-dihydro-1H-pyrrol-1-yl)-4,14-dioxo-7,10-dioxa-3, 13-dialkylamide]-4-[(1-methyl-2-nitro-1H-imidazol-5-yl)methoxy]benzyl ester 4-nitrophenyl ester (L07)

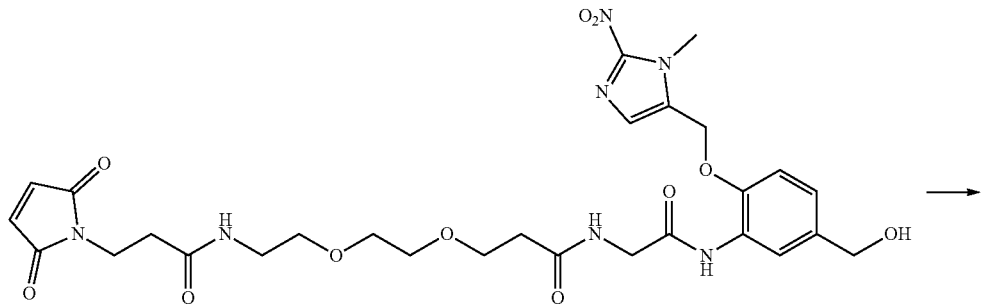

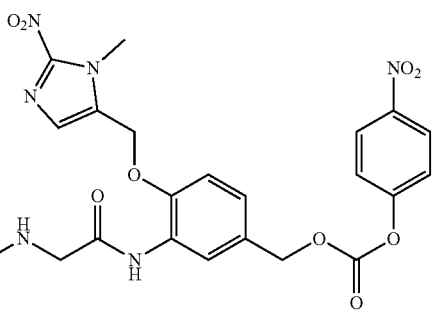

L07

According to the method described in step 17) of Example 1, 3-(2,5-dioxo-2,5-dihydro-1H-pyrrol-1-yl)-N-{2-[2-(3-{[2-({5-(hydroxymethyl)-2-[(1-methyl-2-nitro-1H-imidazol-5-yl) methoxy]phenyl}amino)-2-oxo-ethyl]amino}-3-oxo-propoxy)ethoxy]ethyl}propionamide (crude product, 350 mg, 0.542 mM, 1 eq) was dissolved in DMF (15 mL), bis(p-nitrophenyl) carbonate (2 eq) and DIPEA (2 eq) were added in sequence, and the reaction was carried out under stirring at room temperature for 12 hours. After the reaction was completed, the solvent was removed by concentration under reduced pressure. The resulting residue was purified by column chromatography to obtain the target product as a pale yellow solid powder (180 mg, 0.22 mM, 41% yield). $^1$H-NMR (400M, 400M, DMSO-d6) δ 9.08 (s, 1H), 8.40 (m, 1H), 8.31 (dt, 2H), 8.12 (s, 1H), 8.02 (t, 1H), 7.56 (dt, 2H), 7.41 (s, 1H), 7.30 (m, 1H), 7.23 (dd, 1H), 7.00 (s, 2H), 5.33 (s, 2H), 5.24 (s, 2H), 3.99 (s, 3H), 3.89 (d, 2H), 3.65-3.45 (m, 10H), 3.14 (m, 4H), 2.30 (m, 4H). MS m/z 811.24 ([M+H]$^+$); 833.22 ([M+Na]$^+$).

3) Preparation of L07-MMAE

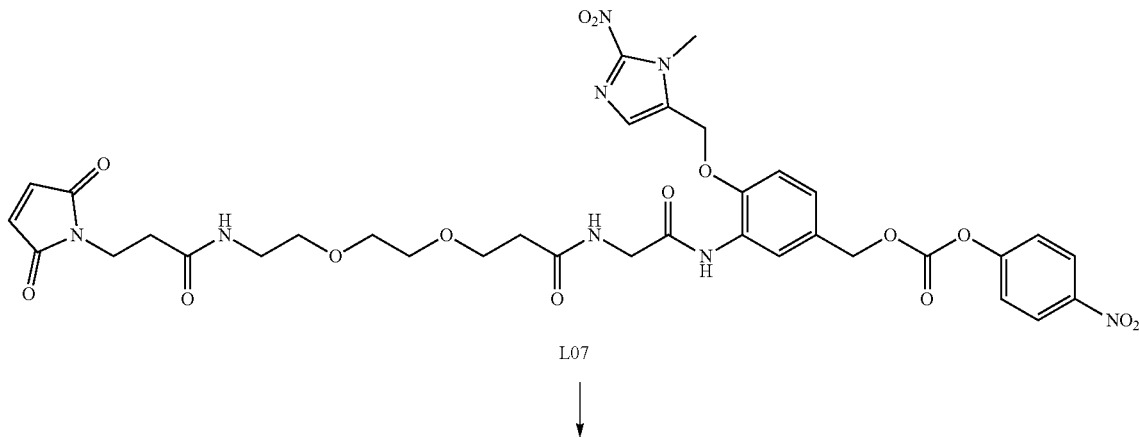

L07

-continued

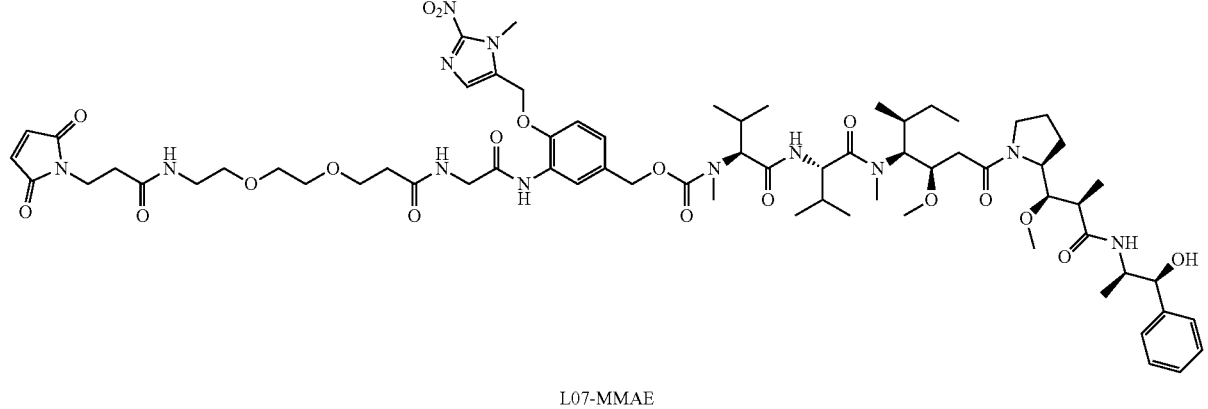

L07-MMAE

According to the method described in step 18) of Example 1, L07 (68.1 mg, 0.084 mmol) was added to a 10 mL eggplant-shaped flask, dissolved in anhydrous DMF (5 mL), then HOBt (9.46 mg, 0.07 mmol), MMAE (50 mg, 0.07 mmol, purchased from Concortis Biosystems) and DIPEA (18.1 mg) were added in sequence, and the reaction was carried out under stirring at room temperature for 18 hours. After the reaction was completed, the solvent was removed by concentration under reduced pressure, and the residue was further purified by column chromatography to obtain the target product as a white solid powder (76 mg, 78% yield). HRMS (ESI) m/z: 1389.7299 [M+H]$^+$; 1411.7091 [M+Na]$^+$.

4) Preparation of ADC-7

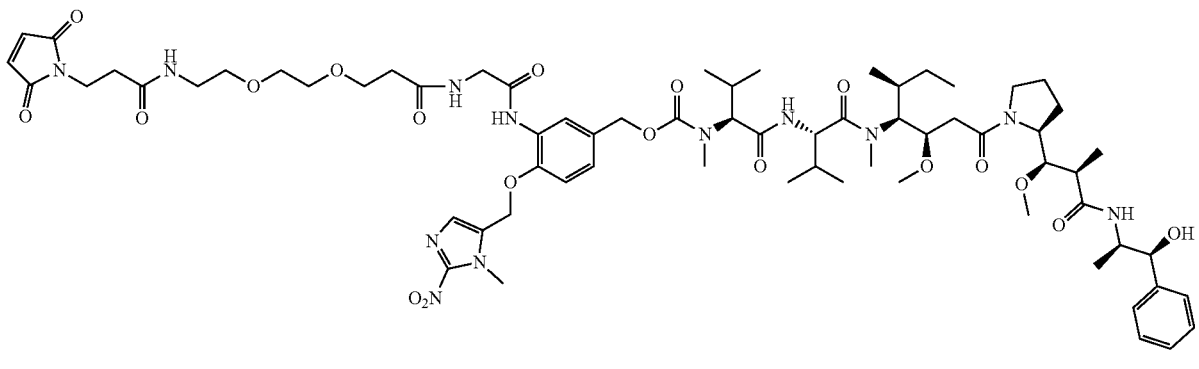

L7-MMAE

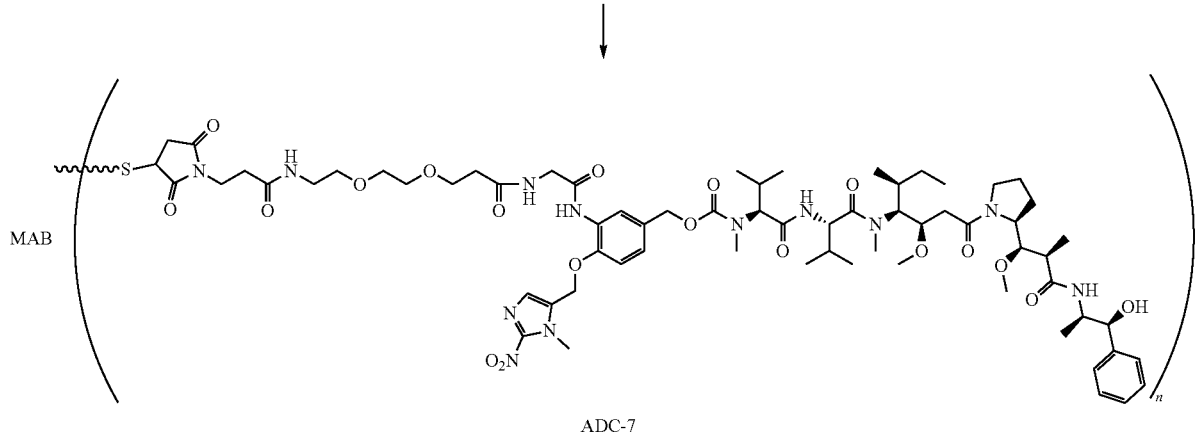

ADC-7

According to the method described in step 19) of Example 1, the L07-MMAE conjugate was coupled to anti-HER2 humanized monoclonal antibody mil40 (purchased from Zhejiang Hisun Pharmaceutical Co., Ltd., a biosimilar of Herceptin) to obtain the target antibody-drug conjugate ADC-7, in which MAB represented monoclonal antibody, and the drug to antibody ratio (DAR) n was about 4.

Example 8: Preparation of ADC-8

1) Preparation of 1-[3-(2,5-dioxo-2,5-dihydro-1H-pyrrol-1-yl)propionylamino]-N-(2-{[5-(hydroxymethyl)-2-(1-methyl-2-nitro-1H-imidazol-5-yl)methoxy)phenyl]amino}-2-oxoethyl-3,6,9,12-tetraoxa-pentadecane-15-amide

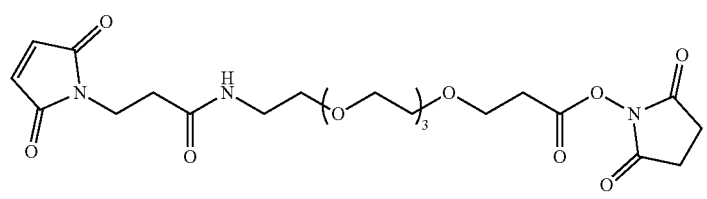
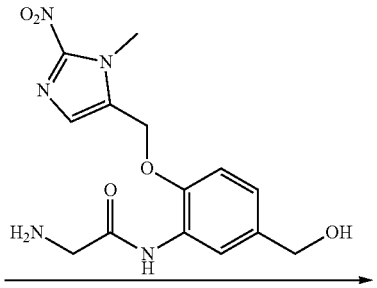

PEG4

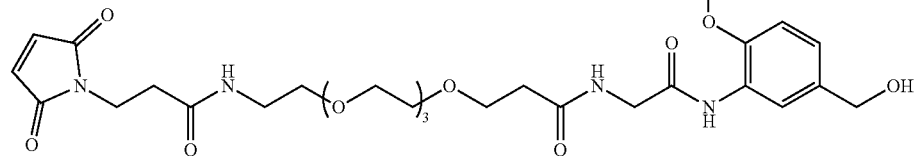

2-Amino-N-[5-hydroxymethyl-2-(3-methyl-2-nitro-3H-imidazol-4-yl-methoxy)-phenyl]-acetamide (134 mg, 0.4 mmol) was added to a 25 mL eggplant-shaped flask, dissolved in DMF (10 mL), an excess of DIPEA (103 mg, 1.193 mmol) was added and stirred at room temperature for 10 minutes, then the intermediate PEG4 (205 mg, 0.4 mmol) was added, and the reaction was carried out under stirring overnight at room temperature. After the reaction was completed, the reaction solution was concentrated and purified by column chromatography to obtain a pale yellow viscous oil (crude product, 400 mg, >100% yield). The resulting oil was used directly in the next reaction. MS m/z 734.30 ([M+H]$^+$); 756.28 ([M+Na]$^+$).

2) Preparation of carbonic acid 3-[22-(2,5-dioxo-2,5-dihydro-1H-pyrrol-1-yl)-4,20-dioxo-7,10,13,16-tetraoxa-3,19-diaza-dibenzamide]-4-[(1-methyl-2-nitro-1H-imidazol-5-yl)methoxy]-benzyl ester 4-nitrophenyl ester (L08)

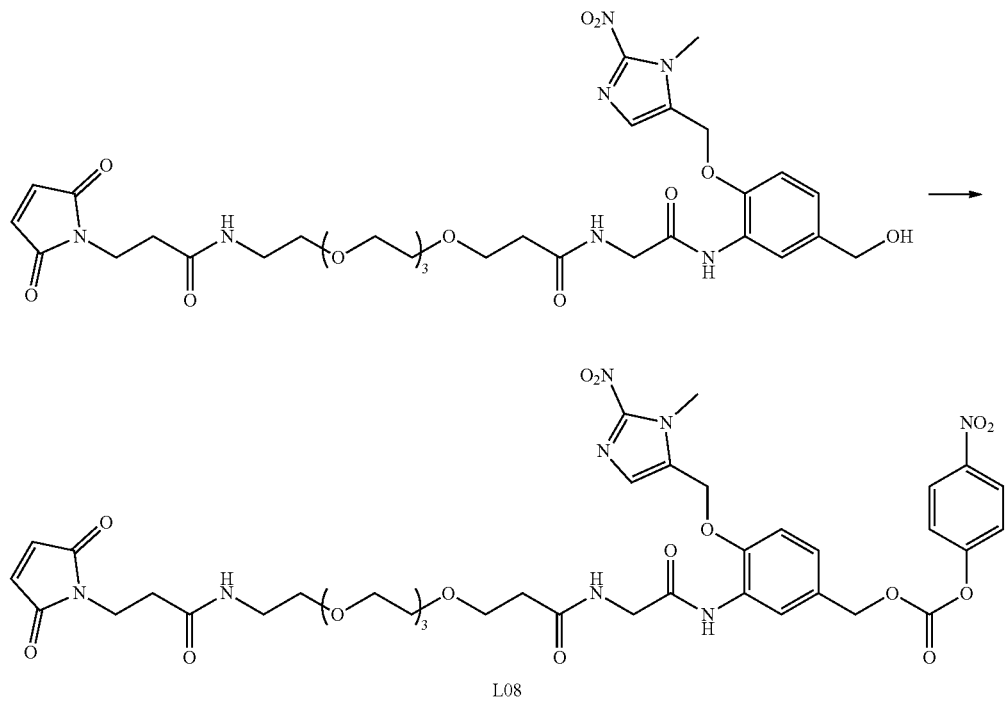

L08

According to the method described in step 17) of Example 1, 1-[3-(2,5-dioxo-2,5-dihydro-1H-pyrrol-1-yl)propionylamino]-N-(2-{[5-(hydroxymethyl)-2-(1-methyl-2-nitro-1H-imidazol-5-yl)methoxy)phenyl]amino}-2-oxoethyl-3,6,9,12-tetraoxa-pentadecane-15-amide (crude product, 0.4 mM, 1 eq) was dissolved in DMF (10 mL), bis(p-nitrophenyl) carbonate (2 eq) and DIPEA (2 eq) were added in sequence, and the reaction was carried out under stirring at room temperature for 12 hours. After the reaction was completed, the solvent was removed by concentration under reduced pressure, the resulting residue was purified by column chromatography to obtain the target product as a yellow oil (200 mg, 0.22 mM, 56% yield). $^1$H-NMR (400M, 400M, DMSO-d6) δ 9.08 (s, 1H), 8.40 (m, 1H), 8.31 (dt, 2H), 8.12 (s, 1H), 8.02 (t, 1H), 7.56 (dt, 2H), 7.41 (s, 1H), 7.30 (m, 1H), 7.23 (dd, 1H), 7.00 (s, 2H), 5.33 (s, 2H), 5.24 (s, 2H), 3.99 (s, 3H), 3.89 (d, 2H), 3.65-3.45 (m, 18H), 3.14 (m, 4H), 2.30 (m, 4H). MS m/z 899.31 ([M+H]$^+$); 921.29 ([M+Na]$^+$).

3) Preparation of L08-MMAE

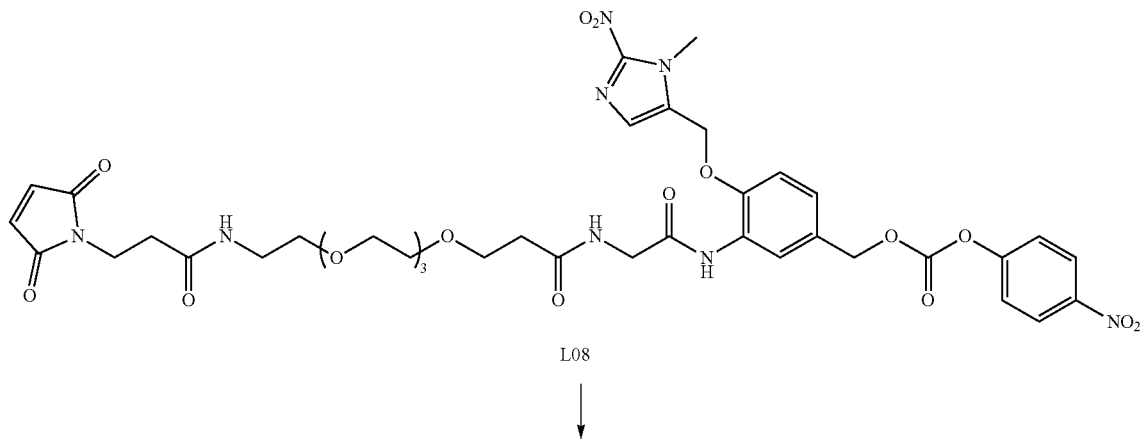

L08

-continued

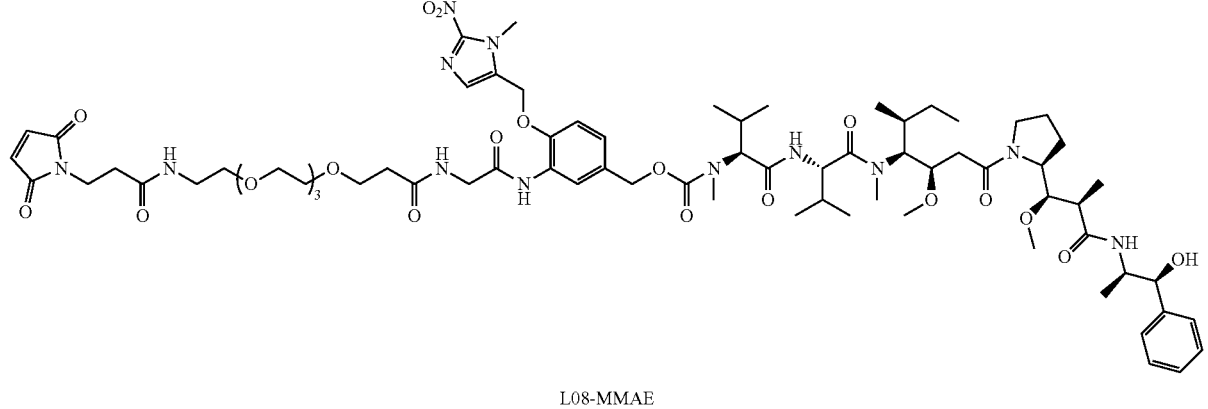

L08-MMAE

According to the method described in step 18) of Example 1, L08 (75.5 mg, 0.084 mmol) was added to a 10 mL eggplant-shaped flask, dissolved in anhydrous DMF (5 mL), then HOBt (9.46 mg, 0.07 mmol), MMAE (50 mg, 0.07 mmol, purchased from Concortis Biosystems) and DIPEA (18.1 mg) were added in sequence, and the reaction was carried out under stirring at room temperature for 18 hours. After the reaction was completed, the solvent was removed by concentration under reduced pressure, and the residue was further purified by column chromatography to obtain the target product as a white solid powder (50.7 mg; 49% yield). HRMS (ESI) m/z: 739.3961 $[M+2H]^{2+}$; 750.3850 $[M+H+Na]^{2+}$; 761.3793 $[M+2Na]^{2+}$.

4) Preparation of ADC-8

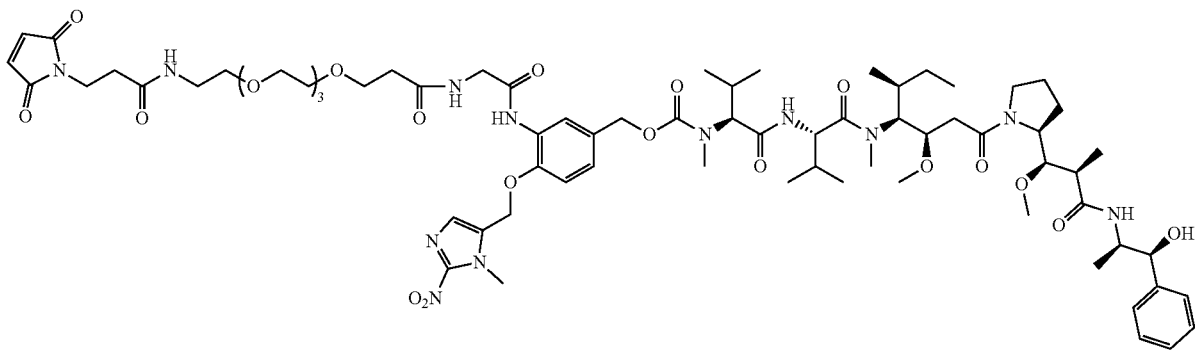

L8-MMAE

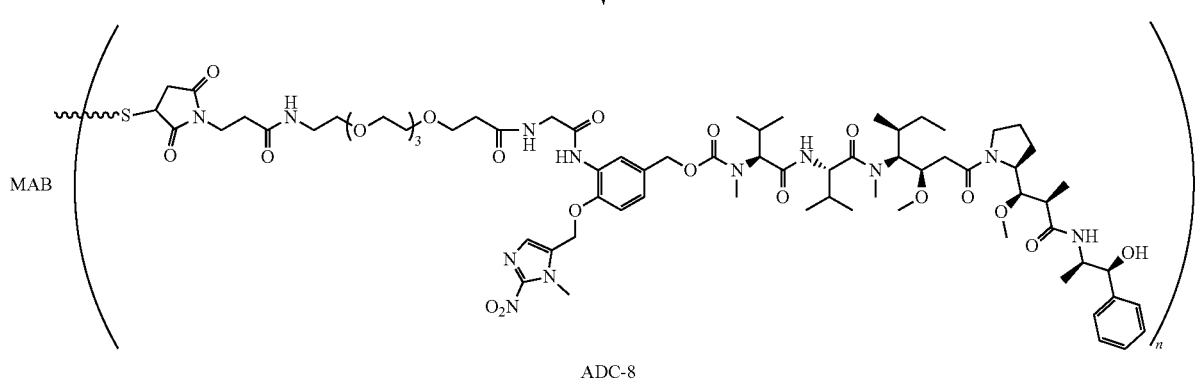

ADC-8

According to the method described in step 19) of Example 1, the L08-MMAE conjugate was coupled to anti-HER2 humanized monoclonal antibody mil40 (purchased from Zhejiang Hisun Pharmaceutical Co., Ltd., a biosimilar of Herceptin) to obtain the target antibody-drug conjugate ADC-8, in which MAB represented monoclonal antibody, and the drug to antibody ratio (DAR) n was about 4.

Example 9: Preparation of ADC-9

1) Preparation of 1-(3-(2,5-dioxo-2,5-dihydro-1H-pyrrol-1-yl)propanamido)-N-(2-((5-(hydroxymethyl)-2-((1-methyl-2-nitro-1H-imidazol-5-yl)methoxy)phenyl)amino)-2-oxoethyl)-3,6,9,12,15,18-hexaoxahenicosan-21-amide

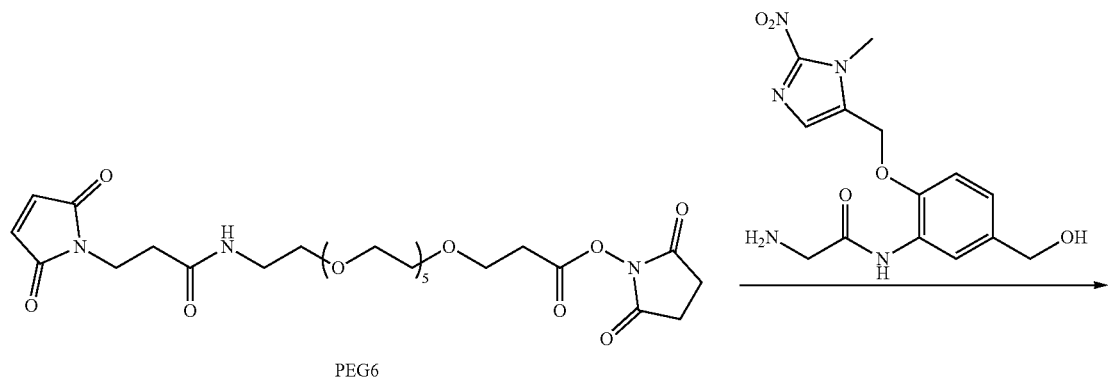

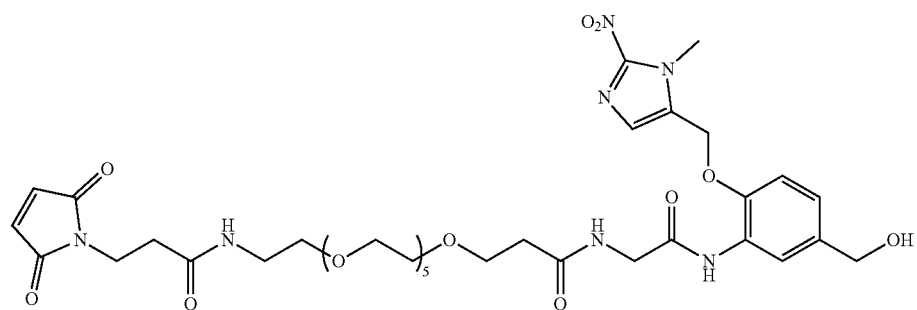

2-Amino-N-[5-hydroxymethyl-2-(3-methyl-2-nitro-3H-imidazol-4-yl-methoxy)-phenyl]-acetamide (134 mg, 0.4 mmol) was added to a 25 mL eggplant-shaped flask, dissolved in DMF (10 mL), an excess of DIPEA (103 mg, 1.193 mmol) was added and stirred for 10 minutes at room temperature, then the intermediate PEG6 (240.64 mg, 0.4 mmol) was added, and the reaction was carried out under stirring overnight at room temperature. After the reaction was completed, the reaction solution was concentrated and purified by column chromatography to obtain a pale yellow viscous oil (crude product, 400 mg, >100% yield). The resulting oil was used directly in the next reaction. MS m/z 822.36 ([M+H]$^+$); 844.33 ([M+Na]$^+$).

2) Preparation of carbonic acid 3-[28-(2,5-dioxo-2,5-dihydro-1H-pyrrol-1-yl)-4,26-dioxo-7,10,13,16,19,22-hexaoxa-3,25-amide]-4-[(1-methyl-2-nitro-1H-imidazol-5-yl)methoxy]benzyl ester 4-nitrophenyl ester (L09)

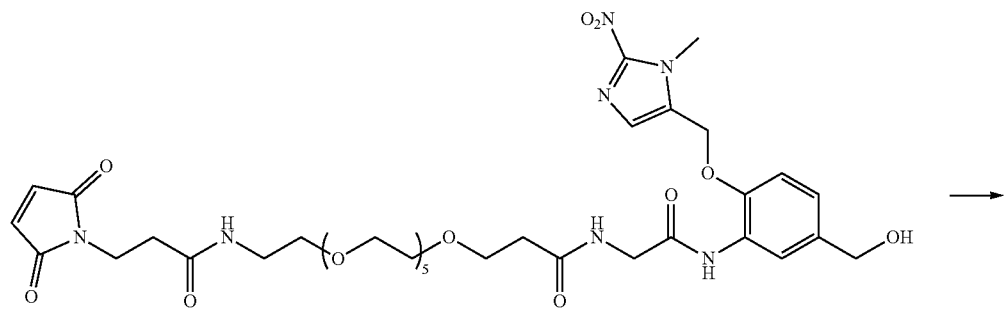

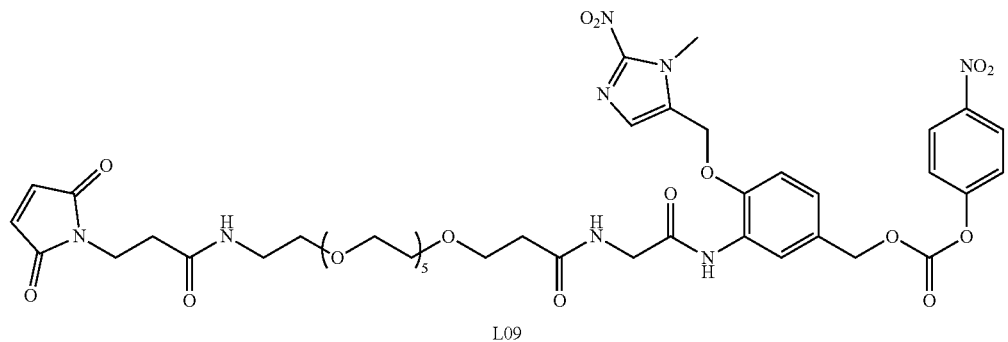

According to the method described in step 17) of Example 1, 1-(3-(2,5-dioxo-2,5-dihydro-1H-pyrrol-1-yl)propanamido)-N-(2-((5-(hydroxymethyl)-2-((1-methyl-2-nitro-1H-imidazol-5-yl)methoxy)phenyl)amino)-2-oxoethyl)-3,6,9,12,15,18-hexaoxahenicosan-21-amide (crude product, 329 mg, 0.4 mM, 1 eq) was dissolved in DMF (10 mL), bis(p-nitrophenyl) carbonate (2 eq) and DIPEA were added (2 eq) in sequence, and the reaction was carried out under stirring at room temperature for 12 hours. After the reaction was completed, the solvent was removed by concentration under reduced pressure, the residue was purified by column chromatography to obtain the target product as a yellow oil (130 mg, 33% yield). $^1$H-NMR (400M, 400M, DMSO-d6) δ 9.08 (s, 1H), 8.40 (m, 1H), 8.31 (dt, 2H), 8.12 (s, 1H), 8.02 (t, 1H), 7.56 (dt, 2H), 7.41 (s, 1H), 7.30 (m, 1H), 7.23 (dd, 1H), 7.00 (s, 2H), 5.33 (s, 2H), 5.24 (s, 2H), 3.99 (s, 3H), 3.89 (d, 2H), 3.65-3.45 (m, 26H), 3.14 (m, 4H), 2.30 (m, 4H). MS m/z 987.36 ([M+H]$^+$); 1009.34 ([M+Na]$^+$).

3) Preparation of L09-MMAE

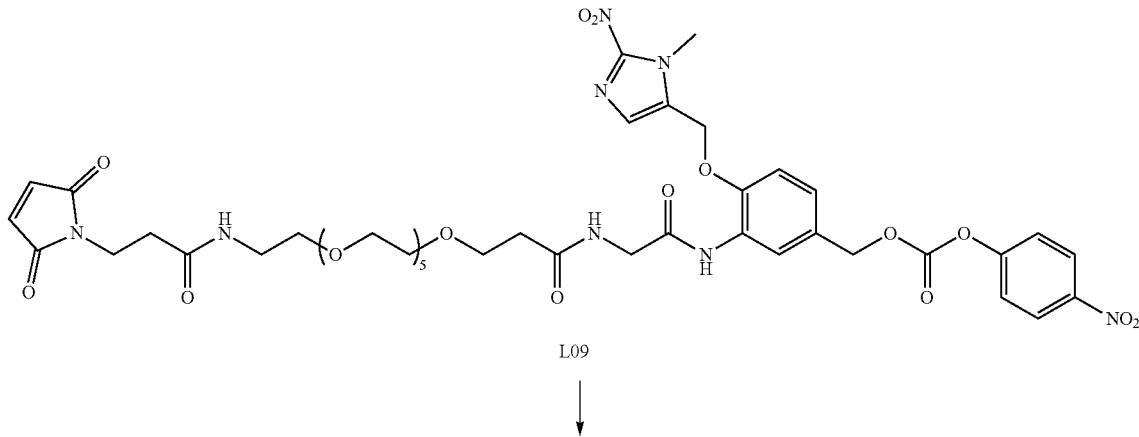

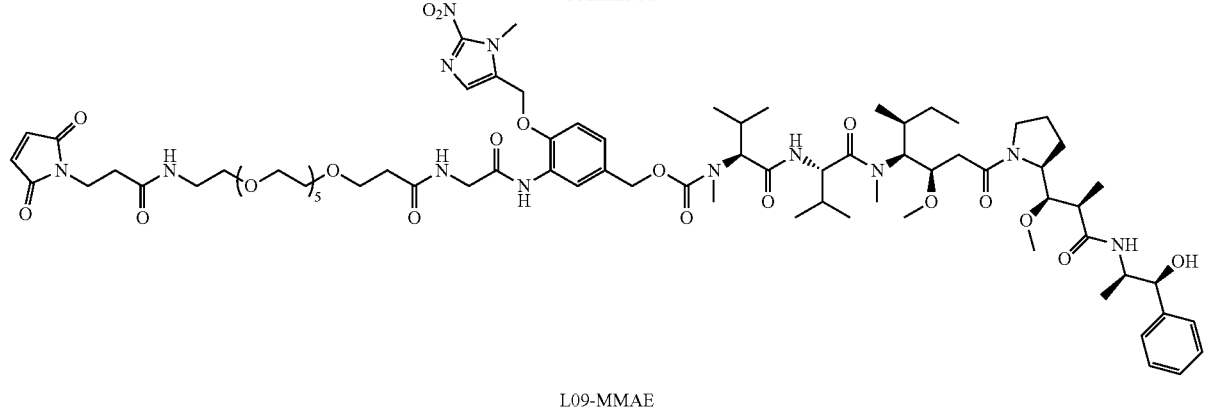

L09-MMAE

According to the method described in step 18) of Example 1, L09 (82.9 mg, 0.084 mmol) was added to a 10 mL eggplant-shaped flask, dissolved in anhydrous DMF (5 mL), HOBt (9.46 mg, 0.07 mmol), MMAE (50 mg, 0.07 mmol, purchased from Concortis Biosystems) and DIPEA (18.1 mg) were added in sequence, and the reaction was carried out under stirring at room temperature for 18 hours. After the reaction was completed, the solvent was removed by concentration under reduced pressure, and the residue was further purified by column chromatography to obtain the target product as a white solid powder (42 mg; 38% yield). HRMS (ESI) m/z: 1587.8142 [M+Na]$^+$; 783.4223 [M+2H]$^{2+}$.

4) Preparation of ADC-9

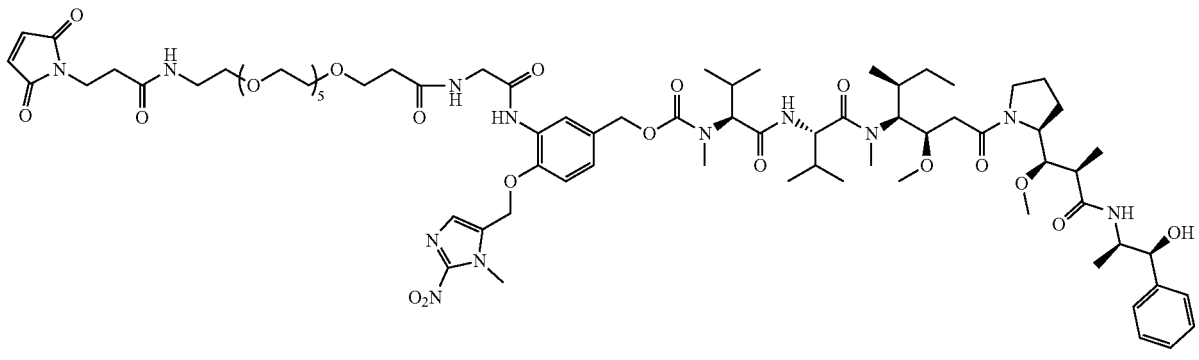

L9-MMAE

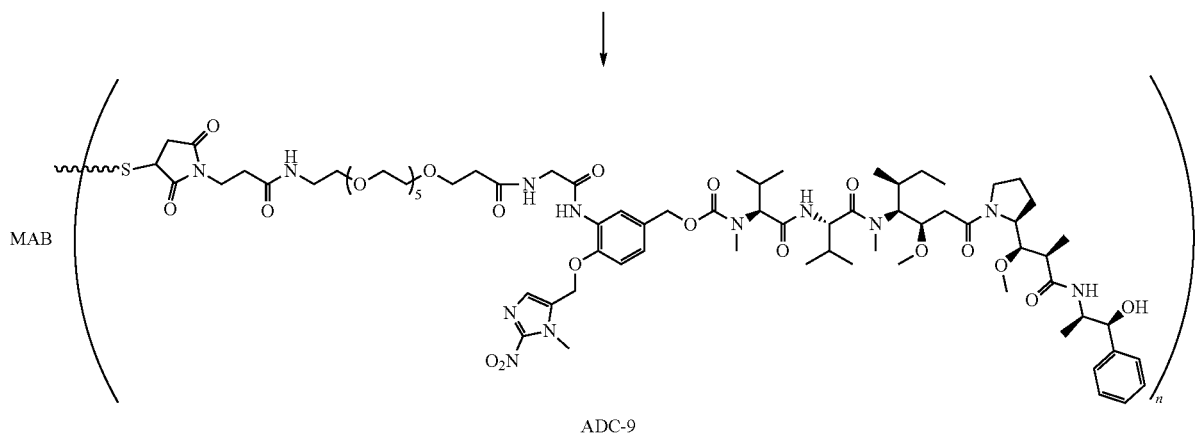

ADC-9

According to the method described in step 19) of Example 1, the L09-MMAE conjugate was coupled to anti-HER2 humanized monoclonal antibody mil40 (purchased from Zhejiang Hisun Pharmaceutical Co., Ltd., a biosimilar of Herceptin) to obtain the target antibody-drug conjugate ADC-9, in which MAB represented monoclonal antibody, and the drug to antibody ratio (DAR) n was about 4.

Example 10: Preparation of ADC-10

1) Preparation of 1-(3-(2,5-dioxo-2,5-dihydro-1H-pyrrol-1-yl)propanamido)-N-(2-((5-(hydroxymethyl)-2-((1-methyl-2-nitro-1H-imidazol-5-yl)methoxy)phenyl)amino)-2-oxoethyl)-3,6,9,12,15,18,21,24-octaoxaheptacosan-27-amide

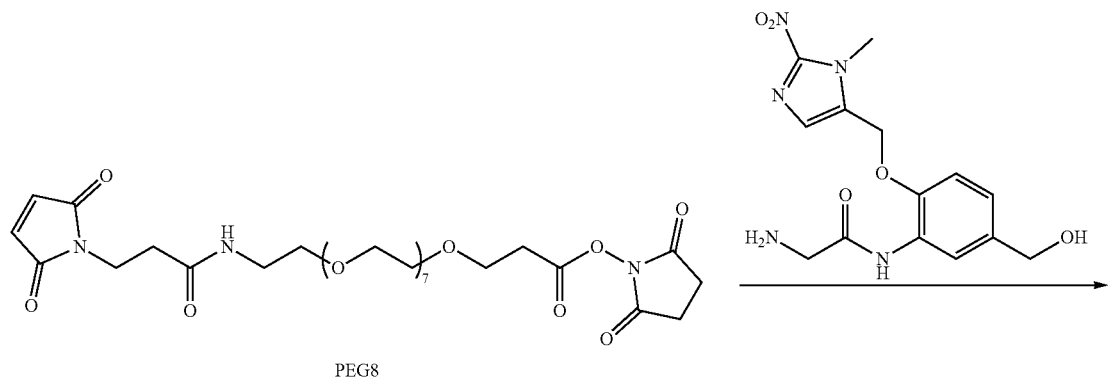

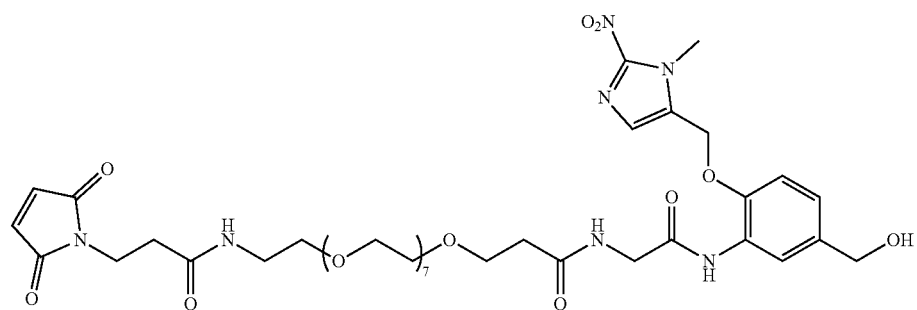

2-Amino-N-[5-hydroxymethyl-2-(3-methyl-2-nitro-3H-imidazol-4-yl-methoxy)-phenyl]-acetamide (134 mg, 0.4 mmol) was added to a 25 mL eggplant-shaped flask, dissolved in DMF (10 mL), an excess of DIPEA (103 mg, 1.193 mmol) was added and stirred for 10 minutes at room temperature, then the intermediate PEG8 (276 mg, 0.4 mmol) was added, and the reaction was carried out under stirring overnight at room temperature. After the reaction was completed, the reaction solution was concentrated and purified by column chromatography to obtain a pale yellow viscous oil (crude product, 410 mg, >100% yield). The resulting oil was used directly in the next reaction. MS m/z 910.41 ([M+H]$^+$); 932.39 ([M+Na]$^+$).

2) Preparation of carbonic acid 3-[34-(2,5-dioxo-2,
5-dihydro-1H-pyrrol-1-yl)-4,32-dioxo-7,10,13,16,19,
22,25,28-octaoxa-3,31-diaza-triazaamido]-4-[(1-
methyl-2-nitro-1H-imidazol-5-yl)methoxy]benzyl
ester 4-nitrophenyl ester (L10)

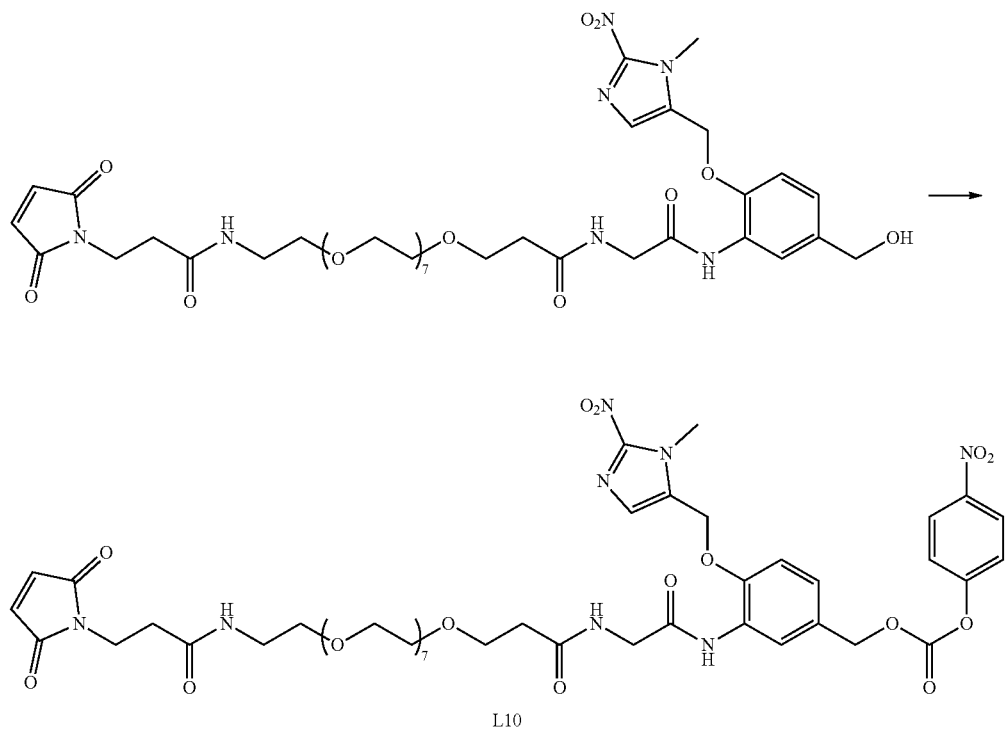

According to the method as described in the step 17) of Example 1, 1-(3-(2,5-dioxo-2,5-dihydro-1H-pyrrol-1-yl)propanamido)-N-(2-((5-(hydroxymethyl)-2-((1-methyl-2-nitro-1H-imidazol-5-yl)methoxy)phenyl)amino)-2-oxoethyl)-3,6,9,12,15,18,21,24-octaoxaheptacosan-27-amide (410 mg, 0.45 mM) was dissolved in DMF (10 mL), bis(p-nitrophenyl) carbonate (2 eq) and DIPEA (2 eq) were added in sequence, and the reaction was carried out under stirring at room temperature for 12 hours. After the reaction was completed, the solvent was removed by concentration under reduced pressure, the residue was purified by column chromatography to obtain the target product as a yellow oil (280 mg, 58% yield). $^1$H-NMR (400M, 400M, DMSO-d6) δ 9.07 (s, 1H), 8.41 (m, 1H), 8.31 (dt, 2H), 8.13 (s, 1H), 8.04 (t, 1H), 7.57 (dt, 2H), 7.41 (s, 1H), 7.31 (m, 1H), 7.23 (dd, 1H), 7.00 (s, 2H), 5.34 (s, 2H), 5.24 (s, 2H), 3.99 (s, 3H), 3.90 (d, 2H), 3.65-3.46 (m, 32H), 3.15 (m, 4H), 2.31 (m, 4H). MS m/z 1075.40 ([M+H]$^+$); 1097.38 ([M+Na]$^+$).

3) Preparation of L10-MMAE

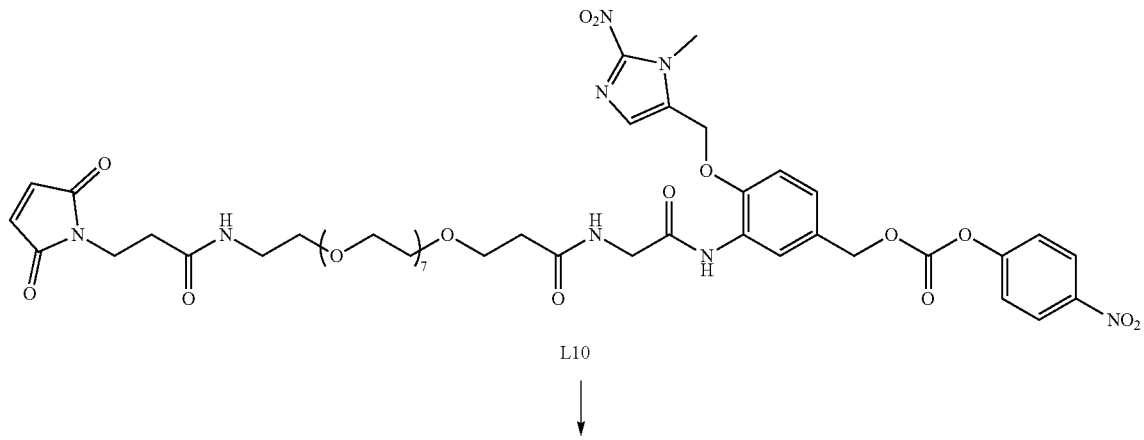

-continued

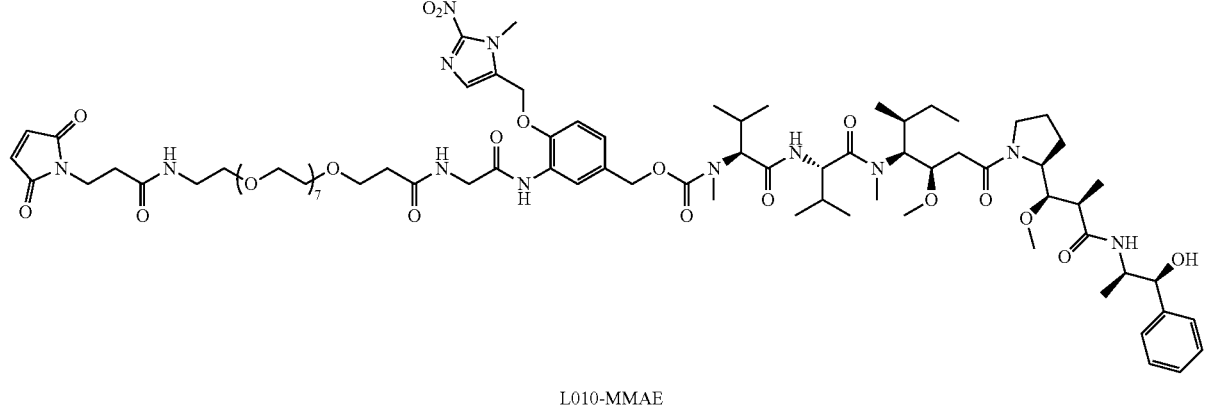

L010-MMAE

According to the method described in step 18) of Example 1, L09 (90.3 mg, 0.084 mmol) was added to a 10 mL eggplant-shaped flask, dissolved in anhydrous DMF (5 mL), then HOBt (9.46 mg, 0.07 mmol), MMAE (50 mg, 0.07 mmol, purchased from Concortis Biosystems) and DIPEA (18.1 mg) were added in sequence, and the reaction was carried out under stirring at room temperature for 18 hours. After the reaction was completed, the solvent was removed by concentration under reduced pressure, and the residue was further purified by column chromatography to obtain the target product as a white solid powder (72 mg; 62% yield). HRMS (ESI) m/z: 827.4484 $[M+2H]^{2+}$; 838.4369 $[M+H+Na]^{2+}$; 849.4286 $[M+2Na]^{2+}$.

4) Preparation of ADC-10

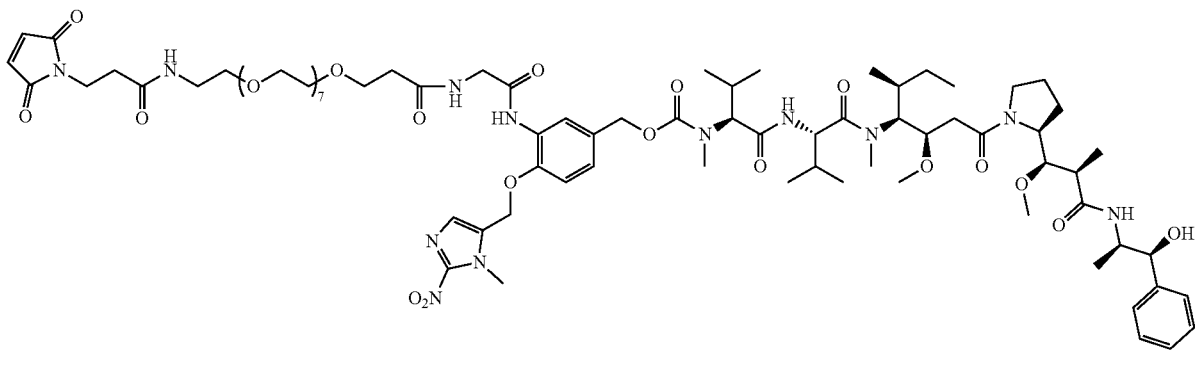

L10-MMAE

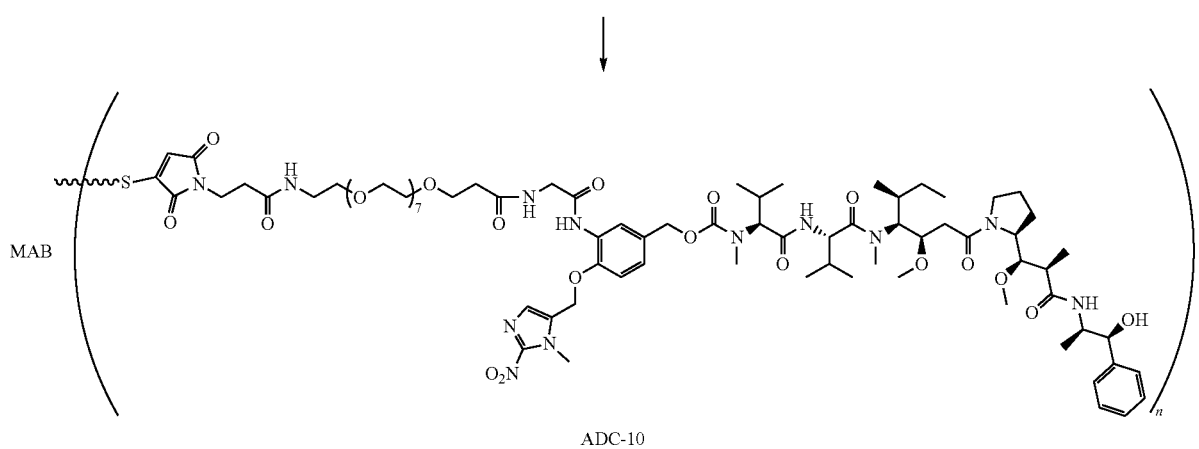

ADC-10

According to the method described in step 19) of Example 1, the L10-MMAE conjugate was coupled to anti-HER2 humanized monoclonal antibody mil40 (purchased from Zhejiang Hisun Pharmaceutical Co., Ltd., which was a biosimilar of Herceptin) to obtain the target antibody-drug conjugate ADC-10, in which MAB represented monoclonal antibody, and the drug to antibody ratio (DAR) n was about 4.

Example 11: Preparation of Antibody-Linker-(Toxin Substitute) Conjugate

1) The Preparation Route and Structure of the Toxin Substitute were as Follows

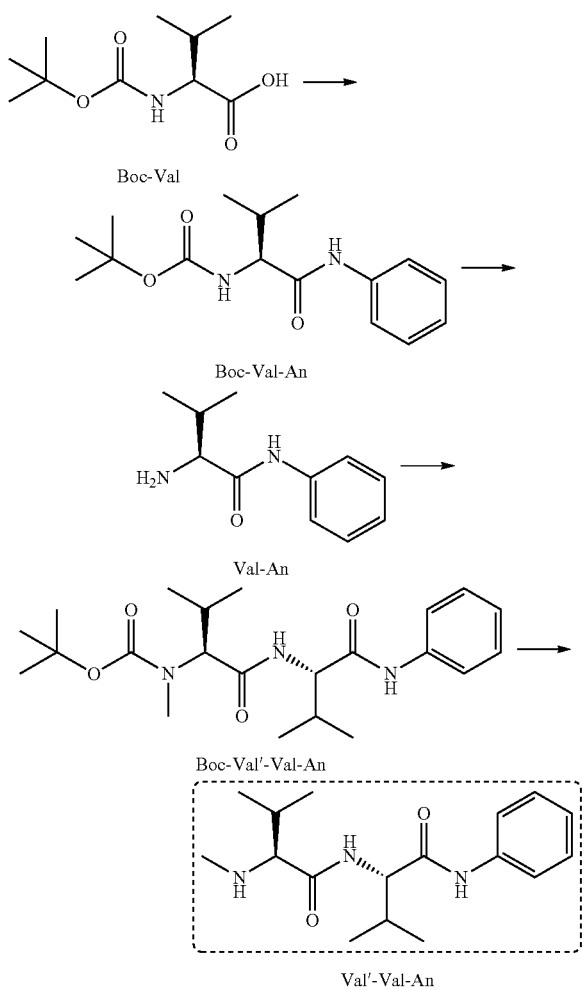

① Preparation of Boc-Val-An

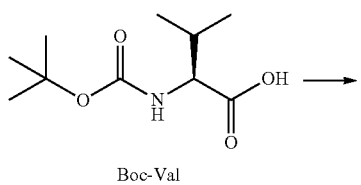

Boc-Val

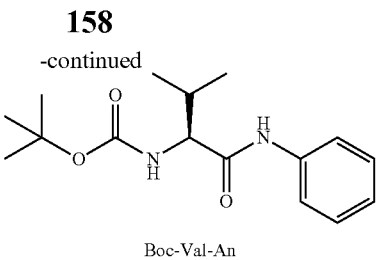

Boc-Val-An

N-Boc-valine (Boc-Val, 2.17 g, 10 mmol/L) was dissolved in anhydrous THF (30 mL), then aniline (0.93 g, 10 mmol/L) and DCC (2.39 g, 11 mmol/L) were added, the reaction was carried out under stirring overnight at room temperature. After the reaction was completed, the insoluble solid by-product dicyclohexylurea (DCU) was removed by filtration, and the obtained filtrate was concentrated under reduced pressure and further purified by column chromatography to obtain the target product as a white solid powder (2.2 g, 75% yield). $^1$H-NMR (400 MHz, DMSO-d6) δ 9.98 (s, 1H), 7.60 (d, J=7.6 Hz, 2H), 7.30 (d, J=8.0 Hz, 2H), 7.04 (t, J=7.4 Hz, 1H), 6.90 (d, J=8.4 Hz, 1H), 3.91 (t, J=7.0 Hz, 1H), 1.96 (m, 1H), 1.39 (s, 9H), 0.88 (d, J=6.7 Hz, 6H). MS (ESI) m/z: 293.1 [M+H]$^+$; 315.2 [M+Na]$^+$.

② Preparation of Val-An

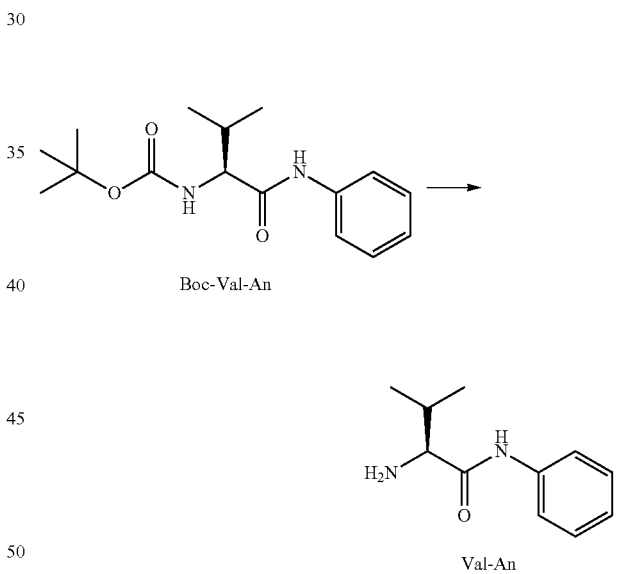

The product Boc-Val-An (5.85 g, 20 mmol/L) obtained in step ① was dissolved in DCM (50 mL), then TFA (12.5 mL) was added to the reaction solution, and the reaction was carried out under stirring overnight at room temperature. After the reaction was completed, the reaction solution was concentrated under reduced pressure and further purified by column chromatography to obtain the target product as a pale yellow oily liquid (2.8 g, 88% yield). $^1$H-NMR (400 MHz, DMSO-d6) δ 9.84 (br, 1H), 7.63 (dd, J=8.7 Hz, 2H), 7.30 (d, J=8.0 Hz, 2H), 7.03 (td, J=7.4 Hz, 1H), 3.10 (d, J=5.6 Hz, 1H), 1.93 (m, 1H), 0.88 (d, J=6.7 Hz, 6H). MS (ESI) m/z: 193.1 [M+H]$^+$; 215.1 [M+Na]$^+$.

③ Preparation of Boc-Val'-Val-An

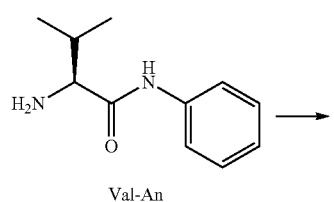

Val-An

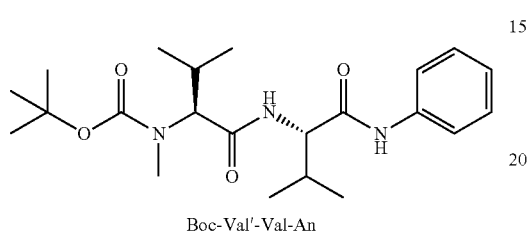

Boc-Val'-Val-An

④ Preparation of Val'-Val-An

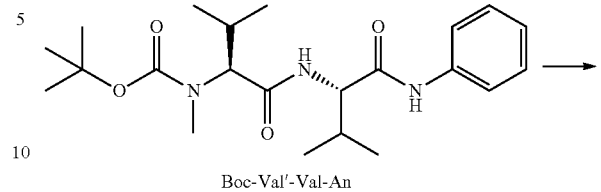

Boc-Val'-Val-An

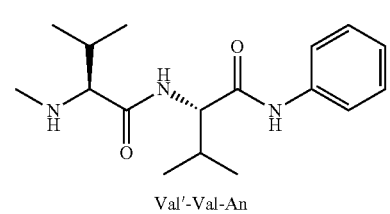

Val'-Val-An

N-methyl-N-Boc-valine (Val', 0.58 g, 2.5 mmol/L) was dissolved in DCM (10 mL), then EDCI (0.58 g, 3 mmol/L), HOBt (0.41 g, 3 mmol/L) and DIPEA (0.51 mL, 3.0 mmol/L) were added in sequence, and the reaction was carried out under stirring at room temperature for 1 hour, then Val-An (0.48 g, 2.5 mmol/L) was added, and the reaction was continued under stirring overnight at room temperature. After the reaction was completed, the solvent was removed by concentration, a crude product was obtained, the crude product was further dried to obtain a pale pink solid powder (0.43 g, 42% yield). $^1$H-NMR (400 MHz, DMSO-d6) δ 10.11 (d, 1H), 7.95 (d, J=8.3 Hz, 2H), 7.58 (d, J=7.6 Hz, 2H), 7.31 (t, J=8.0 Hz, 2H), 7.05 (t, J=7.4 Hz, 3H), 4.23 (t, J=9.4 Hz, 2H), 2.77 (s, 1H), 2.04 (m, 2H), 1.43 (s, 9H), 0.87-0.78 (m, 12H). MS (ESI) m/z: 406.2 [M+H]$^+$; 428.3 [M+Na]$^+$.

Boc-Val'-Val-An (0.42 g, 1.04 mmol/L) obtained in step ③ was dissolved in DCM (5 mL), then TFA (1.25 mL) was added to the reaction solution, and the reaction was carried out under stirring at room temperature for 3 hours. After the reaction was completed, the reaction solution was concentrated under reduced pressure, the residue was re-dissolved with ethyl acetate and washed twice with saturated sodium bicarbonate, and then concentrated, the product was recrystallized from ethyl acetate to obtain the product as a white powdery solid (0.31 g, 99% yield). $^1$H-NMR (400 MHz, DMSO-d6) δ 10.16 (s, 1H), 8.03 (d, J=9.0 Hz, 1H), 7.59 (d, J=8.7 Hz, 2H), 7.30 (t, J=7.1 Hz, 2H), 7.04 (t, J=7.4 Hz, 1H), 4.39 (t, J=8.0 Hz, 1H), 2.69 (d, J=6.2 Hz, 1H), 2.20 (s, 3H), 2.03 (m, 1H), 1.76 (m, 1H), 0.89 (m, 12H). MS (ESI) m/z: 306.22 [M+H]$^+$; 328.20 [M+Na]$^+$.

2)

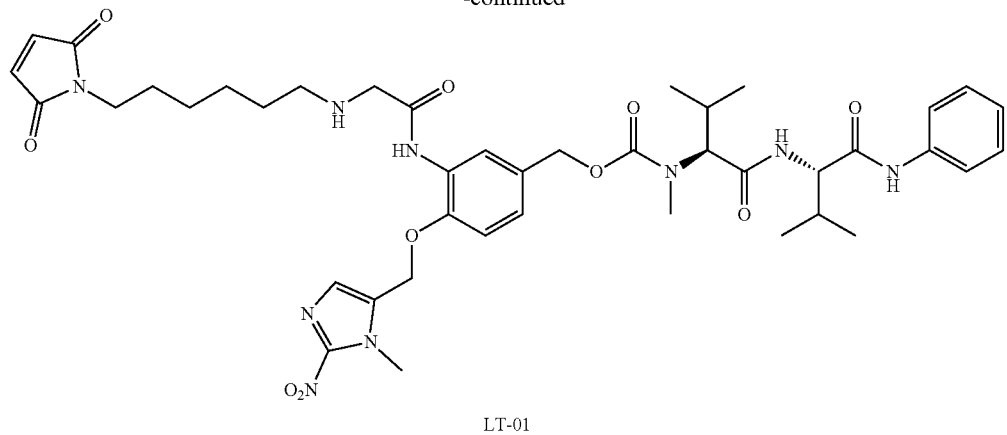

LT-01

By using the linker L01 as raw material, a L01-(toxin substitute) conjugate (LT-01) was synthesized by using a preparation method similar to that of the L01-MMAE conjugate. The target product was obtained as a white solid powder (81% yield). $^1$H-NMR (400 MHz, DMSO-d6) δ 10.00 (d, 1H), 8.99 (s, 1H), 8.32 (s, 1H), 8.08 (s, 1H), 7.94 (d, J=8.9 Hz, 1H), 7.57 (d, J=7.8 Hz, 2H), 7.39 (s, 1H), 7.29 (t, J=7.9 Hz, 2H), 7.24 (d, J=8.4 Hz, 1H), 7.11 (m, 2H), 7.04 (t, J=7.2 Hz, 1H), 6.98 (s, 2H), 5.30 (s, 2H), 5.04 (m, 2H), 4.29 (m, 1H), 4.17 (t, J=8.0 Hz, 1H), 3.98 (s, 3H), 3.84 (d, J=5.6 Hz, 2H), 3.39 (m, 2H), 2.85 (s, 3H), 2.07 (m, 1H), 1.99 (t, J=7.3 Hz, 2H), 1.43 (m, 4H), 1.14 (m, 1H), 1.09 (t, J=7.0 Hz, 2H), 0.89-0.78 (m, 12H). MS (ESI) m/z: 860.6 [M+H]$^+$; 882.6 [M+Na]$^+$; 898.6 [M+K]$^+$; 858.5 [M–H]$^-$; 904.4 [M+Cl]$^-$.

3) Preparation of Antibody-Linker-(Toxin Substitute) Conjugate

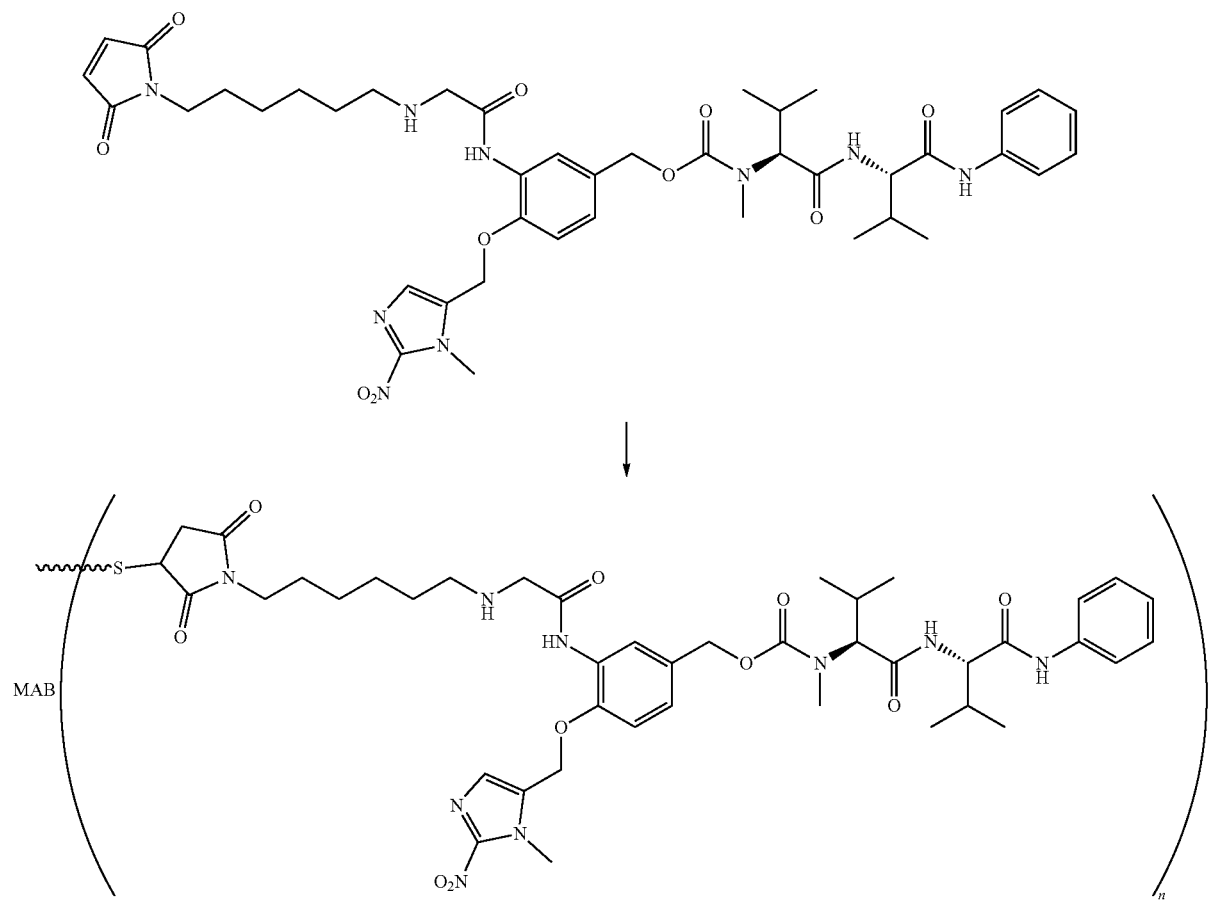

By using the method described in the literature (*Int J Mol Sci.* 2017, 18(9): e1860), the conjugate LT-01 was coupled to anti-HER2 humanized monoclonal antibody mil40 (hereinafter referred to as naked anti-mil40), and the target antibody-drug conjugate was obtained, in which MAB represented monoclonal antibody, and the drug to antibody ratio (DAR) n was about 4.

Example 12: Evaluation of In Vitro Cytotoxicity of ADC (DAR: About 4)

In this example, the ADCs prepared in Examples 1 to 10, toxin MMAE and naked anti-mil40 were evaluated in terms of in vitro cytotoxicity. The cell lines tested included antigen HER2-positive breast cancer cell lines BT-474 and HCC1954, antigen HER2-positive ovarian cancer cell line SK-OV-3, antigen HER2-positive gastric cancer cell line NCI-N87, antigen HER2-weakly positive breast cancer cell line MCF-7, and antigen HER2-negative breast cancer cell line MDA-MB-468 (the above cell lines were all purchased from ATCC).

The reagents, instruments and consumables used in the test were described in the following table:

|  | Vendor | Cat# |
|---|---|---|
| Reagents and consumables | | |
| RPMI 1640 | Invitrogen | A10491-01 |
| FBS | Invitrogen | 10099 |
| Penicillin-Streptomycin | Invitrogen | 15140 |
| Mccoy's 5A | Invitrogen | 16600-082 |
| DMEM | Invitrogen | 10569010 |
| CellTiter Glo kit | Promega | G9243 |
| Instruments | | |
| Enspire | PE | 2300 |

The test process was as follows:

① Cell Thawing

The vial containing the target cells was gently stirred in a 37° C. water bath to be thawed.

After the content was thawed, the vial was taken out from the water bath and decontaminated by immersion or spraying with 70% ethanol.

The content of the vial was transferred into a centrifuge tube containing 9 mL of complete medium (for cell lines BT-474 and MCF-7, DMEM medium was used; for cell lines NCI-N87, HCC1954 and MDA-MB-468, RPMI1640 medium was used; for cell line SK-OV-3, Mccoy's 5A medium was used; the media described below were the same as here), and centrifuged (200 g; 5 min).

The cells were re-suspended in the culture medium, settled and distributed into a culture flask with an area of 75 cm².

The resulting culture was incubated in a Galaxy® $CO_2$ incubator (48R, #C048312044) with 5% $CO_2$ at 37° C., and the oxygen concentration in the incubator was 0.1%.

② Expansion of Cells

The cells were passaged three times a week at a ratio of 1:4 in a medium containing 10% PBS (heat inactivated) and 1% penicillin-streptomycin solution.

For the passaged cells, the adherent cells were firstly rinsed with trypsin/EDTA solution (3 mL), then trypsin/EDTA (3 mL, T75 flask) was added, and spun to coat the cells evenly. The resulting culture was incubated at 37° C. until the cells were detached. It was observed by microscope to verify that the cells had been detached, then an equal volume of cell culture medium was added to inactivate trypsin, the detached cells were collected, and centrifuged at 200 g for 5 minutes, and then re-suspended in a fresh culture medium.

③ Preparation of Compound

The compound stock solution was diluted in series in a ratio of 1:3 to produce 10 diluted solutions (the compound stock solution was an L-His buffer salt solution with a concentration of about 2 mg/mL, which was diluted with PBS, and the initial maximum concentration at test point was about 500 μg/mL);

10 μL of the compound solution was distributed into a 384-well plate.

④ Cell Seeding

The cells were harvested and counted to determine the number of cells;

30 μL of the cell suspension with an adjusted density was added to the specified 384-well cell culture plate; and the final cell density was about 1,000 cells/well;

the plate was covered with a lid, and placed in an incubator to perform incubation at 37° C., 5% $CO_2$ and 0.1% $O_2$ for 168 hours.

⑤ Reading Plate

After 168 hours, the plate was taken out from the incubator and equilibrated at room temperature for 15 minutes;

CellTiter Glo reagent was incubated at 37° C. before experiment;

40 μL of the CellTiter-Glo reagent was added to each well to be tested (the ratio of CellTiter-Glo reagent to medium was 1:1);

the plate was then placed at room temperature for 30 minutes, and then reading was carried out on the EnSpire reader for cell counting.

⑥ Data Analysis

The inhibition percentage was expressed as the following formula:

$$\% \text{ Inhibition} = 100 \times [1-(\text{Sample}-LC)/(HC-LC)]$$

wherein, HC represented the reading of the well in which cells treated with only 0.1% DMSO, and LC represented the reading of the well containing only medium and no cell.

⑦ Experimental Results

The experimental results of the in vitro cytotoxicity of the ADCs prepared in Examples 1 to 5 were shown in Table 1.

TABLE 1

Experimental results of in vitro cytotoxicity

| Cell lines | Test cmpds (IC$_{50}$ nM) | | | | | | |
|---|---|---|---|---|---|---|---|
| | MMAE | MAB | ADC-1 | ADC-2 | ADC-3 | ADC-4 | ADC-5 |
| BT-474 | 0.06 | 84.14 | 0.05 | 0.08 | 0.16 | 0.24 | 0.27 |
| N87 | 0.23 | 28.52 | 0.20 | 0.36 | 0.33 | 0.75 | 0.71 |
| SK-OV-3 | 0.54 | 40.00 | 1.41 | 2.51 | 11.14 | 16.69 | 3.68 |
| HCC1954 | 0.07 | 239.81 | 0.00003 | 0.0007 | 0.18 | 0.41 | 0.002 |
| MCF-7 | 3.81 | 4194 | >1000 | >1000 | >1000 | >1000 | >1000 |
| MDA-MB-468 | 0.13 | 1840 | >1000 | >1000 | >1000 | >1000 | >1000 |

The results showed that through the in vitro activity test of the tested ADCs in hypoxic environment, it was verified that the ADCs prepared in Examples 1 to 5 all had an in vitro cytotoxicity significantly better than that of the corresponding MAB (naked anti-mil40).

The experimental results of in vitro cytotoxicity of the ADC-7, ADC-8 and ADC-10 prepared in Examples 7, 8 and 10 were shown in Table 1-1. The results showed that the ADC-7, ADC-8 and ADC-10 have very significant in vitro cytotoxicity to HER2-positive BT-474 (0.142 to 0.199 nmol/L). Compared with antigen HER2-negative MCF-7, the in vitro cytotoxicity of the ADC-7, ADC-8 and ADC-10 that contain PEG structure linkers to HER2-positive BT-474 is significantly increased by 502 to 704 times, indicating that this type of ADCs has a high antigen selectivity.

TABLE 1-1

In vitro cytotoxicity experiment of ADCs containing PEG structure linker

| ADCs | Test IC$_{50}$ (nM) | |
|---|---|---|
| | BT-474(HER2$^+$) | MCF-7(HER2$^-$) |
| ADC-7 | 0.199 | >100 |
| ADC-8 | 0.142 | >100 |
| ADC-10 | 0.193 | >100 |

Example 13: Hypoxia-Dependent Cytotoxicity of ADC-1

In this example, the hypoxia-dependent in vitro cytotoxicity of hypoxia-activated ADC-1 was studied. The tested cell line was antigen HER2-positive breast cancer cell line BT-474. The cell culture process was as described in Example 12, in which the oxygen concentrations in the cell incubator were separately set to 0.1%, 1.0%, 5.0%, 10.0% and 20.0%. The experimental results were shown in Table 2. The results showed that compared with under normoxic condition (oxygen concentration of 20%), under hypoxic condition (oxygen concentration of 0.1%), the activity of the hypoxia-activated ADC-1 was increased by more than 10 times, while the corresponding MAB (naked anti-mil40) and the linker-toxin conjugate (L01-MMAE) was increased by nearly 2 times respectively.

TABLE 2

Cytotoxicity of ADC-1 to BT-474 cells in different oxygen environments

| O$_2$% | Test cmpds (IC$_{50}$ nM) | | |
|---|---|---|---|
| | MAB | ADC-1 | L01-MMAE |
| 0.1% | 0.6844 | 0.0215 | 3.1041 |
| 1.0% | 0.2402 | 0.0233 | 3.1052 |
| 5.0% | 0.8971 | 0.0463 | 4.3166 |
| 10.0% | 1.3605 | 0.2179 | 8.9445 |
| 20.0% | 1.0831 | 0.2497 | 5.3939 |

Example 14: Time-Dependent Cytotoxicity of ADC-1

In this example, the time-dependent in vitro cytotoxicity of hypoxia-activated ADC-1 was studied. The tested cell line was antigen HER2-positive breast cancer cell line BT-474. The cell culture process was as described in Example 12, in which the oxygen concentration in the incubator was 0.1%, and the incubation time was separately set to 6 h, 12 h, 24 h, 48 h, 72 h and 96 h. The results were shown in Table 3. The results showed that the in vitro cytotoxicity of hypoxia-activated ADC-1 was dependent on the hypoxia time, and the speed of taking effect was significantly faster than that of the corresponding MAB (naked anti-mil40).

TABLE 3

Cytotoxicity of ADC-1 to BT-474 cells at different hypoxia time

| Test cmpds | IC$_{50}$ nM | | | | | |
|---|---|---|---|---|---|---|
| | 6 h | 12 h | 24 h | 48 h | 72 h | 96 h |
| MAB | >1719.12 | >1719.12 | >1719.12 | 0.9785 | 0.7064 | 0.8578 |
| ADC-1 | >1494.89 | >1494.89 | 0.8465 | 1.3550 | 0.2305 | 0.1284 |

Example 15: Stability of ADC-1 in Plasma In Vitro

In this example, the stability of ADC-1 and its corresponding linker-toxin conjugate L01-MMAE in in vitro plasma was studied, ADC with an average DAR value of about 4 was selected, and L01-MMAE was treated with NAC before the experiment to obtain a corresponding NAC-L01-MMAE. The preparation method of NAC-L01-MMAE was referred to Y. Wang, S. Fan, W. Zhong, X. Zhou, S. Li, *Int. J. Mo.l Sci.* 2017, 18, e1860. In short, 125 µL of aqueous solution of NAC (0.1 mmol/L) and 125 µL of PBS buffer (pH=7.4, 30 mmol/L) were added to 900 µL of water, the above mixed liquid was mixed well and 100 µL of NAC in DMSO solution (10 mmol/L) was added, then incubation was carried out at 37° C. for 5 minutes, it was showed that all was converted to NAC-L01-MMAE by HPLC detection.

ADC-1 and NAC-L01-MMAE were diluted with PBS buffer (pH=7.4) to a concentration of 100 μg/mL, and an equal volume of human plasma was added for dilution, the resulting mixture was mixed well and then incubated in a sterile cell incubator at 37° C., and the samples were taken at the specified time points (0 h, 3 h, 6 h, 12 h, 24 h, 36 h, 2 d, 3 d, 4 d, 5 d, 6 d, 7 d), and stored at −80° C. for short-term storage, and subjected to LC/MS analysis after the sampling was completed (the quality of off-target MMAE was quantified according to the standard curve method). The results showed that within 7 days, ADC-1 and NAC-L01-MMAE tested had no significant MMAE off-targeting (see FIG. 1). This example preliminarily confirmed that the type of arylnitro-based enzymatically cleavable ADC provided in the present application had ideal plasma stability.

Example 16: Evaluation of Enzymatic Drug-Release Performance of L01-MMAE Conjugate 1. Reagents and Materials Human NADPH CYP-reducates (purchased from Cypex, #CYP004), NADPH (purchased from ARK), L01-MMAE conjugate, potassium phosphate buffer (100 mmol/L, pH=7.4), DMSO, cold MeOH, etc.

2. Operation

① Preparation of stock solution of sample to be tested: the sample to be tested was the L01-MMAE conjugate, which was treated with NAC before the test to obtain the corresponding NAC-L01-MMAE. NAC-L01-MMAE was dissolved in DMSO to prepare an stock solution of sample to be tested with a concentration of 10 mmol/L;

② preparation of cofactor (NADPH) solution: 50 mg of NADPH was dissolved in phosphate buffer (3 mL) to obtain a NADPH solution with a final concentration of 20 mmol/L;

③ a vial containing 390 μL of potassium phosphate buffer (100 mmol/L, pH=7.4) was fed with nitrogen gas for deoxygenation, and then NADPH solution (75 μL, 20 mM) and Human NADPH CYP-reducates (10 μL, 3 mg/mL; original enzyme was diluted 3 times) were quickly added, the resulting mixture was incubated at 37° C. for 10 minutes; the stock solution (25 μL, 10 mmol/L) of sample to be tested was added to the above incubation solution to initiate the reaction, and then incubated under hypoxia condition (initial concentration of sample to be tested was 0.5 mmol/L; DMSO accounted for 5%);

④ at the specified time points (t=0, 0.5 h, 1 h, 2 h, 4 h, 12 h, 24 h), samples of equal amount (50 μL) were taken from the incubation solution, and 200 μL of cold methanol was added to quench the reaction, and then the resulting incubation solution was centrifuged to remove proteins; the supernatant was taken and analyzed by HPLC to determine the release amount of the target drug;

⑤ each of the peaks of the incubation solution sample was measured by LC/MS to determine the molecular weight thereof as qualitative parameter (including substrate, target product, transition state substance after reduction).

3. Experimental Results

Figure 2:
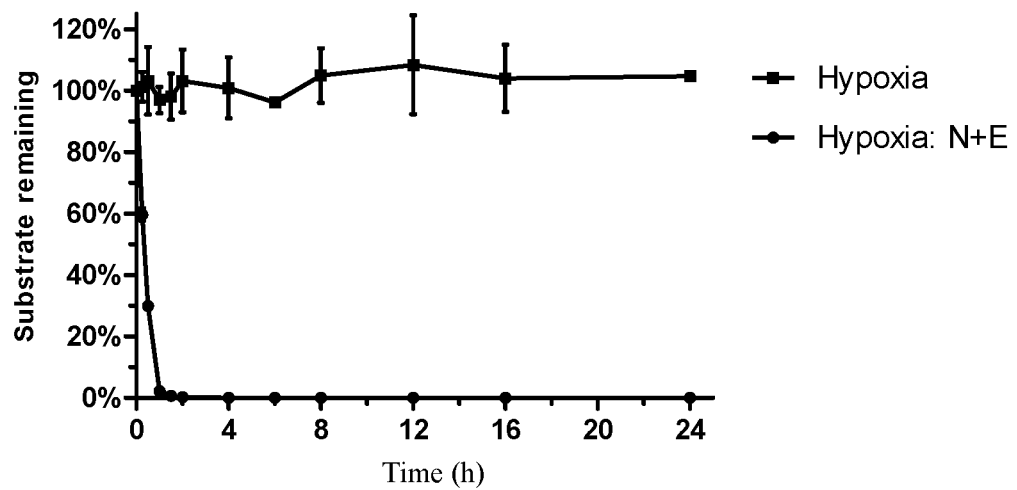
FIG. 2 shows the degradation curve of ADC-1 over time under hypoxic environment, wherein Hypoxia represents a condition in which there is not enough oxygen (oxygen concentration is 0.1%), Oxygen represents normoxia; E represents nitroreductase (Human NADPH CYP-reducates), N represents the reducing substance NADPH.
Figure 3:
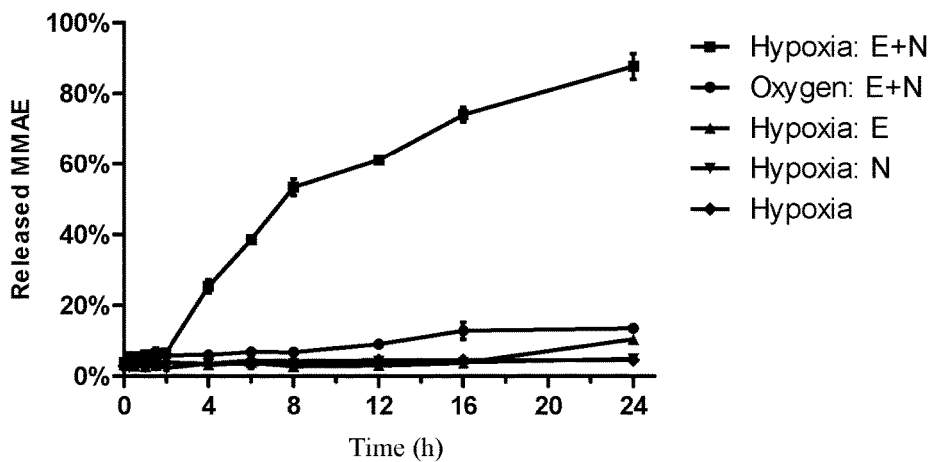
FIG. 3 shows the release curves of ADC-1 toxin MMAE under different conditions, wherein Hypoxia represents a condition in which where is not enough oxygen (oxygen concentration is 0.1%), Oxygen represents normoxia; E represents nitroreductase (Human NADPH CYP-reducates), N represents the reducing substance NADPH.

In this example, the enzymatic drug-release performance of the novel linker that was based on the reduction of arylnitro to drive drug-release was studied. The reduction of arylnitro depended on NADPH-CYP reducates (E.C. 1.6.2.4), reduced NADPH (NADH), and hypoxic environment. In the hypoxic environment, when nitroreductase and reduced NADPH were present at the same time, the substrate (NAC-L01-MMAE) could be rapidly degraded, while the concentration of the corresponding blank group basically showed no significant change within 24 hour (see FIG. 2). At the same time, the release of toxin MMAE also showed dependence on hypoxia, reductase and NADPH (see FIG. 3).

Example 17: Evaluation of the Drug-Release Performance of ADC-1 in Cells In Vitro In order to explore the mechanism of hypoxia-activated ADC-1 taking effect, the performance of ADC-1 to release the toxin MMAE in cells in vitro was further studied in this example. The tested cell lines were antigen HER2-positive breast cancer cell line BT-474 and antigen HER2-positive gastric cancer cell line NCI-N87 (purchased from ATCC).

Test method: BT-474 was taken as an example. BT-474 cells were cultured in DMEM medium containing 10% FBS, 1% PS and 0.01 mg/mL insulin at 37° C., 5% $CO_2$, 95% relative humidity in a flask. When the cells reached 80% to 90% confluence, the cells were separated and inoculated. The BT-474 cells in number of about $2.0 \times 10^6$ were inoculated in a T75 flask, cultured for 2 days at 37° C., 5% $CO_2$ and 95% relative humidity, to reach confluence of 50% to 60%. The cells were also divided into a blank group and ADCs administration groups, and the administration groups each contained two replicates. The medium was replaced, the cells of the administration groups were separately re-cultured with 15 mL of the above-mentioned medium containing about 1500 ng of ADCs, while the cells of the blank control group were cultured with the above-mentioned medium containing no the tested ADCs. After the replacement treatment was completed, the cells were cultured under hypoxia condition (1% $O_2$) for 12 h, 24 h and 48 h, respectively (Table 4 and FIG. 4). The medium was discarded, the cells were separated with trypsin/EDTA, a medium containing excess serum was added to inactivate trypsin, the cells were centrifuged at 120 g for 5 minutes, 10 mL of the corresponding medium was added and mixed. The cells were counted by using automatic cell counter (NexcelomCellometer® VisionCell Profiler), centrifuged and washed with cold PBS solution twice. The cell pellets were extracted by adding 6 mL of cold methanol; then the suspension was kept at −20° C. for 30 minutes and centrifuged at 13000 g for 20 minutes. The supernatant was evaporated by blowing nitrogen gas. The resulting residue was re-dissolved in 600 μL of methanol containing an internal standard (IS=100 nmol/L alprazolam), and the sample was analyzed by LC-MS/MS.

Figure 4:
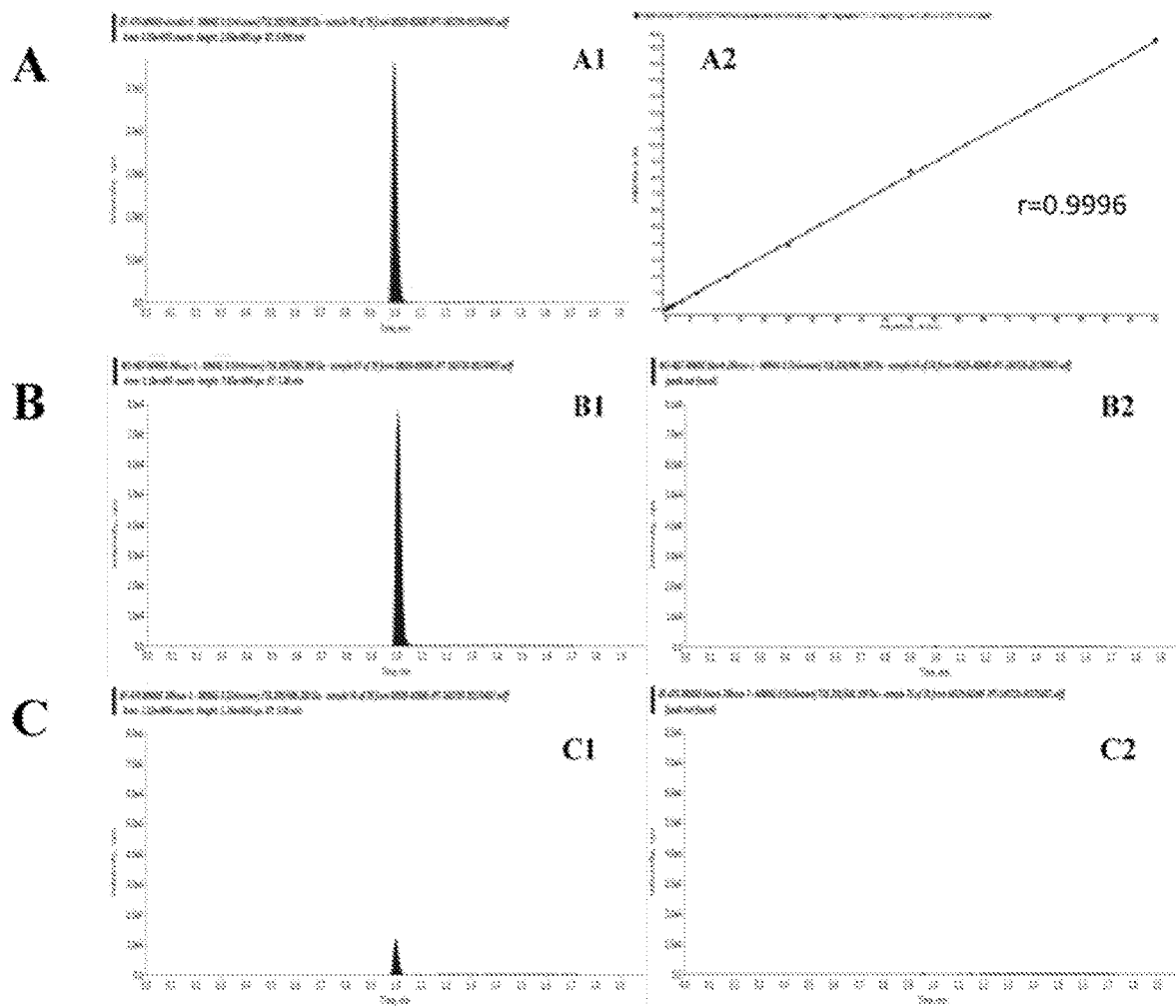
FIG. 4 shows the detection results of MMEA contents in extracts of NCI-N87 and BT-474 cells treated with ADC-1 after 24 hours of administration, in which: A1 represents the detected chromatographic peak of toxin MMAE, A2 represents the quantitative standard curve; B1 represents the detected chromatographic peak of MMAE in NCI-N87 cells, B2 represents the blank control corresponding to B1; C1 represents the detected chromatographic peak of MMAE in BT-474 cells, and C2 represents the blank control corresponding to C1. The results show that the HPLC retention time of the extracts of NCI-N87 and BT-474 cells treated with ADC-1 is very close to the retention time of the MMAE standard, which proves that under the condition of 0.1% $O_2$ partial pressure, ADC-1 can successfully release the carried cytotoxin MMAE in the in vitro cultured NCI-N87 and BT-474 cells, and then induce tumor cell apoptosis through the released cytotoxin.

The experimental results confirmed that after 24 hours of administration, a large amount of intracellular MMAE was detected by LC/MS (see: FIG. 4 and Table 4), while no cytotoxin MMAE was detected in the corresponding blank group. The HPLC retention time of the extracts of NCI-N87 and BT-474 cells treated with ADC-1 was very close to the retention time of MMAE standard, which confirmed that under the condition of 0.1% $O_2$ partial pressure, ADC-1 could successfully release the carried cytotoxin MMAE in NCI-N87 and BT-474 cells that were cultured in vitro, and then induce tumor cell apoptosis through the released cytotoxin (FIG. 4).

TABLE 4

Toxin detection results of ADC-1 group and control group in BT-474 and NCI-N87 cell lines

| Cell | Group | Parallel sample | MMAE peak area (cps) |
|---|---|---|---|
| NCI-N87 | Blank | 1 | 0.00E+00 |
| | | 2 | 0.00E+00 |
| | ADC-1 | 1 | 1.18E+05 |
| | | 2 | 1.13E+05 |
| BT-474 | Blank | 1 | 0.00E+00 |
| | | 2 | 0.00E+00 |
| | ADC-1 | 1 | 1.62E+04 |
| | | 2 | 1.48E+04 |

Example 18: Evaluation of Efficacy of ADC-1 in SCID Mice Xenograft Model of BT-474 Human Breast Cancer Cell In this example, a xenograft model of human breast cancer cell line BT-474 expressed by HER2 (purchased from ATCC) was used to evaluate the in vivo efficacy of the tested drug, in which the tested drug was ADC-1, and 4 dose groups were set, and the doses were 0.75 mg/kg, 1.5 mg/kg, 3 mg/kg and 6 mg/kg, respectively. At the same time, a naked antibody (mil40) positive control group and a vehicle (normal saline) blank control group were set up. The tested drug was dissolved in physiological saline and administered via tail vein injection.

BT-474 human breast cancer cells (purchased from ATCC) were cultured with DMEM medium containing inactivated 10% fetal bovine serum, 100 U/mL penicillin, 100 μg/mL streptomycin, and 2 mmol/L glutamine in an incubator at 37° C., 5% $CO_2$. The initial concentration of cultured cells was $1\times10^6$ cells/ml, and the cells were divided into bottles for passage every 3 to 4 days after the cells were full. The cancer cells in the logarithmic growth phase were inoculated under skin of right lateral thorax of SCID mice (female, 6-8 weeks old, 18-22 g, purchased from Beijing Ankai Yibo Biotechnology Co., Ltd.), and when the tumor grew to a volume of 150 mm³, the modeling was successful. Then the administration was started, 6 mice in each dose group were administered at the specified dose once a week, the administration volume was 5 mL/kg, and the administration was performed 4 times in total. All mice were injected subcutaneously with estrogen (veterinary estradiol benzoate injection, 4 mg/2 mL, purchased from Sichuan Lansheng Pharmaceutical Co., Ltd.) on the day before the cancer cell inoculation until the end of experiment, 2 times per week, 40 μg/20 μL each time. The tumor volume was measured twice a week by measurement of the long and short diameters of tumor with vernier caliper. The volume calculation formula was: volume=0.5×long diameter×short diameter². When the tumor volume was measured, the mice were weighed at the same time. The relationship between the change of mouse body weight and the time of administration was recorded. At the same time, the survival and health status of the mice, such as animal activity and eating during the administration period were observed.

Figure 5:
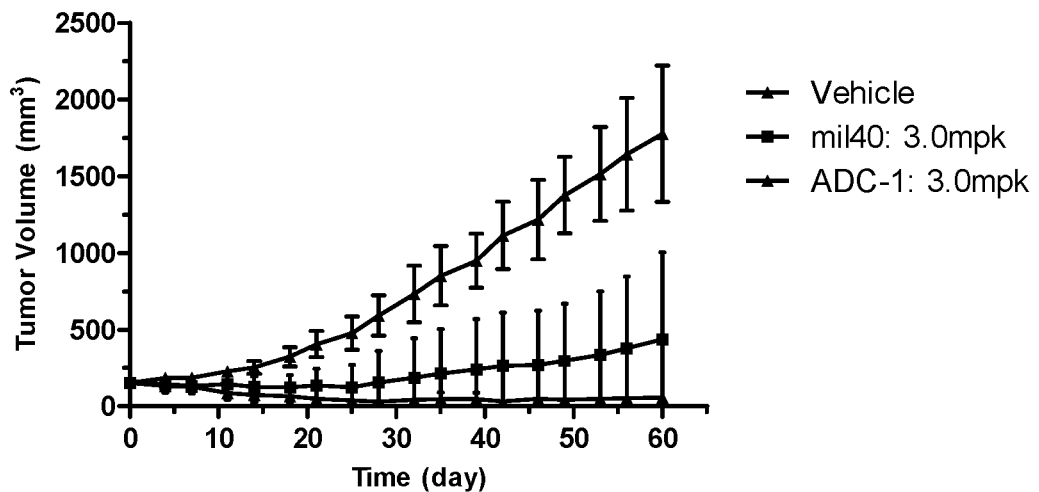
FIG. 5 shows the curves of tumor volume over time in the xenograft model of human breast cancer cell line BT-474 after administration. The results show that ADC-1 shows better in vivo tumor inhibitory activity than the naked antibody, part of the tumors of the test animals in the medium-dose administration group (3 mg/kg) disappeared, and the tumor disappeared continuously after the drug withdraw.
Figure 6:
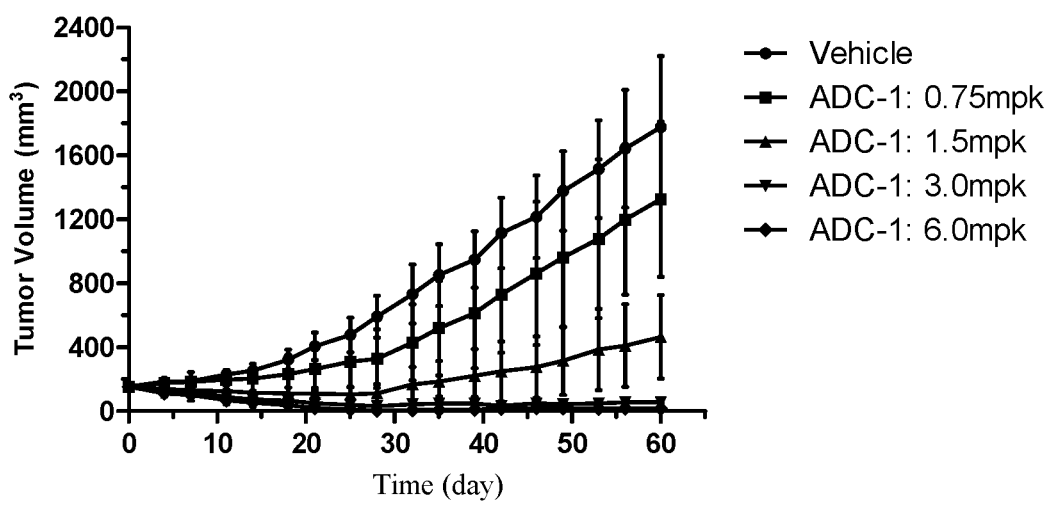
FIG. 6 shows the anti-tumor effect of ADC-1 in the xenograft model of human breast cancer cell line BT-474 under different dosages. The results show that the tumor disappearance of the test animals shows a significant dose-efficacy dependence relationship, the tumors of the test animals in the ADC-1 low- and medium-dose administration groups (0.75 mg/kg, 1.5 mg/kg, 3.0 mg/kg) are inhibited and partially disappeared, while the tumors of the test animals in the high-dose group (6.0 mg/kg) basically completely disappeared and persistently passed away.
Figure 7:
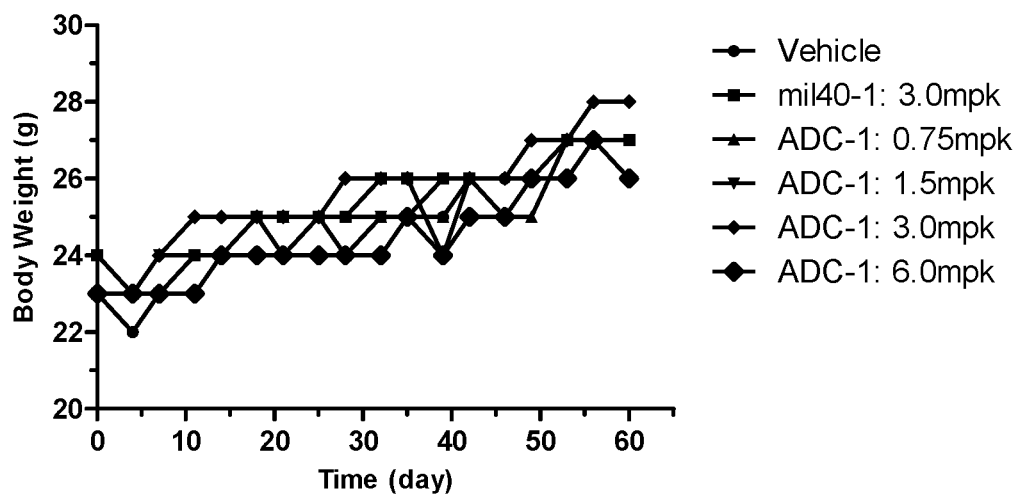
FIG. 7 shows the curves of body weight change of animals in the xenograft model of human breast cancer cell line BT-474 after receiving ADC-1 treatment. The results show that the test animals in the ADC-1 treatment groups show no significant body weight loss during the treatment process and the observation period of drug withdrawal, indicating that ADC-1 has preliminary safety at the therapeutic doses.

The results showed that in the SCID mice xenograft model of BT-474 human breast cancer, ADC-1 showed better in vivo tumor inhibitory activity than the naked antibody, part of the tumors of the test animals in the medium-dose administration group (3 mg/kg) disappeared, and the tumors persistently passed away after drug withdrawal (FIG. 5); at the same time, in the 4 dose groups of ADC-1 (0.75 mg/kg, 1.5 mg/kg, 3.0 mg/kg, 6.0 mg/kg), the tumor disappearance of the test animals showed a significant dose-efficacy dependence relationship (FIG. 6), the tumors of the test animals in the ADC-1 low- and medium-dose administration groups (for example, 0.75 mg/kg, 1.5 mg/kg, 3.0 mg/kg) were inhibited and partially disappeared, while the tumors of the test animals in the high-dose group (for example, 6.0 mg/kg) basically disappeared completely and persistently passed away. In addition, the test animals in the ADC-1 treatment groups showed no significant body weight loss during the treatment process and the observation period of drug withdrawal, indicating that the ADC-1 has preliminary safety at therapeutic doses (FIG. 7). The above studies indicated that the arylnitro-based ADCs provided in the present application have a good therapeutic potentiality for solid tumors.

Example 19: Evaluation of Efficacy of ADC-1 in Nude Mice Xenograft Model of NCI-N87 Human Gastric Cancer Cell In this example, a xenograft model of human gastric cancer cell line NCI-N87 expressed by HER2 (purchased from ATCC) was used to evaluate the efficacy of the tested drug, in which the tested drug was ADC-1, 3 dose groups were set, and the doses were 1 mg/kg, 2.5 mg/kg and 5 mg/kg, respectively. At the same time, a naked antibody (mil40) positive control group, a vehicle (normal saline) blank control group, a chemotherapeutic drug (medicinal Doxetaxel, purchased from Zhejiang Hisun Pharmaceutical Co., Ltd.) control group, and ADC-1/chemotherapeutic drug combined administration group were set. The tested drug was dissolved in physiological saline and administered via tail vein injection.

The NCI-N87 gastric adenocarcinoma cells (purchased from ATCC) were cultured with DMEM medium containing inactivated 10% fetal bovine serum, 100 U/mL penicillin, 100 μg/mL streptomycin, and 2 mM glutamine in an incubator at 37° C. and 5% $CO_2$. The initial concentration of the cultured cell was $1\times10^6$ cells/ml, and the cells were divided into bottles for passage every 3 to 4 days after the cells were full. The cancer cells in the logarithmic growth phase at $5\times10^6$ cells/0.1 mL were inoculated under skin of right lateral thorax of BALB/c nude mice (female, 6-8 weeks old, 18-22 g, purchased from Beijing Ankai Yibo Biotechnology Co., Ltd.). When the tumor grew to a volume of 150 mm³, the modeling was successful. Then the administration was started, 6 mice in each dose group were administered at the specified dose once a week, the administration volume was 5 mL/kg, and the administration was performed 4 times in total. The tumor volume was measured twice a week by measurement of the long and short diameters of tumor with vernier caliper. The volume calculation formula was: volume=0.5×long diameter×short diameter². When the tumor volume was measured, the mice were weighed at the same time. The relationship between the change of mouse body weight and the time of administration was recorded. At the same time, the survival and health status of the mice, such as animal activity and eating during the administration period were observed.

Figure 8:
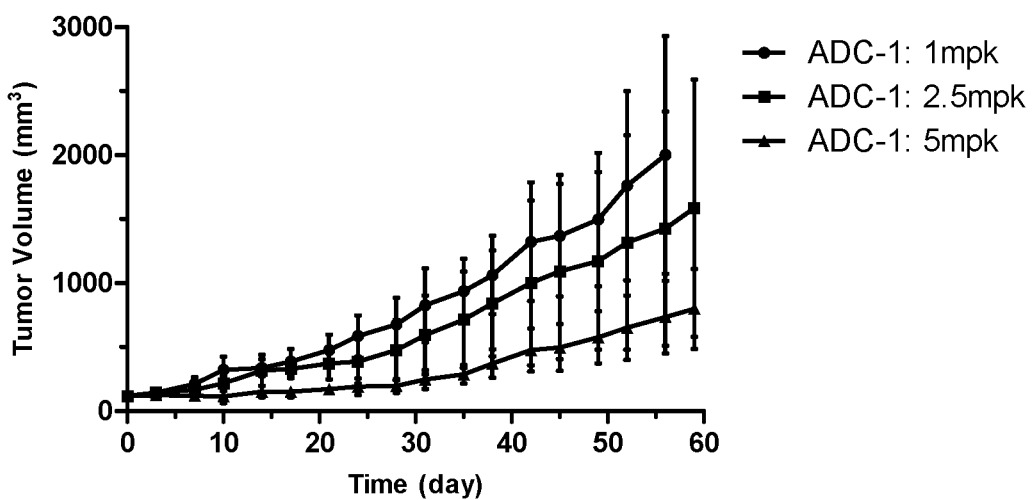
FIG. 8 shows the anti-tumor effect of ADC-1 in the xenograft model of human gastric cancer cell line NCI-N87 under different dosages. The results show that ADC-1 also shows a significant dose-efficacy dependence relationship in the xenograft model of human gastric cancer cell line NCI-N87.
Figure 9:
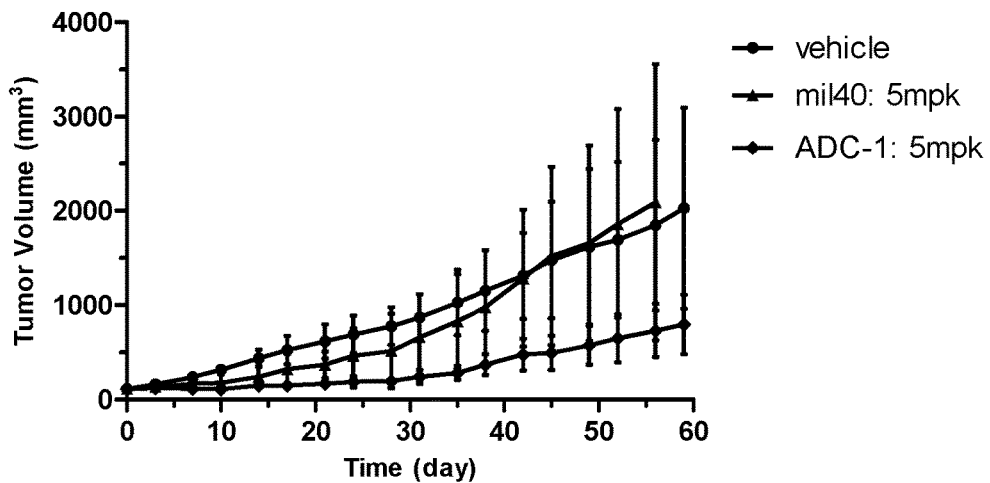
FIGS. 9 and 10 show the curves of tumor volume over time in the xenograft model of human gastric cancer cell line NCI-N87 after administration. The results show that compared with the vehicle blank control group and the naked antibody positive control group at the same dose (5 mg/kg), ADC-1 shows therapeutic advantages with significant differences (P(Vehicle VS ADC)=0.0178, P (mAb VS ADC) =0.0028). In addition, compared with single administration, the combined administration group has the best tumor-inhibitory activity. The drug efficacy of the combined administration group is significantly better than that of the ADC-1 single administration test group (P=0.0097), but it shows no significant therapeutic advantage (P=0.6430) in comparison with chemotherapeutic drugs.
Figure 10:
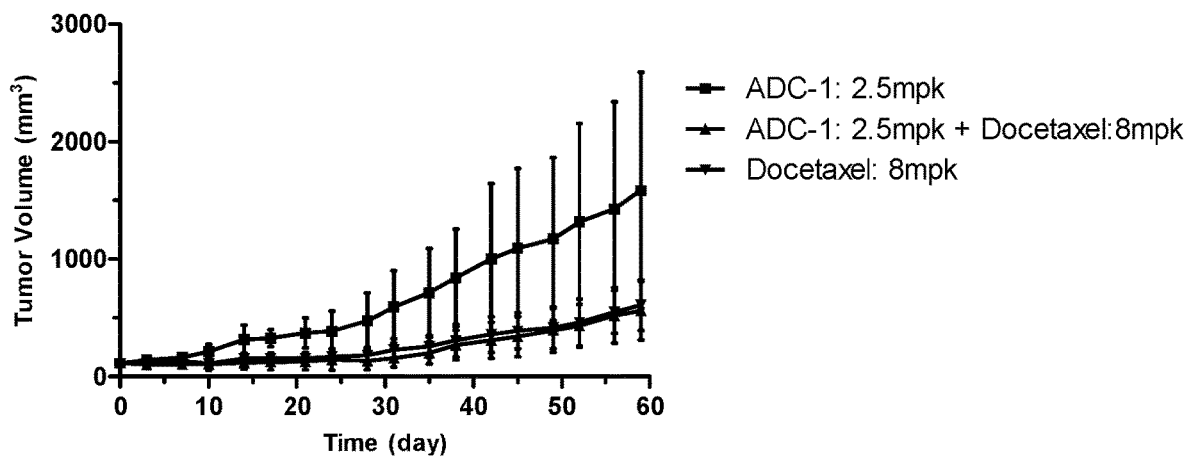
Figure 11:
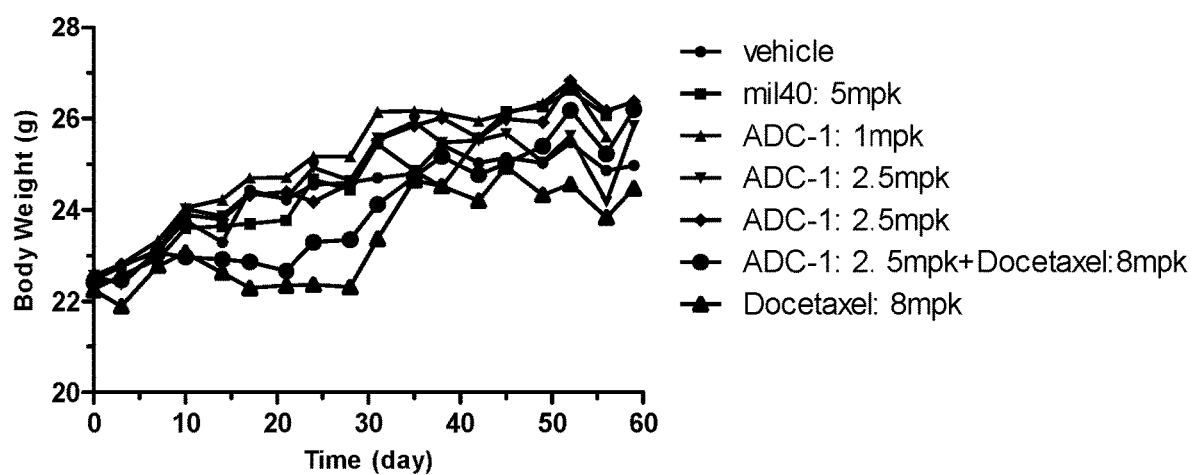
FIG. 11 shows the curves of body weight change of the animals in the xenograft model of human gastric cancer cell line NCI-N87 after receiving ADC-1 treatment. The results show that the body weights of the animals in all ADC-1 test groups increase steadily, while the chemotherapeutic drug (Doxetaxel) shows a significant weight loss (P(Vehicle VS Doxetaxel)=0.0422), which reflects to a certain extent that ADC-1 is safer than the chemotherapy drug.

The results showed that ADC-1 also showed a significant dose-dependent relationship in the xenograft model of human gastric cancer cell line NCI-N87 (FIG. 8). Compared with the vehicle blank group and the naked antibody positive control group at the same dose (5 mg/kg), ADC-1 showed a significantly different therapeutic advantage (P(Vehicle VS ADC)=0.0178, P(mAb VS ADC)=0.0028) (FIG. 9). In addition, compared with single administration, the combined administration group had the best tumor inhibitory activity; although the efficacy of the combined administration group was significantly better than the ADC-1 single administration group (P=0.0097), it had no significant therapeutic advantage in comparison with the chemotherapeutic drug (P=0.6430) (FIG. 10). The reason could be that the selected dose was not reasonable enough. However, in the course of administration and treatment, the animals of all ADC-1 administration groups had steady or slightly increased body weight, while those of the chemotherapeutic drug group (Doxetaxel) showed a significant weight loss (P(Vehicle VS Doxetaxel)=0.0422), which reflected to a certain extent that ADC-1 was safer than the chemotherapeutic drug (FIG. 11).

Example 20: In Vivo Safety Evaluation of ADC-1

In order to further confirm the safety of this type of ADC-1, the maximum tolerated dose (MTD) of ADC-1 in a normal CD-1 mouse model was further evaluated in this example. CD-1 mice were purchased from Beijing Vital River Laboratory Animal Technology Co., Ltd. All animals in the experiment were raised according to the protocol approved by the Institutional Animal Care and Use Committee of Pharmaron Beijing. Each test dose group had 6 CD-1 mice (3 males and 3 females), aged 7-9 weeks, average weight of 22-40 g (male) and 20-35 g (female). ADC-1 or naked antibody mil40 or ADC-a was administered via tail vein injection, and five dose groups were set for each drug, in which the doses of ADC-1 were 10 mg, 20 mg, 40 mg, 80 mg and 160 mg, while the doses of mil40 and ADC-a were 10 mg, 20 mg, 40 mg, 80 mg and 120 mg. After administration, all test animals were monitored for body weight changes once a day, and animal behavior was observed beside cage, twice a day. The observation records included animal death or sudden death, the general health of animals and symptoms of drug toxicity. The detailed clinical observations included changes in skin, fur, eyes and mucous membranes, changes in respiratory system, circulatory system, autonomic and central nervous systems, body movements and behavior patterns of the animals. After the last observation, all surviving animals were euthanized by inhalation 90% to 100% carbon dioxide.

The structural formula of ADC-a was shown below (the preparation method of ADC-a referred to the relevant description in International Journal of Molecular Sciences, 2017, 18(9): 1860).

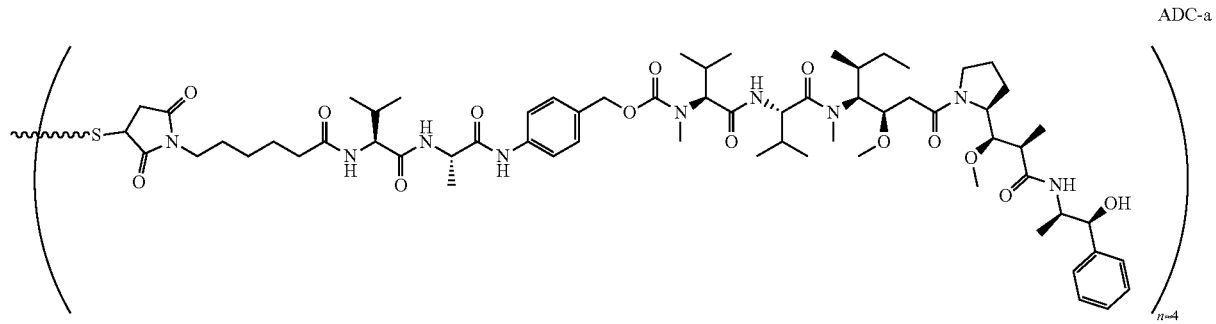

ADC-a

Figure 12:
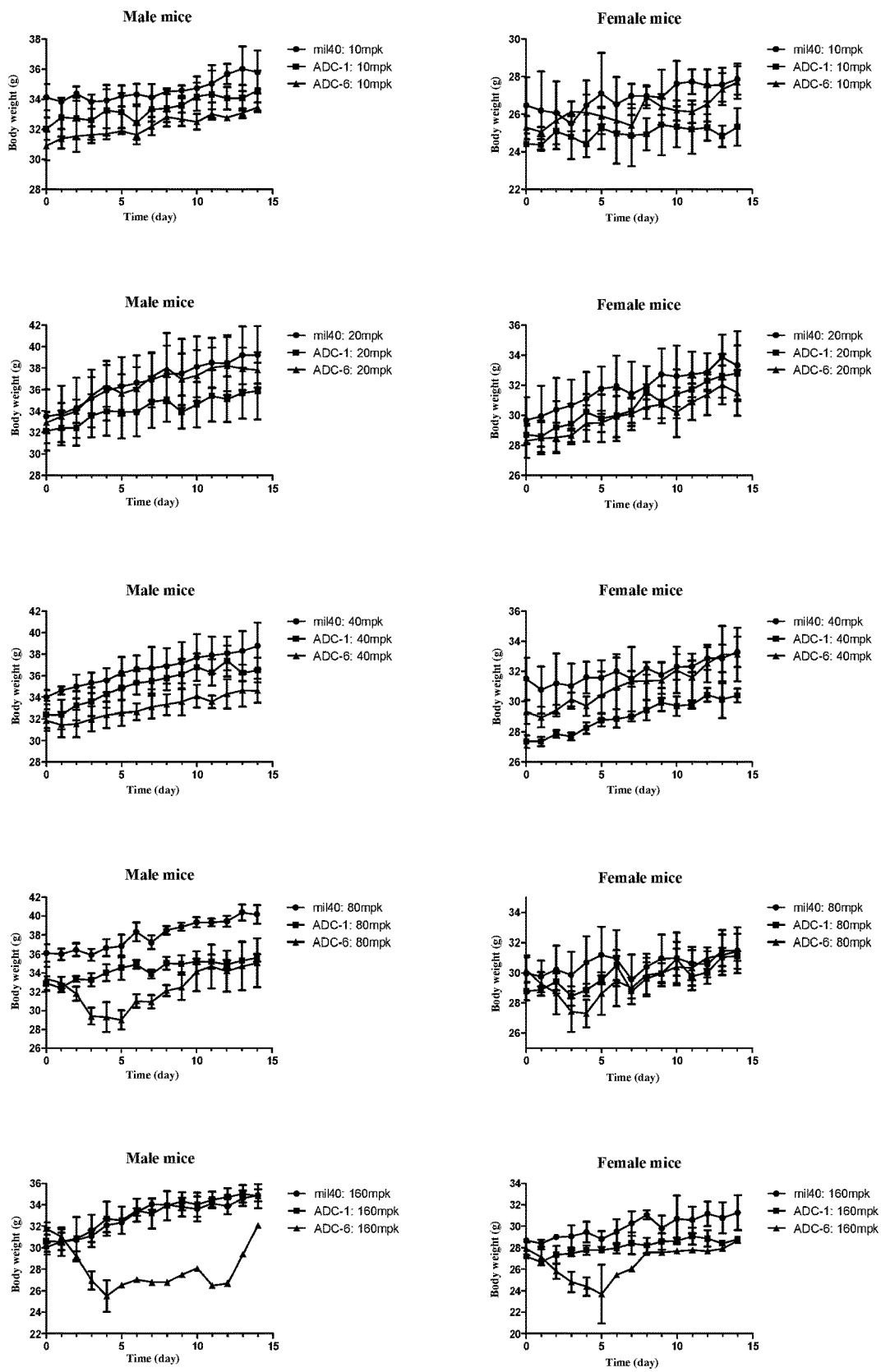
FIG. 12 shows the curves of body weight change of CD-1 mice after receiving drug treatment at different dosages. The results show that the test animals in the ADC-1 administration groups show no obvious adverse reactions, body weight loss and death at the doses of 10 mg/kg, 20 mg/kg, 40 mg/kg, 80 mg/kg and 160 mg/kg, indicating that ADC-1 has a very high therapeutic safety window, and will not cause obvious intolerance in the test animals when it is administered at therapeutic doses or even larger doses.

Referring to FIG. 12, the experimental results showed that similar to the naked antibody mil40, the test animals in the ADC-1 administration groups showed no obvious adverse reactions, body weight loss or death of animals at administration doses of 10 mg/kg, 20 mg/kg, 40 mg/kg, 80 mg/kg and 160 mg/kg, indicating that ADC-1 has a very high therapeutic safety window, and would not cause obvious intolerance in the test animals when it is administered at therapeutic doses or even larger doses. As a control, the traditional cathepsin cleavage dipeptide-type ADC-6 showed continuous weight loss during the first 6 days of administration at a dose of 80 mg/kg, and there were common adverse reactions such as hair loss and scab in the later stage of the test; and at a dose of 120 mg/kg of ADC-6, half of the test animals died within one week after administration. The experimental data of this example showed that the application potentiality of the enzymatically cleavable ADC containing arylnitro linker provided in the present application is better than that of the traditional enzymatically cleavable ADC containing dipeptide linker.

Finally, it should be noted that: the above examples are only used to illustrate the technical solutions of the present application rather than to limit them; although the present application has been described in detail with reference to the preferred examples, those of ordinary skill in the art should understand that: the specific implementation of the present application can be modified or some technical features can be equivalently replaced without departing from the spirit of the technical solution of the present application, and all of them shall be covered by the scope of the technical solution that are sought to be protected by the present application.

What is claimed is:

1. A compound represented by Formula I or a salt thereof,

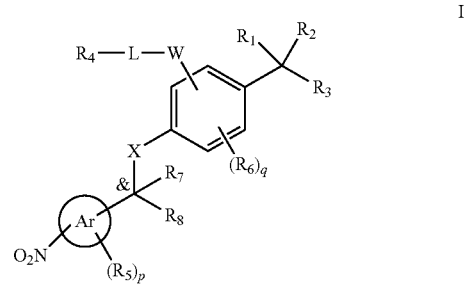

I wherein:
$R_1$ is hydrogen, methyl, ethyl, n-propyl or isopropyl;
$R_2$ is hydrogen, methyl, ethyl, n-propyl or isopropyl;
$R_3$ is

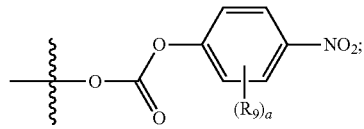

$R_4$ is

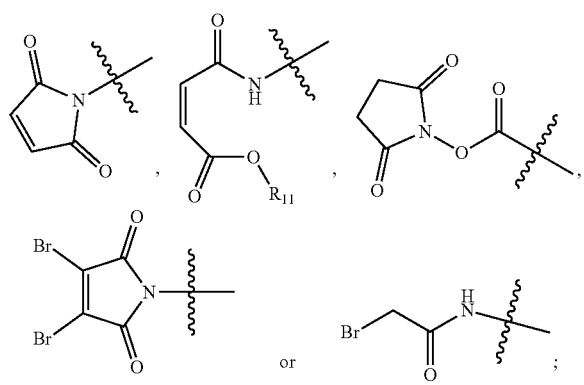

and in

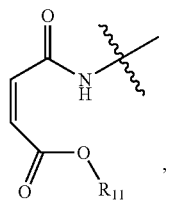

the two carbonyl groups are located on the same side of the C=C double bond, which is a cis structure, $R_{11}$ is a $C_{1-6}$ linear or branched alkyl, and $R_{11}$ is optionally mono- or multi-substituted by one or more substituents selected from the group consisting of: halogen and $C_{1-4}$ alkoxy;
X is oxygen atom (O), nitrogen atom (N) or sulfur atom (S);
Ar is aryl, heteroaryl, aryl-fused-heterocyclyl or heteroaryl-fused-heterocyclyl;
$R_5$ is hydrogen, methyl, ethyl, n-propyl, isopropyl, fluorine, chlorine, bromine, iodine, hydroxyl or cyano;
$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;
$R_7$ is hydrogen, methyl, ethyl, n-propyl or isopropyl;
$R_8$ is hydrogen, methyl, ethyl, n-propyl or isopropyl;
$R_9$ is hydrogen, methyl, ethyl, n-propyl, isopropyl, fluorine, chlorine, bromine, iodine, hydroxyl or cyano;
q is 0, 1, 2 or 3;
p is 0, 1, 2 or 3;
a is 0, 1, 2, 3 or 4;
L is —$(CH_2)_iO(CH_2)_j$—, —$(CH_2)_iO(CH_2)_j$—C(O)—, —$(CH_2)_i$—C(O)NH—$(CH_2)_j$—, —$(CH_2CH_2O)_i$—, —$(CH_2)_j$—C(O)—, —$(CH_2)_i$—$(CH_2CH_2O)_j$—C(O)—, —$(OCH_2CH_2)_i$—, —$(CH_2)_m$—, —$(CH_2)_k$—C(O)NH—$(CH_2CH_2O)_g$—$(CH_2)_h$—C(O)—, —$(CH_2)_r$—C(O)—, —$(CH_2)_b$—C(O)NH—CH[$(CH_2)_d$—NHC(O)—$(CH_2CH_2O)_e$—$(CH_2)_f$—$CH_3$]—,

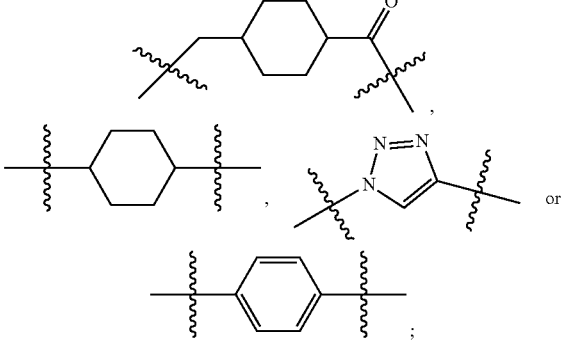

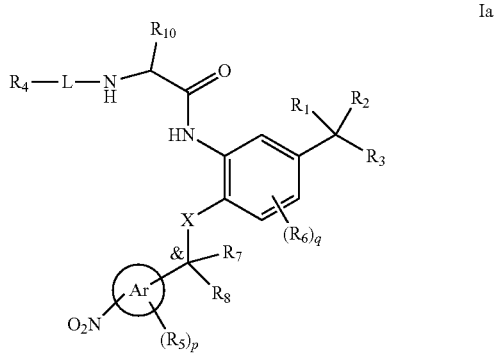

W represents a linking group, and is —NH—$CH_2$—C(O)—NH—, —NH—$CH_2$—$CH_2$—C(O)—NH—, —C(O)—NH—, —NH—C(O)—, —O—, —S—, —NH—, —N($CH_3$)—, —C(O)— or —NH—CH($R_{10}$)—C(O)—NH—;
$R_{10}$ is —H, —$CH_3$, —$C_3H_6$, —CH—$(CH_3)_2$, —$CH_2$—CH$(CH_3)_2$, —CH($CH_3$)—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH($CH_3$)—OH or —$CH_2$—SH;
m is 1, 2, 3, 4, 5, 6, 7, 8 or 9;
each i is independently 1, 2, 3, 4, 5, 6, 7, 8 or 9;
each j is independently 1, 2, 3, 4, 5, 6, 7, 8 or 9;
r is 1, 2, 3, 4, 5, 6, 7, 8 or 9;
k is 1, 2, 3, 4, 5 or 6;
g is 1, 2, 3, 4, 5, 6, 7, 8, 9, 10, 11 or 12;
h is 1, 2, 3, 4, 5 or 6;
b is 1, 2, 3, 4, 5 or 6;
d is 1, 2, 3, 4, 5 or 6;
e is 1, 2, 3, 4, 5, 6, 7, 8, 9, 10, 11 or 12;
f is 1, 2, 3, 4, 5 or 6.

2. The compound or a salt thereof according to claim 1, wherein the compound has a structure represented by Formula Ia, Ia wherein:
$R_1$ is hydrogen, methyl, ethyl, n-propyl or isopropyl;
$R_2$ is hydrogen, methyl, ethyl, n-propyl or isopropyl;

$R_3$ is

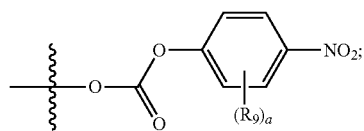

$R_4$ is

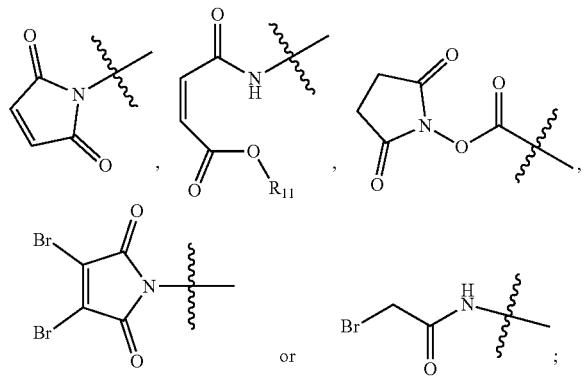

or and in

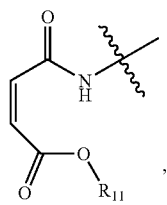

the two carbonyl groups are located on the same side of the C=C double bond, which is a cis structure, $R_{11}$ is a $C_{1-6}$ linear or branched alkyl, and $R_{11}$ is optionally mono- or multi-substituted by one or more substituents selected from the group consisting of: halogen and $C_{1-4}$ alkoxy;

X is oxygen atom (O), nitrogen atom (N) or sulfur atom (S);

Ar is aryl, heteroaryl, aryl-fused-heterocyclyl or heteroaryl-fused-heterocyclyl;

$R_5$ is hydrogen, methyl, ethyl, n-propyl, isopropyl, fluorine, chlorine, bromine, iodine, hydroxyl or cyano;

$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;

$R_7$ is hydrogen, methyl, ethyl, n-propyl or isopropyl;

$R_8$ is hydrogen, methyl, ethyl, n-propyl or isopropyl;

$R_9$ is hydrogen, methyl, ethyl, n-propyl, isopropyl, fluorine, chlorine, bromine, iodine, hydroxyl or cyano;

$R_{10}$ is —H, —$CH_3$, —$C_3H_6$, —CH—$(CH_3)_2$, —$CH_2$—CH$(CH_3)_2$, —CH$(CH_3)$—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH$(CH_3)$—OH or —$CH_2$—SH;

q is 0, 1, 2 or 3;

p is 0, 1, 2 or 3;

a is 0, 1, 2, 3 or 4;

L is —$(CH_2)_iO(CH_2)_j$—, —$(CH_2)_iO(CH_2)_j$—C(O)—, —$(CH_2)_i$—C(O)NH—$(CH_2)_j$—, —$(CH_2CH_2O)_i$—$(CH_2)_j$—C(O)—, —$(CH_2)_i$—$(CH_2CH_2O)_j$—C(O)—, —$(OCH_2CH_2)_i$—, —$(CH_2)_m$—, —$(CH_2)_r$—C(O)—, —$(CH_2)_k$—C(O)NH—$(CH_2CH_2O)_g$—$(CH_2)_h$—C(O)—, —$(CH_2)_b$—C(O)NH—CH[$(CH_2)_d$—NHC(O)—$(CH_2CH_2O)_e$—$(CH_2)_f$—$CH_3$]—,

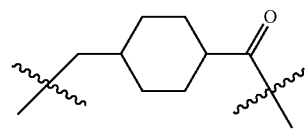

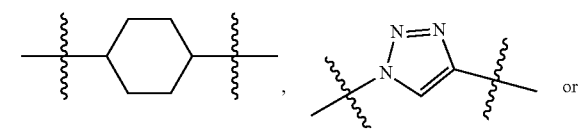

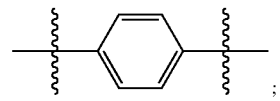

m is 1, 2, 3, 4, 5, 6, 7, 8 or 9;

r is 1, 2, 3, 4, 5, 6, 7, 8 or 9;

each i is independently 1, 2, 3, 4, 5, 6, 7, 8 or 9;

each j is independently 1, 2, 3, 4, 5, 6, 7, 8 or 9;

k is 1, 2, 3, 4, 5 or 6;

g is 1, 2, 3, 4, 5, 6, 7, 8, 9, 10, 11 or 12;

h is 1, 2, 3, 4, 5 or 6;

b is 1, 2, 3, 4, 5 or 6;

d is 1, 2, 3, 4, 5 or 6;

e is 1, 2, 3, 4, 5, 6, 7, 8, 9, 10, 11 or 12;

f is 1, 2, 3, 4, 5 or 6.

3. The compound or a salt thereof according to claim 1, wherein the compound has a structure represented by Formula 1-1, Formula 1-2, Formula 1-3 or Formula 1-4,

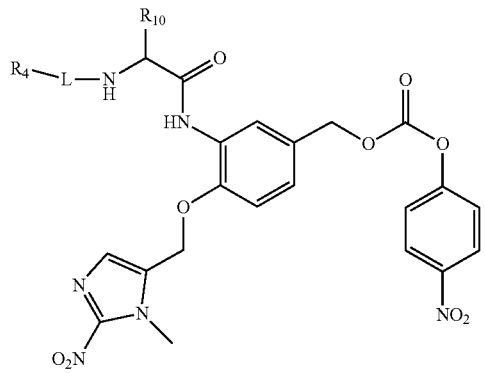

I-1

I-2
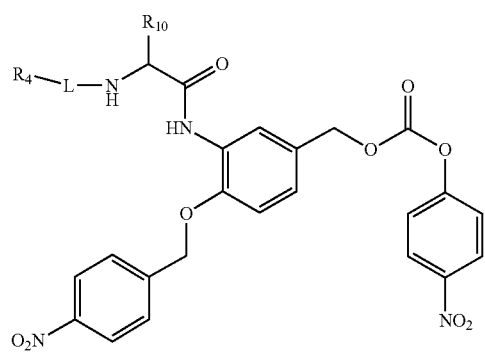
I-3
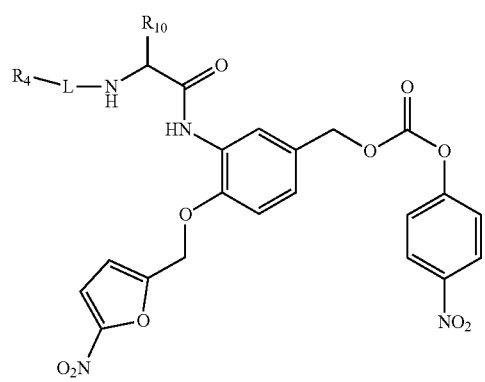
I-4
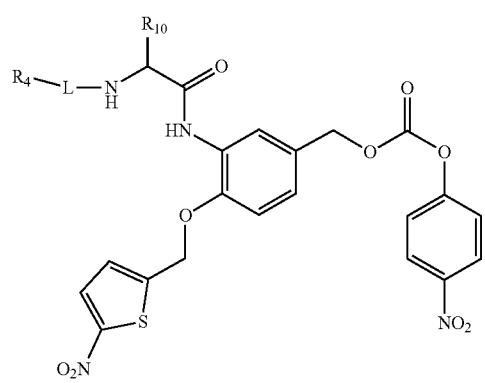
I-5
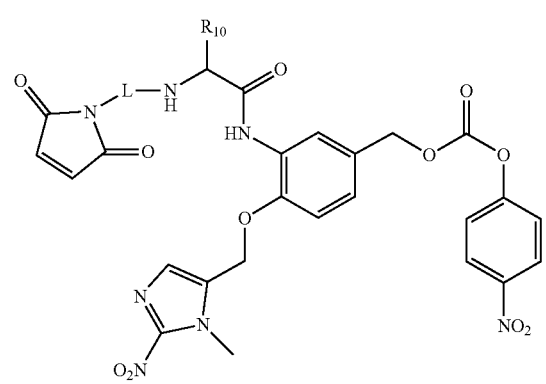
I-6
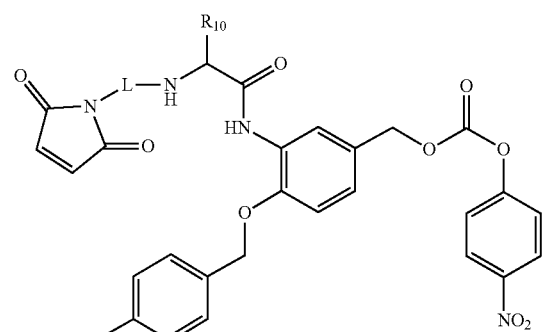
I-7
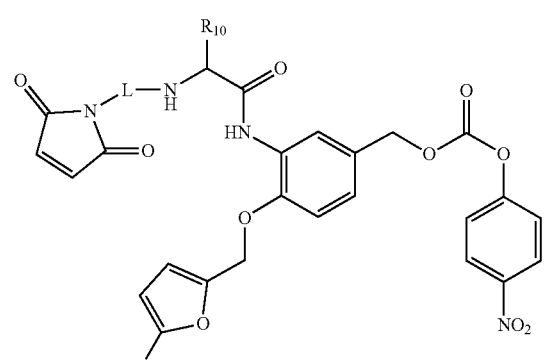
I-8
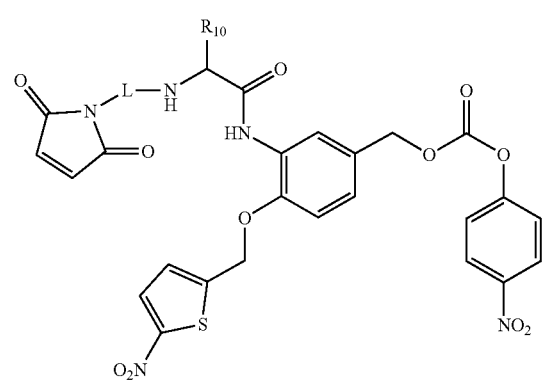
wherein, $R_4$, $R_{10}$ and L are defined as described in claim 1; or
the compound has a structure represented by Formula 1-5, Formula 1-6, Formula 1-7 or Formula 1-8,
wherein, $R_{10}$ and L are defined as described in claim 1; or
the compound represented by Formula I or Formula Ia has a structure represented by Formula 1-9, Formula 1-10, Formula 1-11 or Formula 1-12,

I-9

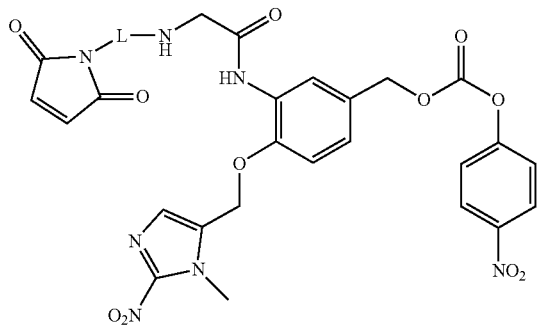

I-10

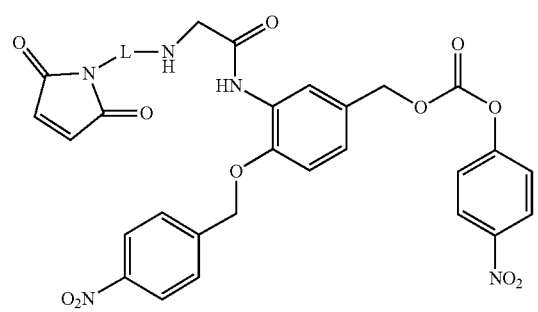

I-11

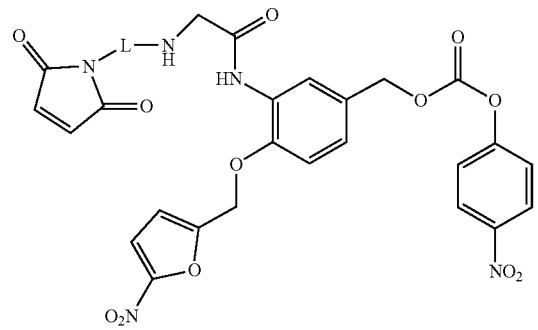

I-12

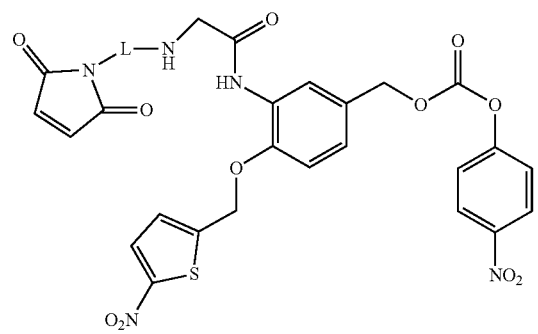

wherein, L is defined as described in claim 1.

4. A compound represented by Formula II or a salt thereof,

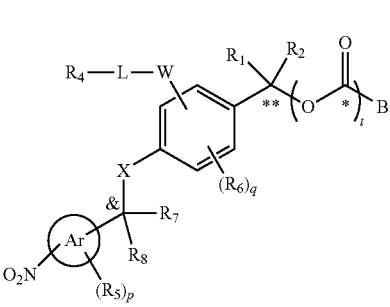

wherein:
$R_1$ is hydrogen, methyl, ethyl, n-propyl or isopropyl;
$R_2$ is hydrogen, methyl, ethyl, n-propyl or isopropyl;
$R_4$ is

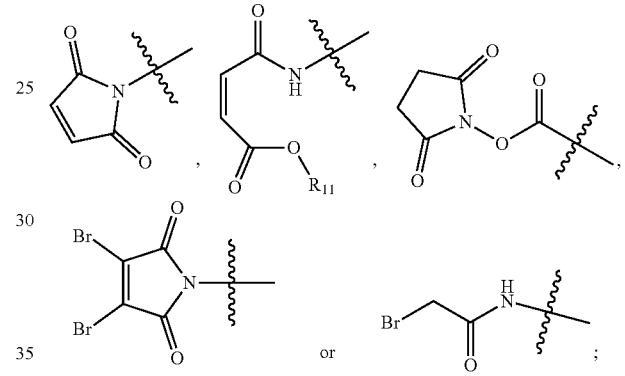

and in

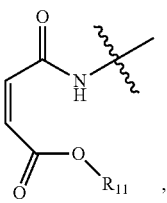

the two carbonyl groups are located on the same side of the C=C double bond, which is a cis structure, $R_{11}$ is a $C_{1-6}$ linear or branched alkyl, and $R_{11}$ is optionally mono- or multi-substituted by one or more substituents selected from the group consisting of: halogen and $C_{1-4}$ alkoxy;
X is oxygen atom (O), nitrogen atom (N) or sulfur atom (S);
Ar is aryl, heteroaryl, aryl-fused-heterocyclyl or heteroaryl-fused-heterocyclyl;
$R_5$ is hydrogen, methyl, ethyl, n-propyl, isopropyl, fluorine, chlorine, bromine, iodine, hydroxyl or cyano;
$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;
$R_7$ is hydrogen, methyl, ethyl, n-propyl or isopropyl;
$R_8$ is hydrogen, methyl, ethyl, n-propyl or isopropyl;
q is 0, 1, 2 or 3;
p is 0, 1, 2 or 3;

L is —(CH$_2$)$_i$O(CH$_2$)$_j$—, —(CH$_2$)$_i$—(CH$_2$)$_j$—C(O)—, —(CH$_2$)$_i$—C(O)NH—(CH$_2$)$_j$—, —(CH$_2$CH$_2$O)$_i$—(CH$_2$)$_j$—C(O)—, —(CH$_2$)$_i$—(CH$_2$CH$_2$O)$_j$—C(O)—, —(OCH$_2$CH$_2$)$_i$—, —(CH$_2$)$_m$—, —(CH$_2$)$_r$—C(O)—, —(CH$_2$)$_k$—C(O)NH—(CH$_2$CH$_2$O)$_g$—(CH$_2$)$_h$—C(O)—, —(CH$_2$)$_b$—C(O)NH—CH[(CH$_2$)$_d$—NHC(O)—(CH$_2$CH$_2$O)$_e$—(CH$_2$)$_f$—CH$_3$]—,

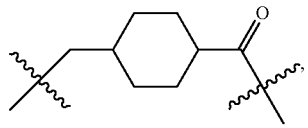

,

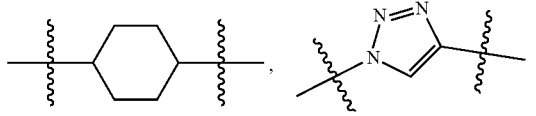

or

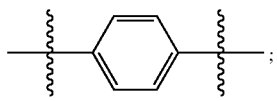

;

W represents a linking group, and is —NH—CH$_2$—C(O)—NH—, —NH—CH$_2$—CH$_2$—C(O)—NH—, —C(O)—NH—, —NH—C(O)—, —O—, —S—, —NH—, —N(CH$_3$)—, —C(O)— or —NH—CH(R$_{10}$)—C(O)—NH—, further preferably —NH—CH$_2$—C(O)—NH—, —C(O)—NH—, —NH—C(O)— or —O—;

R$_{10}$ is —H, —CH$_3$, —C$_3$H$_6$, —CH—(CH$_3$)$_2$, —CH$_2$—CH(CH$_3$)$_2$, —CH(CH$_3$)—CH$_2$—CH$_3$, —CH$_2$—C$_6$H$_5$, —C$_8$NH$_6$, —CH$_2$—C$_6$H$_4$—OH, —CH$_2$—COOH, —CH$_2$—CONH$_2$, —(CH$_2$)$_2$—COOH, —(CH$_2$)$_4$—NH$_2$, —(CH$_2$)$_2$—CONH$_2$, —(CH$_2$)—S—CH$_3$, —CH$_2$—OH, —CH(CH$_3$)—OH or —CH$_2$—SH;

m is 1, 2, 3, 4, 5, 6, 7, 8 or 9;

each i is independently 1, 2, 3, 4, 5, 6, 7, 8 or 9;

each j is independently 1, 2, 3, 4, 5, 6, 7, 8 or 9;

r is 1, 2, 3, 4, 5, 6, 7, 8 or 9;

k is 1, 2, 3, 4, 5 or 6;

g is 1, 2, 3, 4, 5, 6, 7, 8, 9, 10, 11 or 12;

h is 1, 2, 3, 4, 5 or 6;

b is 1, 2, 3, 4, 5 or 6;

d is 1, 2, 3, 4, 5 or 6;

e is 1, 2, 3, 4, 5, 6, 7, 8, 9, 10, 11 or 12;

f is 1, 2, 3, 4, 5 or 6;

B is an active compound, selected from the group consisting of drug, cytotoxin, detection reagent, diagnostic reagent and targeting carrier; B is coupled to the site* or site** through a N atom or O atom in the active compound molecule;

t is 0 or 1.

5. The compound or a salt thereof according to claim 4, wherein the compound has a structure represented by Formula IIa,

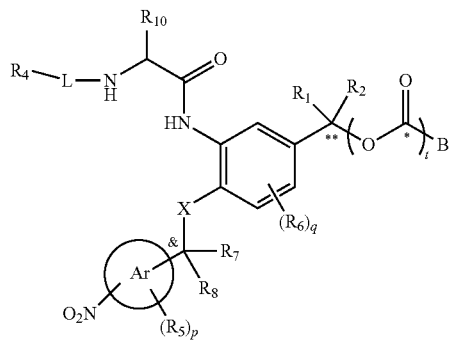

IIa wherein:

R$_1$ is hydrogen, methyl, ethyl, n-propyl or isopropyl;

R$_2$ is hydrogen, methyl, ethyl, n-propyl or isopropyl;

R$_4$ is

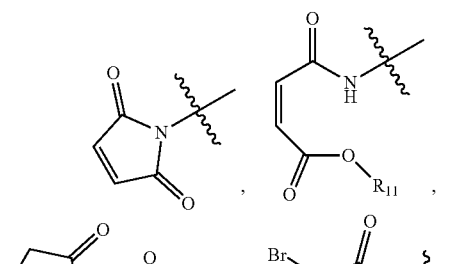

or

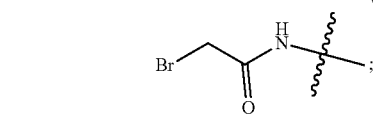

;

and in

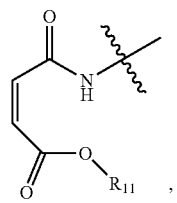

, the two carbonyl groups are located on the same side of the C=C double bond, which is a cis structure, R$_{11}$ is a C$_{1-6}$ linear or branched alkyl, and R$_{11}$ is optionally mono- or multi-substituted by one or more substituents selected from the group consisting of: halogen and C$_{1-4}$ alkoxy;

X is oxygen atom (O), nitrogen atom (N) or sulfur atom (S);

Ar is aryl, heteroaryl, aryl-fused-heterocyclyl or heteroaryl-fused-heterocyclyl;

R$_5$ is hydrogen, methyl, ethyl, n-propyl, isopropyl, fluorine, chlorine, bromine, iodine, hydroxyl or cyano;

R₆ is hydrogen, methyl, ethyl, n-propyl, isopropyl, n-butyl, isobutyl, sec-butyl, tert-butyl, fluorine, chlorine, bromine, iodine, hydroxyl, nitro or cyano;

R₇ is hydrogen, methyl, ethyl, n-propyl or isopropyl;

R₈ is hydrogen, methyl, ethyl, n-propyl or isopropyl;

R₁₀ is —H, —CH₃, —C₃H₆, —CH—(CH₃)₂, —CH₂—CH(CH₃)₂, —CH(CH₃)—CH₂—CH₃, —CH₂—C₆H₅, —C₈NH₆, —CH₂—C₆H₄—OH, —CH₂—COOH, —CH₂—CONH₂, —(CH₂)₂—COOH, —(CH₂)₄—NH₂, —(CH₂)₂—CONH₂, —(CH₂)—S—CH₃, —CH₂—OH, —CH(CH₃)—OH or —CH₂—SH;

q is 0, 1, 2 or 3;

p is 0, 1, 2 or 3;

L is —(CH₂)ᵢO(CH₂)ⱼ—, —(CH₂)ᵢ(CH₂)ⱼ—C(O)—, —(CH₂)ᵢ—C(O)NH—(CH₂)ⱼ—, —(CH₂CH₂O)ᵢ—(CH₂)ⱼ—C(O)—, —(CH₂)ᵢ—(CH₂CH₂O)ⱼ—C(O)—, —(OCH₂CH₂)ᵢ—, —(CH₂)ₘ—, —(CH₂)ᵣ—C(O)—, —(CH₂)ₖ—C(O)NH—(CH₂CH₂O)g—(CH₂)ₕ—C(O)—, —(CH₂)ᵦ—C(O)NH—CH[(CH₂)d—NHC(O)—(CH₂CH₂O)ₑ—(CH₂)f—CH₃]—,

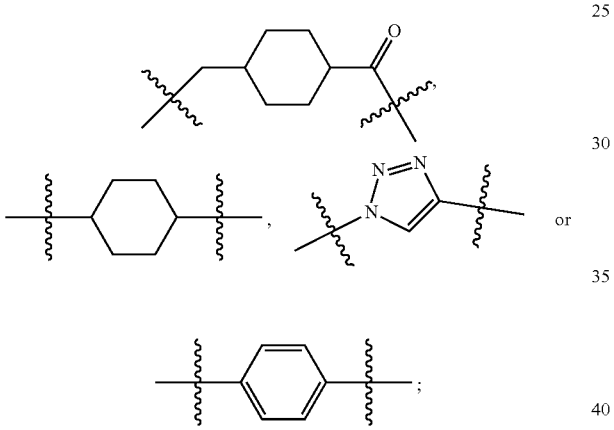

m is 1, 2, 3, 4, 5, 6, 7, 8 or 9;

r is 1, 2, 3, 4, 5, 6, 7, 8 or 9;

each i is independently 1, 2, 3, 4, 5, 6, 7, 8 or 9;

each j is independently 1, 2, 3, 4, 5, 6, 7, 8 or 9;

k is 1, 2, 3, 4, 5 or 6;

g is 1, 2, 3, 4, 5, 6, 7, 8, 9, 10, 11 or 12;

h is 1, 2, 3, 4, 5 or 6;

b is 1, 2, 3, 4, 5 or 6;

d is 1, 2, 3, 4, 5 or 6;

e is 1, 2, 3, 4, 5, 6, 7, 8, 9, 10, 11 or 12;

f is 1, 2, 3, 4, 5 or 6;

B is an active compound, selected from the group consisting of drug, cytotoxin, detection reagent, diagnostic reagent and targeting carrier; B is coupled to the site* or site** through a N atom or O atom in the active compound molecule;

t is 0 or 1.

6. The compound or a salt thereof according to claim 4, wherein the compound has a structure represented by Formula II-1, Formula II-2, Formula II-3 or Formula II-4,

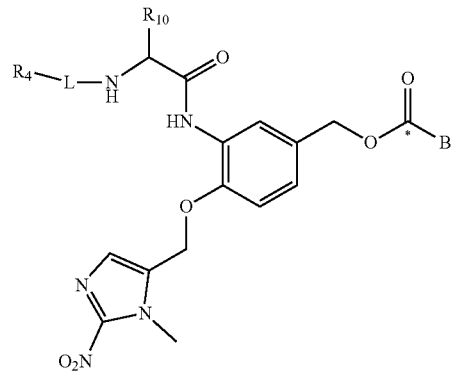

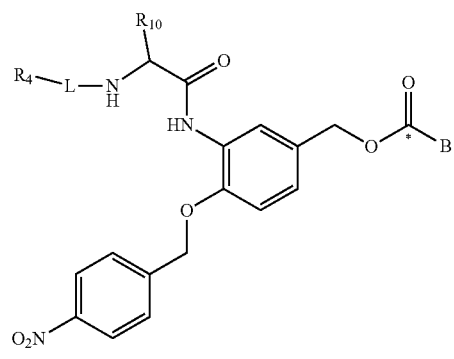

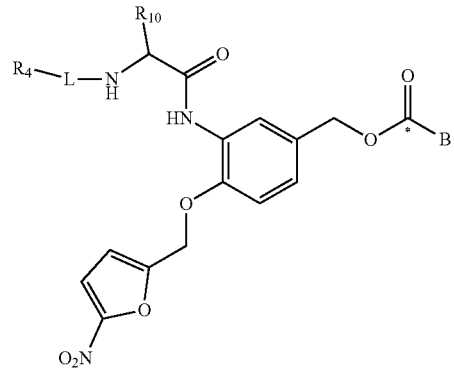

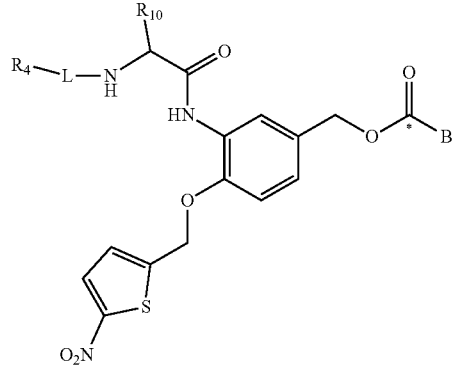

wherein, R₄, R₁₀, L and B are defined as described in claim 4; or the compound has a structure represented by Formula II-5, Formula II-6, Formula II-7 or Formula II-8,

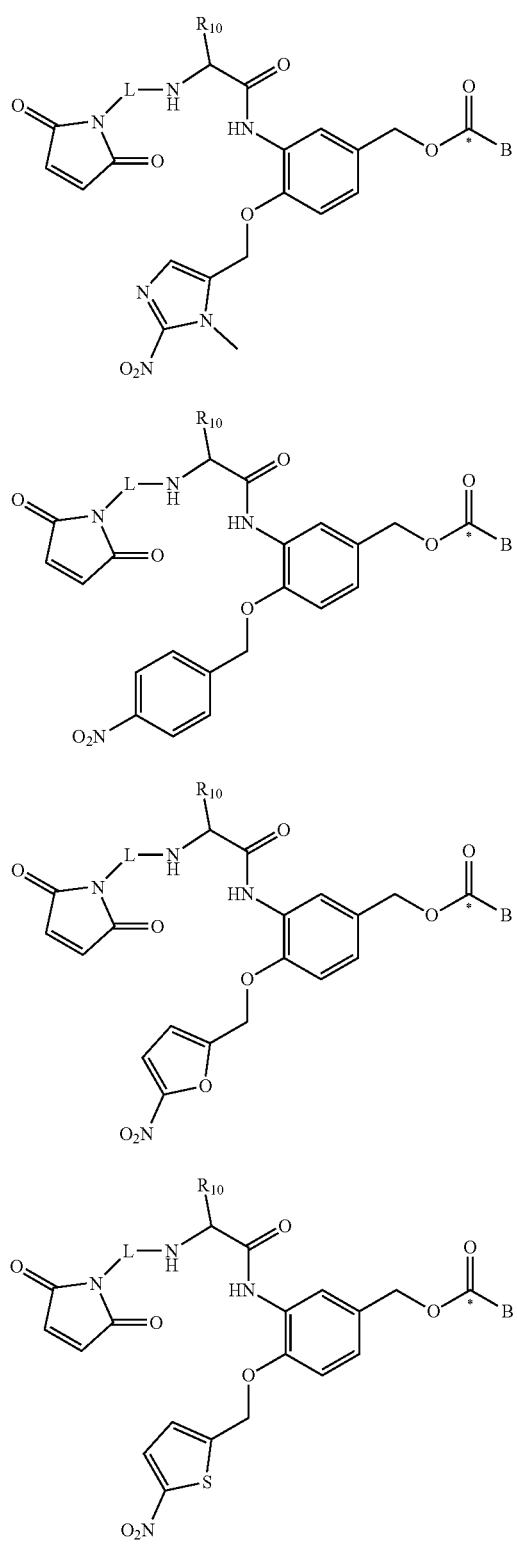
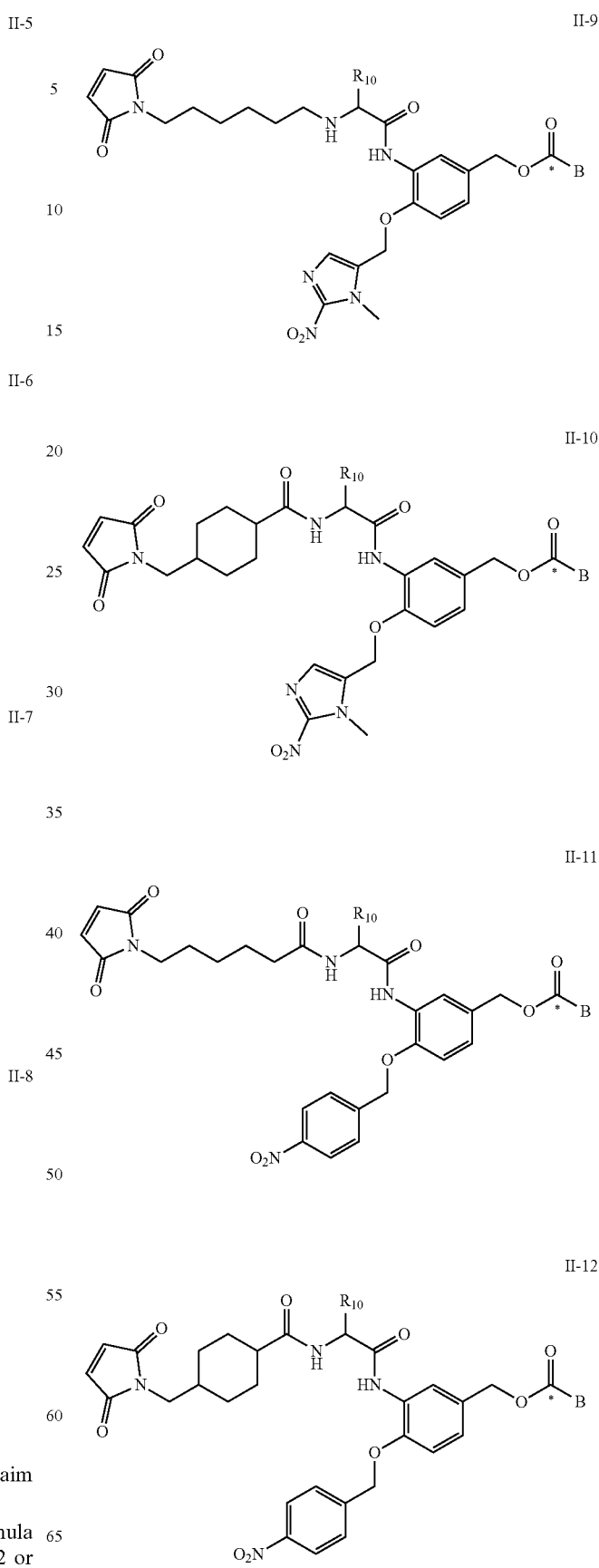
wherein, $R_{10}$, L and B are defined as described in claim 4; or
the compound has a structure represented by Formula II-9, Formula II-10, Formula II-11, Formula II-12 or Formula II-13,

II-13

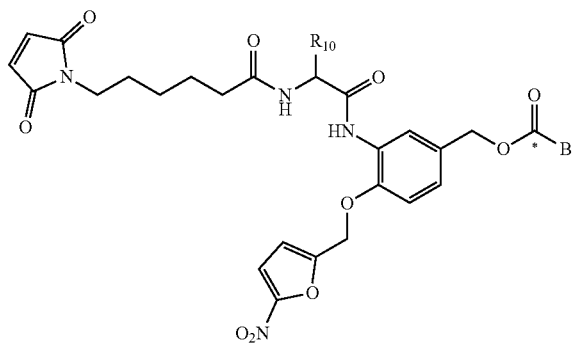

wherein, $R_{10}$ and B are defined as described in claim 4; or the compound represented by Formula II or Formula IIa has a structure represented by Formula II-14, Formula II-15, Formula II-16, Formula II-17 or Formula II-18,

II-14

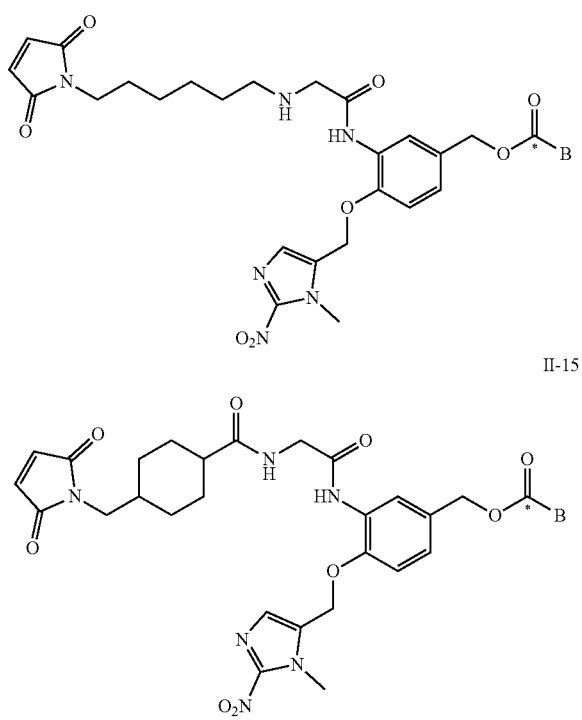

II-15

II-16

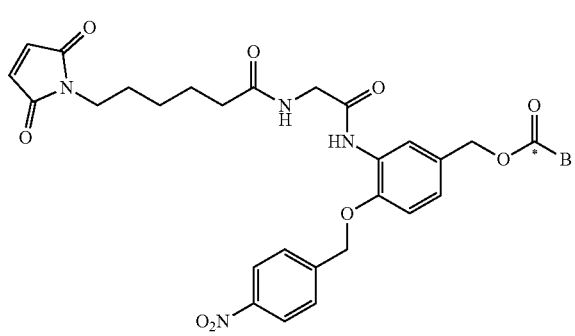

II-17

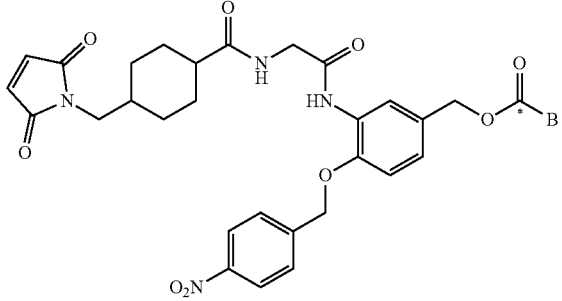

II-18

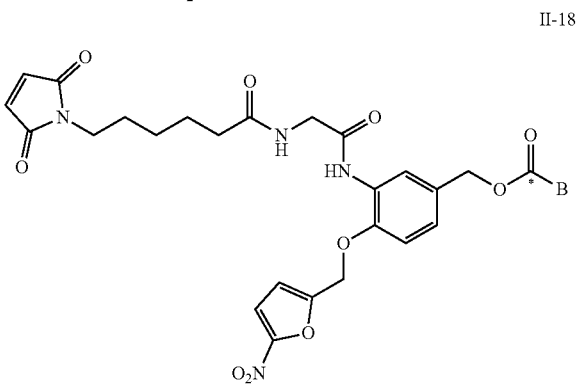

wherein, B is defined as described in claim 4.

7. A compound represented by Formula III or Formula III' or a salt thereof,

III

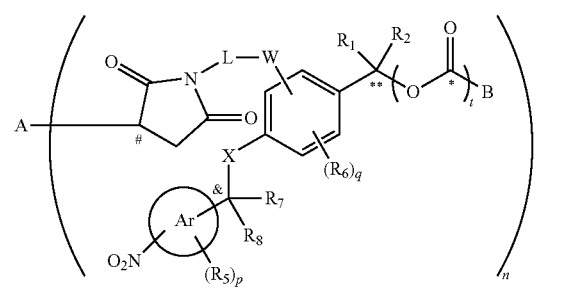

III'

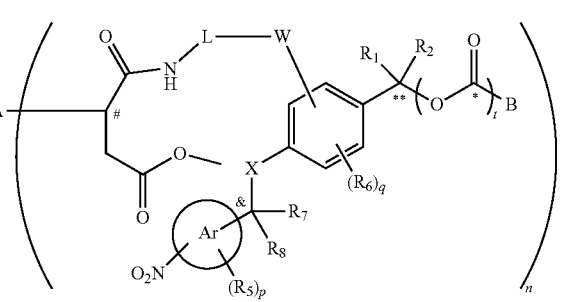

wherein:
$R_1$ is hydrogen, methyl, ethyl, n-propyl or isopropyl;
$R_2$ is hydrogen, methyl, ethyl, n-propyl or isopropyl;
X is oxygen atom (O), nitrogen atom (N) or sulfur atom (S);

Ar is aryl, heteroaryl, aryl-fused-heterocyclyl or heteroaryl-fused-heterocyclyl;
$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;
$R_7$ is hydrogen, methyl, ethyl, n-propyl or isopropyl;
$R_8$ is hydrogen, methyl, ethyl, n-propyl or isopropyl;
q is 0, 1, 2 or 3;
p is 0, 1, 2 or 3;
L is —$(CH_2)_iO(CH_2)_j$—, —$(CH_2)_iO(CH_2)_j$—C(O)—, —$(CH_2)_i$—C(O)NH—$(CH_2)_j$—, —$(CH_2CH_2O)_i$—$(CH_2)_j$—C(O)—, —$(CH_2)_i$—$(CH_2CH_2O)_j$—C(O)—, —$(OCH_2CH_2)_i$—, —$(CH_2)_m$—, —$(CH_2)_r$—C(O)—, —$(CH_2)_k$—C(O)NH—$(CH_2CH_2O)_g$—$(CH_2)_h$—C(O)—, —$(CH_2)_b$—C(O)NH—CH[$(CH_2)_d$—NHC(O)—$(CH_2CH_2O)_e$—$(CH_2)_f$—$CH_3$]—,

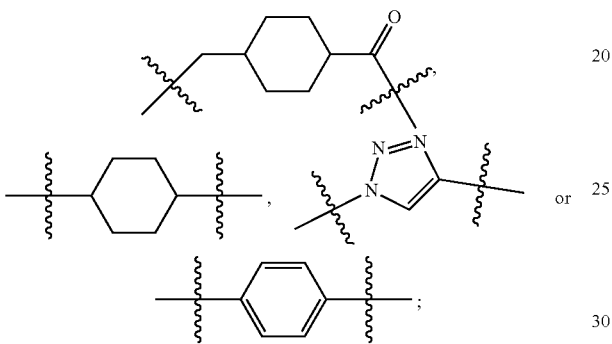

W represents a linking group, and is —NH—$CH_2$—C(O)—NH—, —NH—$CH_2$—$CH_2$—C(O)—NH—, —C(O)—NH—, —NH—C(O)—, —O—, —S—, —NH—, —N($CH_3$)—, —C(O)— or —NH—CH($R_{10}$)—C(O)—NH—, further preferably —NH—$CH_2$—C(O)—NH—, —C(O)—NH—, —NH—C(O)— or —O—;
$R_{10}$ is —H, —$CH_3$, —$C_3H_6$, —CH—$(CH_3)_2$, —$CH_2$—CH($CH_3$)$_2$, —CH($CH_3$)—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH($CH_3$)—OH or —$CH_2$—SH, preferably;
m is 1, 2, 3, 4, 5, 6, 7, 8 or 9;
each i is independently 1, 2, 3, 4, 5, 6, 7, 8 or 9;
each j is independently 1, 2, 3, 4, 5, 6, 7, 8 or 9;
r is 1, 2, 3, 4, 5, 6, 7, 8 or 9;
k is 1, 2, 3, 4, 5 or 6;
g is 1, 2, 3, 4, 5, 6, 7, 8, 9, 10, 11 or 12;
h is 1, 2, 3, 4, 5 or 6;
b is 1, 2, 3, 4, 5 or 6;
d is 1, 2, 3, 4, 5 or 6;
e is 1, 2, 3, 4, 5, 6, 7, 8, 9, 10, 11 or 12;
f is 1, 2, 3, 4, 5 or 6;
B is an active compound, selected from the group consisting of drug, cytotoxin, detection reagent, diagnostic reagent and targeting carrier;
B is coupled to the site* or site** through a N atom or O atom in the active compound molecule;
t is 0 or 1;
A is a targeting compound, selected from the group consisting of: protein, antibody, polypeptide, enzyme and small molecule;
n is a number between 0.5 and 8.5.

8. The compound or a salt thereof according to claim 7, wherein the compound has a structure represented by Formula IIIa,

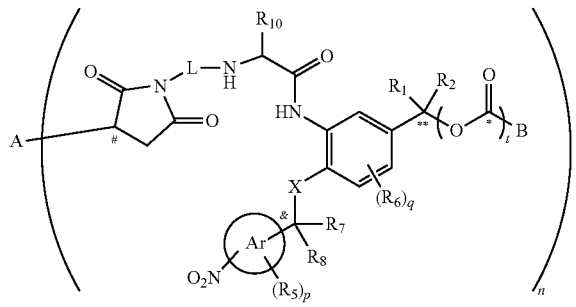

wherein:
$R_1$ is hydrogen, methyl, ethyl, n-propyl or isopropyl;
$R_2$ is hydrogen, methyl, ethyl, n-propyl or isopropyl;
X is oxygen atom (O), nitrogen atom (N) or sulfur atom (S);
Ar is aryl, heteroaryl, aryl-fused-heterocyclyl or heteroaryl-fused-heterocyclyl;
$R_5$ is hydrogen, methyl, ethyl, n-propyl, isopropyl, fluorine, chlorine, bromine, iodine, hydroxyl or cyano;
$R_6$ is hydrogen, methyl, ethyl, n-propyl, isopropyl, n-butyl, isobutyl, sec-butyl, tert-butyl, fluorine, chlorine, bromine, iodine, hydroxyl, nitro or cyano;
$R_7$ is hydrogen, methyl, ethyl, n-propyl or isopropyl;
$R_8$ is hydrogen, methyl, ethyl, n-propyl or isopropyl;
$R_{10}$ is —H, —$CH_3$, —$C_3H_6$, —CH—$(CH_3)_2$, —$CH_2$—CH($CH_3$)$_2$, —CH($CH_3$)—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH($CH_3$)—OH or —$CH_2$—SH;
q is 0, 1, 2 or 3;
p is 0, 1, 2 or 3;
L is —$(CH_2)_iO(CH_2)_j$—, —$(CH_2)_iO(CH_2)_j$—C(O)—, —$(CH_2)_i$—C(O)NH—$(CH_2)_j$—, —$(CH_2CH_2O)_i$—$(CH_2)_j$—C(O)—, —$(CH_2)_i$—$(CH_2CH_2O)_j$—C(O)—, —$(OCH_2CH_2)_i$—, —$(CH_2)_m$—, —$(CH_2)_r$—C(O)—, —$(CH_2)_k$—C(O)NH—$(CH_2CH_2O)_g$—$(CH_2)_h$—C(O)—, —$(CH_2)_b$—C(O)NH—CH[$(CH_2)_d$—NHC(O)—$(CH_2CH_2O)_e$—$(CH_2)_f$—$CH_3$]—,

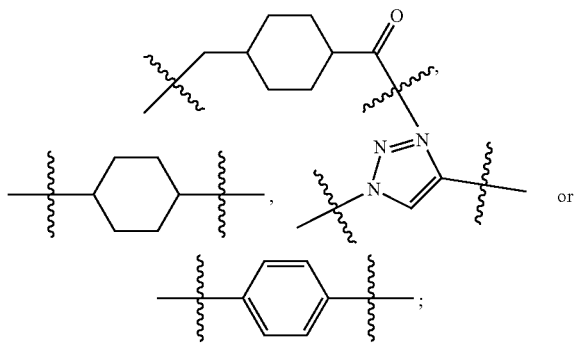

m is 1, 2, 3, 4, 5, 6, 7, 8 or 9;

r is 1, 2, 3, 4, 5, 6, 7, 8 or 9;

each i is independently 1, 2, 3, 4, 5, 6, 7, 8 or 9;

each j is independently 1, 2, 3, 4, 5, 6, 7, 8 or 9;

k is 1, 2, 3, 4, 5 or 6;

g is 1, 2, 3, 4, 5, 6, 7, 8, 9, 10, 11 or 12;

h is 1, 2, 3, 4, 5 or 6;

b is 1, 2, 3, 4, 5 or 6;

d is 1, 2, 3, 4, 5 or 6;

e is 1, 2, 3, 4, 5, 6, 7, 8, 9, 10, 11 or 12;

f is 1, 2, 3, 4, 5 or 6;

B is an active compound, selected from the group consisting of drug, cytotoxin, detection reagent, diagnostic reagent and targeting carrier; B is coupled to the site* or site** through a N atom or O atom in the active compound molecule;

t is 0 or 1;

A is a targeting compound, selected from the group consisting of: protein, antibody, polypeptide, enzyme and small molecule;

n is a number between 0.5 and 8.5.

9. The compound or a salt thereof according to claim 7, wherein the compound has a structure represented by Formula III-1, Formula III-2, Formula III-3 or Formula III-4,

III-1

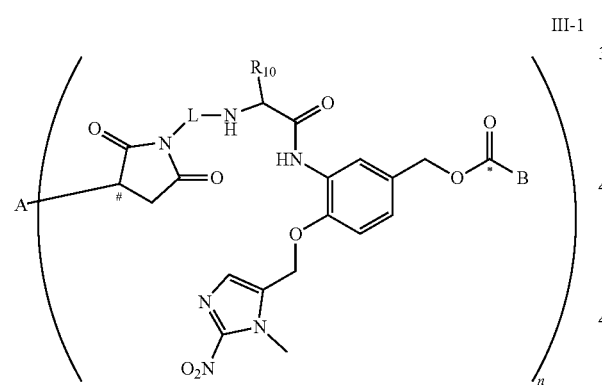

III-2

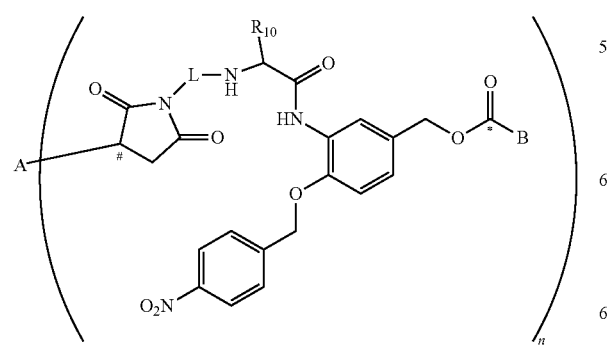

III-3

III-4

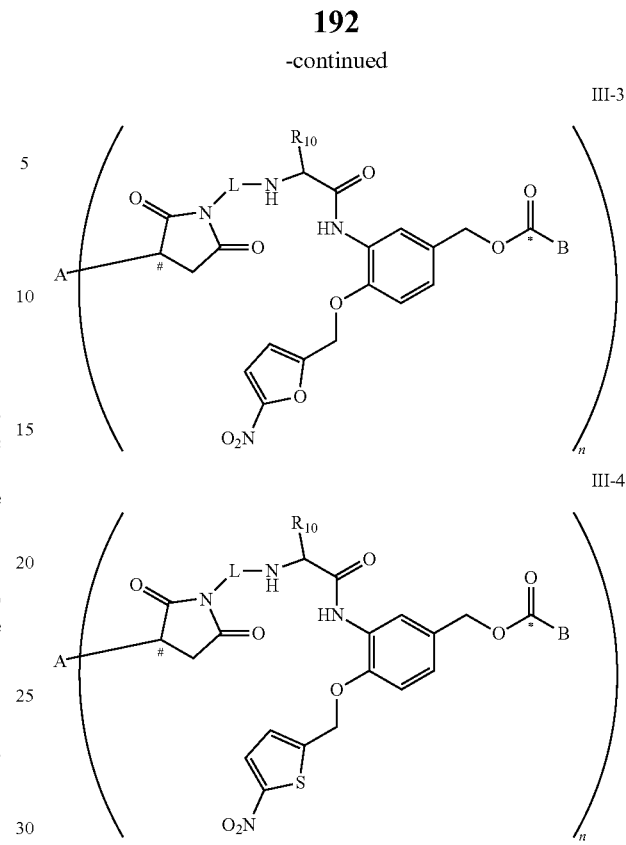

wherein, A, $R_{10}$, L, B and n are defined as described in claim 7; or the compound has a structure represented by Formula III-5, Formula III-6, Formula III-7, Formula III-8 or Formula III-9,

III-5

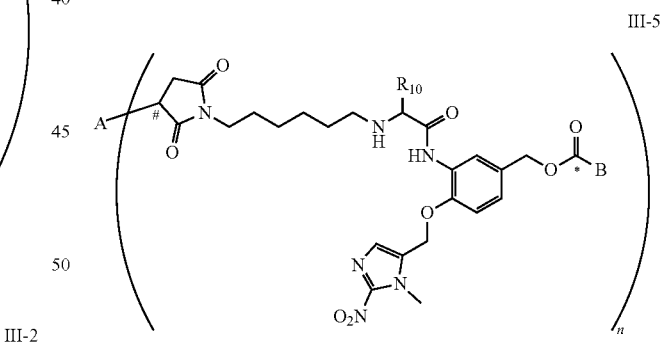

III-6

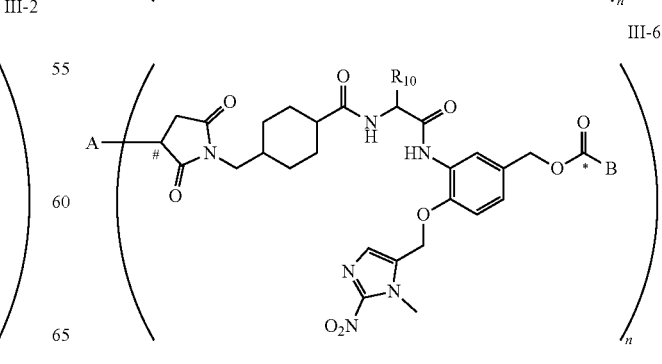

III-7

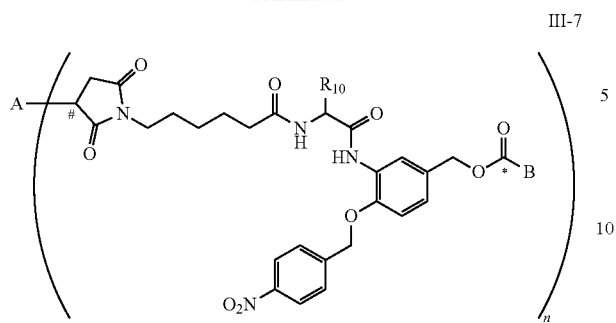

III-8

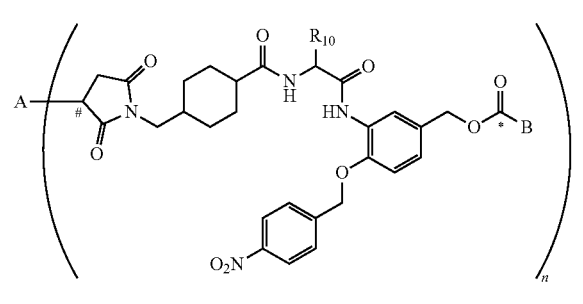

III-9

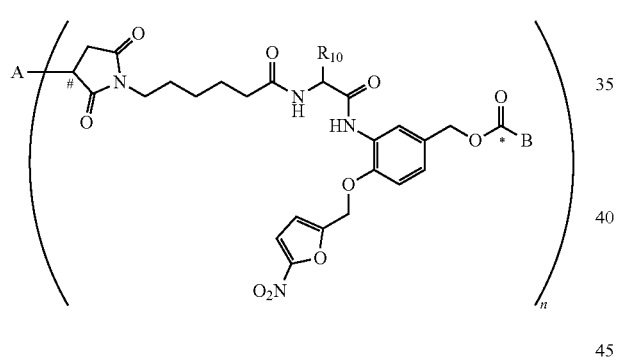

wherein, A, B, R$_{10}$ and n are defined as described in claim 7; or the compound represented by Formula III or Formula IIIa has a structure represented by Formula III-10, Formula III-11, Formula III-12, Formula III-13 or Formula III-14,

III-10

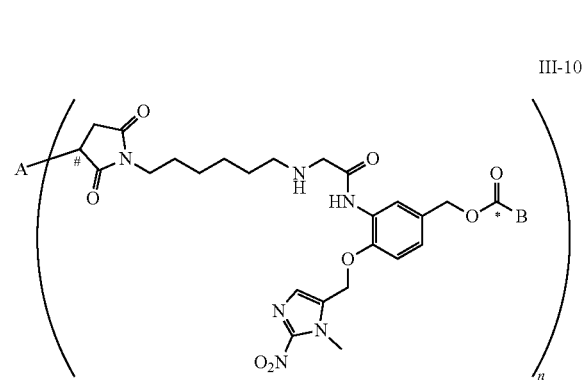

III-11

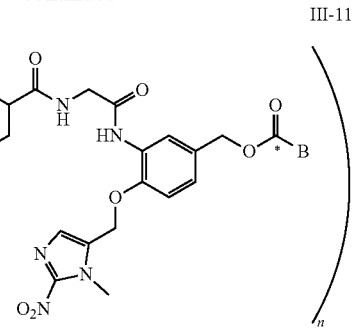

III-12

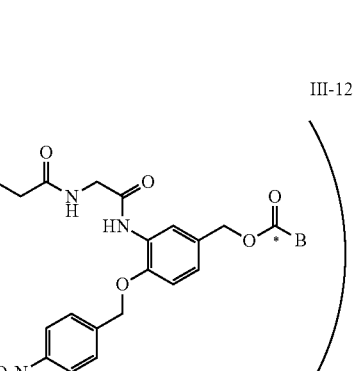

III-13

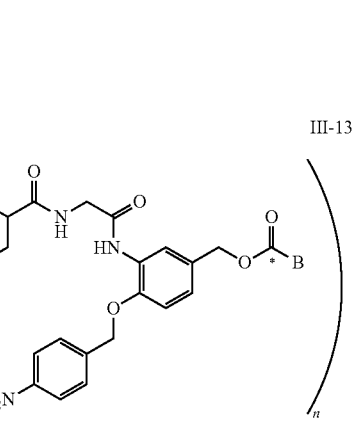

III-14

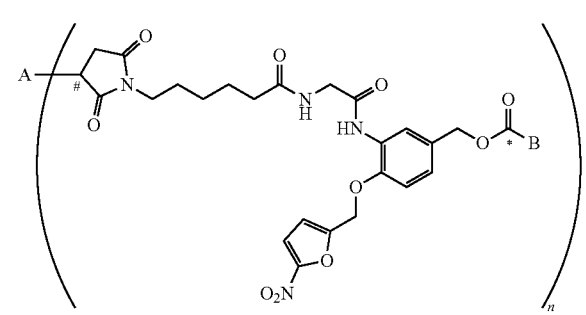

wherein, A, B and n are defined as described in claim 7.

10. The compound or a salt thereof according to claim 1, wherein the compound is selected from the group consisting of:

L01
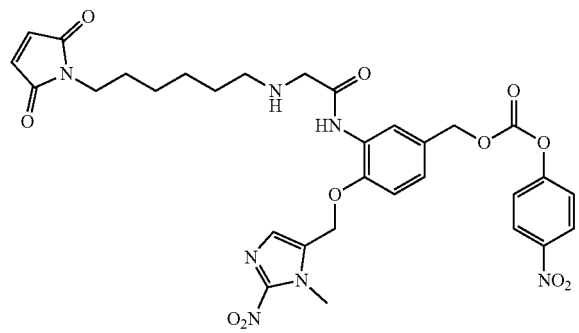
L02
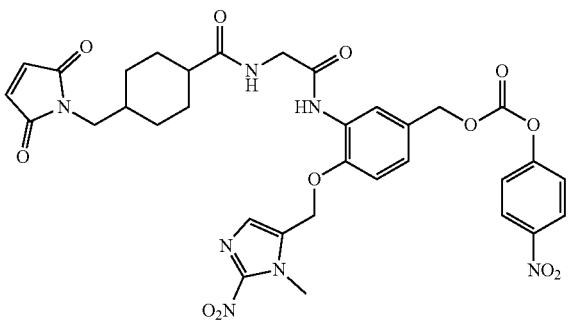
L03
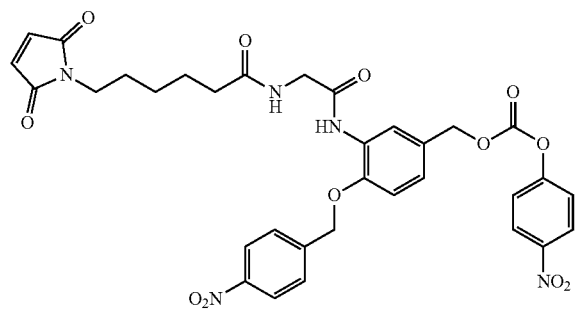
L04
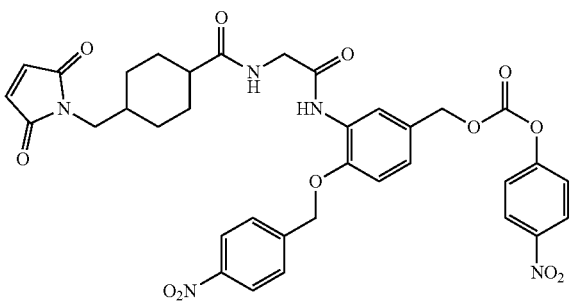
L05
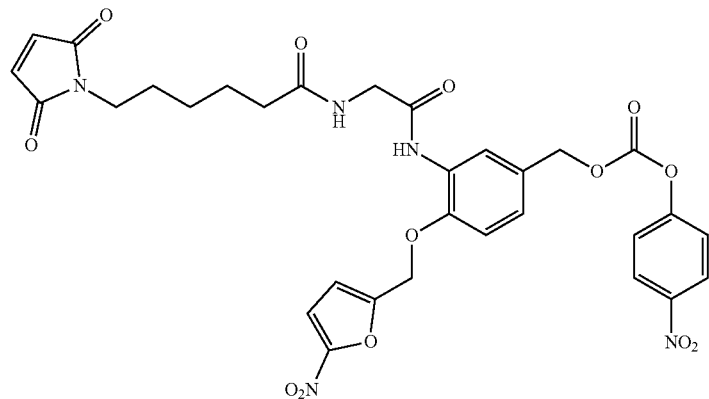
L06
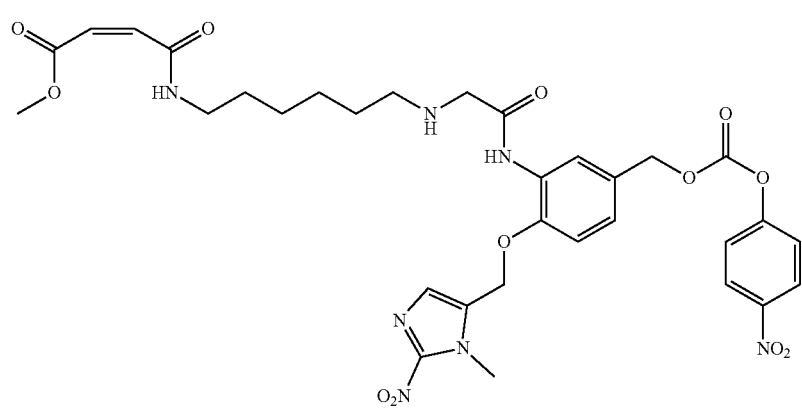

-continued
L07
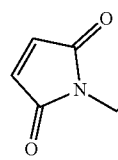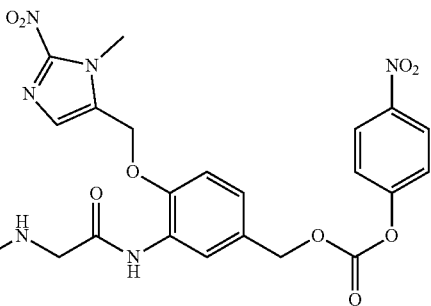
L08
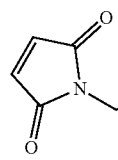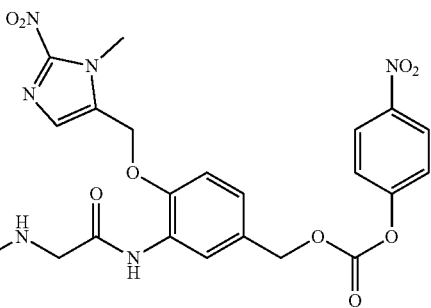
L09
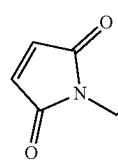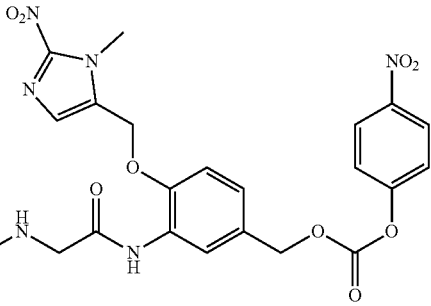
L10
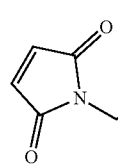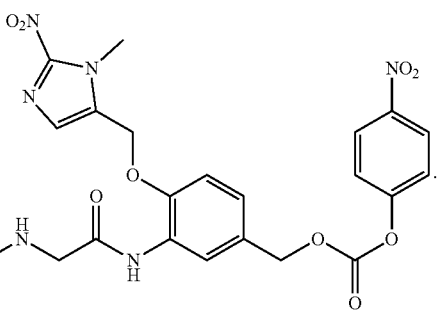

11. The compound or a salt thereof according to claim 4, wherein the compound is selected from the group consisting of:
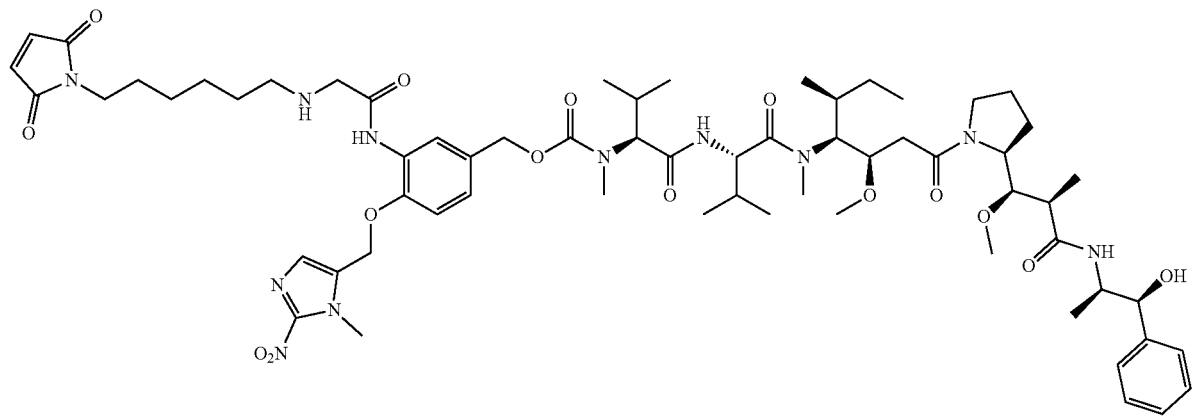
L01-MMAE
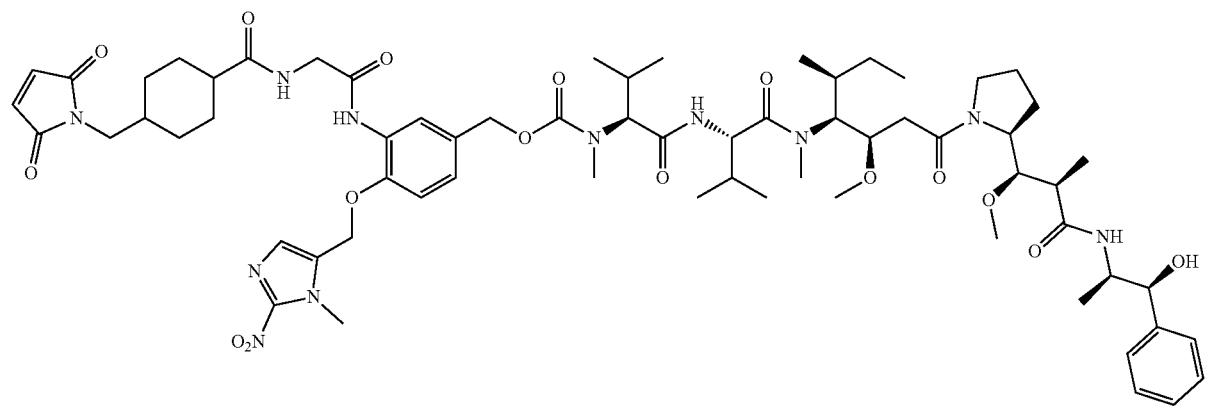
L02-MMAE
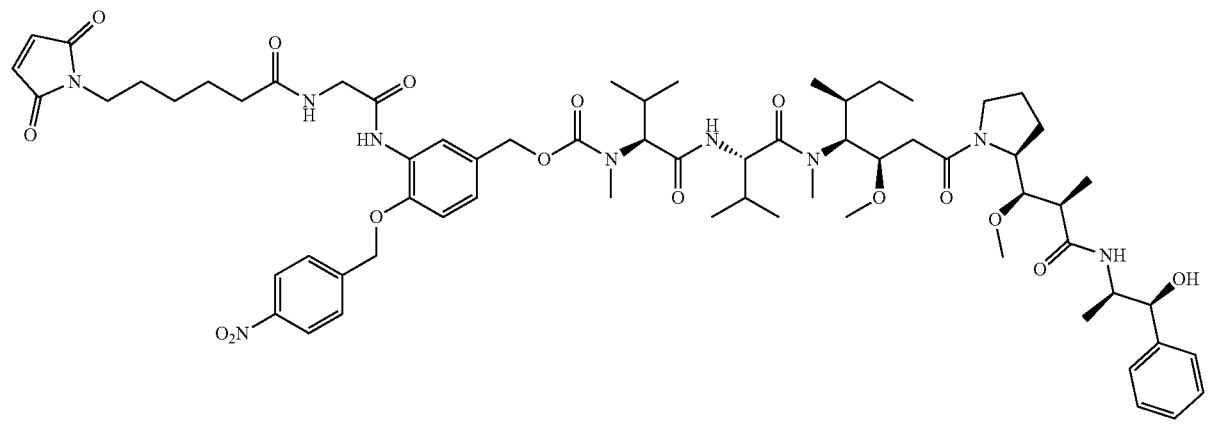
L03-MMAE -continued
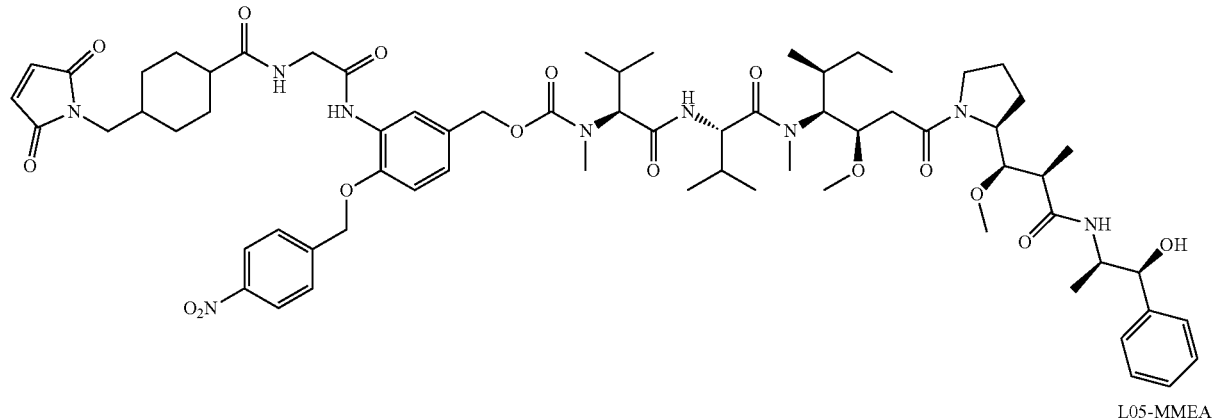
L04-MMEA
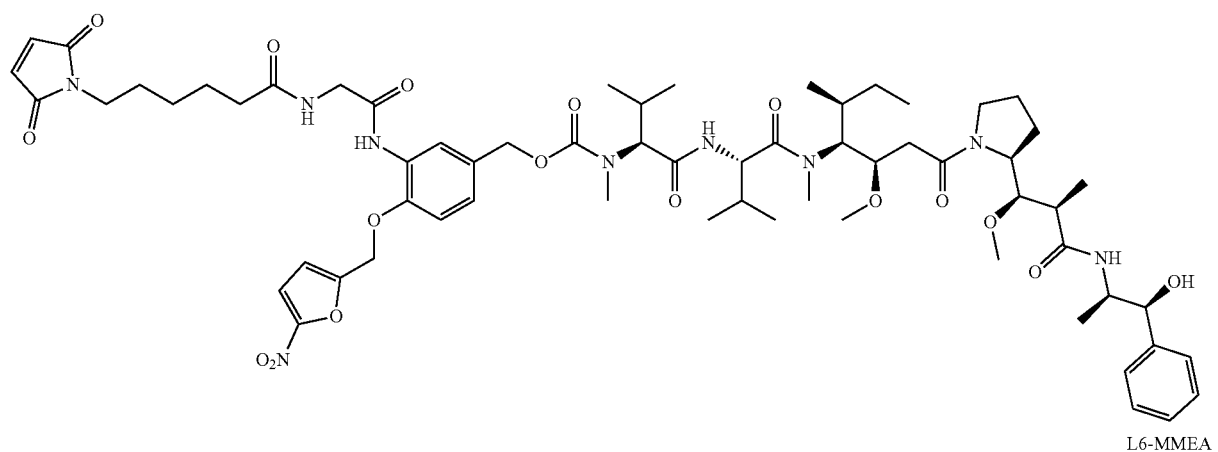
L05-MMEA
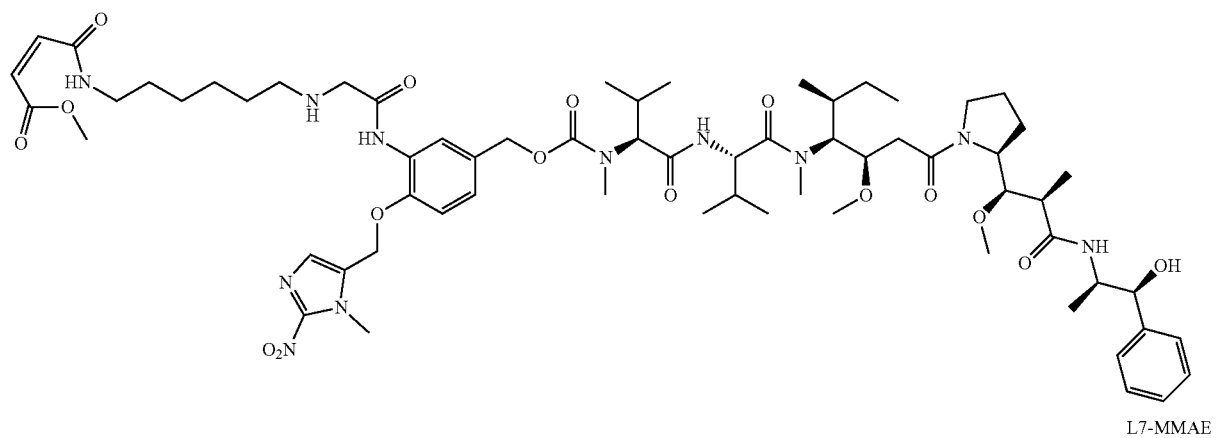
L6-MMEA
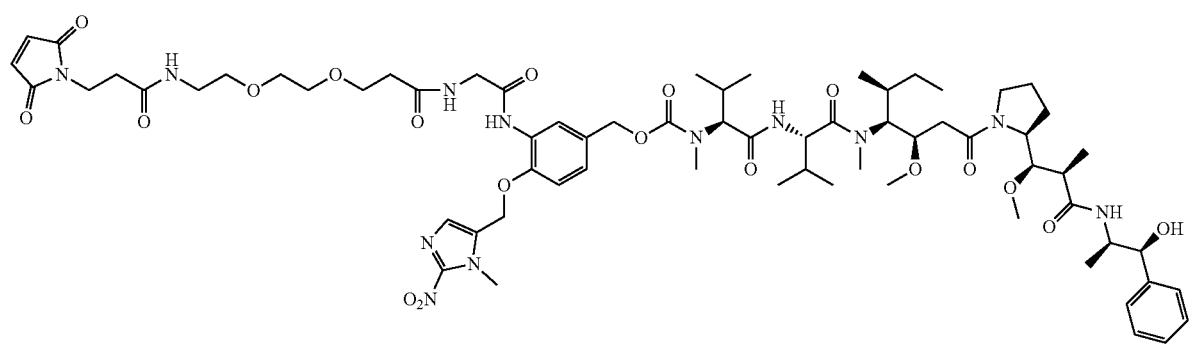
L7-MMAE -continued
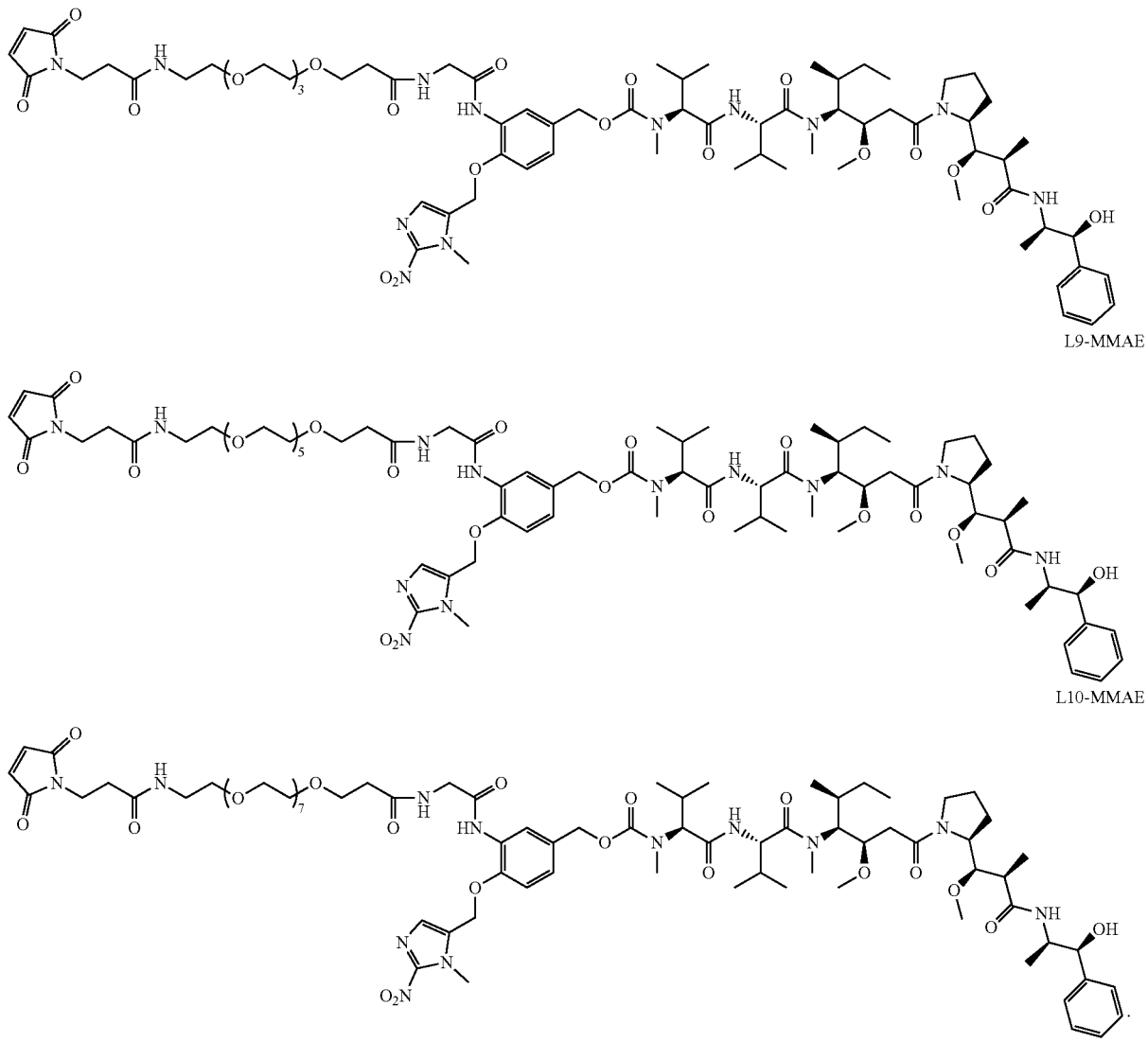
12. The compound or a salt thereof according to claim 7, wherein the compound is selected from the group consisting of:
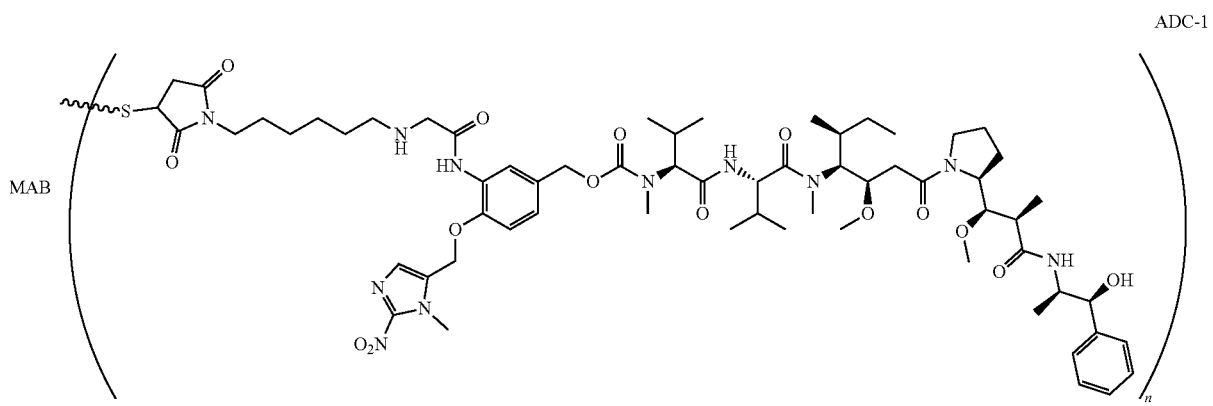

-continued
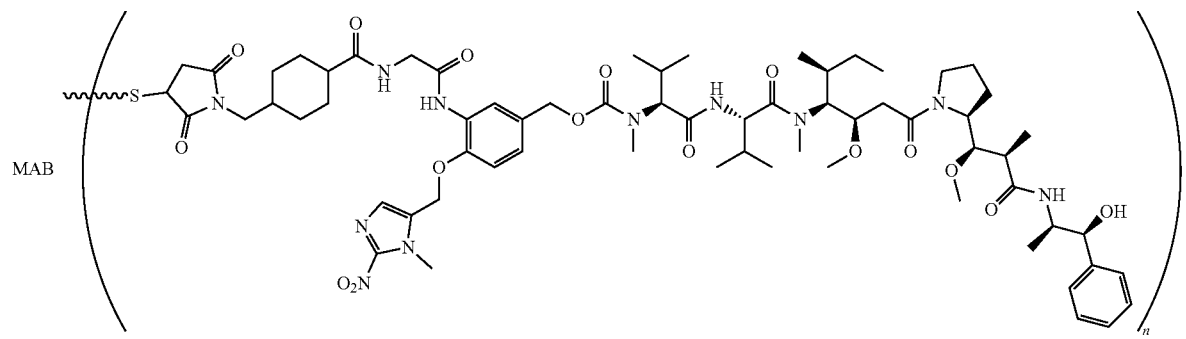
ADC-2
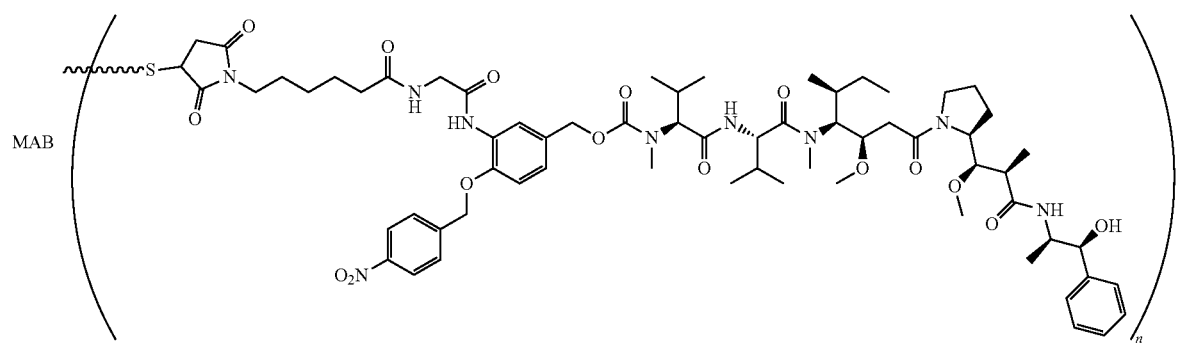
ADC-3
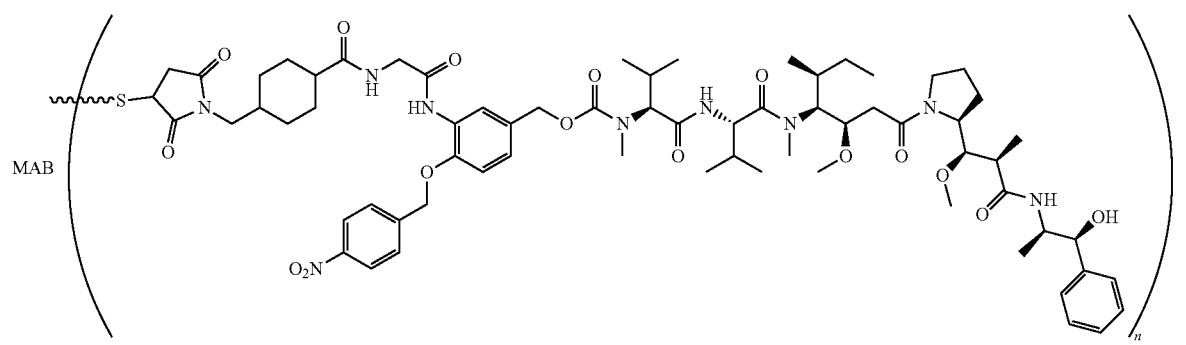
ADC-4
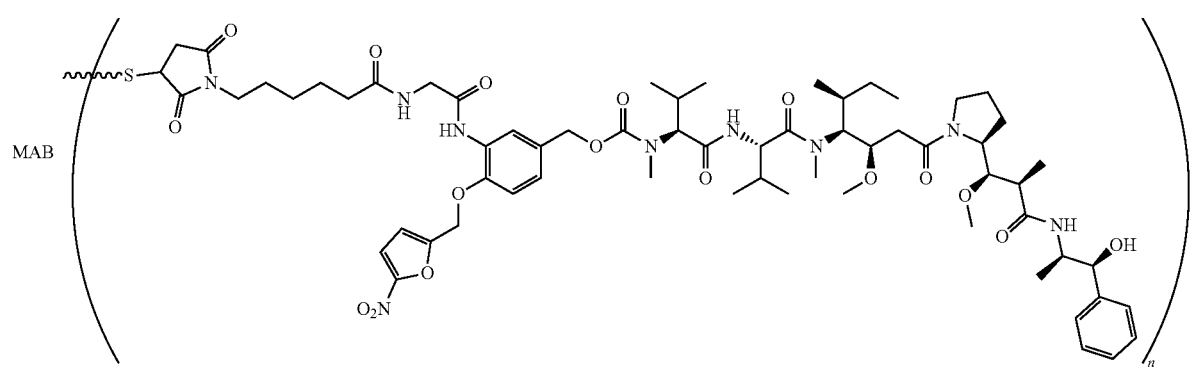
ADC-5

-continued
ADC-6
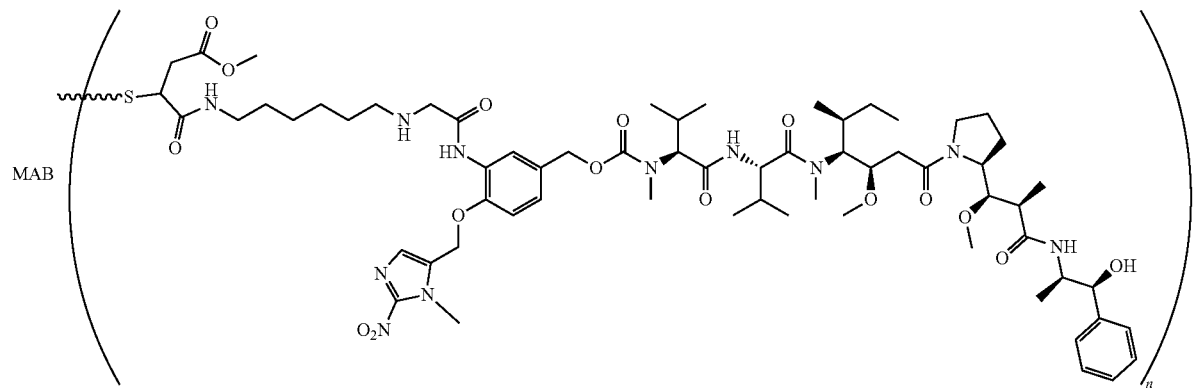
ADC-7
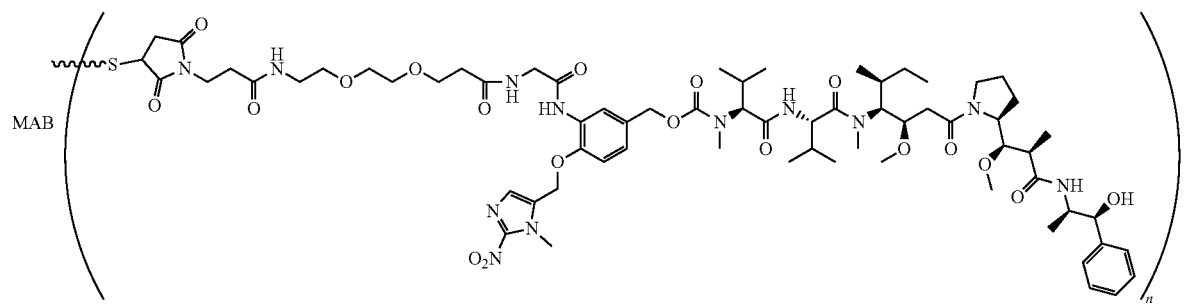
ADC-8
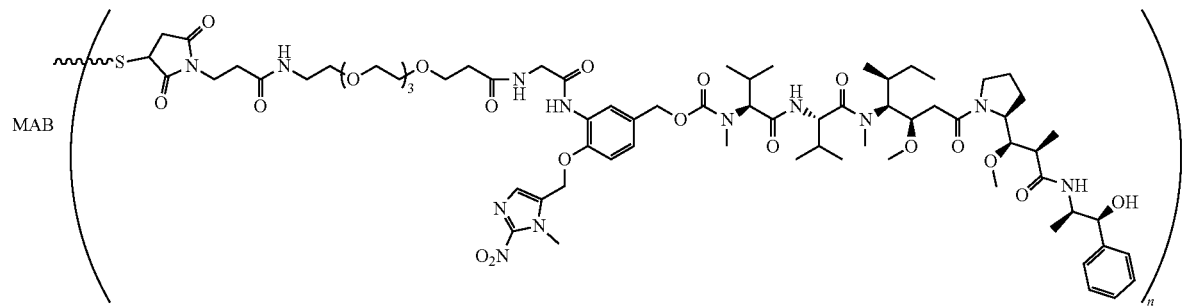
ADC-9
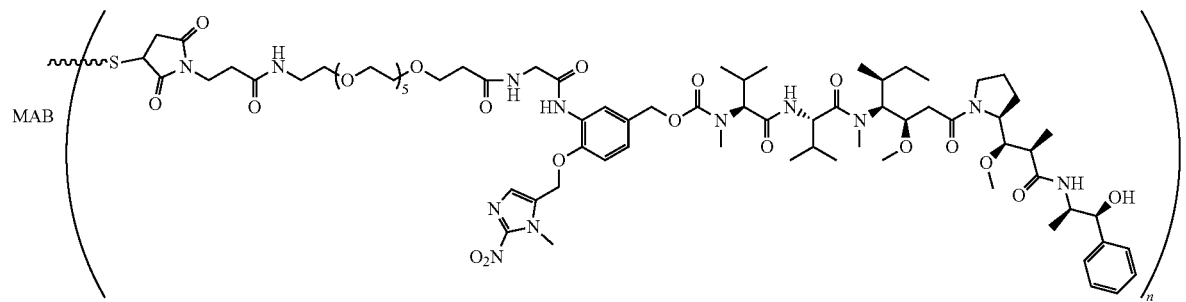

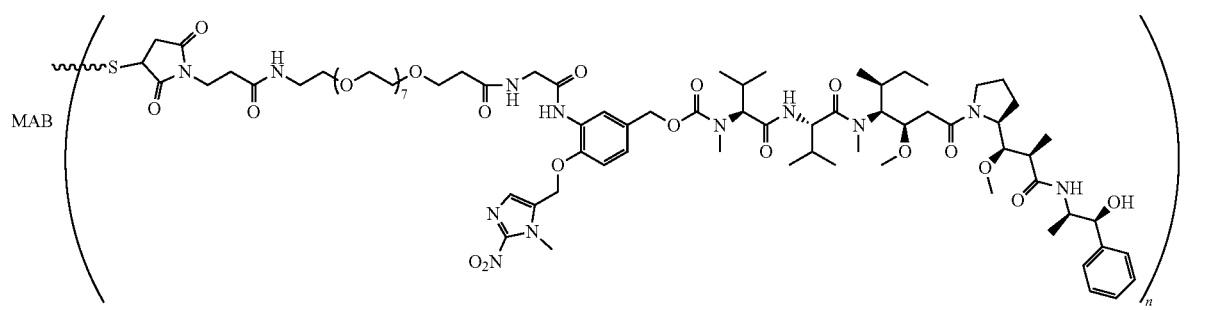

ADC-10 wherein, MAB is a monoclonal antibody, and n is defined as described in claim 7.

13. The compound or a salt thereof according to claim 7, wherein B is selected from the group consisting of: auristatin, monomethyl-auristatin E (MMAE), maytansine or derivatives thereof (such as maytansinoids, DM1, DM3, DM4), paclitaxel, calicheamicin, duocarmycin, doxorubicin, camptothecin, PBD (pyrrolobenzodiazepines) cytotoxin and derivatives thereof.

14. The compound or a salt thereof according to claim 7, wherein A is selected from the group consisting of: anti-HER2 humanized monoclonal antibody mil40, trastuzumab (HERCEPTIN), pertuzumab (PERJETA), cetuximab (ERBITUX), panitumumab (VECTIBIX), rituximab (RITUXAN), alemtuzumab (CAMPATH), ibritumomab (ZEVALIN), tositumomab (BEXXAR), ofatumumab (ARZERRA), bevacizumab (AVASTIN), ipilimumab (YERVOY), denosumab (XGEVA), pembrolizumab (KEYTRUDA), nivolumab (Opdivo), Avelumab (Bavencio), Atezolizumab (Tecentriq), durvalumab (Imfinzi), sacituzumab, rovalpituzumab, and biological analogues thereof, and A is coupled to the site # through a S atom in the targeting compound molecule.

15. A pharmaceutical composition comprising at least one of the compound or a salt thereof according to claim 7, and one or more pharmaceutically acceptable carriers or excipients.

16. A method for treatment of a disease or condition or alleviation of a severity of the disease or condition, the method comprising administering to a patient in need of such treatment an effective amount of the compound or a salt thereof according to claim 7, wherein the disease or condition is selected from the group consisting of tumor, infectious disease, hematological disease, metabolic disease, and inflammation.

17. The method according to claim 16, the tumor is selected from the group consisting of cancer, lymphoma, lymphoid tumor, blastoma, sarcoma and leukemia.

18. The method according to claim 17, the cancer is selected from the group consisting of: breast cancer; squamous cell carcinoma; lung cancer, including small cell lung cancer, non-small cell lung cancer, adenocarcinoma of lung and squamous cell carcinoma of lung; peritoneal cancer; liver cancer; gastric cancer; gastrointestinal cancer; pancreatic cancer; glioblastoma; cervical cancer; ovarian cancer; liver cancer; bladder cancer; urethral cancer; hepatocellular tumor; breast cancer; intestinal cancer; colon cancer; rectal cancer; colorectal cancer; endometrial cancer; uterine cancer; salivary gland cancer; kidney cancer; prostate cancer; vulvar cancer; thyroid cancer; liver cancer; anal cancer; penile cancer; melanoma; multiple myeloma and B-cell lymphoma; brain cancer; gallbladder cancer; esophageal cancer; cholangiocarcinoma; head and neck cancer and related metastatic tumor.

* * * * *